Figure 1:

US006060594A

United States Patent [19]
English et al.

[11] Patent Number: 6,060,594
[45] Date of Patent: May 9, 2000

[54] NUCLEIC ACID SEGMENTS ENCODING MODIFIED BACILLUS THURINGIENSIS COLEOPTERAN-TOXIC CRYSTAL PROTEINS

[75] Inventors: Leigh H. English, Churchville; Susan M. Brussock, New Hope, both of Pa.; Thomas M. Malvar, St. Louis, Mo.; James W. Bryson, Langhorne, Pa.; Caroline A. Kulesza, Charlottesville, Va.; Frederick S. Walters, Beaver Falls, Pa.; Stephen L. Slatin, Fair Lawn; Michael A. Von Tersch, Ewing Township, both of N.J.; Charles Romano, Ballwin, Mo.

[73] Assignees: Ecogen, Inc., Langhorn, Pa.; Monsanto Company, St. Louis, Mo.

[21] Appl. No.: 08/993,722

[22] Filed: Dec. 18, 1997

[51] Int. Cl.$^7$ .............................. C12N 15/32; C12N 15/82
[52] U.S. Cl. ..................................... 536/23.71; 435/320.1; 435/440
[58] Field of Search ................................ 435/320.1, 440; 536/23.71, 24.1

[56] References Cited

U.S. PATENT DOCUMENTS

| | | | |
|---|---|---|---|
| 4,797,279 | 1/1989 | Karamata et al. | 424/93 |
| 4,910,016 | 3/1990 | Gaertner et al. | 424/93 |
| 5,024,837 | 6/1991 | Donovan et al. | 424/93 |
| 5,071,654 | 12/1991 | English | 424/405 |
| 5,187,091 | 2/1993 | Donovan et al. | 435/240.4 |
| 5,500,365 | 3/1996 | Fischhoff et al. | 435/240.4 |
| 5,567,862 | 10/1996 | Adang et al. | 800/205 |
| 5,659,123 | 8/1997 | Van Rie et al. | 800/205 |

OTHER PUBLICATIONS

Almond and Dean, "Suppression of protein structure destabilizing mutations in *Bacillus thuringiensis* δ–Endotoxins by second site mutations," *Biochemistry*, 32:1040–1046, 1993.

Angsuthanasamnbat et al., "Effects on toxicity of eliminating a cleavage site in a predicted interhelical loop in *Bacillus thuringiensis* CryIVB δ–endotoxin," *FEMS Microbiol. Lett.*, 111:255–262, 1993.

Aronson et al., "Mutagenesis of specificity and toxicity regions of a *Bacillus thuringiensis* protoxin gene." *J. Bacteriol.*, 177:4059–4065, 1995.

Baum, "TnpI recombinase: Identification of sites within Tn5401 required for TnpI binding and site–specific recombination," *J. Bacteriol.*, 177(14):4036–4042, 1995.

Caramori et al., "In vivo generation of hybrids between two *Bacillus thuringiensis* insect–toxin–encoding genes," *Gene*, 98:37–44, 1991.

Carroll et al., "Proteolytic processing of a coleopteran–specific δ–endotoxin produced by *Bacillus thuringiensis* var. *tenebrionis*," *Biochem. J.*, 261:99–105, 1989.

Chen et al., "Mutations in domain I of *Bacillus thuringiensis* δ–endotoxin CryIAb reduce the irreversible binding of toxin to *Manduca sexta* brush border membrane vesicles," *J. Biol. Chem.*, 270:6412–6419, 1995.

Chen et al., "Site–directed mutations in a highly conserved region of *Bacillus thuringiensis* δ–endotoxin affect inhibition of short circuit current across *Bombyx mori* midguts," *Proc. Natl. Acad. Sci. USA*, 90:9041–9045, 1993.

Chowrira and Burke, "Extensive phosphorothioate substitution yields highly active and nuclease–resistant hairpin ribozymes," *Nucl. Acids Res.*, 20(11):2835–2840, 1992.

Cody et al., "Purification and crystallization of insecticidal δ–endotoxin CryIIIB2 from *Bacillus thuringiensis*," *Proteins: Struct. Funct. Genet.*, 14:324, 1992.

Cummings and Ellar, "Chemical modification of *Bacillus thuringiensis* activated δ–endotoxin and its effect on toxicity and binding to *Manduca sexta* midgut membranes," *Microbiol.*, 140:2737–2747, 1994.

Diehn et al., "Problems that can limit the expression of foreign genes in plants: lessons to be learned from B.t. toxin genes," *Genet. Engineer.*, 18:83–99, 1996.

Donovan et al., "Isolation and characterization of EG2158, a new strain of *Bacillus thuringiensis* toxic to coleopteran larvae, and nucleotide sequence of the toxin gene," *Mol. Gen. Genet.*, 214:365–372, 1988.

English and Slatin, "Mode of action of delta–endotoxins from *Bacillus thuringiensis*: A comparison with other bacterial toxins," *Insect Biochem. Mol. Biol.*, 22(1):1–7, 1992.

English et al., "Mode of action of CryIIA: a *Bacillus thuringiensis* Delta–endotoxin," *Insect Biochem. Molec. Biol.*, 24(10):1025–1035, 1994.

Gazit and Shai, "Structural and functional characterization of the α–5 segment of *Bacillus thuringiensis* δ–endotoxin," *Biochemistry*, 32:3429–3436, 1993.

Gazit and Shai, "The assembly and organization of the α5 and α7 helices from the pore–forming domain of *Bacillus thuringiensis* δ–endotoxin," *J. Biol. Chem.*, 270:2571–2578, 1995.

Ge et al., "Functional domains of *Bacillus thuringiensis* insecticidal crystal proteins: refinement of *Heliothis virescens* and *Trichoplusia ni* specificity domains on CryIA(c)," *J. Biol. Chem.*, 266:17954–17958, 1991.

Grochulski et al., "*Bacillus thuringiensis* CryIA(a) insecticidal toxin: crystal structure and channel formation," *J. Mol. Biol.*, 254:447–464, 1995.

Höfte et al., "Structural and functional analysis of a cloned delta endotoxin of *Bacillus thuringiensis berliner* 1715," *Eur. J. Biochem.*, 161:273–280, 1986.

(List continued on next page.)

Primary Examiner—Lynette R. F. Smith
Assistant Examiner—Amy J. Nelson
Attorney, Agent, or Firm—Arnold White & Durkee

[57] ABSTRACT

Disclosed are nucleic acid segments comprising synthetically-modified genes encoding Coleopteran-toxic *B. thuringiensis* δ-endotoxins. Also disclosed are methods of using these genes for the recombinant expression of polypeptides, the preparation of vectors containing the genes, and methods for transforming suitable host cells.

97 Claims, 19 Drawing Sheets

OTHER PUBLICATIONS

Johnson et al., "Insecticidal activity of EG4961, a novel strain of *Bacillus thuringiensis* toxic to larvae and adults of Southern Corn Rootworm (Coleoptera: Chrysomelidae) and Colorado Potato Beetle (Coleoptera: Chrysomelidae)," *J. Econ. Entomol.,* 86(2):330–333, 1993.

Kwak et al., "Exploration of receptor binding of *Bacillus thuringiensis* toxins," *Mem. Inst. Oswaldo,* 90:75–79, 1995.

Lambert et al., "A *Bacillus thuringiensis* insecticidal crystal protein with a high activity against members of the family Noctuidae," *Appl. Environ. Microbiol.,* 62:80–86, 1996.

Lee et al., "Domain III exchanges of *Bacillus thuringiensis* CryIA toxins affect binding to different gypsy moth midgut receptors," *Biochem. Biophys. Res. Commun.,* 216:306–312, 1995.

Lee et al., "Location of a *Bombyx mori* receptor binding region on a *Bacillus thuringiensis* δ–endotoxin," *J. Biol. Chem.,* 267:3115–3121, 1992.

Lu et al., "Identification of amino acid residues of *Bacillus thuringiensis* δ–endotoxin CryIAa associated with membrane binding and toxicity to *Bombyx mori,*" *J. Bacteriol.,* 176:5554–5559, 1994.

Rajamohan et al., "Role of domain II, loop 2 residues of *Bacillus thuringiensis* CryIAb δ–endotoxin in reversible and irreversible binding to *Manduca sexta* and *Heliothis virescens,*" *J. Biol. Chem.,* 271:2390–2397, 1996.

Rajamohan et al., "Single amino acid changes in domain II of *Bacillus thuringiensis* CryIAb δ–endotoxin affect irreversible binding to *Manduca sexta* midgut membrane vesicles," *J. Bacteriol.,* 177:2276–2282, 1995.

Rupar et al., "Two novel strains of *Bacillus thuringiensis* toxic to Coleopterans," *Applied Environ. Microbiol.,* 57(11):3337–3344, 1991.

Slaney et al., "Mode of action of *Bacillus thuringiensis* toxin CryIIIA: An analysis of toxicity in *Leptinotarsa decemlineata* (Say) and *Diabrotica undecimpunctata howardi* Barber," *Insect Biochem. Molec. Biol.,* 22:9–18, 1992.

Slatin et al., "Delta–endotoxins form cation–selective channels in planar lipid bilayers," *Biochem. Biophys. Res. Comm.,* 169(2):765–772, 1990.

Smedley and Ellar, "Mutagenesis of three surface–exposed loops of a *Bacillus thuringiensis* insecticidal toxin reveals residues important for toxicity, receptor recognition and possibly membrane insertion," *Microbiology,* 142:1617–1624, 1996.

Smith et al., "Mosquitocidal activity of the CryIC δ–endotoxin from *Bacillus thuringiensis* subsp. aizawai," *Appl. Environ. Microbiol.,* 62(2):680–684, 1996.

Smith and Ellar, "Mutagenesis of two surface–exposed loops of the *Bacillus thuringiensis* Cry1C δ–endotoxin affects insecticidal specificity," *Biochem. J.,* 302:611–616, 1994.

Von Tersch et al., "Membrane permeabilizing activity of *Bacillus thuringiensis* Coleopteran–active toxins CryIIIB2 and CryIIIB2 domain 1 peptides," *Appl. Env Microbiol.,* 60:3711–3717, 1994.

Walters et al., "Ion channel activity of N–terminal fragments from CryIA(c) delta–endotoxin," *Biochem. Biophys. Res. Commun.,* 196(2):921–926, 1993.

Wolfersberger et al., "Site–directed mutations in the third domain of *Bacillus thuringiensis* δ–endotoxin CryIAa affect its ability to increase the permeability of *Bombyx mori* midgut brush border membrane vesicles," *Appl. Environ. Microbiol.,* 62(1):279–282, 1996.

Wu and Dean, "Functional significance of loops in the receptor binding domain of *Bacillus thuringiensis* CryIIIA δ–endotoxin," *J. Mol. Biol.,* 255:628–640, 1996.

Wu and Aronson, "Localized mutagenesis defines regions of the *Bacillus thuringiensis* δ–endotoxin involved in toxicity and specificity," *J. Biol. Chem.,* 267:2311–2317, 1992.

Zhang and Matthews, "Conservations of solvent–binding sites in 10 crystal forms of T4 lysozyme," *Prot. Sci.,* 3:1031–1039, 1994.

| alpha helix | Amino acid Residues |
|---|---|
| α1 | 63-79 |
| α2a | 85-98 |
| α2b | 105-118 |
| α3 | 124-153 |
| α4 | 161-186 |
| α5 | 194-215 |
| α6 | 223-255 |
| α7 | 260-286 |

FIG. 4

Sheet 1

| β Strand | Amino Acid Residue |
|---|---|
| β2 | 339-350 |
| β3a | 256-360 |
| β3b | 362-368 |
| β4 | 375-379 |
| β5 | 390-395 |

Sheet 2

| β Strand | Amino Acid Residue |
|---|---|
| β6 | 402-412 |
| β7a | 416-419 |
| β7b | 423-430 |
| β8 | 435-442 |
| β9 | 452-456 |

Sheet 3

| β Strand | Amino Acid Residue |
|---|---|
| β1 | 296-306 |
| β10 | 472-483 |
| β11 | 492-498 |

FIG. 6

| Strand Number | Amino Acid Residues |
|---|---|
| β12 | 505-509 |
| β13 | 512-515 |
| β14 | 522-528 |
| β15 | 539-544 |
| β16 | 550-557 |
| β17 | 563-574 |
| β18 | 578-584 |
| β19 | 590-596 |
| β20 | 609-614 |
| β21 | 616-619 |
| β22 | 626-636 |
| β23 | 638-650 |

FIG. 8

FIG. 14

ALIGNMENT OF CRY3 SEQUENCES (Numbered according to Cry3BB)
(alpha helices underlined, beta sheets marked with +++'s)

```
                 1        10        20        30        40
CRY3C:           MNPNNRSEHDTIKATENNEVSNNHAQYPLADTP--TLEELNY
CRYCBB2:         MNPNNRSEHDTIKVTPNSELPTNHNQYPLADNPNSTLEELNY
CRY3BB:          MNPNNRSEHDTIKVTPNSELQTNHNQYPLADNPNSTLEELNY
CRY3BA:      MIRMGGRKMNPNNRSEYDTIKVTPNSELPTNHNQYPLADNPNSTLEELNY
CRY3A:       MIRKGGRKMNPNNRSEHDTIKTTENNEVPTNHVQYPLAETPNPTLEDLNY 50        60        70        80        90
CRY3C:       KEFLRRTTDNNVEALDSSTTKDAIQKGISIIGDLLGVVGFPYGGALVSFY
CRYCBB2:     KEFLRMTEDSSTEVLDNSTVKDAVGTGISVVGQILGVVGVPFAGALTSFY
CRY3BB:      KEFLRMTEDSSTEVLDNSTVKDAVGTGISVVGQILGVVGVPFAGALTSFY
CRY3BA:      KEFLRMTADNSTEVLDSSTVKDAVGTGISVVGQILGVVGVPFAGALTSFY
CRY3A:       KEFLRMTADNNTEALDSSTTKDVIQKGISVVGDLLGVVGFPFGGALVSFY 100       110       120       130       140
CRY3C:       TNLLNTIWPGE-DPLKAFMQQVEALIDQKIADYAKDKATAELQGLKNVFK
CRY3BB2:     QSFLDTIWPSDADPWKAFMAQVEVLIDKKIEEYAKSKALAELQGLQNNFE
CRY3BB:      QSFLNTIWPSDADPWKAFMAQVEVLIDKKIEEYAKSKALAELQGLQNNFE
CRY3BA:      QSFLNAIWPSDADPWKAFMAQVEVLIDKKIEEYAKSKALAELQGLQNNFE
CRY3A:       TNFLNTIWPSE-DPWKAFMEQVEALMDQKIADYAKNKALAELQGLQNNVE 150       160       170       180       190
CRY3C:       DYVSALDSWDKTPLTLRDGRSQGRIRELFSQAESHFRRSMPSFAVSGYEV
CRY3BB2:     DYVNALNSWKKTPLSLRSKRSQDRIRELFSQAESHFRNSMPSFAVSKFEV
CRY3BB:      DYVNALNSWKKTPLSLRSKRSQDRIRELFSQAESHFRNSMPSFAVSKFEV
CRY3BA:      DYVNALDSWKKAPVNLRSRRSQDRIRELFSQAESHFRNSMPSFAVSKFEV
CRY3A:       DYVSALSSWQKNPVSSRNPHSQGRIRELFSQAESHFRNSMPSFAISGYEV
```

FIG. 17A

```
                200       210       220       230       240
CRY3C:    LFLPTYAQAANTHLLLLKDAQIYGTDWGYSTDDLNEFHTKQKDLTIEYTN
CRY3BB2:  LFLPTYAQAANTHLLLLKDAQVFGEEWGYSSEDVAEFYHRQLKLTQQYTD
CRY3BB:   LFLPTYAQAANTHLLLLKDAQVFGEEWGYSSEDVAEFYHRQLKLTQQYTD
CRY3BA:   LFLPTYAQAANTHLLLLKDAQVFGEEWGYSSEDIAEFYQRQLKLTQQYTD
CRY3A:    LFLTTYAQAANTHLFLLKDAQIYGEEWGYEKEDIAEFYKRQLKLTQEYTD 250       260       270       280       290
CRY3C:    HCAKWYKAGLDKLRGSTYEEWVKFNRYRREMTLTVLDLITLFPLYDVRTY
CRYS3BB2: HCVNWYNVGLNGLRGSTYDAWVKFNRFRREMTLTVLDLIVLFPFYDVRLY
CRY3BB:   HCVNWYNVGLNGLRGSTYDAWVKFNRFRREMTLTVLDLIVLFPFYDIRLY
CRY3BA:   HCVNWYNVGLNSLRGSTYDAWVKFNRFRREMTLTVLDLIVLFPFYDVRLY
CRY3A:    HCVKWYNVGLDKLRGSSYESWVNFNRYRREMTLTVLDLIALFPLYours
truly.DVRLY 300       310       320       330       340
CRY3C:    TKGVKTELTRDVLTDPIVAVNNMNGYGTTFSNIENYIRKPHLFDYLHAIQ
CRY3BB2:  SKGVKTELTRDIFTDPIFSLNTLQEYGPTFLSIENSIRKPHLFDYLQGIE
CRY3BB:   SKGVKTELTRDIFTDPIFSLNTLQEYGPTFLSIENSIRKPHLFDYLQGIE
CRY3BA:   SKGVKTELTRDIFTDPIFTLNALQEYGPTFSSIENSIRKPHLFDYLRGIE
CRY3A:    PKEVKTELTRDVLTDPIVGVNNLRGYGTTFSNIENYIRKPHLFDYLHRIQ
          +++++++++++                                  ++++

350       360       370       380       390
CRY3C:    FHSRLQPGYFGTDSFNYWSGNYVSTRSSIGSDEIIRSPFYGNKSTLDVQN
CRY3BB2:  FHTRLQPGYSGKDSFNYWSGNYVETRPSIGSSKTITSPFYGDKSTEPVQK
CRY3BB:   FHTRLQPGYFGKDSFNYWSGNYVETRPSIGSSKTITSPFYGDKSTEPVQK
CRY3BA:   FHTRLRPGYSGKDSFNYWSGNYVETRPSIGSNDTITSPFYGDKSIEPIQK
CRY3A:    FHTRFQPGYYGNDSFNYWSGNYVSTRPSIGSNDIITSPFYGNKSSEPVQN
          ++++++++    +++++ +++++++      +++++          +++

400       410       420       430
CRY3C:    LEFNGEKVFRAVANGNLAVWPVGTGGTKIHSGVTKVQFSQYNDRKDEVRT
CRY3BB2:  LSFDGQKVYRTIANTDVAAWPNG----KIYFGVTKVDFSQYDDQKNETST
CRY3BB:   LSFDGQKVYRTIANTDVAAWPNG----KVYLGVTKVDFSQYDDQKNETST
CRY3BA:   LSFDGQKVYRTIANTDIAAFPDG----KIYFGVTKVDFSQYDDQKNETST
CRY3A:    LEFNGEKVYRAVANTNLAVWPSA-----VYSGVTKVEFSQYNDQTDEAST
          +++      ++++++++++    ++++  ++++++++    ++++
```

FIG. 17B

```
         440       450       460       470       480
CRY3C:   QTYDSKRNVGGIV-FDSIDQLPPITTDESLEKAYSHQLNYVRCFLLQGGR
CRY3BB2: QTYDSKRNNGHVGAQDSIDQLPPETTDEPLEKAYSHQLNYAECFLMQDRR
CRY3BB:  QTYDSKRNNGHVSAQDSIDQLPPETTDEPLEKAYSHQLNYAECFLMQDRR
CRY3BA:  QTYDSKRYNGYLGAQDSIDQLPPETTDEPLEKAYSHQLNYAECFLMQDRR
CRY3A:   QTYDSKRNVGAVS-WDSIDQLPPETTDEPLEKGYSHQLNYVMCFLMQGSR
         ++++      +++++                        +++++++

490       500       510       520       530
CRY3C:   GIIPVFTWTHKSVDFYNTLDSEKITQIPFVKAFILVNSTSVVAGPGFTGG
CRY3BB2: GTIPFFTWTHRSVDFFNTIDAEKITQLPVVKAYALSSGASIIEGPGFTGG
CRY3BB:  GTIPFFTWTHRSVDFFNTIDAEKITQLPVVKAYALSSGASIIEGPGFTGG
CRY3BA:  GTIPFFTWTHRSVDFFNTIDAEKITQLPVVKAYALSSGASIIEGPGFTGG
CRY3A:   GTIPVLTWTHKSVDFFNMIDSKKITQLPLVKAYKLQSGASVVAGPRFTGG
           +++++++      +++++  ++++       +++++++

540       550       560       570       580
CRY3C:   DII-KCT-NGSGLTLYVTPAPDLTYSKTYKIRIRYASTSQVRFGIDLGSY
CRY3BB2: NLLFLKESSNSIAKFKVTL-NSAALLQRYRVRIRYASTTNLRLFVQNSNN
CRY3BB:  NLLFLKESSNSIAKFKVTL-NSAALLQRYRVRIRYASTTNLRLFVQNSNN
CRY3BA:  NLLFLKESSNSIAKFKVTL-NSAALLQRYRVRIRYASTTNLRLFVQNSNN
CRY3A:   DII-QCTENGSAATIYVTPD--VSYSQKYRARIHYASTSQITFTLSLDGA
         ++++++    ++++++++    ++++++++++++    +++++++

590       600       610       620       630
CRY3C:   THSISYFDKTMDKGNTLTYNSFNLSSVSRPIEISG-GNKIGVSVGGIGSG
CRY3BB2: DFIVIYINKTMNIDDDLTYQTFDLATTNSNMGFSGDTNELIIGAESFVSN
CRY3BB:  DFLVIYINKTMNKDDDLTYQTFDLATTNSNMGFSGDKNELIIGAESFVSN
CRY3BA:  DFLVIYINKTMNIDGDLTYQTFDFATSNSNMGFSGDTNDFIIGAESFVSN
CRY3A:   PFNQYYFDKTINKGDTLTYNSFNLASFSTPFELSG--NNLQIGVTGLSAG
            +++++++      +++++++ ++++       +++++++++++

640       650
CRY3C:   DEVYIDKIEFIPMD
CRY3BB2: EKIYIDKIEFIPVQL
CRY3BB:  EKIYIDKIEFIPVQL
CRY3BA:  EKIYIDKIEFIPVQ
CRY3A:   DKVYIDKIEFIPVN
         ++++++++++++
```

FIG. 17C

NUCLEIC ACID SEGMENTS ENCODING MODIFIED BACILLUS THURINGIENSIS COLEOPTERAN-TOXIC CRYSTAL PROTEINS

1.0 BACKGROUND OF THE INVENTION

1.1 Field of the Invention

This invention relates to transformed host cells and vectors which comprise nucleic acid segments encoding genetically-engineered, recombinant *Bacillus thuringiensis* δ-endotoxins which are active against Coleopteran insects.

1.2 Description of the Related Art

Almost all field crops, plants, and commercial farming areas are susceptible to attack by one or more insect pests. Particularly problematic are Coleopteran and Lepidoptern pests. For example, vegetable and cole crops such as artichokes, kohlrabi, arugula, leeks, asparagus, lentils, beans, lettuce (e.g., head, leaf, romaine), beets, bok choy, malanga, broccoli, melons (e.g., muskmelon, watermelon, crenshaw, honey dew, cantaloupe), brussels sprouts, cabbage, cardoni, carrots, napa, cauliflower, okra, onions, celery, parsley, chick peas, parsnips, chicory, peas, chinese cabbage, peppers, collards, potatoes, cucumber, pumpkins, cucurbits, radishes, dry bulb onions, rutabaga, eggplant, salsify, escarole, shallots, endive, soybean, garlic, spinach, green onions, squash, greens, sugar beets, sweet potatoes, turnip, swiss chard, horseradish, tomatoes, kale, turnips, and a variety of spices are sensitive to infestation by one or more of the following insect pests: alfalfa looper, armyworm, beet armyworm, artichoke plume moth, cabbage budworm, cabbage looper, cabbage webworm, corn earworm, celery leafeater, cross-striped cabbageworm, european corn borer, diamondback moth, green cloverworm, imported cabbageworm, melonworm, omnivorous leafroller, pickleworm, rindworm complex, saltmarsh caterpillar, soybean looper, tobacco budworm, tomato fruitworm, tomato hornworm, tomato pinworm, velvetbean caterpillar, and yellowstriped armyworm. Likewise, pasture and hay crops such as alfalfa, pasture grasses and silage are often attacked by such pests as armyworm, beef armyworm, alfalfa caterpillar, European skipper, a variety of loopers and webworms, as well as yellowstriped armyworms.

Fruit and vine crops such as apples, apricots, cherries, nectarines, peaches, pears, plums, prunes, quince almonds, chestnuts, filberts, pecans, pistachios, walnuts, citrus, blackberries, blueberries, boysenberries, cranberries, currants, loganberries, raspberries, strawberries, grapes, avocados, bananas, kiwi, persimmons, pomegranate, pineapple, tropical fruits are often susceptible to attack and defoliation by achema sphinx moth, amorbia, armyworm, citrus cutworm, banana skipper, blackheaded fireworm, blueberry leafroller, cankerworm, cherry fruitworm, citrus cutworm, cranberry girdler, eastern tent caterpillar, fall webworm, fall webworm, filbert leafroller, filbert webworm, fruit tree leafroller, grape berry moth, grape leaffolder, grapeleaf skeletonizer, green fruitworm, gummososbatrachedra commosae, gypsy moth, hickory shuckworm, hornworms, loopers, navel orangeworm, obliquebanded leafroller, omnivorous leafroller. omnivorous looper, orange tortrix, orangedog, oriental fruit moth, pandemis leafroller, peach twig borer, pecan nut casebearer, redbanded leafroller, redhumped caterpillar, roughskinned cutworm, saltmarsh caterpillar, spanworm, tent caterpillar, thecla-thecla basillides, tobacco budworm, tortrix moth, tufted apple budmoth, variegated leafroller, walnut caterpillar, western tent caterpillar, and yellowstriped armyworm.

Field crops such as canola/rape seed, evening primrose, meadow foam, corn (field, sweet, popcorn), cotton, hops, jojoba, peanuts, rice, safflower, small grains (barley, oats, rye, wheat, etc.), sorghum, soybeans, sunflowers, and tobacco are often targets for infestation by insects including armyworm, asian and other corn borers, banded sunflower moth, beet armyworm, bollworm, cabbage looper, corn rootworm (including southern and western varieties), cotton leaf perforator, diamondback moth, european corn borer, green cloverworm, headmoth, headworm, imported cabbageworm, loopers (including Anacamptodes spp.), obliquebanded leafroller, omnivorous leaftier, podworm, podworm, saltmarsh caterpillar, southwestern corn borer, soybean looper, spotted cutworm, sunflower moth, tobacco budworm, tobacco hornworm, velvetbean caterpillar, Bedding plants, flowers, ornamentals, vegetables and container stock are frequently fed upon by a host of insect pests such as armyworm, azalea moth, beet armyworm, diamondback moth, ello moth (hornworm), Florida fern caterpillar, Io moth, loopers, oleander moth, omnivorous leafroller, omnivorous looper, and tobacco budworm.

Forests, fruit, ornamental, and nut-bearing trees, as well as shrubs and other nursery stock are often susceptible to attack from diverse insects such as bagworm, blackheaded budworm, browntail moth, california oakworm, douglas fir tussock moth, elm spanworm, fall webworm, fruittree leafroller, greenstriped mapleworm, gypsy moth, jack pine budworm, mimosa webworm, pine butterfly, redhumped caterpillar, saddleback caterpillar, saddle prominent caterpillar, spring and fall cankerworm, spruce budworm, tent caterpillar, tortrix, and western tussock moth. Likewise, turf grasses are often attacked by pests such as armyworm, sod webworm, and tropical sod webworm.

Because crops of commercial interest are often the target of insect attack, environmentally-sensitive methods for controlling or eradicating insect infestation are desirable in many instances. This is particularly true for farmers, nurserymen, growers, and commercial and residential areas which seek to control insect populations using eco-friendly compositions.

The most widely used environmentally-sensitive insecticidal formulations developed in recent years have been composed of microbial pesticides derived from the bacterium *Bacillus thuringiensis*. *B. thuringiensis* is a Gram-positive bacterium that produces crystal proteins or inclusion bodies which are specifically toxic to certain orders and species of insects. Many different strains of *B. thuringiensis* have been shown to produce insecticidal crystal proteins. Compositions including *B. thuringiensis* strains which produce insecticidal proteins have been commercially-available and used as environmentally-acceptable insecticides because they are quite toxic to the specific target insect, but are harmless to plants and other non-targeted organisms.

1.2.1 δ-ENDOTOXINS

δ-endotoxins are used to control a wide range of leaf-eating caterpillars and beetles, as well as mosquitoes. These proteinaceous parasporal crystals, also referred to as insecticidal crystal proteins, crystal proteins, *Bt* inclusions, crystaline inclusions, inclusion bodies, and *Bt* toxins, are a large collection of insecticidal proteins produced by *B. thuringiensis* that are toxic upon ingestion by a susceptible insect host. Over the past decade research on the structure and function of *B. thuringiensis* toxins has covered all of the major toxin categories, and while these toxins differ in specific structure and function, general similarities in the structure and function are assumed. Based on the accumulated knowledge of *B. thuringiensis* toxins, a generalized mode of action for *B. thuringiensis* toxins has been created and includes: ingestion by the insect, solubilization in the insect midgut (a combination stomach and small intestine), resistance to digestive enzymes sometimes with partial digestion actually "activating" the toxin, binding to the midgut cells, formation of a pore in the insect cells and the disruption of cellular homeostasis (English and Slatin, 1992).

1.2.2 GENES ENCODING CRYSTAL PROTEINS

Many of the δ-endotoxins are related to various degrees by similarities in their amino acid sequences. Historically, the proteins and the genes which encode them were classified based largely upon their spectrum of insecticidal activity. The review by Höfte and Whiteley (1989) discusses the genes and proteins that were identified in *B. thuringiensis* prior to 1990, and sets forth the nomenclature and classification scheme which has traditionally been applied to *B. thuringiensis* genes and proteins: cryI genes encode lepidopteran-toxic CryI proteins. cryII genes encode CryII proteins that are toxic to both lepidopterans and dipterans. cryIII genes encode coleopteran-toxic CryII proteins, while cryIV genes encode dipteran-toxic CryIV proteins, etc. Based on the degree of sequence similarity, the proteins were further classified into subfamilies; more highly related proteins within each family were assigned divisional letters such as CryIA, CryIB, CryIC, etc. Even more closely related proteins within each division were given names such as CryIC1, CryIC2, etc.

Recently a new nomenclature was developed which systematically classifies the Cry proteins based upon amino acid sequence homology rather than upon insect target specificities. This classification scheme, including most of the known toxins but not including allelic variations in individual polypeptides, is summarized in Table 1.

TABLE 1

KNOWN *B. THURINGIENSIS* δ-ENDOTOXINS, GENBANK ACCESSION NUMBERS, AND REVISED NOMENCLATURE[A]

| New | Old | GenBank Accession # |
|---|---|---|
| Cry1Aa1 | CryIA(a) | M11250 |
| Cry1Aa2 | CryIA(a) | M10917 |
| Cry1Aa3 | CryIA(a) | D00348 |
| Cry1Aa4 | CryIA(a) | X13535 |
| Cry1Aa5 | CryIA(a) | D17518 |
| Cry1Aa6 | CryIA(a) | U43605 |
| Cry1Ab1 | CryIA(b) | M13898 |
| Cry1Ab2 | CryIA(b) | M12661 |
| Cry1Ab3 | CryIA(b) | M15271 |
| Cry1Ab4 | CryIA(b) | D00117 |
| Cry1Ab5 | CryIA(b) | X04698 |
| Cry1Ab6 | CryIA(b) | M37263 |
| Cry1Ab7 | CryIA(b) | X13233 |
| Cry1Ab8 | CryIA(b) | M16463 |
| Cry1Ab9 | CryIA(b) | X54939 |
| Cry1Ab10 | CryIA(b) | |
| Cry1Ac1 | CryIA(c) | M11068 |
| Cry1Ac2 | CryIA(c) | M35524 |
| Cry1Ac3 | CryIA(c) | X54159 |
| Cry1Ac4 | CryIA(c) | M73249 |
| Cry1Ac5 | CryIA(c) | M73248 |
| Cry1Ac6 | CryIA(c) | U43606 |
| Cry1Ac7 | CryIA(c) | U87793 |
| Cry1Ac8 | CryIA(c) | U87397 |
| Cry1Ac9 | CryIA(c) | U89872 |
| Cry1Ac10 | CryIA(c) | AJ002514 |
| Cry1Ad1 | CryIA(d) | M73250 |
| Cry1Ae1 | CryIA(e) | M65252 |
| Cry1Ba1 | CryIB | X06711 |
| Cry1Ba2 | | X95704 |
| Cry1Bb1 | ET5 | L32020 |

TABLE 1-continued

KNOWN *B. THURINGIENSIS* δ-ENDOTOXINS, GENBANK ACCESSION NUMBERS, AND REVISED NOMENCLATURE[A]

| New | Old | GenBank Accession # |
|---|---|---|
| Cry1Bc1 | CryIb(c) | Z46442 |
| Cry1Bd1 | CryE1 | |
| Cry1Ca1 | CryIC | X07518 |
| Cry1Ca2 | CryIC | X13620 |
| Cry1Ca3 | CryIC | M73251 |
| Cry1Ca4 | CryIC | A27642 |
| Cry1Ca5 | CryIC | X96682 |
| Cry1Ca6 | CryIC | X96683 |
| Cry1Ca7 | CryIC | X96684 |
| Cry1Cb1 | CryIC(b) | M97880 |
| Cry1Da1 | CryID | X54160 |
| Cry1Db1 | PrtB | Z22511 |
| Cry1Ea1 | CryIE | X53985 |
| Cry1Ea2 | CryIE | X56144 |
| Cry1Ea3 | CryIE | M73252 |
| Cry1Ea4 | | U94323 |
| Cry1Eb1 | CryIE(b) | M73253 |
| Cry1Fa1 | CryIF | M63897 |
| Cry1Fa2 | CryIF | M63897 |
| Cry1Fb1 | PrtD | Z22512 |
| Cry1Ga1 | PrtA | Z22510 |
| Cry1Ga2 | CryIM | Y09326 |
| Cry1Gb1 | CryH2 | |
| Cry1Ha1 | PrtC | Z22513 |
| Cry1Hb1 | | U35780 |
| Cry1Ia1 | CryV | X62821 |
| Cry1Ia2 | CryV | M98544 |
| Cry1Ia3 | CryV | L36338 |
| Cry1Ia4 | CryV | L49391 |
| Cry1Ia5 | CryV | Y08920 |
| Cry1Ib1 | CryV | U07642 |
| Cry1Ja1 | ET4 | L32019 |
| Cry1Jb1 | ET1 | U31527 |
| Cry1Ka1 | | U28801 |
| Cry2Aa1 | CryIIA | M31738 |
| Cry2Aa2 | CryIIA | M23723 |
| Cry2Aa3 | | D86084 |
| Cry2Ab1 | CryIIB | M23724 |
| Cry2Ab2 | CryIIB | X55416 |
| Cry2Ac1 | CryIIC | X57252 |
| Cry3Aa1 | CryIIIA | M22472 |
| Cry3Aa2 | CryIIIA | J02978 |
| Cry3Aa3 | CryIIIA | Y00420 |
| Cry3Aa4 | CryIIIA | M30503 |
| Cry3Aa5 | CryIIIA | M37207 |
| Cry3Aa6 | CryIIIA | U10985 |
| Cry3Ba1 | CryIIIB | X17123 |
| Cry3Ba2 | CryIIIB | A07234 |
| Cry3Bb1 | CryIIIB2 | M89794 |
| Cry3Bb2 | CryIIIC(b) | U31633 |
| Cry3Ca1 | CryIIID | X59797 |
| Cry4Aa1 | CryIVA | Y00423 |
| Cry4Aa2 | CryIVA | D00248 |
| Cry4Ba1 | CryIVB | X07423 |
| Cry4Ba2 | CryIVB | X07082 |
| Cry4Ba3 | CryIVB | M20242 |
| Cry4Ba4 | CryIVB | D00247 |
| Cry5Aa1 | CryVA(a) | L07025 |
| Cry5Ab1 | CryVA(b) | L07026 |
| Cry5Ba1 | PS86Q3 | U19725 |
| Cry6Aa1 | CryVIA | L07022 |
| Cry6Ba1 | CryVIB | L07024 |
| Cry7Aa1 | CryIIIC | M64478 |
| Cry7Ab1 | CryIIICb | U04367 |
| Cry8Aa1 | CryIIIE | U04364 |
| Cry8Ba1 | CryIIIG | U04365 |
| Cry8Ca1 | CryIIIF | U04366 |
| Cry9Aa1 | CryIG | X58120 |
| Cry9Aa1 | CryIG | X58534 |
| Cry9Ba1 | CryIX | X75019 |
| Cry9Ca1 | CryIH | Z37527 |
| Cry9Da1 | N141 | D85560 |
| Cry10Aa1 | CryIVC | M12662 |
| Cry11Aa1 | CryIVD | M31737 |

TABLE 1-continued

KNOWN *B. THURINGIENSIS* δ-ENDOTOXINS, GENBANK
ACCESSION NUMBERS, AND REVISED NOMENCLATURE[a]

| New | Old | GenBank Accession # |
|---|---|---|
| Cry11Aa2 | CryIVD | M22860 |
| Cry11Ba1 | Jeg80 | X86902 |
| Cry12Aa1 | CryVB | L07027 |
| Cry13Aa1 | CryVC | L07023 |
| Cry14Aa1 | CryVD | U13955 |
| Cry15Aa1 | 34kDa | M76442 |
| Cry16Aa1 | cbm71 | X94146 |
| Cry17Aa1 | cbm71 | X99478 |
| Cry18Aa1 | CryBP1 | X99049 |
| Cry19Aa1 | Jeg65 | Y08920 |
| Cry20Aa1 | | U82518 |
| Cry21Aa1 | | 132932 |
| Cry22Aa1 | | 134547 |
| Cyt1Aa1 | CytA | X03182 |
| Cyt1Aa2 | CytA | X04338 |
| Cyt1Aa3 | CytA | Y00135 |
| Cyt1Aa4 | CytA | M35968 |
| Cyt1Ab1 | CytM | X98793 |
| Cyt1Ba1 | | U37196 |
| Cyt2Aa1 | CytB | Z14147 |
| Cyt2Ba1 | "CytB" | U52043 |
| Cyt2Ba2 | "CytB" | AF020789 |
| Cyt2Ba3 | "CytB" | AF022884 |
| Cyt2Ba4 | "CytB" | AF022885 |
| Cyt2Ba5 | "CytB" | AF022886 |
| Cyt2Bb1 | | U82519 |

[a]Adapted from: http://epunix.biols.susx.ac.uk/Home/Neil_Crickmore/Bt/index.html

1.2.3 BIOINSECTICIDE POLYPEPTIDE COMPOSITIONS

The utility of bacterial crystal proteins as insecticides was extended beyond lepidopterans and dipteran larvae when the first isolation of a coleopteran-toxic *B. thuringiensis* strain was reported (Krieg et al., 1983; 1984). This strain (described in U.S. Pat. No. 4,766,203, specifically incorporated herein by reference), designated *B. thuringiensis* var. *tenebrionis*, is reported to be toxic to larvae of the coleopteran insects *Agelastica alni* (blue alder leaf beetle) and *Leptinotarsa decemlineata* (Colorado potato beetle).

U.S. Pat. No. 5,024,837 also describes hybrid *B. thuringiensis* var. *kurstaki* strains which showed activity against lepidopteran insects. U.S. Pat. No. 4,797,279 (corresponding to EP 0221024) discloses a hybrid *B. thuringiensis* containing a plasmid from *B. thuringiensis* var. *kurstaki* encoding a lepidopteran-toxic crystal protein-encoding gene and a plasmid from *B. thuringiensis tenebrionis* encoding a coleopteran-toxic crystal protein-encoding gene. The hybrid *B. thuringiensis* strain produces crystal proteins characteristic of those made by both *B. thuringiensis kurstaki* and *B. thuringiensis tenebrionis*. U.S. Pat. No. 4,910,016 (corresponding to EP 0303379) discloses a *B. thuringiensis* isolate identified as *B. thuringiensis* MT 104 which has insecticidal activity against coleopterans and lepidopterans.

1.2.4 MOLECULAR GENETIC TECHNIQUES FACILITATE PROTEIN ENGINEERING

The revolution in molecular genetics over the past decade has facilitated a logical and orderly approach to engineering proteins with improved properties. Site specific and random mutagenesis methods, the advent of polymerase chain reaction (PCR™) methodologies, and related advances in the field have permitted an extensive collection of tools for changing both amino acid sequence, and underlying genetic sequences for a variety of proteins of commercial, medical, and agricultural interest.

Following the rapid increase in the number and types of crystal proteins which have been identified in the past decade, researchers began to theorize about using such techniques to improve the insecticidal activity of various crystal proteins. In theory, improvements to δ-endotoxins should be possible using the methods available to protein engineers working in the art, and it was logical to assume that it would be possible to isolate improved variants of the wild-type crystal proteins isolated to date. By strengthening one or more of the aforementioned steps in the mode of action of the toxin, improved molecules should provide enhanced activity, and therefore, represent a breakthrough in the field. If specific amino acid residues on the protein are identified to be responsible for a specific step in the mode of action, then these residues can be targeted for mutagenesis to improve performance

1.2.5 STRUCTURAL ANALYSES OF CRYSTAL PROTEINS

The combination of structural analyses of *B. thuringiensis* toxins followed by an investigation of the function of such structures, motifs, and the like has taught that specific regions of crystal protein endotoxins are, in a general way, responsible for particular functions.

Domain 1, for example, from Cry3Bb and Cry1Ac has been found to be responsible for ion channel activity, the initial step in formation of a pore (Walters et al., 1993; Von Tersch et al., 1994). Domains 2 and 3 have been found to be responsible for receptor binding and insecticidal specificity (Aronson et al., 1995; Caramori et al., 1991; Chen et al. 1993; de Maagd et al., 1996; Ge et al., 1991; Lee et al., 1992; Lee et al., 1995; Lu et al., 1994; Smedley and Ellar, 1996; Smith and Ellar, 1994; Rajamohan et al., 1995; Rajamohan et al., 1996; Wu and Dean, 1996). Regions in domain 2 and 3 can also impact the ion channel activity of some toxins (Chen et al., 1993, Wolfersberger et al., 1996; Von Tersch et al., 1994).

1.3 DEFICIENCIES IN THE PRIOR ART

Unfortunately, while many laboratories have attempted to make mutated crystal proteins, few have succeeded in making mutated crystal proteins with improved lepidopteran toxicity. In almost all of the examples of genetically-engineered *B. thuringiensis* toxins in the literature, the biological activity of the mutated crystal protein is no better than that of the wild-type protein, and in many cases, the activity is decreased or destroyed altogether (Almond and Dean, 1993; Aronson et al., 1995; Chen et al., 1993, Chen et al., 1995; Ge et al., 1991; Kwak et al., 1995; Lu et al., 1994; Rajamohan et al., 1995; Rajamohan et al., 1996; Smedley and Ellar, 1996; Smith and Ellar, 1994; Wolfersberger et al., 1996; Wu and Aronson, 1992).

For a crystal protein having approximately 650 amino acids in the sequence of its active toxin, and the possibility of 20 different amino acids at each position in this sequence, the likelihood of arbitrarily creating a successful new structure is remote, even if a general function to a stretch of 250–300 amino acids can be assigned. Indeed, the above prior art with respect to crystal protein gene mutagenesis has been concerned primarily with studying the structure and function of the crystal proteins, using mutagenesis to perturb some step in the mode of action, rather than with engineering improved toxins.

Collectively, the limited successes in the art to develop synthetic toxins with improved insecticidal activity have stifled progress in this area and confounded the search for improved endotoxins or crystal proteins. Rather than following simple and predictable rules, the successful engineering of an improved crystal protein may involve different strategies, depending on the crystal protein being improved and the insect pests being targeted. Thus, the process is highly empirical.

Accordingly, traditional recombinant DNA technology is clearly not routine experimentation for providing improved insecticidal crystal proteins. What are lacking in the prior art are rational methods for producing genetically-engineered *B. thuringiensis* crystal proteins that have improved insecticidal activity and, in particular, improved toxicity towards a wide range of lepidopteran insect pests.

2.0 SUMMARY OF THE INVENTION

The present invention seeks to overcome these and other drawbacks inherent in the prior art by providing genetically-engineered modified *B. thuringiensis* δ-endotoxins (Cry*), and in particular modified Cry3 δ-endotoxins (designated Cry3* endotoxins). Also provided are nucleic acid sequences comprising one or more genes which encode such modified proteins. Particularly preferred genes include cry3* genes such as cry3A, cry3B*, and cry3C* genes, particularly cry3B* genes, and more particularly, cry3Bb* genes, that encode modified crystal proteins having improved insecticidal activity against target pests.

Also disclosed are novel methods for constructing synthetic Cry3* proteins, synthetically-modified nucleic acid sequences encoding such proteins, and compositions arising therefrom. Also provided are synthetic cry3* expression vectors and various methods of using the improved genes and vectors. In a preferred embodiment, the invention discloses and claims Cry3B* proteins and cry3B* genes which encode improved insecticidal polypeptides.

In preferred embodiments, channel-forming toxin design methods are disclosed which have been used to produce a specific set of designed Cry3Bb* toxins with improved biological activity. These improved Cry3Bb* proteins are listed in Table 2 along with their respective amino acid changes from wild-type (WT) Cry3Bb, the nucleotide changes present in the altered cry3Bb* gene encoding the protein, the fold increase in bioactivity over WT Cry3Bb, the structural site of the alteration, and the design method(s) used to create the new toxins.

Accordingly, the present invention provides in an overall and general sense, mutagenized Cry3 protein-encoding genes and methods of making and using such genes. As used herein the term "mutagenized cry3 gene(s)" means one or more cry3 genes that have been mutagenized or altered to contain one or more nucleotide sequences which are not present in the wild type sequences, and which encode mutant Cry3 crystal proteins (Cry3*) showing improved insecticidal activity. Such mutagenized cry3 genes have been referred to in the Specification as cry3* genes. Exemplary cry3* genes include cry3A*, cry3B*, and cry3C* genes.

Exemplary mutagenized Cry3 protein-encoding genes include cry3B genes. As used herein the term "mutagenized cry3B gene(s)" means one or more genes that have been mutagenized or altered to contain one or more nucleotide sequences which are not present in the wild type sequences, and which encode mutant Cry3B crystal proteins (Cry3B*) showing improved insecticidal activity. Such genes have been designated cry3B* genes. Exemplary cry3B* genes include cry3Ba* and cry3Bb* genes, which encode Cry3Ba* and Cry3Bb* proteins, respectively.

Likewise, the present invention provides mutagenized Cry3A protein-encoding genes and methods of making and using such genes. As used herein the term "mutagenized cry3A gene(s)" means one or more genes that have been mutagenized or altered to contain one or more nucleotide sequences which are not present in the wild type sequences, and which encode mutant Cry3A crystal proteins (Cry3A*) showing improved insecticidal activity. Such mutagenized genes have been designated as cry3A * genes.

In similar fashion, the present invention provides mutagenized Cry3C protein-encoding genes and methods of making and using such genes. As used herein the term "mutagenized cry3C gene(s)" means one or more genes that have been mutagenized or altered to contain one or more nucleotide sequences which are not present in the wild type sequences, and which encode mutant Cry3C crystal proteins (Cry3C*) showing improved insecticidal activity. Such mutagenized genes have been designated as cry3C* genes.

Preferably the novel sequences comprise nucleic acid sequences in which at least one, and preferably, more than one, and most preferably, a significant number, of wild-type cry3 nucleotides have been replaced with one or more nucleotides, or where one or more nucleotides have been added to or deleted from the native nucleotide sequence for the purpose of altering, adding, or deleting the corresponding amino acids encoded by the nucleic acid sequence so mutagenized. The desired result, therefore, is alteration of the amino acid sequence of the encoded crystal protein to provide toxins having improved or altered activity and/or specificity compared to that of the unmodified crystal protein.

Examples of preferred Cry2Bb*-encoding genes include cry3Bb.60, cry3Bb.11221, cry3Bb.11222, cry3Bb.11223, cry3Bb.11224, cry3Bb.11225, cry3Bb.11226, cry3Bb.11227, cry3Bb.11228, cry3Bb.11229, cry3Bb.11230, cry3Bb.11231, cry3Bb.11232, cry3Bb.11233, cry3Bb.11234, cry3Bb.11235, cry3Bb.11236, cry3Bb.11237, cry3Bb.11238, cry3Bb.11239, cry3Bb.11241, cry3Bb.11242, cry3Bb.11032, cry3Bb.11035, cry3Bb.11036, cry3Bb.11046, cry3Bb.11048, cry3Bb.11051, cry3Bb.11057, cry3Bb.11058, cry3Bb.11081, cry3Bb.11082, cry3Bb.11083, cry3Bb.11084, cry3Bb.11095, and cry3Bb.11098.

TABLE 2

CRY3BB* PROTEINS EXHIBITING IMPROVED ACTIVITY AGAINST SCRW LARVAE

| Cry3Bb* Protein Designation | cry3Bb* Plasmid Designation | cry3Bb* Nucleotide Sequence Changes | Cry3Bb* Amino Acid Changes | Structural Site of Changes | Fold Increase Over WT Activity | Design Method Used |
|---|---|---|---|---|---|---|
| Cry3Bb.60 | — | — | Δ1–159 | ΔE1–α3 | 3.6× | 1, 6, 8 |
| Cry3Bb.11221 | pEG1707 | A460T, C461T, A462T, C464A, T465C, T466C, T467A, A468T, A469T, G470C, T472C, T473G, | T154F, P155H, L156H, L158R | 1α3, 4 | 6.4× | 1, 8 |

TABLE 2-continued

CRY3BB* PROTEINS EXHIBITING IMPROVED ACTIVITY AGAINST SCRW LARVAE

| Cry3Bb* Protein Designation | cry3Bb* Plasmid Designation | cry3Bb* Nucleotide Sequence Changes | Cry3Bb* Amino Acid Changes | Structural Site of Changes | Fold Increase Over WT Activity | Design Method Used |
|---|---|---|---|---|---|---|
| Cry3Bb.11222 | pEG1708 | G474T, A477T, A478T, G479C T687C, T688C, A689T, C691A, A692G | Y230L, H231S | α6 | 4.0× | 3, 7 |
| Cry3Bb.11223 | pEG1709 | T667C, T687C, T688A, A689G, C691A, A692G | S223P, Y230S | α6 | 2.8× | 3 |
| Cry3Bb.11224 | pEG1710 | T687C, A692G | H231R | α6 | 5.0× | 7, 8 |
| Cry3Bb.11225 | pEG1711 | T687C, C691A | H231N, T241S | α6 | 3.6× | 7 |
| Cry3Bb.11226 | pEG1712 | T687C, C691A, A692C, T693C | H231T | α6 | 3.0× | 7, 8 |
| Cry3Bb.11227 | pEG1713 | C868A, G869A, G870T | R290N | 1α7, β1 | 1.9× | 2, 3, 4 6 |
| Cry3Bb.11228 | pEG1714 | C932T, A938C, T942G, G949A, T954C | S311L, N313T, E317K | 1β1, α8 | 4.1× | 2, 4 |
| Cry3Bb.11229 | pEG1715 | T931A, A933C, T942A, T945A, G949A, A953G, T954C | S311T, E317K, Y318C | 1β1, α8 | 2.5× | 2, 4 |
| Cry3Bb.11230 | pEG1716 | T931G, A933C, C934G, T945G, C946T, A947T, G951A, T954C | S311A, L312V, Q316W | 1β1, α8 | 4.7× | 2, 4 8 |
| Cry3Bb.11231 | pEG1717 | T687C, A692G, C932T, A938C, T942G, G949A, T954C | H231R, S311L, N313T, E317K | α6; 1β1, α8 | 7.9× | 2, 4, 7, 8, 10 |
| Cry3Bb.11232 | pEG1718 | T931A, A933C, T935C, T936A, A938C, T939C, T942C, T945A, G951T, T954C | S311L, L312P, N313T, E317N | 1β1, α8 | 5.1× | 4 |
| Cry3Bb.11233 | pEG1719 | T931G, A933C, T936G, T942C, C943T, T945A, C946G, G948C, T954C | S311A, Q316D | 1β1, α8 | 2.2× | 2, 4 |
| Cry3Bb.11234 | pEG1720 | T861C, T866C, C868A, T871C, T872G, A875T, T877A, C878G, A882G | I289T, L291R, Y292F, S293R | 1α7, β1 | 4.1× | 4 |
| Cry3Bb.11235 | pEG1721 | T687C, A692G, C932T | H231R, S311L | α6; 1β1, α8 | 3.2× | 2, 4, 7, 8 10 |
| Cry3Bb.11236 | pEG1722 | T931A, C932T, A933C, T936C, T942G, T945A, T954C | S311I | 1β1, α8 | 3.1× | 2, 4 |
| Cry3Bb.11237 | pEG1723 | T931A, C932T, A933C, T936C, A937G, A938T, C941A, T942C, T945A, C946A, A947T, A950T, T954C | S311I, N313H | 1β1, α8 | 5.4× | 2, 4 |
| Cry3Bb.11238 | pEG1724 | A933C, T936C, A937G, A938T, C941A, T942C, T945A, C946A, A947T, A950T, T954C | N313V, T314N, Q316M, E317V | 1β1, α8 | 2.6× | 2, 4 |
| Cry3Bb.11239 | pEG1725 | A933C, A938G, T939G, T942A, T944C, T945A, A947T, G948T, A950C, T954C | N313R, L315P, Q316L, E317A | 1β1, α8 | 2.8× | 2, 4 |
| Cry3Bb.11241 | pEG1726 | A860T, T861C, G862A, C868T, G869T, T871C, A873T, T877A, C878G, A879T | Y287F, D288N, R290L | 1α7, β1 | 2.6× | 2, 3, 4, 6 |
| Cry3Bb.11242 | pEG1727 | C868G, G869T | R290V | 1α7, β1 | 2.5× | 2, 3, 4, 6, 8 |
| Cry3Bb.11032 | pEG1041 | A494G | D165G | α4 | 3.1× | 2, 4, 8 |
| Cry3Bb.11035 | pEG1046 | G479A, A481C, A482C, A484C, G485A, A486C, A494G | S160N, K161P, P162H, D165G | α4 | 2.7× | 8 |
| Cry3Bb.11036 | pEG1047 | A865G, T877C | I289V, S293P | 1α7, β1 | 4.3× | 4 |
| Cry3Bb.11046 | pEG1052 | G479A, A481C, A482C, A484C, G485A, A486C, A494G, A865G, T877C | S160N, K161P, P162H, D165G, I289V, S293P | α4; 1α7, β1 | 2.6× | 2, 4, 8, 10 |
| Cry3Bb.11048 | pEG1054 | T309A, Δ310, Δ311, Δ312 | D103E, ΔA104 | 1α2a, 2b | 4.3× | 8 |
| Cry3Bb.11051 | pEG1057 | A565G, A566G | K189G | 1α4, 5 | 3.0× | 2, 3, 4 |
| Cry3Bb.11057 | pEG1062 | T309A, Δ310, Δ311, Δ312, G479A, A481C, A482C, A484C, G485A, A486C, A494G | D103E, ΔA104, S160N, K161P, P162H, D165G | 1α2a, 2b; α4 | 3.4× | 2, 4, 8, 10 |
| Cry3Bb.11058 | pEG1063 | T309A, Δ310, Δ311, Δ312 A460T, C461T, A462T, C464A, T465C, T466C, T467A, A468T, A469T, G470C, T472C, T473G, G474T, A477T, A478T, G479C | D103E, ΔA104, T154F, P155H, L156H, L158R | 1α2a, 2b; 1α3, 4 | 3.5× | 1, 8, 10 |
| Cry3Bb.11081 | pEG1084 | A494G, T931A, A933C, T942A, T945A, G949A, T954C | D165G, S311T, E317K | α4; 1β1, α8 | 6.1× | 2, 4, 8, 10 |
| Cry3Bb.11082 | pEG1085 | A494G, A865G, T877C, T914C, T931G, A933C, C934G, T945G, C946T, A947G, G951A, T954C, A1043G, T1094C | D165G, I289V, S293P, F305S, S311A, L312V, Q316W, Q348R, V365A | α4; 1α7, β1; β1; 1β1, α8; β2; β3b | 4.9× | 2, 4, 5, 8, 9, 10 |
| Cry3Bb.11083 | pEG1086 | A865G, T877C, A1043G | I289V, S293P, Q348R | 1α7, β1; β2 | 7.4× | 4, 5, 9, 10 |
| Cry3Bb.11084 | pEG1087 | A494G, C932T | D165G, S311L | α4; 1β1, α8 | 7.2× | 2, 4, 8, 10 |
| Cry3Bb.11095 | pEG1095 | A1043G | Q348R | β2 | 4.6× | 5, 9 |

TABLE 2-continued

CRY3BB* PROTEINS EXHIBITING IMPROVED ACTIVITY AGAINST SCRW LARVAE

| Cry3Bb* Protein Designation | cry3Bb* Plasmid Designation | cry3Bb* Nucleotide Sequence Changes | Cry3Bb* Amino Acid Changes | Structural Site of Changes | Fold Increase Over WT Activity | Design Method Used |
|---|---|---|---|---|---|---|
| Cry3Bb.11098 | pEG1098 | A494G, T687C, A692G, C932T, A938C, T942G, G949A, T954C | D165G, H231R, S311L, N313T, E317K | α4; α6, 1β1, α8 | 7.9× | 2, 4, 7, 8 |

In a variety of illustrative embodiments, the inventors have shown remarkable success in generating toxins with improved insecticidal activity using these methods. In particular, the inventors have identified unique methods of analyzing and designing toxins having improved or enhanced insecticidal properties both in vitro and in vivo.

In addition to modifications of Cry3Bb peptides, those having benefit of the present teaching are now also able to make mutations in a variety of channel-forming toxins, and particularly in crystal proteins which are related to Cry3Bb either functionally or structurally. In fact, the inventors contemplate that any B. thuringiensis crystal protein or peptide can be analyzed using the methods disclosed herein and may be altered using the methods disclosed herein to produce crystal proteins having improved insecticidal specificity or activity. Alternatively, the inventors contemplate that those of skill in the art having the benefit of the teachings disclosed herein will be able to prepare not only mutated Cry3 toxins with improved activity, but also other crystal proteins including all of those proteins identified in Table 1, herein. In particular, the inventors contemplate the creation of Cry3* variants using one or more of the methods disclosed herein to produce toxins with improved activity. For example, the inventors note Cry3A, Cry3B, and Cry3C crystal proteins (which are known in the art) may be modified using one or more of the design strategies employed herein, to prepare synthetically-modifiedcrystal proteins with improved properties. Likewise, one of skill in the art will even be able to utilize the teachings of the present disclosure to modify other channel forming toxins, including channel forming toxins other than B. thuringiensis crystal proteins, and even to modify proteins and channel toxins not yet described or characterized.

Because the structures for insecticidal crystal proteins show a remarkable conservation of protein tertiary structure (Grochulski et al., 1995), and because many crystal proteins show significant amino acid sequence identity to the Cry3Bb amino acid sequence within domain 1, including proteins of the Cry1, Cry2, Cry3, Cry4, Cry5, Cry7, Cry8, Cry9, Cry10, Cry11, Cry12, Cry13, Cry14, and Cry16 classes (Table 1), now in light of the inventors' surprising discovery, for the first time, those of skill in the art having benefit of the teachings disclosed herein will be able to broadly apply the methods of the invention to modifying a host of crystal proteins with improved activity or altered specificity. Such methods will not only be limited to the insecticidal crystal proteins disclosed in Table 1, but may also been applied to any other related crystal protein, including those yet to be identified.

In particular, the high degree of homology between Cry3A, Cry3B, and Cry3C proteins is evident in the alignment of the primary amino acid sequence of the three proteins (FIG. 17A, FIG. 17B, and FIG. 17C).

As such, the disclosed methods may be now applied to preparation of modified crystal proteins having one or more alterations introduced using one or more of the mutational design methods as disclosed herein. The inventors further contemplate that regions may be identified in one or more domains of a crystal protein, or other channel forming toxin which may be similarly modified through site-specific or random mutagenesis to generate toxins having improved activity, or alternatively, altered specificity.

In certain applications, the creation of altered toxins having increased activity against one or more insects is desired. Alternatively, it may be desirable to utilize the methods described herein for creating and identifying altered insecticidal crystal proteins which are active against a wider spectrum of susceptible insects. The inventors further contemplate that the creation of chimeric insecticidal crystal proteins comprising one or more of these mutations may be desirable for preparing "super" toxins which have the combined advantages of increased insecticidal activity and concomitant broad spectrum activity.

In light of the present disclosure, the mutagenesis of one or more codons within the sequence of a toxin may result in the generation of a host of related insecticidal proteins having improved activity. While exemplary mutations have been described for each of the design strategies employed in the present invention, the inventors contemplate that mutations may also be made in insecticidal crystal proteins, including the loop regions, helices regions, active sites of the toxins, regions involved in protein oligomerization, and the like, which will give rise to functional bioinsecticidal crystal proteins. All such mutations are considered to fall within the scope of this disclosure.

In one illustrative embodiment, mutagenized cry3Bb* genes are obtained which encode Cry3Bb* variants that are generally based upon the wild-type Cry3Bb sequence, but that have one or more changes incorporated into the amino acid sequence of the protein using one or more of the design strategies described and claimed herein.

In these and other embodiments, the mutated genes encoding the crystal proteins may be modified so as to change about one, two, three, four, or five or so amino acids in the primary sequence of the encoded polypeptide. Alternatively even more changes from the native sequence may be introduced, such that the encoded protein may have at least about 1% or 2%, or alternatively about 3% or about 4%, or even about 5% to about 10%, or about 10% to about 15%, or even about 15% to about 20% or more of the codons either altered, deleted, or otherwise modified. In certain situations, it may even be desirable to alter substantially more of the primary amino acid sequence to obtain the desired modified protein. In such cases the inventors contemplate that from about 25%, to about 50%, or even from about 50% to about 75%, or more of the native (or wild-type) codons either altered, deleted, or otherwise modified. Alternatively, mutations in the amino acid sequences or underlying DNA gene sequences which result in the insertion or deletion of one or more amino acids within one or more regions of the crystal protein or peptide.

To effect such changes in the primary sequence of the encoded polypeptides, it may be desirable to mutate or delete one or more nucleotides from the nucleic acid sequences of the genes encoding such polypeptides, or alternatively, under certain circumstances to add one or more nucleotides into the primary nucleic acid sequence at one or more sites in the sequence. Frequently, several nucleotide residues may be altered to produce the desired polypeptide. As such, the inventors contemplate that in certain embodiments it may be desirable to alter only one, two, three, four, or five or so nucleotides in the primary sequence. In other embodiments, which more changes are desired, the mutagenesis may involve changing, deleting, or inserting 6, 7, 8, 9, 10, 11, 12, 13, 14, 15, 16, 17, 18, 19, or even 20 or so nucleotide residues in the gene sequence. In still other embodiments, one may desire to mutate, delete, or insert 21, 22, 23, 24, 25, 26, 27, 28, 29, 30–40, 40–50, 50–60, 60–70, 70–80, 80–90, or even 90–100, 150, 200, 250, 300, 350, 400, 450, or more nucleotides in the sequence of the gene in order to prepare a cry3* gene which produces a Cry3* polypeptide having the desired characteristics. In fact, any number of mutations, deletions, and/or insertions may be made in the primary sequence of the gene, so long as the encoded protein has the improved insecticidal activity or specificity characteristics described herein.

Changing a large number of the codons in the nucleotide sequence of an endotoxin-encoding gene may be particularly desirable and often necessary to achieve the desired results, particularly in the situation of "plantizing" a DNA sequence in order to express a DNA of non-plant origin in a transformed plant cell. Such methods are routine to those of skill in the plant genetics arts, and frequently many residues of a primary gene sequence will be altered to facilitate expression of the gene in the plant cell. Preferably, the changes in the gene sequence introduce no changes in the amino acid sequence, or introduce only conservative replacements in the amino acid sequence such that the polypeptide produced in the plant cell from the "plantized" nucleotide sequence is still fully functional, and has the desired qualities when expressed in the plant cell.

Genes and encoded proteins mutated in the manner of the invention may also be operatively linked to other protein-encoding nucleic acid sequences, or expressed as fusion proteins. Both N-terminal and C-terminal fusion proteins are contemplated. Virtually any protein- or peptide-encoding DNA sequence, or combinations thereof, may be fused to a mutated cry3* sequence in order to encode a fusion protein. This includes DNA sequences that encode targeting peptides, proteins for recombinant expression, proteins to which one or more targeting peptides is attached, protein subunits, domains from one or more crystal proteins, and the like. Such modifications to primary nucleotide sequences to enhance, target, or optimize expression of the gene sequence in a particular host cell, tissue, or cellular localization, are well-known to those of skill in the art of protein engineering and molecular biology, and it will be readily apparent to such artisans, having benefit of the teachings of this specification, how to facilitate such changes in the nucleotide sequence to produce the polypeptides and polynucleotides disclosed herein.

In one aspect, the invention discloses and claims host cells comprising one or more of the modified crystal proteins disclosed herein, and in particular, cells of B. thuringiensis strains EG11221, EG11222, EG11223, EG11224, EG11225, EG11226, EG11227, EG11228, EG11229, EG11230, EG11231, EG11232, EG11233, EG11234, EG11235, EG11236, EG11237, EG11238, EG11239, EG11241, EG11242, EG11032, EG11035, EG11036, EG11046, EG11048, EG11051, EG11057, EG11058, EG11081, EG11082, EG11083, EG11084, EG11095, and EG11098 which comprise recombinant DNA segments encoding synthetically-modified Cry3Bb* crystal proteins which demonstrates improved insecticidal activity.

Likewise, the invention also discloses and claims cell cultures of B. thuringiensis EG11221, EG11222, EG11223, EG11224, EG11225, EG11226, FG11227, EG11228, EG11229, EG11230, EG11231, EG11232, EG11233, EG11234, EG11235, EG11236, EG11237, EG11238, EG11239, EG11241, EG11242, EG11032, EG11035, EG11036, EG11046, EG11048, EG11051, EG11057, EG11058, EG11081, EG11082, EG11083, EG11084, and EG11095, and 11098.

Such cell cultures may be biologically-pure cultures consisting of a single strain, or alternatively may be cell co-cultures consisting of one or more strains. Such cell cultures may be cultivated under conditions in which one or more additional B. thuringiensis or other bacterial strains are simultaneously co-cultured with one or more of the disclosed cultures, or alternatively, one or more of the cell cultures of the present invention may be combined with one or more additional B. thuringiensis or other bacterial strains following the independent culture of each. Such procedures may be useful when suspensions of cells containing two or more different crystal proteins are desired.

The subject cultures have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits are available as required by foreign patent laws in countries wherein counterparts of the subject application, or its progeny, are filed. However, it should be understood that the availability of a deposit does not constitute a license to practice the subject invention in derogation of patent rights granted by governrmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the finishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Cultures shown in Table 3 were deposited in the permanent collection of the Agricultural Research Service Culture Collection, Northern Regional Research Laboratory (NRRL) under the terms of the Budapest Treaty.

TABLE 3

STRAINS OF THE PRESENT INVENTION DEPOSITED UNDER THE TERMS OF THE BUDAPEST TREATY

| Strain | Deposit Date | Protein | Accession Number (NRRL Number) |
|---|---|---|---|
| EG11032 | 5/27/97 | Cry3Bb.11032 | B-21744 |
| EG11035 | 5/27/97 | Cry3Bb.11035 | B-21745 |
| EG11036 | 5/27/97 | Cry3Bb.11036 | B-21746 |
| EG11037 | 5/27/97 | Cry3Bb.11037 | B-21747 |
| EG11046 | 5/27/97 | Cry3Bb.11046 | B-21748 |
| EG11048 | 5/27/97 | Cry3Bb.11048 | B-21749 |
| EG11051 | 5/27/97 | Cry3Bb.11051 | B-21750 |
| EG11057 | 5127/97 | Cry3Bb.11057 | B-21751 |
| EG11058 | 5/27/97 | Cry3Bb.11058 | B-21752 |
| EG11081 | 5/27/97 | Cry3Bb.11081 | B-21753 |
| EG11082 | 5/27/97 | Cry3Bb.11082 | B-21754 |
| EG11083 | 5/27/97 | Cry3Bb.11083 | B-21755 |
| EG11084 | 5/27/97 | Cry3Bb.11084 | B-21756 |
| EG11095 | 5/27/97 | Cry3Bb.11095 | B-21757 |
| EG11204 | 5/27/97 | Cry3Bb.11204 | B-21758 |
| EG11221 | 5/27/97 | Cry3Bb.11221 | B-21759 |
| EG11222 | 5/27/97 | Cry3Bb.11222 | B-21760 |
| EG11223 | 5/27/97 | Cry3Bb.11223 | B-21761 |
| EG11224 | 5/27/97 | Cry3Bb.11224 | B-21762 |
| EG11225 | 5/27/97 | Cry3Bb.11225 | B-21763 |
| EG11226 | 5/27/97 | Cry3Bb.11226 | B-21764 |
| EG11227 | 5/27/97 | Cry3Bb.11227 | B-12765 |
| EG11228 | 5/27/97 | Cry3Bb.11228 | B-12766 |
| EG11229 | 5/27/97 | Cry3Bb.11229 | B-21767 |
| EG11230 | 5/27/97 | Cry3Bb.11230 | B-21768 |
| EG11231 | 5/27/97 | Cry3Bb.11231 | B-21769 |
| EG11232 | 5/27/97 | Cry3Bb.11232 | B-12770 |
| EG11233 | 5/27/97 | Cry3Bb.11233 | B-21771 |
| EG11234 | 5/27/97 | Cry3Bb.11234 | B-21772 |
| EG11235 | 5/27/97 | Cry3Bb.11235 | B-21773 |
| EG11236 | 5/27/97 | Cry3Bb.11236 | B-21774 |
| EG11237 | 5/27/97 | Cry3Bb.11237 | B-21775 |
| EG11238 | 5/27/97 | Cry3Bb.11238 | B-21776 |
| EG11239 | 5/27/97 | Cry3Bb.11239 | B-21777 |
| EG11241 | 5/27/97 | Cry3Bb.11241 | B-21778 |
| EG11242 | 5/27/97 | Cry3Bb.11242 | B-21779 |

Also disclosed are methods of controlling or eradicating an insect population from an environment. Such methods generally comprise contacting the insect population to be controlled or eradicated with an insecticidally-effective amount of a Cry3* crystal protein composition. Preferred Cry3* compositions include Cry3A*, Cry3B*, and Cry3C* polypeptide compositions, with Cry3B* compositions being particularly preferred. Examples of such polypeptides include proteins selected from the group consisting of Cry3Bb-60, Cry3Bb.11221, Cry3Bb.11222, Cry3Bb.11223, Cry3Bb.11224, Cry3Bb.11225, Cry3Bb.11226, Cry3Bb.11227, Cry3Bb.11228, Cry3Bb.11229, Cry3Bb.11230, Cry3Bb.11231, Cry3Bb.11232, Cry3Bb.11233, Cry3Bb.11234, Cry3Bb.11235, Cry3Bb.11236, Cry3Bb.11237, Cry3Bb.11238, Cry3Bb.11239, Cry3Bb.11241, Cry3Bb.11242, Cry3Bb.11032, Cry3Bb.11035, Cry3Bb.11036, Cry3Bb.11046, Cry3Bb.11048, Cry3Bb.11051, Cry3Bb.11057, Cry3Bb.11058, Cry3Bb.11081, Cry3Bb.11082, Cry3Bb.11083, Cry3Bb.11084, Cry3Bb.11095, and Cry3Bb.11098.

In preferred embodiments, these Cry3Bb* crystal protein compositions comprise the amino acid sequence of any of SEQ ID NO:2, SEQ ID NO:4, SEQ ID NO:6. SEQ ID NO:8, SEQ ID NO:10, SEQ ID NO:12, SEQ ID NO:14. SEQ ID NO:16 SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102 or SEQ ID NO:108.

2.1 METHODS FOR PRODUCING MODIFIED CRY* PROTEINS

The modified Cry* polypeptides of the present invention are preparable by a process which generally involves the steps of obtaining a nucleic acid sequence encoding a Cry* polypeptide; analyzing the structure of the polypeptide to identify particular "target" sites for mutagenesis of the underlying gene sequence; introducing one or more mutations into the nucleic acid sequence to produce a change in one or more amino acid residues in the encoded polypeptide sequence; and expressing in a transformed host cell the mutagenized nucleic acid sequence under conditions effective to obtain the modified Cry* protein encoded by the cry* gene.

Means for obtaining the crystal structures of the polypeptides of the invention are well-known. Exemplary high resolution crystal structure solution sets are given in Section 9.0 of the disclosure, and include the crystal structure of both the Cry3A and Cry3B polypeptides disclosed herein. The information provided in Section 9.0 permits the analyses disclosed in each of the methods herein which rely on the 3D crystal structure information for targeting mutagenesis of the polypeptides to particular regions of the primary amino acid sequences of the δ-endotoxins to obtain mutants with increased insecticidal activity or enhanced insecticidal specificity.

A first method for producing a modified B. thuringiensis Cry3Bb δ-endotoxin having improved insecticidal activity or specificity disclosed herein generally involves obtaining a high-resolution 3D crystal structure of the endotoxin, locating in the crystal structure one or more regions of bound water wherein the bound water forms a contiguous hydrated surfaces separated by no more than about 16 Å; increasing the number of water molecules in this surface by increasing the hydrophobicity of one or more amino acids of the protein in the region; and obtaining the modified δ-endotoxin so produced. Exemplary δ-endotoxins include Cry3Bb.11032, Cry3Bb.11227, Cry3Bb.11241, Cry3Bb.11051, Cry3Bb.11242, and Cry3Bb.11098.

A second method for producing a modified B. thuringiensis Cry3Bb δ-endotoxin having improved insecticidal activity comprises identifying a loop region in a δ-endotoxin; modifying one or more amino acids in the loop to increase the hydrophobicity of the amino acids; and obtaining the modified δ-endotoxin so produced. Preferred δ-endotoxinproduced by this method include Cry3Bb.11241, Cry3Bb.11242, Cry3Bb.11228, Cry3Bb.11229, Cry3Bb.11230, Cry3Bb.11231, Cry3Bb.11233, Cry3Bb.11236, Cry3Bb.11237, Cry3Bb.11238, and Cry3Bb.11239.

A method for increasing the mobility of channel forming helices of a B. thuringiensis Cry3B δ-endotoxin is also provided by the present invention. The method generally comprises disrupting one or more hydrogen bonds formed between a first amino acid of one or more of the channel forming helices and a second amino acid of the δ-endotoxin. The hydrogen bonds may be formed inter- or intramolecularly, and the disrupting may consist of replacing a first or second amino acid with a third amino acid whose spatial distance is greater than about 3 Å, or whose spatial orientation bond angle is not equal to 180±60 degrees relative to the hydrogen bonding site of the first or second amino acid. δ-endotoxins produced by this method and disclosed herein include Cry3Bb.11222, Cry3Bb.11223, Cry3Bb.11224, Cry3Bb.11225, Cry3Bb.11226, Cry3Bb.11227, Cry3Bb.11231, Cry3Bb.11241, and Cry3Bb.11242, and Cry3Bb.11098.

Also disclosed is a method of increasing the flexibility of a loop region in a channel forming domain of a *B. thuringiensis* Cry3Bb δ-endotoxin. This method comprises obtaining a crystal structure of a Cry3Bb δ-endotoxin having one or more loop regions; identifying the amino acids comprising the loop region; and altering one or more of the amino acids to reduce steric hindrance in the loop region, wherein the altering increases flexibility of the loop region in the δ-endotoxin. Examples of δ-endotoxins produced using this method include Cry3Bb.11032, Cry3Bb.11051, Cry3Bb.11228, Cry3Bb.11229, Cry3Bb.11230, Cry3Bb.11231, Cry3Bb.11232, Cry3Bb.11233, Cry3Bb.11236, Cry3Bb.11237, Cry3Bb.11238, Cry3Bb.11239, Cry3Bb.11227, Cry3Bb.11234, Cry3Bb.11241, Cry3Bb.11242, Cry3Bb.11036, and Cry3Bb.11098.

Another aspect of the invention is a method for increasing the activity of a δ-endotoxin, comprising reducing or eliminating binding of the δ-endotoxin to a carbohydrate in a target insect gut. The eliminating or reducing may be accomplished by removal of one or more α helices of domain 1 of the δ-endotoxin, for example, by removal of α helices α1, α2a/b, and α3. An exemplary δ-endotoxin produced using the method is Cry3Bb.60.

Alternatively, the reducing or eliminating may be accomplished by replacing one or more amino acids within loop β1,α8, with one or more amino acids having increased hydrophobicity. Such a method gives rise to δ-endotoxins such as Cry3Bb.11228, Cry3Bb.11230, Cry3B.11231, Cry3Bb.11237, and Cry3Bb.11098, which are described in detail, herein.

Alternatively, the reducing or eliminating is accomplished by replacing one or more specific amino acids, with any other amino acid. Such replacements are described in Table 2, and in the examples herein. One example is the δ-endotoxin designated herein as Cry3Bb.11221.

A method of identifying a region of a Cry3Bb δ-endotoxin for targeted mutagenesis comprising: obtaining a crystal structure of the δ-endotoxin; identifying from the crystal structure one or more surface-exposed amino acids in the protein; randomly substituting one or more of the surface-exposed amino acids to obtain a plurality of mutated polypeptides, wherein at least 50% of the mutated polypeptides have diminished insecticidal activity; and identifying from the plurality of mutated polypeptides one or more regions of the Cry3Bb δ-endotoxin for targeted mutagenesis. The method may further comprise determining the amino acid sequences of a plurality of mutated polypeptides having diminished activity, and identifying one or more amino acid residues required for insecticidal activity.

In another embodiment, the invention provides a process for producing a Cry3Bb δ-endotoxin having improved insecticidal activity. The process generally involves the steps of obtaining a high-resolution crystal structure of the protein; determining the electrostatic surface distribution of the protein; identifying one or more regions of high electrostatic diversity; modifying the electrostatic diversity of the region by altering one or more amino acids in the region; and obtaining a Cry3Bb δ-endotoxin which has improved insecticidal activity. In one embodiment, the electrostatic diversity may be decreased relative to the electrostatic diversity of a native Cry3Bb δ-endotoxin. Exemplary δ-endotoxins with decreased electrostatic diversity include Cry3Bb.11227, Cry3Bb.11241, and Cry3Bb.11242. Alternatively, the electrostatic diversity may be increased relative to the electrostatic diversity of a native Cry3Bb δ-endotoxin. An exemplary δ-endotoxin with increased electrostatic diversity is Cry3Bb.11234.

Furthermore, the invention also provides a method of producing a Cry3Bb δ-endotoxin having improved insecticidal activity which involves obtaining a high-resolution crystal structure; identifying the presence of one or more metal binding sites in the protein; altering one or more amino acids in the binding site; and obtaining an altered protein, wherein the protein has improved insecticidal activity. The altering may involve the elimination of one or more metal binding sites. Exemplary δ-endotoxin include Cry3Bb.11222, Cry3Bb.11224, Cry3Bb.11225, and Cry3Bb.11226.

A further aspect of the invention involves a method of identifying a *B. thuringiensis* Cry3Bb δ-endotoxin having improved channel activity. This method in an overall sense involves obtaining a Cry3Bb δ-endotoxin suspected of having improved channel activity; and determining one or more of the following characteristics in the δ-endotoxin, and comparing such characteristics to those obtained for the wild-type unmodified δ-endotoxin: (1) the rate of channel formation, (2) the rate of growth of channel conductance or (3) the duration of open channel state. From this comparison, one may then select a δ-endotoxin which has an increased rate of channel formation compared to the wild-type δ-endotoxin. Examples of Cry3Bb δ-endotoxins prepared by this method include Cry3Bb.60, Cry3Bb.11035, Cry3Bb.11048, Cry3Bb.11032, Cry3Bb.11223, Cry3Bb.11224, Cry3Bb.11226, Cry3Bb.11221, Cry3Bb.11242, Cry3Bb.11230, and Cry3Bb.11098.

Also provided is a method for producing a modified Cry3Bb δ-endotoxin, having improved insecticidal activity which involves altering one or more non-surface amino acids located at or near the point of greatest convergence of two or more loop regions of the Cry3Bb δ-endotoxin, such that the altering decreases the mobility of one or more of the loop regions. The mobility may conveniently be determined by comparing the thermal denaturation of the modified protein to a wild-type Cry3Bb δ-endotoxin. An exemplary crystal protein produced by this method is Cry3Bb.11095.

A further aspect of the invention involves a method for preparing a modified Cry3Bb δ-endotoxin, having improved insecticidal activity comprising modifying one or more amino acids in the loop to increase the hydrophobicity of said amino acids; and altering one or more of said amino acids to reduce steric hindrance in the loop region, wherein the altering increases flexibility of the loop region in the endotoxin. Exemplary Cry3Bb δ-endotoxins produced is selected from the group consisting of Cry3Bb.11057, Cry3Bb.11058, Cry3Bb.11081, Cry3Bb.11082, Cry3 Bb.11083, Cry3 Bb.11084, Cry3Bb.11231, Cry3Bb.11235, and Cry3Bb.11098.

The invention also provides a method of improving the insecticidal activity of a *B. thuringiensis* Cry3Bb δ-endotoxin, which generally comprises inserting one or more protease sensitive sites into one or more loop regions of domain 1 of the δ-endotoxin. Preferably, the loop region is α3,4, and an exemplary δ-endotoxin so produced is Cry3Bb.11221.

2.2 POLYPEPTIDE COMPOSITIONS

The crystal proteins so produced by each of the methods described herein also represent important aspects of the invention. Such crystal proteins preferably include a protein or peptide selected from the group consisting of Cry3Bb-60, Cry3Bb.11221, Cry3Bb.11222, Cry3Bb.11223, Cry3Bb.11224, Cry3Bb.11225, Cry3Bb.11226, Cry3Bb.11227, Cry3Bb.11228, Cry3Bb.11229, Cry3Bb.11230, Cry3Bb.11231, Cry3Bb.11232, Cry3Bb.11233, Cry3Bb.11234, Cry3Bb.11235, Cry3Bb.11236, Cry3Bb.11237, Cry3Bb.11238, Cry3Bb.11239, Cry3Bb.11241, Cry3Bb.11242, Cry3Bb.11032, Cry3Bb.11035, Cry3Bb.11036, Cry3Bb.11046, Cry3Bb.11048, Cry3Bb.11051, Cry3Bb.11057, Cry3Bb.11058, Cry3Bb.11081, Cry3Bb.11082, Cry3Bb.11083, Cry3Bb.11084, Cry3Bb.11095, and Cry3Bb.11098.

In preferred embodiments, the protein comprises a contiguous amino acid sequence selected from the group consisting of SEQ ID NO:2, SEQ ID NO:4, SEQ ID NO:6. SEQ ID NO:8, SEQ ID NO:10, SEQ ID NO:12, SEQ ID NO:14. SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, and SEQ ID NO:108.

Highly preferred are those crystal proteins which are encoded by the nucleic acid sequence of SEQ ID NO:1, SEQ ID NO:3, SEQ ID NO:5. SEQ ID NO:7, SEQ ID NO:9, SEQ ID NO:11, SEQ ID NO:13. SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101; or SEQ ID NO:107, or a nucleic acid sequence which hybridizes to the nucleic acid sequence of SEQ ID NO:1, SEQ ID NO:3, SEQ ID NO:5. SEQ ID NO:7, SEQ ID NO:9, SEQ ID NO:11, SEQ ID NO:13. SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107 under conditions of moderate stringency.

Amino acid, peptide and protein sequences within the scope of the present invention include, and are not limited to the sequences set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46 SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, and SEQ ID NO:108, and alterations in the amino acid sequences including alterations, deletions, mutations, and homologs.

Compositions which comprise from about 0.5% to about 99% by weight of the crystal protein, or more preferably from about 5% to about 75%, or from about 25% to about 50% by weight of the crystal protein are provided herein. Such compositions may readily be prepared using techniques of protein production and purification well-known to those of skill, and the methods disclosed herein. Such a process for preparing a Cry3Bb* crystal protein generally involves the steps of culturing a host cell which expresses the Cry3Bb* protein (such as a *B. thuringiensis* EG11221, EG11222, EG11223, EG11224, EG11225, EG11226, EG11227, EG11228, EG11229, EG11230, EG11231, EG11232, EG11233, EG11234, EG11235, EG11236, EG11237, EG11238, EG11239, EG11241, EG11242, EG11032, EG11035, EG11036, EG11046, EG11048, EG11051, EG11057, EG11058, EG11081, EG11082, EG11083, EG11084, EG11095, or EG11098 cell) under conditions effective to produce the crystal protein, and then obtaining the crystal protein so produced.

The protein may be present within intact cells, and as such, no subsequent protein isolation or purification steps may be required. Alternatively, the cells may be broken, sonicated, lysed, disrupted, or plasmolyzed to free the crystal protein(s) from the remaining cell debris. In such cases, one may desire to isolate, concentrate, or further purify the resulting crystals containing the proteins prior to use, such as, for example, in the formulation of insecticidal compositions. The composition may ultimately be purified to consist almost entirely of the pure protein, or alternatively, be purified or isolated to a degree such that the composition comprises the crystal protein(s) in an amount of from between about 0.5% and about 99% by weight, or in an amount of from between about 5% and about 95% by weight, or in an amount of from between about 15% and about 85% by weight, or in an amount of from between about 25% and about 75% by weight, or in an amount of from between about 40% and about 60% by weight etc.

2.3 RECOMBINANT VECTORS EXPRESSING CRY3* GENES

One important embodiment of the invention is a recombinant vector which comprises a nucleic acid segment encoding one or more of the novel *B. thuringiensis* crystal proteins disclosed herein. Such a vector may be transferred to and replicated in a prokaryotic or eukaryotic host, with bacterial cells being particularly preferred as prokaryotic hosts, and plant cells being particularly preferred as eukaryotic hosts.

In preferred embodiments, the recombinant vector comprises a nucleic acid segment encoding the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108. Highly preferred nucleic acid segments are those which have the sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107.

Another important embodiment of the invention is a transformed host cell which expresses one or more of these recombinant vectors. The host cell may be either prokaryotic or eukaryotic, and particularly preferred host cells are those which express the nucleic acid segment(s) comprising the recombinant vector which encode one or more B. thuringiensis crystal protein comprising modified amino acid sequences in one or more loop regions of domain 1, or between α helix 7 of domain 1 and β strand 1 of domain 2. Bacterial cells are particularly preferred as prokaryotic hosts, and plant cells are particularly preferred as eukaryotic hosts In an important embodiment, the invention discloses and claims a host cell wherein the modified amino acid sequences comprise one or more loop regions between α helices 1 and 2, α helices 2 and 3, α helices 3 and 4, α helices 4 and 5, α helices 5 and 6 or α helices 6 and 7 of domain 1, or between α helix 7 of domain 1 and β strand 1 of domain 2. A particularly preferred host cell is one that comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108, and more preferably, one that comprises the nucleic acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107.

Bacterial host cells transformed with a nucleic acid segment encoding a modified Cry3Bb crystal protein according to the present invention are disclosed and claimed herein, and in particular, a B. thuringiensis cell having designation EG11221, EG11222, EG11223, EG11224, EG11225, EG11226, EG11227, EG11228, EG11229, EG11230, EG11231, EG11232, EG11233, EG11234, EG11235, EG11236, EG11237, EG11238, EG11239, EG11241, EG11242, EG11032, EG11035, EG11036, EG11046, EG11048, EG11051, EG11057, EG11058, EG11081, EG11082, EG11083, EG11084, EG11095, or EG11098.

In another embodiment, the invention encompasses a method of using a nucleic acid segment of the present invention that encodes a cry3Bb* gene. The method generally comprises the steps of: (a) preparing a recombinant vector in which the cry3Bb* gene is positioned under the control of a promoter; (b) introducing the recombinant vector into a host cell; (c) culturing the host cell under conditions effective to allow expression of the Cry3Bb* crystal protein encoded by said cry3Bb* gene; and (d) obtaining the expressed Cry3Bb* crystal protein or peptide.

A wide variety of ways are available for introducing a B. thuringiensis gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, more preferably at least about 1000 bp, and usually not more than about 2000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lost the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the $\lambda_L$ and $\lambda_R$ promoters, the tac promoter, the naturally-occurring promoters associated with the δ-endotoxin gene, where functional in the host. See for example, U.S. Pat. Nos. 4,332,898; 4,342,832; and 4,356,270 (each of which is specifically incorporated herein by reference). The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pR01614, and the like. See for example, Olson et al. (1982); Bagdasarian et al. (1981), Baum et al., 1990, and U.S. Pat. Nos. 4,356,270; 4,362,817; 4,371,625, and 5,441,884, each incorporated specifically herein by reference.

The B. thuringiensis gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity. If desired, unwanted or ancillary DNA sequences may be selectively removed from the recombinant bacterium by employing site-specific recombination systems, such as those described in U.S. Pat. No. 5,441,884 (specifically incorporated herein by reference).

2.4 CRY3 DNA SEGMENTS

A B. thuringiensis cry3* gene encoding a crystal protein having one or more mutations in one or more regions of the peptide represents an important aspect of the invention. Preferably, the cry3* gene encodes an amino acid sequence in which one or more amino acid residues have been changed based on the methods disclosed herein, and particularly those changes which have been made for the purpose of altering the insecticidal activity or specificity of the crystal protein.

In accordance with the present invention, nucleic acid sequences include and are not limited to DNA, including and not limited to cDNA and genomic DNA, genes; RNA, including and not limited to mRNA and tRNA; antisense sequences, nucleosides, and suitable nucleic acid sequences such as those set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107, and alterations in the nucleic acid sequences including alterations, deletions, mutations, and homologs capable of expressing the B. thuringiensis modified toxins of the present invention.

As such the present invention also concerns DNA segments, that are free from total genomic DNA and that encode the novel synthetically-modified crystal proteins disclosed herein. DNA segments encoding these peptide species may prove to encode proteins, polypeptides, subunits, functional domains, and the like of crystal protein-related or other non-related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding a crystal protein or peptide refers to a DNA segment that contains crystal protein coding sequences yet is isolated away from, or purified free from, total genomic DNA of the species from which the DNA segment is obtained, which in the instant case is the genome of the Gram-positive bacterial genus, Bacillus, and in particular, the species of Bacillus known as B. thuringiensis. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified crystal protein-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, operon sequences and smaller engineered gene segments that express, or may be adapted to express, proteins, polypeptides or peptides.

"Isolated substantially away from other coding sequences" means that the gene of interest, in this case, a gene encoding a bacterial crystal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

Particularly preferred DNA sequences are those encoding Cry3Bb.60, Cry3Bb.11221, Cry3Bb.11222, Cry3Bb.11223, Cry3Bb.11224, Cry3Bb.11225, Cry3Bb.11226, Cry3Bb.11227, Cry3Bb.11228, Cry3Bb.11229, Cry3Bb.11230, Cry3Bb.11231, Cry3Bb.11232, Cry3Bb.11233, Cry3Bb.11234, Cry3Bb.11235, Cry3Bb.11236, Cry3Bb.11237, Cry3Bb.11238, Cry3Bb.11239, Cry3Bb.11241, Cry3Bb.11242, Cry3Bb.11032, Cry3Bb.11035, Cry3Bb.11036, Cry3Bb.11046, Cry3Bb.11048, Cry3Bb.11051, Cry3Bb.11057, Cry3Bb.11058, Cry3Bb.11081, Cry3 Bb.11082, Cry3 Bb.11083, Cry3 Bb.11084, Cry3 Bb.11095 and Cry3Bb.11098 crystal proteins, and in particular cry3Bb* genes such as cry3Bb.60, cry3Bb.11221, cry3Bb.11222, cry3Bb.11223, cry3Bb.11224, cry3Bb.11225, cry3Bb.11226, cry3Bb.11227, cry3Bb.11228, cry3Bb.11229, cry3Bb.11230, cry3Bb.11231, cry3Bb.11232, cry3Bb.11233, cry3Bb.11234, cry3Bb.11235, cry3Bb.11236, cry3Bb.11237, cry3Bb.11238, cry3Bb.11239, cry3Bb.11241, cry3Bb.11242, cry3Bb.11032, cry3Bb.11035, cry3Bb.11036, cry3Bb.11046, cry3Bb.11048, cry3Bb.11051, cry3Bb.11057, cry3Bb.11058, cry3Bb.11081, cry3Bb.11082, cry3Bb.11083, cry3Bb.11084, cry3Bb.1095 and cry3Bb.11098. In particular embodiments, the invention concerns isolated DNA segments and recombinant vectors incorporating DNA sequences that encode a Cry peptide species that includes within its amino acid sequence an amino acid sequence essentially as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108.

The term "a sequence essentially as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108" means that the sequence substantially corresponds to a portion of the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30,SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108, and has relatively few amino acids that are not identical to, or a biologically functional equivalent of, the amino acids of any of these sequences. The term "biologically functional equivalent" is well understood in the art and is further defined in detail herein (e.g., see Illustrative Embodiments).

Accordingly, sequences that have between about 70% and about 75% or between about 75% and about 80%, or more preferably between about 81% and about 90%, or even more preferably between about 91% or 92% or 93% and about 97% or 98% or 99% amino acid sequence identity or functional equivalence to the amino acids of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102 or SEQ ID NO:108 will be sequences that are "essentially as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i. e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a short contiguous stretch encoding the peptide sequence disclosed in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108, or that are identical to or complementary to DNA sequences which encode the peptide disclosed in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108, and particularly the DNA segments disclosed in SEQ ID NO:1, SEQ ID NO:3, SEQ ID NO:5, SEQ ID NO:7, SEQ ID NO:9, SEQ ID NO:1, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107.

Highly preferred nucleic acid segments of the present invention comprise one or more cry genes of the invention, or a portion of one or more cry genes of the invention. For certain application, relatively small contiguous nucleic acid sequences are preferable, such as those which are about 14 or 15 or 16 or 17 or 18 or 19, or 20, or 30–50, 51–80, 81–100 or so nucleotides in length. Alternatively, in some embodiments, and particularly those involving preparation of recombinant vectors, transformation of suitable host cells, and preparation of transgenic plant cell, longer nucleic acid segments are preferred, particularly those that include the entire coding region of one or more cry genes. As such, the preferred segments may include those that are up to about 20,000 or so nucleotides in length, or alternatively, shorter sequences such as those about 19,000, about 18,000, about 17,000, about 16,000, about 15,000, about 14,000, about 13,000, about 12,000, 11,000, about 10,000, about 9,000, about 8,000, about 7,000, about 6,000, about 5,000, about 4,500, about 4,000, about 3,500, about 3,000, about 2,500, about 2,000, about 1,500, about 1,000, about 500, or about 200 or so base pairs in length. Of course, these numbers are not intended to be exclusionary of all possible intermediate lengths in the range of from about 20,000 to about 15 nucleotides, as all of these intermediate lengths are also contemplated to be useful, and fall within the scope of the present invention. It will be readily understood that "intermediate lengths", in these contexts, means any length between the quoted ranges, such as 14, 15, 16, 17, 18, 19, 20, etc.; 21, 22, 23, 24, 25, 26, 27, 28, 29, etc.; 30, 31, 32, 33, 34, 35, 36 . . . etc.; 40, 41, 42, 43, 44 . . . etc., 50, 51, 52, 53 . . . etc.; 60,61, 62, 63 . . . etc., 70, 80, 90, 100, 110, 120, 130 . . . etc.; 200, 210, 220, 230,240, 250 . . . etc.; including all integers in the entire range from about 14 to about 10,000, including those integers in the ranges 200–500; 500–1,000; 1,000–2,000; 2,000–3,000; 3,000–5,000 and the like.

In a preferred embodiment, the nucleic acid segments comprise a sequence of from about 1800 to about 18,000 base pair in length, and comprise one or more genes which encode a modified Cry3* polypeptide disclosed herein which has increased activity against Coleopteran insect pests.

It will also be understood that this invention is not limited to the particular nucleic acid sequences which encode peptides of the present invention, or which encode the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108, including the DNA sequences which are particularly disclosed in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level If desired, one may also prepare fusion proteins and peptides, e.g., where the peptide-coding regions are aligned within the same expression unit with other proteins or peptides having desired functions, such as for purification or immunodetection purposes (e.g, proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.5 VECTORS, HOST CELLS, AND PROTEIN EXPRESSION

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a crystal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of crystal peptides or epitopic core regions, such as may be used to generate anti-crystal protein antibodies, also falls within the scope of the invention. DNA segments that encode peptide antigens from about 8, 9, 10, or 11 or so amino acids, and up to and including those of about 30, 40, or 50 or so amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequence from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, or SEQ ID NO:108.

2.6 TRANSFORMED HOST CELLS AND TRANSGENIC PLANTS

In one embodiment, the invention provides a transgenic plant having incorporated into its genome a transgene that encodes a contiguous amino acid sequence selected from the group consisting of SEQ ID NO:2, SEQ ID NO:4, SEQ ID NO:6. SEQ ID NO:8, SEQ ID NO:10, SEQ ID NO:12, SEQ ID NO:14. SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, SEQ ID NO:102, and SEQ ID NO:108.

A further aspect of the invention is a transgenic plant having incorporated into its genome a cry3Bb* transgene, provided the transgene comprises a nucleic acid sequence selected from the group consisting of SEQ ID NO:1, SEQ ID NO:3, SEQ ID NO:5. SEQ ID NO:7, SEQ ID NO:9, SEQ ID NO:11, SEQ ID NO:13. SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, and SEQ ID NO:107. Also disclosed and claimed are progeny of such a transgenic plant, as well as its seed, progeny from such seeds, and seeds arising from the second and subsequent generation plants derived from such a transgenic plant.

The invention also discloses and claims host cells, both native, and genetically engineered, which express the novel cry3Bb* genes to produce Cry3Bb* polypeptides. Preferred examples of bacterial host cells include *B. thuringiensis* EG11221, EG11222, EG11223, EG11224, EG11225, EG11226, EG11227, EG11228, EG11229, EG11230, EG11231, EG11232, EG11233, EG11234, EG11235, EG11236, EG11237, EG11238, EG11239, EG11241, EG11242, EG11032, EG11035, EG11036, EG11046, EG11048, EG11051, EG11057, EG11058, EG11081, EG11082, EG11083, EG11084, EG11095, and EG1098.

Methods of using such cells to produce Cry3* crystal proteins are also disclosed. Such methods generally involve culturing the host cell (such as *B. thuringiensis* EG11221, EG11222, EG11223, EG11224, EG11225, EG11226, EG11227, EG11228, EG11229, EG11230, EG11231, EG11232, EG11233, EG11234, EG11235, EG11236, EG11237, EG11238, EG11239, EG11241, EG11242, EG11032, EG11035, EG11036, EG11046, EG11048, EG11051, EG11057, EG11058, EG11081, EG11082, EG11083, EG11084, or EG11095, or EG11098) under conditions effective to produce a Cry3* crystal protein, and obtaining the Cry3* crystal protein from said cell.

In yet another aspect, the present invention provides methods for producing a transgenic plant which expresses a nucleic acid segment encoding the novel recombinant crystal proteins of the present invention. The process of producing transgenic plants is well-known in the art. In general, the method comprises transforming a suitable host cell with one or more DNA segments which contain one or more promoters operatively linked to a coding region that encodes one or more of the disclosed *B. thuringiensis* crystal proteins. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Another aspect of the invention comprises a transgenic plant which express a gene or gene segment encoding one or more of the novel polypeptide compositions disclosed herein. As used herein, the term “transgenic plant” is intended to refer to a plant that has incorporated DNA sequences, including but not limited to genes which are perhaps not normally present, DNA sequences not normally transcribed into RNA or translated into a protein (“expressed”), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more Cry3Bb*-encoding transgenes, either native, synthetically modified, or mutated. In some instances, more than one transgene will be incorporated into the genome of the transformed host plant cell. Such is the case when more than one crystal protein-encoding DNA segment is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant.

A preferred gene which may be introduced includes, for example, a crystal protein-encoding a DNA sequence from bacterial origin, and particularly one or more of those described herein which are obtained from Bacillus spp. Highly preferred nucleic acid sequences are those obtained from *B. thuringiensis*, or any of those sequences which have been genetically engineered to decrease or increase the insecticidal activity of the crystal protein in such a transformed host cell.

Means for transforming a plant cell and the preparation of a transgenic cell line are well-known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified crystal protein, which will be expressed in the resultant recombinant cells, and/or which will impart an improved phenotype to the regenerated plant Such transgenic plants may be desirable for increasing the insecticidal resistance of a monocotyledonous or dicotyledonous plant, by incorporating into such a plant, a transgenic DNA segment encoding a Cry3Bb* crystal protein which is toxic to coleopteran insects. Particularly preferred plants include grains such as corn, wheat, rye, rice, barley, and oats; legumes such as soybeans; tubers such as potatoes; fiber crops such as flax and cotton; turf and pasture grasses; ornamental plants; shrubs; trees; vegetables, berries, citrus, fruits, cacti, succulents, and other commercially-important crops including garden and houseplants.

In a related aspect, the present invention also encompasses a seed produced by the transformed plant, a progeny from such seed, and a seed produced by the progeny of the original transgenic plant, produced in accordance with the above process. Such progeny and seeds will have one or more crystal protein transgene(s) stably incorporated into its genome, and such progeny plants will inherit the traits afforded by the introduction of a stable transgene in Mendelian fashion. All such transgenic plants having incorporated into their genome transgenic DNA segments encoding one or more Cry3Bb* crystal proteins or polypeptides are aspects of this invention. Particularly preferred transgenes for the practice of the invention include nucleic acid segments comprising one or more cry3Bb* gene(s).

2.7 BIOLOGICAL FUNCTIONAL EQUIVALENTS

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 4.

TABLE 4

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic Acid | Asp | D | GAC | GAU | | |
| Glutamic Acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |

TABLE 4-continued

| Amino Acids | | | Codons | | | | | |
|---|---|---|---|---|---|---|---|---|
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, specifically incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1 Schematic representation of the monomeric structure of Cry3Bb.

FIG. 2 Stereoscopic view of the monomeric structure of Cry3Bb with associated water molecules (represented by dots).

FIG. 3A Schematic representation of domain 1 of Cry3Bb

FIG. 3B Diagram of the positions of the 7 helices that comprise domain 1.

FIG. 4 Domain 1 of Cry3Bb is organized into seven α helices illustrated in FIG. 3A (schematic representation) and FIG. 3B (schematic diagram). The α helices and amino acids residues are shown.

FIG. 5A Schematic representation of domain 2 of Cry3Bb.

FIG. 5B Diagram of the positions of the 11 β strands that compose the 3 β sheets of domain 2.

FIG. 6 Domain 2 of Cry3Bb is a collection of three anti-parallel β sheets illustrated in FIG. 5. The amino acids that define these sheets is listed below (α8, amino aids 322–328, also is included in domain 2):

FIG. 7A Schematic representation of domain 3 of Cry3Bb.

FIG. 7B Diagram of the positions of the β strands that comprise domain 3.

FIG. 8 Domain 3 (FIG. 7) is a loosely organized collection of β strands and loops; no β sheets are present. The β stands contain the amino acids limited below:

FIG. 9A A "side" view of the dimeric structure of Cry3Bb. The helical bundles of domains 1 can be seem in the middle of the molecule.

FIG. 9B A "top" view of the dimeric structure of Cry3Bb. The helical bundles of domains 1 can be seem in the middle of the molecule.

FIG. 10 A graphic representation of the growth in conductance with time of channels formed by Cry3A and Cry3Bb in planar lipid bilayers. Cry3A forms channels with higher conductances much more rapidly than Cry3Bb.

Figure 11:
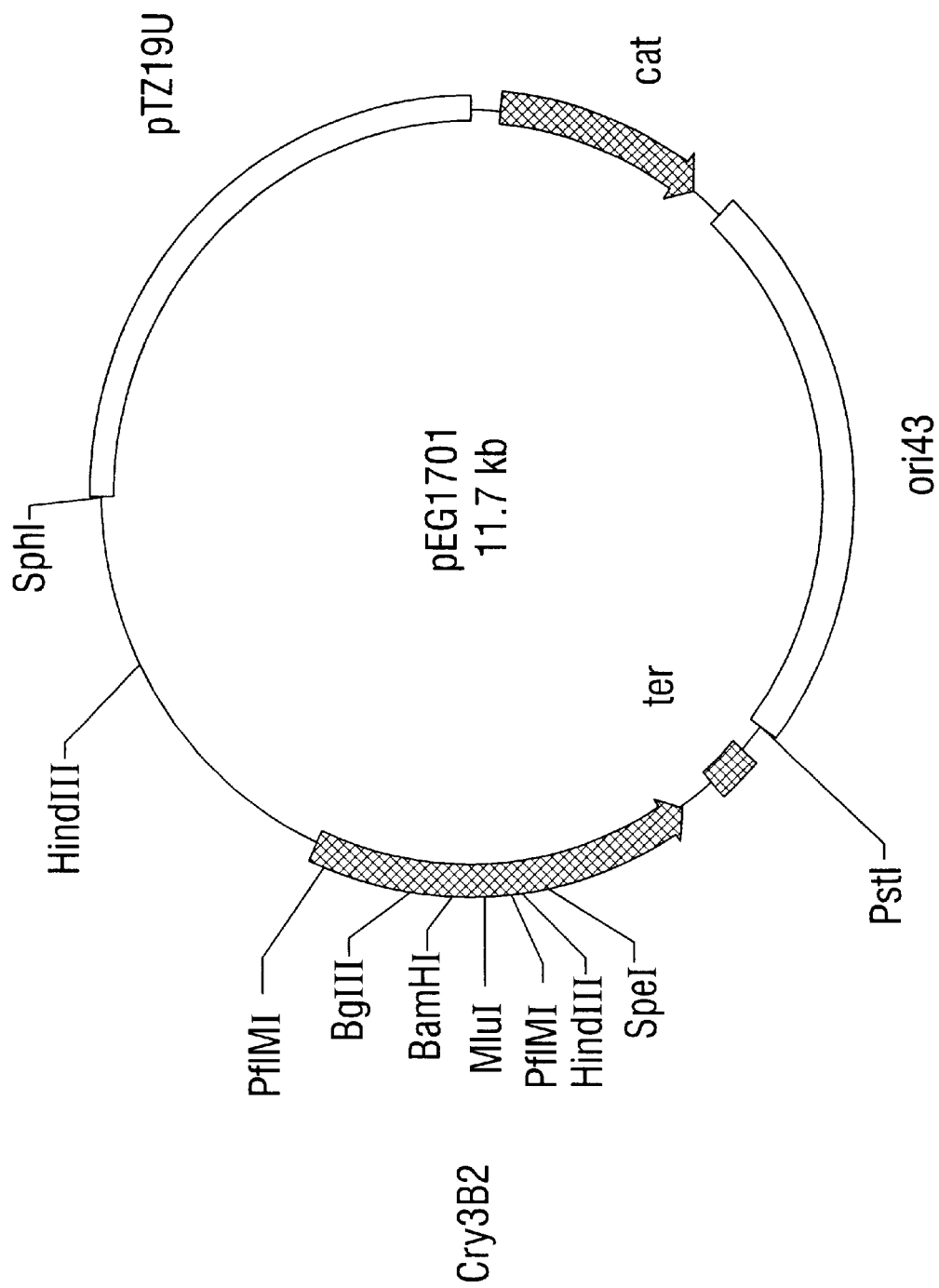

FIG. 11 A map of pEG1701 which contains the Cry3Bb gene with the cry1F terminator.

Figure 12:
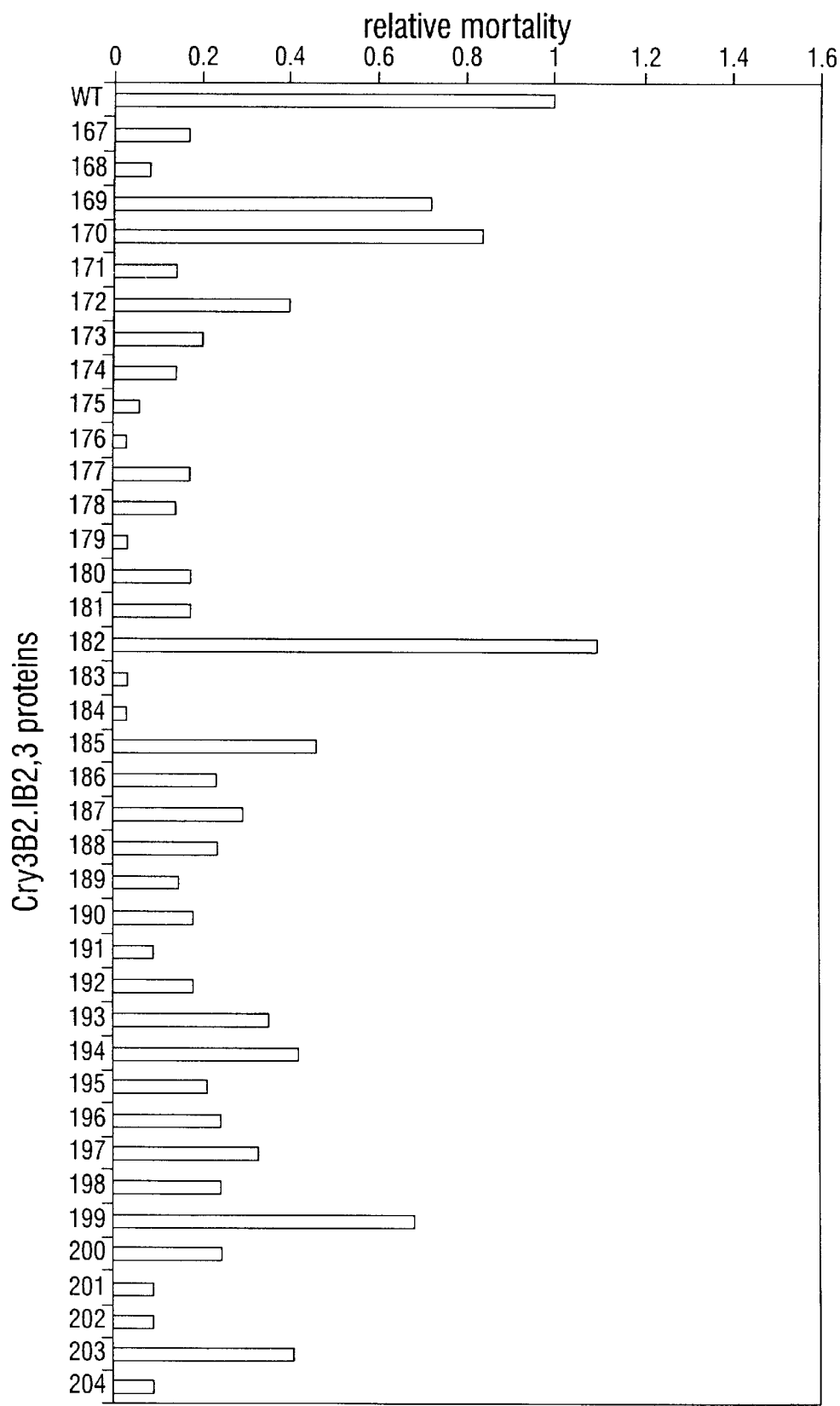

FIG. 12 The results of replicated 1-dose assays against SCRW larvae of Cry3Bb proteins altered in the 1B2,3 region.

Figure 13:
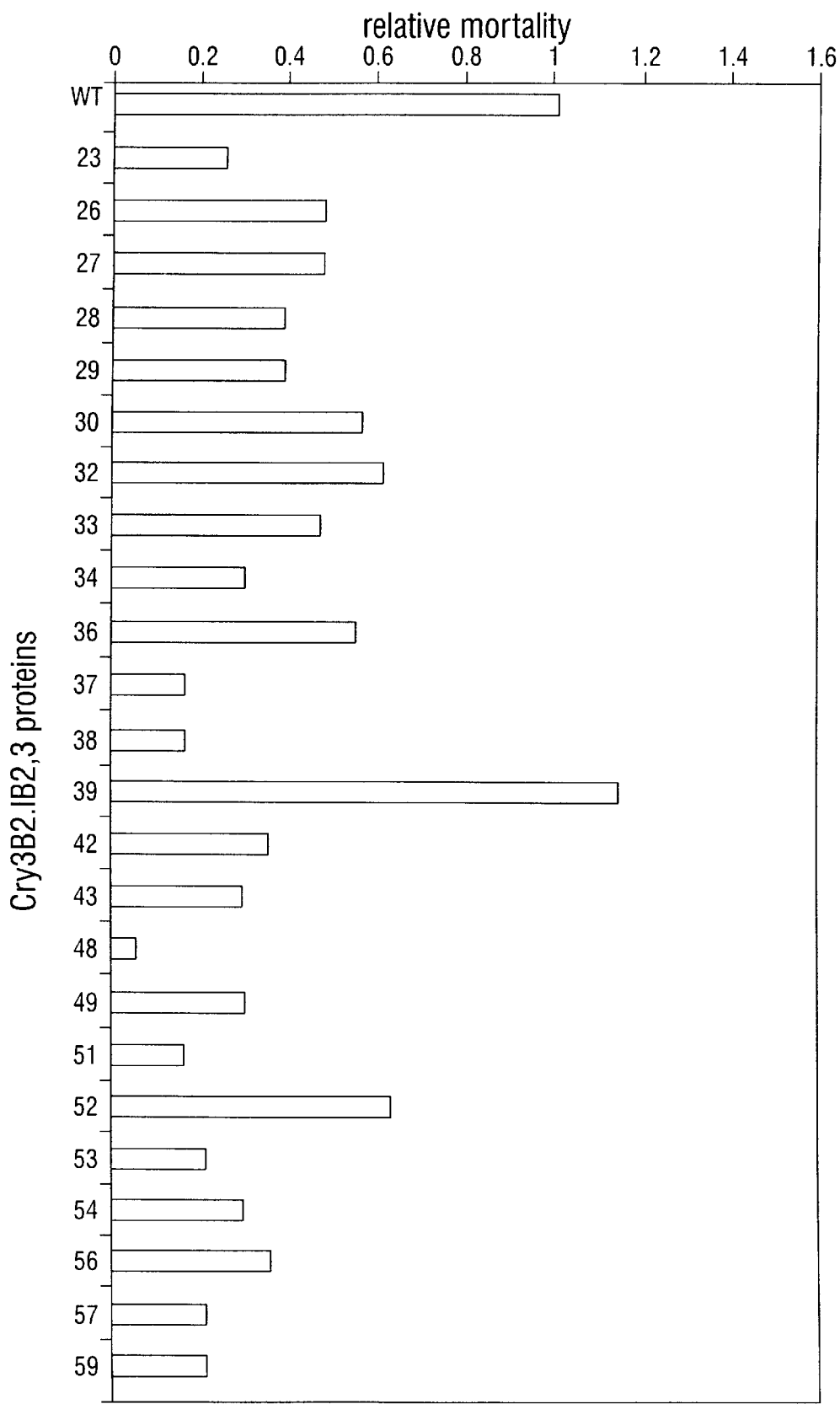

FIG. 13 The results of replicated, 1-dose assays against SCRW larvae of Cry3Bb proteins altered in the 1B6, 7 region.

Figure 14:
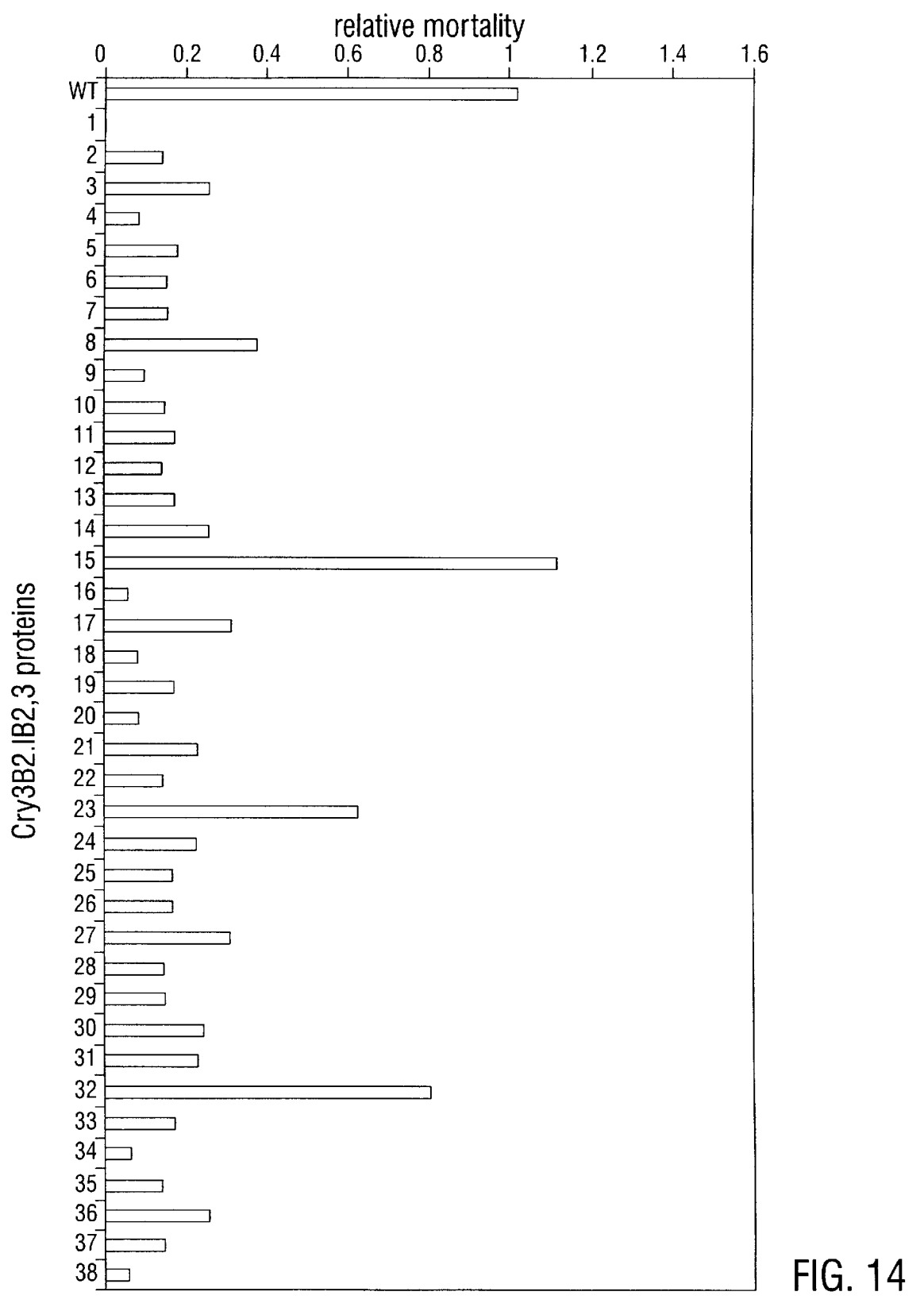

FIG. 14 The results of replicated, 1-dose screens against SCRW larvae of Cry3Bb proteins altered in the 1B10,11 region.

Figure 15:
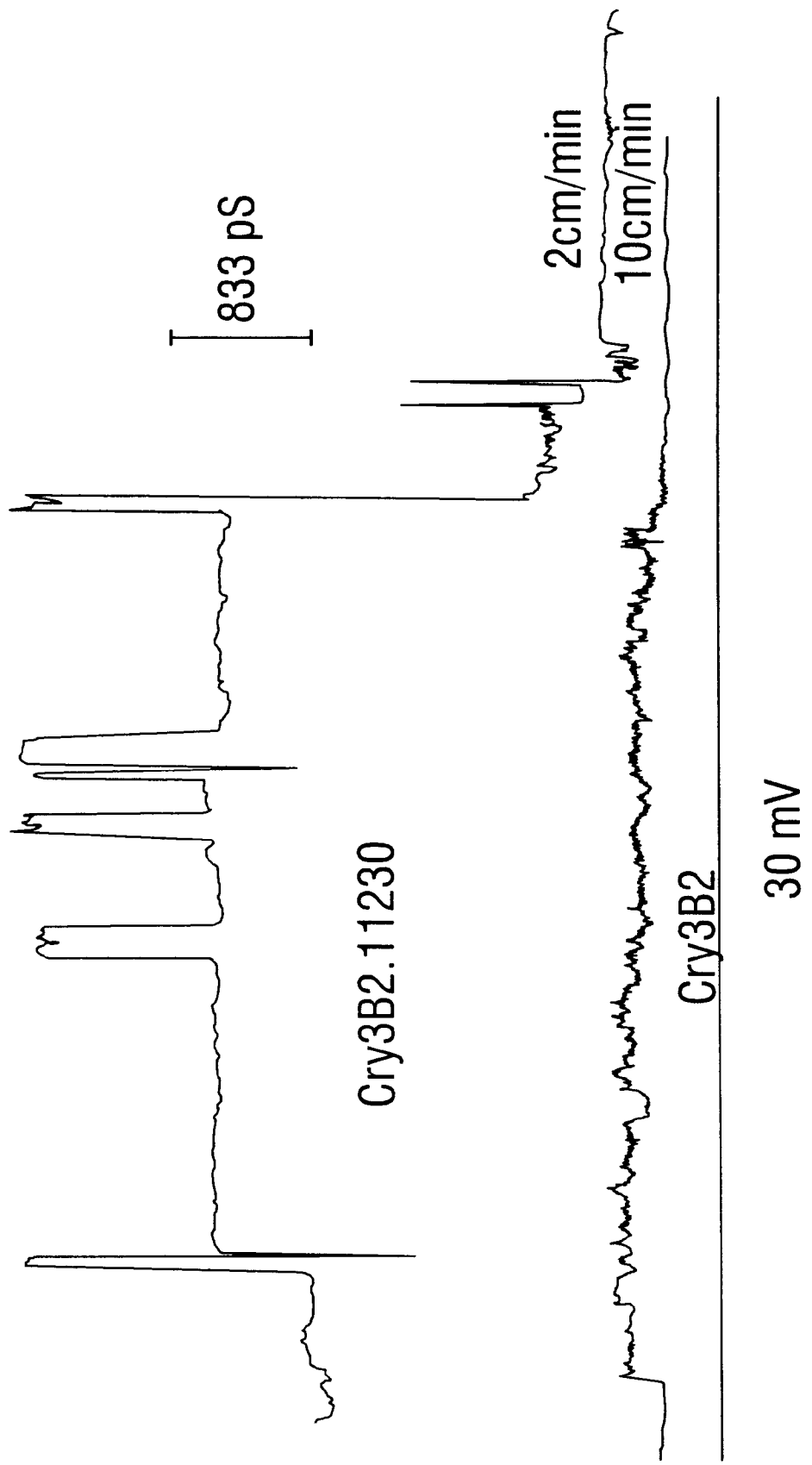

FIG. 15 Single channel recordings of channels formed by Cry3Bb.11230 and WT Cry3Bb in planar lipid bilayers. Cry3Bb.11230 forms channels with well resolved open and closed states while Cry3Bb rarely does.

Figure 16:
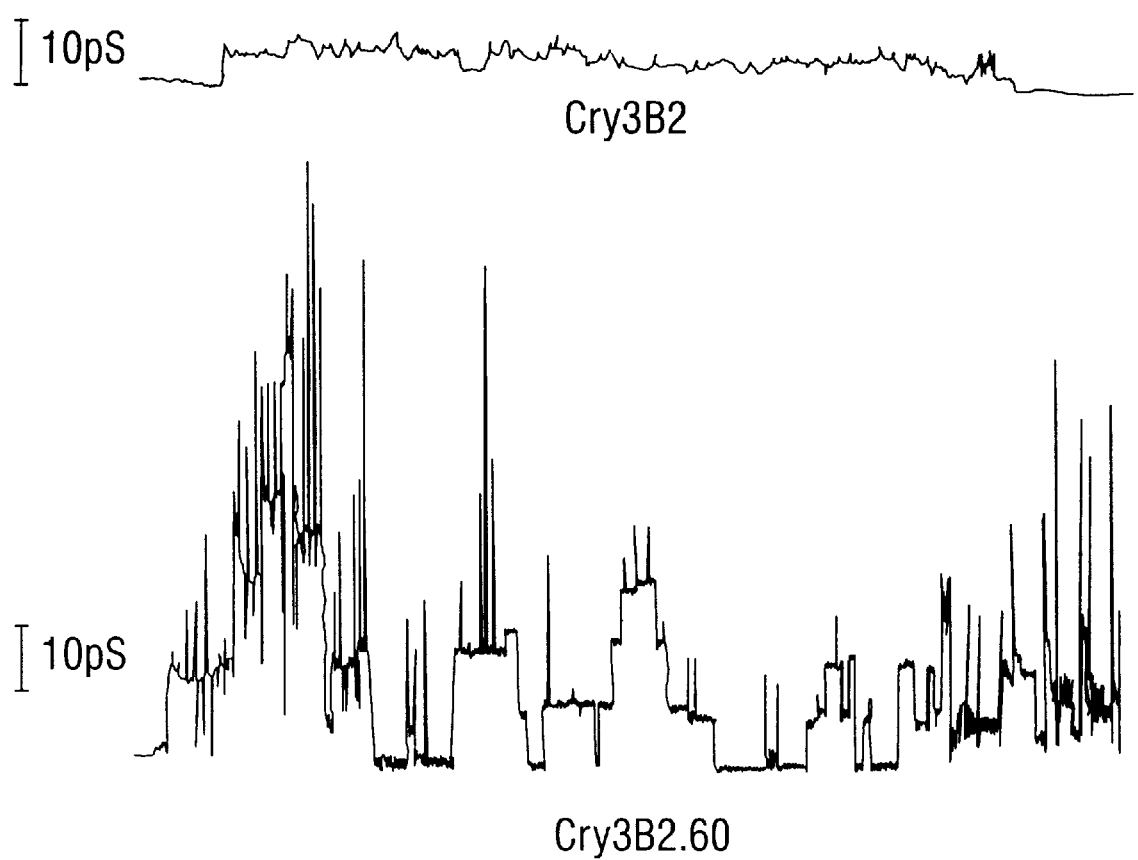

FIG. 16 Single channel recordings of channels formed by Cry3Bb and Cry3Bb.60, a truzncated form of Cry3Bb. Cry3Bb.60 forms channels more quickly than Cry3Bb and, unlike Cry3Bb, produces channels with well resolved open and closed states.

FIGS. 17A–17C Sequence alignment of the amino acid sequence of Cry3A, Cry3B, and Cry3C.

4.0 DESCRIPTION OF ILLUSTRATIVE EMBODIMENTS

The invention defines new *B. thuringiensis* (*Bt*) insecticidal δ-endotoxin proteins and the biochemical and biophysical strategies used to design the new proteins. Delta-endotoxins are a class of insecticdal proteins produced by *B. thuringiensis* that form cation-selective channels in planar lipid bilayers (English and Slatin, 1992). The new δ-endotoxins are based on the parent structure of the coleopteran-active, δ-endotoxin Cry3Bb. Like other members of the coleopteran-active class of δ-endotoxins, including Cry3A and Cry3B, Cry3Bb exhibits excellent insecticidal activity against the Colorado Potato Beetle (*Leptinotarsa decemlineata*). However, unlike Cry3A and Cry3B, Cry3Bb is also active against the southern corn rootworm or SCRW (*Diabrotica undecimpunctata howardi* Barber) and the western corn rootworm or WCRW (*Diabrotica virgifera virgifera* LeConte). The new insecticidal proteins described herein were specifically designed to improve the biological activity of the parent Cry3Bb protein. In addition, the design strategies themselves are novel inventions capable of being applied to and improving *B. thuringiensis* δ-endotoxins in general. *B. thuringiensis* δ-endotoxins are also members of a larger class of bacterial toxins that form ion channels (see English and Slatin 1992, for a review). The inventors, therefore, believe that these design strategies can also be applied to any biologically active, channel-forming protein to improve its biological properties.

The designed Cry3Bb proteins were engineered using one or more of the following strategies including (1) identification and alteration of protease-sensitive sites and proteolytic processing; (2) analysis and manipulation of bound water; (3) manipulation of hydrogen bonds around mobile regions; (4) loop analysis and loop redesign around flexible helices; (5) loop design around β strands and β sheets; (6) identification and redesign of complex electrostatic surfaces; (7) identification and removal of metal binding sites; (8) alteration of quaternary structure; (9) identification and design of structural residues; and (10) combinations of any and all sites defined by strategies 1–9. These design strategies permit the identification and redesign of specific sites on Cry3Bb, ultimately creating new proteins with improved insecticidal activities. These new proteins are designated Cry3Bb designed proteins and are named Cry3Bb followed by a period and a suffix (e.g., Cry3Bb.60, Cry3Bb.11231). The new proteins are listed in Table 2 along with the specific sites on the molecule that were modified, the amino-acid sequence changes at those sites that improve biological activity, the improved insecticidal activities and the design method used to identify that specific site.

4.1 SOME ADVANTAGES OF THE INVENTION

Mutagenesis studies with cry genes have failed to identify a significant number of mutant crystal proteins which have improved broad-spectrum insecticidal activity, that is, with improved toxicity towards a range of insect pest species. Since agricultural crops are typically threatened by more than one insect pest species at any given time, desirable mutant crystal proteins are preferably those that exhibit improvements in toxicity towards multiple insect pest species. Previous failures to identify such mutants may be attributed to the choice of sites targeted for mutagenesis. For example, with respect to the related protein, Cry1C, sites within domain 2 and domain 3 have been the principal targets of mutagenesis efforts, primarily because these domains are believed to be important for receptor binding and in determining insecticidal specificity (Aronson et al., 1995; Chen et al. 1993; de Maagd et al., 1996; Lee et al., 1992; Lee et al., 1995; Lu et al., 1994; Smedley and Ellar, 1996; Smith and Ellar, 1994; Rajamohan et al., 1995; Rajamohan et al., 1996)

In contrast, the present inventors reasoned that the toxicity of Cry3 proteins, and specifically the toxicity of the Cry3Bb protein, may be improved against a broader array of target pests by targeting regions involved in ion channel function rather than regions of the molecule directly involved in receptor interactions, namely domains 2 and 3. Accordingly, the inventors opted to target regions within domain 1 of Cry3Bb for mutagenesis for the purpose of isolating Cry3Bb mutants with improved broad spectrum toxicity. Indeed, in the present invention, Cry3Bb mutants are described that show improved toxicity towards several coleopteran pests.

At least one, and probably more than one, α helix of domain 1 is involved in the formation of ion channels and pores within the insect midgut epithelium (Gazit and Shai, 1993; Gazit and Shai, 1995). Rather than target for mutagenesis the sequences encoding the α helices of domain 1 as others have (Wu and Aronson, 1992; Aronson et al., 1995; Chen et al., 1995), the present inventors opted to target exclusively sequences encoding amino acid residues adjacent to or lying within the predicted loop regions of Cry3Bb that separate these α helices. Amino acid residues within these loop regions or amino acid residues capping the end of an α helix and lying adjacent to these loop regions may affect the spatial relationships among these α helices. Consequently, the substitution of these amino acid residues may result in subtle changes in tertiary structure, or even quaternary structure, that positively impact the function of the ion channel. Amino acid residues in the loop regions of domain 1 are exposed to the solvent and thus are available for various molecular interactions. Altering these amino acids could result in greater stability of the protein by eliminating or occluding protease-sensitive sites. Amino acid substitutions that change the surface charge of domain 1 could alter ion channel efficiency or alter interactions with the brush border membrane or with other portions of the toxin molecule, allowing binding or insertion to be more effective.

According to this invention, base substitutions are made in the underlying cry3Bb nucleic acid residues in order to change particular codons of the corresponding polypeptides, and particularly, in those loop regions between α-helices. The insecticidal activity of a crystal protein ultimately dictates the level of crystal protein required for effective insect control. The potency of an insecticidal protein should be maximized as much as possible in order to provide for its economic and efficient utilization in the field. The increased potency of an insecticidal protein in a bioinsecticide formulation would be expected to improve the field performance of the bioinsecticide product. Alternatively, increased potency of an insecticidal protein in a bioinsecticide formulation may promote use of reduced amounts of bioinsecticide per unit area of treated crop, thereby allowing for more cost-effective use of the bioinsecticide product. When expressed in planta, the production of crystal proteins with improved insecticidal activity can be expected to improve plant resistance to susceptible insect pests.

4.2 METHODS FOR CULTURING B. THURINGIENSIS TO PRODUCE CRYSTAL PROTEINS

The B. thuringiensis strains described herein may be cultured using standard known media and fermentation techniques. Upon completion of the fermentation cycle, the bacteria may be harvested by first separating the B. thuringiensis spores and crystals from the fermentation broth by means well known in the art. The recovered B. thuringiensis spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art.

4.3 RECOMBINANT HOST CELLS FOR EXPRESSION OF CRY* GENES

The nucleotide sequences of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the sites of coleopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B. thuringiensis toxin.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility or toxicity to a mammalian host. As hosts, of particular interest will be the prokaryotes and the lower eukaryotes, such as fungi. Illustrative prokaryotes, both Gram-negative and Gram-positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B. thuringiensis gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include Pseudomonas aeruginosa, Pseudomonas fluorescens, Saccharomyces cerevisiae, B. thuringiensis, Escherichia coli, B. subtilis, B. megaterium, B. cereus, Streptomyces lividans and the like.

Treatment of the microbial cell, e.g., a microbe containing the B. thuringiensis toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol's iodine, Bouin's fixative, and Helly's fixatives, (see e.g., Humason, 1967); or a combination of physical (heat) and chemical agents that preserve and prolong the activity of the toxin produced in the cell when the cell is administered to the host animal. Examples of physical means are short wavelength radiation such as γ-radiation and X-radiation, freezing, UV irradiation, lyophilization, and the like. The cells employed will usually be intact and be substantially in the proliferative form when treated, rather than in a spore form, although in some instances spores may be employed.

Where the B. thuringiensis toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus (including the species and subspecies *B. thuringiensis kurstaki* HD-1, *B. thuringiensis kurstaki* HD-73, *B. thuringiensis sotto, B. thuringiensis berliner, B. thuringiensis thuringiensis, B. thuringiensis tolworthi, B. thuringiensis dendrolimus, B. thuringiensis alesti, B. thuringiensis galleriae, B. thuringiensis aizawai, B. thuringiensis subtoxicus, B. thuringiensis entomocidus, B. thuringiensis tenebrionis* and *B. thuringiensis san diego*); Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodobacter sphaeroides, Xanthomonas campestris, Rhizobium melioti, Alcaligenes eutrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans.*

4.4 DEFINITIONS

In accordance with the present invention, nucleic acid sequences include and are not limited to DNA (including and not limited to genomic or extragenomic DNA), genes, RNA (including and not limited to mRNA and tRNA), nucleosides, and suitable nucleic acid segments either obtained from native sources, chemically synthesized, modified, or otherwise prepared by the hand of man. The following words and phrases have the meanings set forth below.

A, an: In accordance with long standing patent law convention, the words "a" and "an" when used in this application, including the claims, denotes "one or more".

Broad-spectrum: Refers to a wide range of insect species.

Broad-spectrum activity: The toxicity towards a wide range of insect species.

Expression: The combination of intracellular processes, including transcription and translation undergone by a coding DNA molecule such as a structural gene to produce a polypeptide.

Insecticidal activity: The toxicity towards insects.

Insecticidal specificity: The toxicity exhibited by a crystal protein or proteins, microbe or plant, towards multiple insect species.

Intraorder specificity: The toxicity of a particular crystal protein towards insect species within an Order of insects (e.g., Order Coleoptera).

Interorder specificity: The toxicity of a particular crystal protein towards insect species of different Orders (e.g., Orders Coleoptera and Diptera).

$LC_{50}$: The lethal concentration of crystal protein that causes 50% mortality of the insects treated.

$LC_{95}$: The lethal concentration of crystal protein that causes 95% mortality of the insects treated.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

As used herein, the designations "CryIII" and "Cry3" are synonymous, as are the designations "CryIIIB2" and "Cry3Bb." Likewise, the inventors have utilized the generic term Cry3Bb* to denote any and all Cry3Bb variants which comprise amino acid sequences modified in the protein. Similarly, cry3Bb* is meant to denote any and all nucleic acid segments and/or genes which encode a Cry3Bb* protein, etc.

4.5 PREPARATION OF CRY3* POLYNUCLEOTIDES

Once the structure of the desired peptide to be mutagenized has been analyzed using one or more of the design strategies disclosed herein, it will be desirable to introduce one or more mutations into either the protein or, alternatively, into the DNA sequence encoding the protein for the purpose of producing a mutated protein with altered bioinsecticidal properties.

To that end, the present invention encompasses both site-spccific mutagenesis methods and random mutagenesis of a nucleic acid segment encoding a crystal protein in the manner described herein. In particular, methods are disclosed for the mutagenesis of nucleic acid segments encoding the amino acid sequences using one or more of the design strategies described herein. Using the assay methods described herein, one may then identify mutants arising from these procedures which have improved insecticidal properties or altered specificity, either intraorder or interorder.

The means for mutagenizing a DNA segment encoding a crystal protein are well-known to those of skill in the art. Modifications may be made by random, or site-specific mutagenesis procedures. The nucleic acid may be modified by altering its structure through the addition or deletion of one or more nucleotides from the sequence.

Mutagenesis may be performed in accordance with any of the techniques known in the art such as and not limited to synthesizing an oligonucleotide having one or more mutations within the sequence of a particular crystal protein. A "suitable host" is any host which will express Cry3Bb, such as and not limited to *B. thuringiensis* and *E. coli*. Screening for insecticidal activity, in the case of Cry3Bb includes and is not limited to coleopteran-toxic activity which may be screened for by techniques known in the art.

In particular, site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™ mediated mutagenesis procedures of Tomic et al. (1990) and Upender et al. (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159 (each of which is specifically incorporated herein by reference in its entirety). Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, specifically incorporated herein by reference in its entirety, describes an alternative method of amplification similar to LCR for binding probe pairs to a target sequence.

Qbeta Replicase™, described in Intl. Pat. Appl. Publ. No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA Sequences can also be detected using a cyclic probe reaction (CPR). In CPR, a probe having 3' and 5' end sequences of non-Cry-specific DNA and an internal sequence of a Cry-specific RNA is hybridized to DNA which is present in a sample. Upon hybridization, the reaction is treated with RNaseH, and the products of the probe identified as distinctive products generating a signal which are released after digestion. The original template is annealed to another cycling probe and the reaction is repeated. Thus, CPR involves amplifying a signal generated by hybridization of a probe to a cry-specific expressed nucleic acid Still other amplification methods described in Great Britain Pat. Appl. No. 2 202 328, and in Intl. Pat. Appl. Publ. No. PCT/US89/01025, each of which is incorporated herein by reference in its entirety, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence Other nucleic acid amplification procedures include transcription-based amplification systems (TAS) (Kwoh et al., 1989; Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has crystal protein-specific sequences. Following polymerization, DNA/RNA hybrids are digested with RNase H while double stranded DNA molecules are heat denatured again. In either case the single stranded DNA is made fully double stranded by addition of second crystal protein-specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate crystal protein-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e., new templates are not produced from the resultant RNA transcripts. Other amplification methods include "RACE" (Frohman, 1990), and "one-sided PCR™" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

4.6 PHAGE-RESISTANT VARIANTS

In certain embodiments, one may desired to prepare one or more phage resistant variants of the *B. thuringiensis* mutants prepared by the methods described herein. To do so, an aliquot of a phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

4.7 CRYSTAL PROTEIN COMPOSITIONS AS INSECTICIDES AND METHODS OF USE

Order Coleoptera comprises numerous beetle species including ground beetles, reticulated beetles, skin and larder beetles, long-horned beetles, leaf beetles, weevils, bark beetles, ladybird beetles, soldier beetles, stag beetles, water scavenger beetles, and a host of other beetles. A brief taxonomy of the Order is given at the website http://www.ncbi.nlm.nih.gov/Taxonomy/tax.html.

Particularly important among the Coleoptera are the agricultural pests included within the infraorders Chrysomeliformia and Cucujiformia. Members of the infraorder Chrysomeliformia, including the leaf beetles (Chrysomelidae) and the weevils (Curculionidae), are particularly problematic to agriculture, and are responsible for a variety of insect damage to crops and plants. The infraorder Cucujiformia includes the families Coccinellidae, Cucujidae, Lagridae, Meloidae, Rhipiphoridae, and Tenebrionidae. Within this infraorder, members of the family Chrysomelidae (which includes the genera Exema, Chrysomela, Oreina, Chrysolina, Leptinotarsa, Gonioctena, Oulema, Monozia, Ophraella, Cerotoma, Diabrotica, and Lachnaia), are well-known for their potential to destroy agricultural crops.

As the toxins of the present invention have been shown to be effective in combatting a variety of members of the order Coleoptera, the inventors contemplate that the insects of many Coleopteran genera may be controlled or eradicated using the polypeptide compositions described herein. Likewise, the methods described herein for generating modified polypeptides having enhanced insect specificity may also be useful in extending the range of the insecticidal activity of the modified polypeptides to other insect species within, and outside of, the Order Coleoptera.

As such, the inventors contemplate that the crystal protein compositions disclosed herein will find particular utility as insecticides for topical and/or systemic application to field crops, including but not limited to rice, wheat, alfalfa, corn (maize), soybeans, tobacco, potato, barley, canola (rapeseed), sugarbeet, sugarcane, flax, rye, oats, cotton, sunflower; grasses, such as pasture and turf grasses; fruits, citrus, nuts, trees, shrubs and vegetables; as well as ornamental plants, cacti, succulents, and the like.

Disclosed and claimed is a composition comprising an insecticidally-effective amount of a Cry3Bb* crystal protein composition. The composition preferably comprises the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50 SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, or SEQ ID NO:108 or biologically-functional equivalents thereof.

The insecticide composition may also comprise a Cry3Bb* crystal protein that is encoded by a nucleic acid sequence having the sequence of SEQ ID NO:1, SEQ ID NO:3, SEQ ID NO:5. SEQ ID NO:7, SEQ ID NO:9, SEQ ID NO:11, SEQ ID NO:13. SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, or SEQ ID NO:108, or, alternatively, a nucleic acid sequence which hybridizes to the nucleic acid sequence of SEQ ID NO:1, SEQ ID NO:3, SEQ ID NO:5. SEQ ID NO:7, SEQ ID NO:9, SEQ ID NO:11, SEQ ID NO:13. SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, or SEQ ID NO:107 under conditions of moderate stringency.

The insecticidal compositions may comprise one or more *B. thuringiensis* cell types, or one or more cultures of such cells, or, alternatively, a mixture of one or more *B. thuringiensis* cells which express one or more of the novel crystal proteins of the invention in combination with another insecticidal composition. In certain aspects it may be desirable to prepare compositions which contain a plurality of crystal proteins, either native or modified, for treatment of one or more types of susceptible insects. The *B. thuringiensis* cells of the invention can be treated prior to formulation to prolong the insecticidal activity when the cells are applied to the environment of the target insect(s). Such treatment can be by chemical or physical means, or by a combination of chemical and/or physical means, so long as the technique does not deleteriously affect the properties of the insecticide, nor diminish the cellular capability in protecting the insecticide. Examples of chemical reagents are halogenerating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (see Humason, 1967); or a combination of physical (heat) and chemical agents that prolong the activity of the δ-endotoxin produced in the cell when the cell is applied to the environment of the target pest(s). Examples of physical means are short wavelength radiation such as gamma-radiation and X-radiation, freezing, UV irradiation, lyophilization, and the like.

The inventors contemplate that any formulation methods known to those of skill in the art may be employed using the proteins disclosed herein to prepare such bioinsecticide compositions. It may be desirable to formulate whole cell preparations, cell extracts, cell suspensions, cell homogenates, cell lysates, cell supernatants, cell filtrates, or cell pellets of a cell culture (preferably a bacterial cell culture such as a *B. thuringiensis* cell culture described in Table 3) that expresses one or more cry3Bb* DNA segments to produce the encoded Cry3Bb* protein(s) or peptide(s). The methods for preparing such formulations are known to those of skill in the art, and may include, e.g., desiccation, lyophilization, homogenization, extraction, filtration, centrifugation, sedimentation, or concentration of one or more cultures of bacterial cells, such as *B. thuringiensis* cells described in Table 3, which express the Cry3Bb* peptide(s) of interest.

In one preferred embodiment, the bioinsecticide composition comprises an oil flowable suspension comprising lysed or unlysed bacterial cells, spores, or crystals which contain one or more of the novel crystal proteins disclosed herein. Preferably the cells are *B. thuringiensis* cells, however, any such bacterial host cell expressing the novel nucleic acid segments disclosed herein and producing a crystal protein is contemplated to be useful, such as Bacillus spp., including *B. megaterium, B. subtilis; B. cereus*, Escherichia spp., including *E. coli*, and/or Pseudomonas spp., including *P. cepacia, P. aeruginosa*, and *P. fluorescens*. Alternatively, the oil flowable suspension may consist of a combination of one or more of the following compositions: lysed or unlysed bacterial cells, spores, crystals, and/or purified crystal proteins.

In a second preferred embodiment, the bioinsecticide composition comprises a water dispersible granule or powder. This granule or powder may comprise lysed or unlysed bacterial cells, spores, or crystals which contain one or more of the novel crystal proteins disclosed herein. Preferred sources for these compositions include bacterial cells such as *B. thuringiensis* cells, however, bacteria of the genera Bacillus, Escherichia, and Pseudomonas which have been transformed with a DNA segment disclosed herein and expressing the crystal protein are also contemplated to be useful. Alternatively, the granule or powder may consist of a combination of one or more of the following compositions: lysed or unlysed bacterial cells, spores, crystals, and/or purified crystal proteins.

In a third important embodiment, the bioinsecticide composition comprises a wettable powder, spray, emulsion, colloid, aqueous or organic solution, dust, pellet, or collodial concentrate. Such a composition may contain either unlysed or lysed bacterial cells, spores, crystals, or cell extracts as described above, which contain one or more of the novel crystal proteins disclosed herein. Preferred bacterial cells are *B. thuringiensis* cells, however, bacteria such as *B. megaterium, B. subtilis, B. cereus, E coli*, or Pseudomonas spp. cells transformed with a DNA segment disclosed herein and expressing the crystal protein are also contemplated to be useful. Such dry forms of the insecticidal compositions may be formulated to dissolve immediately upon wetting, or alternatively, dissolve in a controlled-release, sustained-release, or other time-dependent manner. Alternatively, such a composition may consist of a combination of one or more of the following compositions: lysed or unlysed bacterial cells, spores, crystals, and/or purified crystal proteins.

In a fourth important embodiment, the bioinsecticide composition comprises an aqueous solution or suspension or cell culture of lysed or unlysed bacterial cells, spores, crystals, or a mixture of lysed or unlysed bacterial cells, spores, and/or crystals, such as those described above which contain one or more of the novel crystal proteins disclosed herein. Such aqueous solutions or suspensions may be provided as a concentrated stock solution which is diluted prior to application, or alternatively, as a diluted solution ready-to-apply.

For these methods involving application of bacterial cells, the cellular host containing the Crystal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can be treated prior to harvesting.

When the insecticidal compositions comprise *B. thuringiensis* cells, spores, and/or crystals containing the modified crystal protein(s) of interest, such compositions may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel Cry3Bb-derived mutated crystal proteins may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the crystal protein and apply solutions, suspensions, or collodial preparations of such crystals and/or spores as the active bioinsecticidal composition.

Another important aspect of the invention is a method of controlling coleopteran insects which are susceptible to the novel compositions disclosed herein. Such a method generally comprises contacting the insect or insect population, colony, etc., with an insecticidally-effective amount of a Cry3Bb* crystal protein composition. The method may utilize Cry3Bb* crystal proteins such as those disclosed in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, or SEQ ID NO:108, or biologically functional equivalents thereof.

Alternatively, the method may utilize one or more Cry3Bb* crystal proteins which are encoded by the nucleic acid sequences of SEQ ID NO:1, SEQ ID NO:3, SEQ ID NO:5. SEQ ID NO:7, SEQ ID NO:9, SEQ ID NO:11, SEQ ID NO:13. SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107, or by one or more nucleic acid sequences which hybridize to the sequences of SEQ ID NO:1, SEQ ID NO:3, SEQ ID NO:5. SEQ ID NO:7, SEQ ID NO:9, SEQ ID NO:11, SEQ ID NO:13. SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107, under conditions of moderate, or higher, stringency. The methods for identifying sequences which hybridize to those disclosed under conditions of moderate or higher stringency are well-known to those of skill in the art, and are discussed herein.

Regardless of the method of application, the amount of the active component(s) are applied at an insecticidally-effective amount, which will vary depending on such factors as, for example, the specific coleopteran insects to be controlled, the specific plant or crop to be treated, the environmental conditions, and the method, rate, and quantity of application of the insecticidally-active composition.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions of this invention are applied to the environment of the target coleopteran insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, soil tilling, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or foliar application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the compositions may be from about 1% to about 99% or more by weight of the composition, while liquid fonnulations may generally comprise from about 1% to about 99% or more of the active ingredient by weight. Formulations which comprise intact bacterial cells will generally contain from about $10^4$ to about $10^{12}$ cells/mg The insecticidal formulation may be administered to a particular plant or target area in one or more applications as needed, with a typical field application rate per hectare ranging on the order of from about 1 g to about 1 kg, 2 kg, 5, kg, or more of active ingredient.

4.8 NUCLEIC ACID SEGMENTS AS HYBRIDIZATION PROBES AND PRIMERS

In addition to their use in directing the expression of crystal proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1, SEQ ID NO:3, SEQ ID NO:5. SEQ ID NO:7, SEQ ID NO:9, SEQ ID NO:11, SEQ ID NO:13. SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107 will find particular utility. Longer contiguous identical or complementary sequences, e.g., those of about 20, 30, 40, 50, 100, 200, 500, 1000, 2000, 5000, 10000 etc. (including all intermediate lengths and up to and including full-length sequences will also be of use in certain embodiments.

The ability of such nucleic acid probes to specifically hybridize to crystal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to DNA sequences of SEQ ID NO:1, SEQ ID NO:3, SEQ ID NO:5. SEQ ID NO:7, SEQ ID NO:9, SEQ ID NO:11, SEQ ID NO:13. SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, SEQ ID NO:101, or SEQ ID NO:107 are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementary stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating crystal protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate crystal protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

4.9 CHARACTERISTICS OF MODIFIED CRY3 δ-ENDOTOXINS

The present invention provides novel polypeptides that define a whole or a portion of a *B. thuringiensis* cry3Bb.60, cry3Bb.11221, cry3Bb.11222, cry3Bb.11223, cry3Bb.11224, cry3Bb.11225, cry3Bb.11226, cry3Bb.11227, cry3Bb.11228, cry3Bb.11229, cry3Bb.11230, cry3Bb.11231, cry3Bb.11232, cry3Bb.11233, cry3Bb.11234, cry3Bb.11235, cry3Bb.11236, cry3Bb.11237, cry3Bb.11238, cry3Bb.11239, cry3Bb.11241, cry3Bb.11242, cry3Bb.11032, cry3Bb.11035, cry3Bb.11036, cry3Bb.11046, cry3Bb.11048, cry3Bb.11051, cry3Bb.11057, cry3Bb.11058, cry3Bb.11081, cry3Bb.11082, cry3Bb.11083, cry3Bb.11084, cry3Bb.11095 and cry3Bb.11098-encoded crystal protein.

4.10 CRYSTAL, PROTEIN NOMENCLATURE

The inventors have arbitrarily assigned the designations Cry3Bb.60, Cry3Bb.11221, Cry3Bb.11222, Cry3 Bb.11223, Cry3Bb.11224, Cry3Bb.11225, Cry3Bb.11226, Cry3Bb.11227, Cry3Bb.11228, Cry3Bb.11229, Cry3Bb.11230, Cry3Bb.11231, Cry3Bb.11232, Cry3Bb.11233, Cry3Bb.11234, Cry3Bb.11235, Cry3Bb.11236, Cry3Bb.11237, Cry3Bb.11238, Cry3Bb.11239, Cry3Bb.11241, Cry3Bb.11242, Cry3Bb.11032, Cry3Bb.11035, Cry3Bb.11036, Cry3Bb.11046, Cry3Bb.11048, Cry3Bb.11051, Cry3Bb.11057, Cry3Bb.11058, Cry3Bb.11081, Cry3Bb.11082, Cry3Bb.11083, Cry3Bb.11084, Cry3Bb.11095 and Cry3Bb.11098 to the novel proteins of the invention.

Likewise, the arbitrary designations of cry3Bb.60, cry3Bb.11221, cry3Bb.11222, cry3Bb.11223, cry3Bb.11224, cry3Bb.11225, cry3Bb.11226, cry3Bb.11227, cry3Bb.11228, cry3Bb.11229, cry3Bb.11230, cry3Bb.11231, cry3Bb.11232, cry3Bb.11233, cry3Bb.11234, cry3Bb.11235, cry3Bb.11236, cry3Bb.11237, cry3Bb.11238, cry3Bb.11239, cry3Bb.11241, cry3Bb.11242, cry3Bb.11032, cry3Bb.11035, cry3Bb.11036, cry3Bb.11046, cry3Bb.11048, cry3Bb.11051, cry3Bb.11057, cry3Bb.11058, cry3Bb.11081, cry3Bb.11082, cry3Bb.11083, cry3Bb.11084, cry3Bb.11095 and Cry3Bb.11098 have been assigned to the novel nucleic acid sequences which encode these polypeptides, respectively. While formal assignment of gene and protein designations based on the revised nomenclature of crystal protein endotoxins (Table 1) may be made by the committee on the nomenclature of *B. thuringiensis*, any re-designations of the compositions of the present invention are also contemplated to be fully within the scope of the present disclosure.

4.11 TRANSFORMED HOST CELLS AND TRANSGENIC PLANTS

A bacterium, a yeast cell, or a plant cell or a plant transformed with an expression vector of the present invention is also contemplated. A transgenic bacterium, yeast cell, plant cell or plant derived from such a transformed or transgenic cell is also one aspect of the invention.

Such transformed host cells are often desirable for use in the production of endotoxins and for expression of the various DNA gene constrcuts disclosed herein. In some aspects of the invention, it is often desirable to modulate, regulate, or otherwise control the expression of the gene segments disclosed herein. Such methods are routine to those of skill in the molecular genetic arts. Typically, when increased or over-expression of a particular gene is desired, various manipulations may be employed for enhancing the expression of the messenger RNA, particularly by using an active promoter, as well as by employing sequences, which enhance the stability of the messenger RNA in the particular transformed host cell.

Typically, the initiation and translational termination region will involve stop codon(s), a terminator region, and optionally, a polyadenylation signal. In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the δ-endotoxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the δ-endotoxin. In this manner, the enhanced expression of a siderophore may provide for a competitive advantage for the δ-endotoxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the δ-endotoxin gene will be in close proximity to the gene providing for complementation as well as the gene providing for the competitive advantage. Therefore, in the event that a δ-endotoxin gene is lost, the resulting organism will be likely to also lose the complementing gene and/or the gene providing for the competitive advantage, so that it will be unable to compete in the environment with the gene retaining the intact construct.

The crystal protein-encoding gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the δ-endotoxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the δ-endotoxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibdo, Spirillum; Lactobacillaceae; phylloplane organisms such as members of the Pseudomonadaceae (including Pseudomonas spp. and Acetobacter spp.); Azotobacteraceae and Nitrobacteraceae; Flavobacterium spp.; members of the Bacillaceae such as Lactobacillus spp., Bifidobacterium, and Bacillus spp., and the like. Particularly preferred host cells include *Pseudomonas aeruginosa, Pseudomonas fluorescens, Bacillus thuringiensis, Escherichia coli, Bacillus subtilis*, and the like.

Among eukaryotes are fungi, such as Phycomyceles and Ascomycetes, which includes yeast, such as Schizosaccharomyces; and Basidiomycetes, Rhodotorula, Aureobasidium, Sporobolomyces, Saccharomyces spp., and Sporobolomyces spp.

Characteristics of particular interest in selecting a host cell for purposes of production include ease of introducing the δ-endotoxin gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the δ-endotoxin; and the like. Other considerations include ease of formulation and handling, economics, storage stability, and the like.

The cell will usually be intact and be substantially in the proliferative form when treated, rather than in a spore form, although in some instances spores may be employed. Treatment of the recombinant microbial cell can be done as disclosed infra. The treated cells generally will have enhanced structural stability which will enhance resistance to environmental conditions.

Genes or other nucleic acid segments, as disclosed herein, can be inserted into host cells using a variety of techniques which are well known in the art. For example, a large number of cloning vectors comprising a replication system in *E. coli* and a marker that permits selection of the transformed cells are available for preparation for the insertion of foreign genes into higher organisms, including plants. The vectors comprise, for example, pBR322, pUC series, M13mp series, pACYC184, etc. Accordingly, the sequence coding for the δ-endotoxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary.

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

Suitable methods are believed to include virtually any method by which DNA can be introduced into a cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988; Eglitis et al., 1988); and (4) receptor-mediated mechanisms (Curiel et al., 1991; 1992; Wagner et al., 1992).

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA.

Intermediate vectors cannot replicate themselves in agrobacteria. The intermediate vector can be transferred into Agrobacterium tumefaciens by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al., 1978). The agrobacterium used as host cell is to comprise a plasmid carrying a vir region. The vir region is necessary for the transfer of the T-DNA into the plant cell. Additional t-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in Eur. Pat. Appl. No. EP 120 516; Hockema (1985); An et al., 1985, Herrera-Estrella et al., (1983), Bevan et al., (1983), and Klee et al., (1985).

A particularly useful Ti plasmid cassette vector for transformation of dicotyledonous plants consists of the enhanced CaMV35S promoter (EN35S) and the 3' end including polyadenylation signals from a soybean gene encoding the α'-subunit of β-conglycinin. Between these two elements is a multilinker containing multiple restriction sites for the insertion of genes of interest.

The vector preferably contains a segment of pBR322 which provides an origin of replication in *E. coli* and a region for homologous recombination with the disarmed T-DNA in Agrobacterium strain ACO; the oriV region from the broad host range plasmid RK1; the streptomycin/spectinomycin resistance gene from Tn7; and a chimeric NPTII gene, containing the CaMV35S promoter and the nopaline synthase (NOS) 3' end, which provides kanamycin resistance in transformed plant cells.

Optionally, the enhanced CaMV35S promoter may be replaced with the 1.5 kb mannopine synthase (MAS) promoter (Velten et al., 1984). After incorporation of a DNA construct into the vector, it is introduced into *A. tumefaciens* strain ACO which contains a disarmed Ti plasmid. Cointegrate Ti plasmid vectors are selected and subsequentially may be used to transform a dicotyledonous plant.

*A. tumefaciens* ACO is a disarmed strain similar to pTiB6SE described by Fraley et al. (1985). For construction of ACO the starting Agrobacterium strain was the strain A208 which contains a nopaline-type Ti plasmid. The Ti plasmid was disarmed in a manner similar to that described by Fraley et al. (1985) so that essentially all of the native T-DNA was removed except for the left border and a few hundred base pairs of T-DNA inside the left border. The remainder of the T-DNA extending to a point just beyond the right border was replaced with a novel piece of DNA including (from left to right) a segment of pBR322, the oriV region from plasmid RK2, and the kanamycin resistance gene from Tn601. The pBR322 and oriV segments are similar to these segments and provide a region of homology for cointegrate formation.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

4.11.1 ELECTROPORATION

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.11.2 MICROPROJECTILE BOMBARDMENT

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/ microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.11.3 AGROBACTERIUM-MEDIATED TRANSFER

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al., 1987). Therefore, commercially important cereal grains such as rice, corn, and wheat must usually be transformed using alternative methods. However, as mentioned above, the transformation of asparagus using Agrobacterium can also be achieved (see, for example, Bytebier et al., 1987).

A transgenic plant formed using Agrobaciterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1985; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

4.11.4 GENE EXPRESSION IN PLANTS

Although great progress has been made in recent years with respect to preparation of transgenic plants which express bacterial proteins such as *B. thuringiensis* crystal proteins, the results of expressing native bacterial genes in plants are often disappointing. Unlike microbial genetics, little was known by early plant geneticists about the factors which affected heterologous expression of foreign genes in plants. In recent years, however, several potential factors have been implicated as responsible in varying degrees for the level of protein expression from a particular coding sequence. For example, scientists now know that maintaining a significant level of a particular mRNA in the cell is indeed a critical factor. Unfortunately, the causes for low steady state levels of mRNA encoding foreign proteins are many. First, full length RNA synthesis may not occur at a high frequency. This could, for example, be caused by the premature termination of RNA during transcription or due to unexpected mRNA processing during transcription. Second, full length RNA may be produced in the plant cell, but then processed (splicing, polyA addition) in the nucleus in a fashion that creates a nonfunctional mRNA. If the RNA is not properly synthesized, terminated and polyadenylated, it cannot move to the cytoplasm for translation. Similarly, in the cytoplasm, if mRNAs have reduced half lives (which are determined by their primary or secondary sequence) insufficient protein product will be produced. In addition, there is an effect, whose magnitude is uncertain, of translational efficiency on mRNA half-life. In addition, every RNA molecule folds into a particular structure, or perhaps family of structures, which is determined by its sequence. The particular structure of any RNA might lead to greater or lesser stability in the cytoplasm. Structure per se is probably also a determinant of mRNA processing in the nucleus. Unfortunately, it is impossible to predict, and nearly impossible to determine, the structure of any RNA (except for tRNA) in vitro or in vivo. However, it is likely that dramatically changing the sequence of an RNA will have a large effect on its folded structure It is likely that structure per se or particular structural features also have a role in determining RNA stability.

To overcome these limitations in foreign gene expression, researchers have identified particular sequences and signals in RNAs that have the potential for having a specific effect on RNA stability. In certain embodiments of the invention, therefore, there is a desire to optimize expression of the disclosed nucleic acid segments in planta. One particular method of doing so, is by alteration of the bacterial gene to remove sequences or motifs which decrease expression in a transformed plant cell. The process of engineering a coding sequence for optimal expression in planta is often referred to as "plantizing" a DNA sequence.

Particularly problematic sequences are those which are A+T rich. Unfortunately, since *B. thuringiensis* has an A+T rich genome, native crystal protein gene sequences must often be modified for optimal expression in a plant. The sequence motif ATTTA (or AUUUA as it appears in RNA) has been implicated as a destabilizing sequence in mammalian cell mRNA (Shaw and Kamen, 1986). Many short lived mRNAs have A+T rich 3' untranslated regions, and these regions often have the ATTTA sequence, sometimes present in multiple copies or as multimers (e.g., ATTTATTTA . . . ). Shaw and Kamen showed that the transfer of the 3' end of an unstable mRNA to a stable RNA (globin or VA1) decreased the stable RNA's half life dramatically. They further showed that a pentamer of ATTTA had a profound destabilizing effect on a stable message, and that this signal could exert its effect whether it was located at the 3' end or within the coding sequence. However, the number of ATTTA sequences and/or the sequence context in which they occur also appear to be important in determining whether they function as destabilizing sequences. Shaw and Kamen showed that a trimer of ATTTA had much less effect than a pentamer on mRNA stability and a dimer or a monomer had no effect on stability (Shaw and Kamen, 1987). Note that multimers of ATTTA such as a pentamer automatically create an A+T rich region. This was shown to be a cytoplasmic effect, not nuclear. In other unstable mRNAs, the ATTTA sequence may be present in only a single copy, but it is often contained in an A+T rich region. From the animal cell data collected to date, it appears that ATTTA at least in some contexts is important in stability, but it is not yet possible to predict which occurrences of ATTTA are destabiling elements or whether any of these effects are likely to be seen in plants.

Some studies on mRNA degradation in animal cells also indicate that RNA degradation may begin in some cases with nucleolytic attack in A+T rich regions. It is not clear if these cleavages occur at ATTTA sequences. There are also examples of mRNAs that have differential stability depending on the cell type in which they are expressed or on the stage within the cell cycle at which they are expressed. For example, histone mRNAs are stable during DNA synthesis but unstable if DNA synthesis is disrupted. The 3' end of some histone mRNAs seems to be responsible for this effect (Pandey and Marzluff, 1987). It does not appear to be mediated by ATTTA, nor is it clear what controls the differential stability of this mRNA. Another example is the differential stability of IgG mRNA in B lymphocytes during B cell maturation (Genovese and Milcarek, 1988). A final example is the instability of a mutant β-thallesemic globin mRNA. In bone marrow cells, where this gene is normally expressed, the mutant mRNA is unstable, while the wild-type mRNA is stable. When the mutant gene is expressed in HeLa or L cells in vitro, the mutant mRNA shows no instability (Lim et al., 1988). These examples all provide evidence that mRNA stability can be mediated by cell type or cell cycle specific factors. Furthermore this type of instability is not yet associated with specific sequences. Given these uncertainties, it is not possible to predict which RNAs are likely to be unstable in a given cell. In addition, even the ATTTA motif may act differentially depending on the nature of the cell in which the RNA is present. Shaw and Kamen (1987) have reported that activation of protein kinase C can block degradation mediated by ATTTA.

The addition of a polyadenylate string to the 3' end is common to most eukaryotic mRNAs, both plant and animal. The currently accepted view of polyA addition is that the nascent transcript extends beyond the mature 3' terminus. Contained within this transcript are signals for polyadenylation and proper 3' end formation. This processing at the 3' end involves cleavage of the mRNA and addition of polyA to the mature 3' end. By searching for consensus sequences near the polyA tract in both plant and animal mRNAs, it has been possible to identify consensus sequences that apparently are involved in polyA addition and 3' end cleavage. The same consensus sequences seem to be important to both of these processes. These signals are typically a variation on the sequence AATAAA. In animal cells, some variants of this sequence that are functional have been identified; in plant cells there seems to be an extended range of functional sequences (Wickens and Stephenson, 1984; Dean et al., 1986). Because all of these consensus sequences are variations on AATAAA, they all are A+T rich sequences. This sequence is typically found 15 to 20 bp before the polyA tract in a mature mRNA. Studies in animal cells indicate that this sequence is involved in both polyA addition and 3' maturation. Site directed mutations in this sequence can disrupt these functions (Conway and Wickens, 1988; Wickens et al., 1987). However, it has also been observed that sequences up to 50 to 100 bp 3' to the putative polyA signal are also required; i.e., a gene that has a normal AATAAA but has been replaced or disrupted downstream does not get properly polyadenylated (Gil and Proudfoot, 1984; Sadofsky and Alwine, 1984; McDevitt et al., 1984). That is, the polyA signal itself is not sufficient for complete and proper processing. It is not yet known what specific downstream sequences are required in addition to the polyA signal, or if there is a specific sequence that has this function. Therefore, sequence analysis can only identify potential polyA signals.

In naturally occurring mRNAs that are normally polyadenylated, it has been observed that disruption of this process, either by altering the polyA signal or other sequences in the mRNA, profound effects can be obtained in the level of functional mRNA. This has been observed in several naturally occurring mRNAs, with results that are gene-specific so far.

It has been shown that in natural mRNAs proper polyadenylation is important in mRNA accumulation, and that disruption of this process can effect mRNA levels significantly. However, insufficient knowledge exists to predict the effect of changes in a normal gene. In a heterologous gene, it is even harder to predict the consequences. However, it is possible that the putative sites identified are dysfunctional. That is, these sites may not act as proper polyA sites, but instead function as aberrant sites that give rise to unstable mRNAs.

In animal cell systems, AATAAA is by far the most common signal identified in mRNAs upstream of the polyA, but at least four variants have also been found (Wickens and Stephenson, 1984). In plants, not nearly so much analysis has been done, but it is clear that multiple sequences similar to AATAAA can be used. The plant sites in Table 5 called major or minor refer only to the study of Dean et al. (1986) which analyzed only three types of plant gene. The designation of polyadenylation sites as major or minor refers only to the frequency of their occurrence as functional sites in naturally occurring genes that have been analyzed. In the case of plants this is a very limited database. It is hard to predict with any certainty that a site designated major or minor is more or less likely to function partially or completely when found in a heterologous gene such as those encoding the crystal proteins of the present invention.

TABLE 5

POLYADENYLATION SITES IN PLANT GENES

| PA | AATAAA | Major consensus site |
|---|---|---|
| P1A | AATAAT | Major plant site |
| P2A | AACCAA | Minor plant site |
| P3A | ATATAA | " |
| P4A | AATCAA | " |
| P5A | ATACTA | " |
| P6A | ATAAAA | " |
| P7A | ATGAAA | " |
| P8A | AAGCAT | " |
| P9A | ATTAAT | " |
| P10A | ATACAT | " |
| P11A | AAAATA | " |

TABLE 5-continued

POLYADENYLATION SITES IN PLANT GENES

| P12A | ATTAAA | Minor animal site |
|---|---|---|
| P13A | AATTAA | " |
| P14A | AATACA | " |
| P15A | CATAAA | " |

The present invention provides a method for preparing synthetic plant genes which genes express their protein product at levels significantly higher than the wild-type genes which were commonly employed in plant transformation heretofore. In another aspect, the present invention also provides novel synthetic plant genes which encode non-plant proteins.

As described above, the expression of native *B. thuringiensis* genes in plants is often problematic. The nature of the coding sequences of *B. thuringiensis* genes distinguishes them from plant genes as well as many other heterologous genes expressed in plants. In particular, *B. thuringiensis* genes are very rich (~62%) in adenine (A) and thymine (T) while plant genes and most other bacterial genes which have been expressed in plants are on the order of 45–55% A+T.

Due to the degeneracy of the genetic code and the limited number of codon choices for any amino acid, most of the "excess" A+T of the structural coding sequences of some Bacillus species are found in the third position of the codons. That is, genes of some Bacillus species have A or T as the third nucleotide in many codons. Thus A+T content in part can determine codon usage bias. In addition, it is clear that genes evolve for maximum function in the organism in which they evolve. This means that particular nucleotide sequences found in a gene from one organism, where they may play no role except to code for a particular stretch of amino acids, have the potential to be recognized as gene control elements in another organism (such as transcriptional promoters or terminators, polyA addition sites, intron splice sites, or specific mRNA degradation signals). It is perhaps surprising that such misread signals are not a more common feature of heterologous gene expression, but this can be explained in part by the relatively homogeneous A+T content (~50%) of many organisms. This A+T content plus the nature of the genetic code put clear constraints on the likelihood of occurrence of any particular oligonucleotide sequence. Thus, a gene from *E. coli* with a 50% A+T content is much less likely to contain any particular A+T rich segment than a gene from *B. thuringiensis*.

Typically, to obtain high-level expression of the S-endotoxin genes in plants, existing structural coding sequence ("structural gene") which codes for the S-endotoxin are modified by removal of ATTTA sequences and putative polyadenylation signals by site directed mutagenesis of the DNA comprising the structural gene. It is most preferred that substantially all the polyadenylation signals and ATTTA sequences are removed although enhanced expression levels are observed with only partial removal of either of the above identified sequences. Alternately if a synthetic gene is prepared which codes for the expression of the subject protein, codons are selected to avoid the ATTTA sequence and putative polyadenylation signals. For purposes of the present invention putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA. In replacing the ATTTA sequences and polyadenylation signals, codons are preferably utilized which avoid the codons which are rarely found in plant genomes.

The selected DNA sequence is scanned to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is preferably altered to remove these signals while maintaining the original encoded amino acid sequence.

The second step is to consider the about 15 to about 30 or so nucleotide residues surrounding the A+T rich region identified in step one. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal.

The extended region is examined for the presence of plant polyadenylation signals. The polyadenylation signals are removed by site-directed mutagenesis of the DNA sequence. The extended region is also examined for multiple copies of the ATTTA sequence which are also removed by mutagenesis.

It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

4.11.5 SYNTHETIC OLIGONUCLEOTIDES FOR MUTAGENESIS

When oligonucleotides are used in the mutagenesis, it is desirable to maintain the proper amino acid sequence and reading frame, without introducing common restriction sites such as BglII, HindIII, SacI, KpnI, EcoRI, NcoI, PstI and SalI into the modified gene. These restriction sites are found in poly-linker insertion sites of many cloning vectors. Of course, the introduction of new polyadenylation signals, ATTTA sequences or consecutive stretches of more than five A+T or G+C, should also be avoided. The preferred size for the oligonucleotides is about 40 to about 50 bases, but fragments ranging from about 18 to about 100 bases have been utilized. In most cases, a minimum of about 5 to about 8 base pairs of homology to the template DNA on both ends of the synthesized fragment are maintained to insure proper hybridization of the primer to the template. The oligonucleotides should avoid sequences longer than five base pairs A+T or G+C. Codons used in the replacement of wild-type codons should preferably avoid the TA or CG doublet wherever possible. Codons are selected from a plant preferred codon table (such as Table 6 below) so as to avoid codons which are rarely found in plant genomes, and efforts should be made to select codons to preferably adjust the G+C content to about 50%.

TABLE 6

PREFERRED CODON USAGE IN PLANTS

| Amino Acid | Codon | Percent Usage in Plants |
|---|---|---|
| ARG | CGA | 7 |
|  | CGC | 11 |
|  | CGG | 5 |
|  | CGU | 25 |
|  | AGA | 29 |
|  | AGG | 23 |
| LEU | CUA | 8 |
|  | CUC | 20 |
|  | CUG | 10 |
|  | CUU | 28 |
|  | UUA | 5 |
|  | UUG | 30 |
| SER | UCA | 14 |
|  | UCC | 26 |
|  | UCG | 3 |
|  | UCU | 21 |
|  | AGC | 21 |
|  | AGU | 15 |
| THR | ACA | 21 |
|  | ACC | 41 |
|  | ACG | 7 |
|  | ACU | 31 |
| PRO | CCA | 45 |
|  | CCC | 19 |
|  | CCG | 9 |
|  | CCU | 26 |
| ALA | GCA | 23 |
|  | GCC | 32 |
|  | GCG | 3 |
|  | GCU | 41 |
| GLY | GGA | 32 |
|  | GGC | 20 |
|  | GGG | 11 |
|  | GGU | 37 |
| ILE | AUA | 12 |
|  | AUC | 45 |
|  | AUU | 43 |
| VAL | GUA | 9 |
|  | GUC | 20 |
|  | GUG | 28 |
|  | GUU | 43 |
| LYS | AAA | 36 |
|  | AAG | 64 |
| ASN | AAC | 72 |
|  | AAU | 28 |
| GLN | CAA | 64 |
|  | CAG | 36 |
| HIS | CAC | 65 |
|  | CAU | 35 |
| GLU | GAA | 48 |
|  | GAG | 52 |
| ASP | GAC | 48 |
|  | GAU | 52 |
| TYR | UAC | 68 |
|  | UAU | 32 |
| CYS | UGC | 78 |
|  | UGU | 22 |
| PHE | UUC | 56 |
|  | UUU | 44 |
| MET | AUG | 100 |
| TRP | UGG | 100 |

Regions with many consecutive A+T bases or G+C bases are predicted to have a higher likelihood to form hairpin structures due to self-complementarity. Disruption of these regions by the insertion of heterogeneous base pairs is preferred and should reduce the likelihood of the formation of self-complementary secondary structures such as hairpins which are known in some organisms to inhibit transcription (transcriptional terminators) and translation (attenuators).

Alternatively, a completely synthetic gene for a given amino acid sequence can be prepared, with regions of five or more consecutive A+T or G+C nucleotides being avoided. Codons are selected avoiding the TA and CG doublets in codons whenever possible. Codon usage can be normalized against a plant preferred codon usage table (such as Table 6) and the G+C content preferably adjusted to about 50%. The resulting sequence should be examined to ensure that there are minimal putative plant polyadenylation signals and ATTTA sequences. Restriction sites found in commonly used cloning vectors are also preferably avoided. However, placement of several unique restriction sites throughout the gene is useful for analysis of gene expression or construction of gene variants.

4.11.6 "PLANTIZED" GENE CONSTRUCTS

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter." The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of Agrobacterium tumefaciens), the Cauliflower Mosaic Virus (CaMV) 19S and 35S promoters, the light-inducible promoter from the small subunit of ribulose bis-phosphate carboxylase (ssRUBISCO, a very abundant plant polypeptide) and the mannopine synthase (MAS) promoter (Velten et al., 1984 and Velten and Schell, 1985). All of these promoters have been used to create various types of DNA constructs which have been expressed in plants (see e.g., Int. Pat. Appl. Publ. No. WO 84/02913).

Promoters which are known or are found to cause transcription of RNA in plant cells can be used in the present invention. Such promoters may be obtained from plants or plant viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of protein.

The promoters used in the DNA constructs (i.e. chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples. Rather, the non-translated leader sequence can be part of the 5' end of the non-translated region of the coding sequence for the virus coat protein, or part of the promoter sequence, or can be derived from an unrelated promoter or coding sequence. In any case, it is preferred that the sequence flanking the initiation site conform to the translational consensus sequence rules for enhanced translation initiation reported by Kozak (1984).

The cry DNA constructs of the present invention may also contain one or more modified or fully-synthetic structural coding sequences which have been changed to enhance the performance of the cry gene in plants. The structural genes of the present invention may optionally encode a fusion protein comprising an amino-terminal chloroplast transit peptide or secretory signal sequence.

The DNA construct also contains a 3' non-translated region. The 3' non-translated region contains a polyadenylation signal which functions in plants to cause the addition of polyadenylate nucleotides to the 3' end of the viral RNA. Examples of suitable 3' regions are (1) the 3' transcribed, non-translated regions containing the polyadenylation signal of Agrobacterium tumor-inducing (Ti) plasmid genes, such as the nopaline synthase (NOS) gene, and (2) plant genes like the soybean storage protein (7S) genes and the small subunit of the RuBP carboxylase (E9) gene.

4.12 METHODS FOR PRODUCING INSECT-RESISTANT TRANSGENIC PLANTS

By transforming a suitable host cell, such as a plant cell, with a recombinant cry* gene-containing segment, the expression of the encoded crystal protein (i.e., a bacterial crystal protein or polypeptide having insecticidal activity against coleopterans) can result in the formation of insect-resistant plants.

By way of example, one may utilize an expression vector containing a coding region for a B. thuringiensis crystal protein and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the insecticidal proteins.

The formation of transgenic plants may also be accomplished using other methods of cell transformation which are known in the art such as Agrobacterium-mediated DNA transfer (Fraley et al., 1983). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

Such plants can form germ cells and transmit the transformed trait(s) to progeny plants. Likewise, transgenic plants can be grown in the normal manner and crossed with plants that have the same transformed hereditary factors or other hereditary factors. The resulting hybrid individuals have the corresponding phenotypic properties. A transgenic plant of this invention thus has an increased amount of a coding region (e.g., a mutated cry gene) that encodes the mutated Cry polypeptide of interest. A preferred transgenic plant is an independent segregant and can transmit that gene and its activity to its progeny. A more preferred transgenic plant is homozygous for that gene, and transmits that gene to all of its offspring on sexual mating.

Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against coleopteran insects, preferably in the field, under a range of environmental conditions. The inventors contemplate that the present invention will find particular utility in the creation of transgenic plants of commercial interest including various grasses, grains, fibers, tubers, legumes, ornamental plants, cacti, succulents, fruits, berries, and vegetables, as well as a number of nut- and fruit-bearing trees and plants.

4.13 METHODS FOR PRODUCING COMBINATORIAL CRY3* VARIANTS

Crystal protein mutants containing substitutions in one or more domains may be constructed via a number of techniques. For instance, sequences of highly related genes can be readily shuffled using the PCR™-based technique described by Stemmer (1994). Alternatively, if suitable restriction sites are available, the mutations of one cry gene may be combined with the mutations of a second cry gene by routine subcloning methodologies. If a suitable restriction site is not available, one may be generated by oligonucleotide directed mutagenesis using any number of procedures known to those skilled in the art. Alternatively, splice-overlap extension PCR™ (Horton et al., 1989) may be used to combine mutations in different regions of a crystal protein. In this procedure, overlapping DNA fragments generated by the PCR™ and containing different mutations within their unique sequences may be annealed and used as a template for amplification using flanking primers to generate a hybrid gene sequence. Finally, cry* mutants may be combined by simply using one cry mutant as a template for oligonucleotide-directed mutagenesis using any number of protocols such as those described herein.

4.14 ISOLATING HOMOLOGOUS GENE AND GENE FRAGMENTS

The genes and δ-endotoxins according to the subject invention include not only the full length sequences disclosed herein but also fragments of these sequences, or fusion proteins, which retain the characteristic insecticidal activity of the sequences specifically exemplified herein.

It should be apparent to a person skill in this art that insecticidal δ-endotoxins can be identified and obtained through several means. The specific genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these δ-endotoxins.

Equivalent δ-endotoxins and/or genes encoding these equivalent δ-endotoxins can also be isolated from Bacillus strains and/or DNA libraries using the teachings provided herein. For example, antibodies to the δ-endotoxins disclosed and claimed herein can be used to identify and isolate other δ-endotoxins from a mixture of proteins. Specifically, antibodies may be raised to the portions of the δ-endotoxins which are most constant and most distinct from other *B. thuringiensis* δ-endotoxins. These antibodies can then be used to specifically identify equivalent δ-endotoxins with the characteristic insecticidal activity by immunoprecipitation, enzyme linked immunoassay (ELISA), or Western blotting.

A further method for identifying the δ-endotoxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying formicidal δ-endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}$P, $^{125}$, $^{35}$S, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the *B. thuringiensis* δ-endotoxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of a δ-endotoxin encoding a gene of the invention. Such mutants can be made by techniques well known to persons skilled in the art. For example, UV irradiation can be used to prepare mutants of host organisms. Likewise, such mutants may include asporogenous host cells which also can be prepared by procedures well known in the art.

4.15 RIBOZYMES

Ribozymes are enzymatic RNA molecules which cleave particular mRNA species. In certain embodiments, the inventors contemplate the selection and utilization of ribozymes capable of cleaving the RNA segments of the present invention, and their use to reduce activity of target mRNAs in particular cell types or tissues.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992); examples of hairpin motifs are described by Hampel et al (Eur. Pat. EP 0360257), Hampel and Tritz (1989), Hampel et al. (1990) and Cech et al. (U.S. Pat. No. 5,631,359; an example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described by Cech et al. (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

The invention provides a method for producing a class of enzymatic cleaving agents which exhibit a high degree of specificity for the RNA of a desired target. The enzymatic nucleic acid molecule is preferably targeted to a highly conserved sequence region of a target mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Draper et al., Int. Pat. Appl. Publ. No. WO 93/23569, and Sullivan et al., Int. Pat. Appl. Publ. No. WO 94/02595, both hereby incorporated in their totality by reference herein; Ohkawa et al., 1992; Taira et al., 1991; Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Draper et al. (Int. Pat. Appl. Publ. No. WO 93/23569), or Sullivan et al., (Int. Pat. Appl. Publ. No. WO 94/02595) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nucicase resistant groups, for example, 2'-amino, 2'-C-allyl, 2'-flouro, 2'-o-methyl, 2'-H (for a review see Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al. (Int. Pat. Appl. Publ. No. WO 94/02595) and Draper et al. (Int. Pat. Appl. Publ. No. WO 93/23569) which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes of this invention may be used as diagnostic tools to examine genetic drift and mutations within cell lines or cell types. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in particular cells or cell types.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 EXAMPLE 1—THREE-DIMENSIONAL STRUCTURE OF CRY3BB

The three-dimensional structure of Cry3Bb was determined by X-ray crystallography. Crystallization of Cry3Bb and X-ray diffraction data collection were performed as described by Cody et al. (1992). The crystal structure of Cry3Bb was refined to a residual R factor of 18.0% using data collected to 2.4 Å resolution. The crystals belong to the space group C222$_1$, with unit cell dimensions a=122.44, b=131.81, and c=105.37 Å and contain one molecule in the asymmetric unit. Atomic coordinates for Cry3Bb are described in Example 31 and listed in Section 9.

Figure 2:
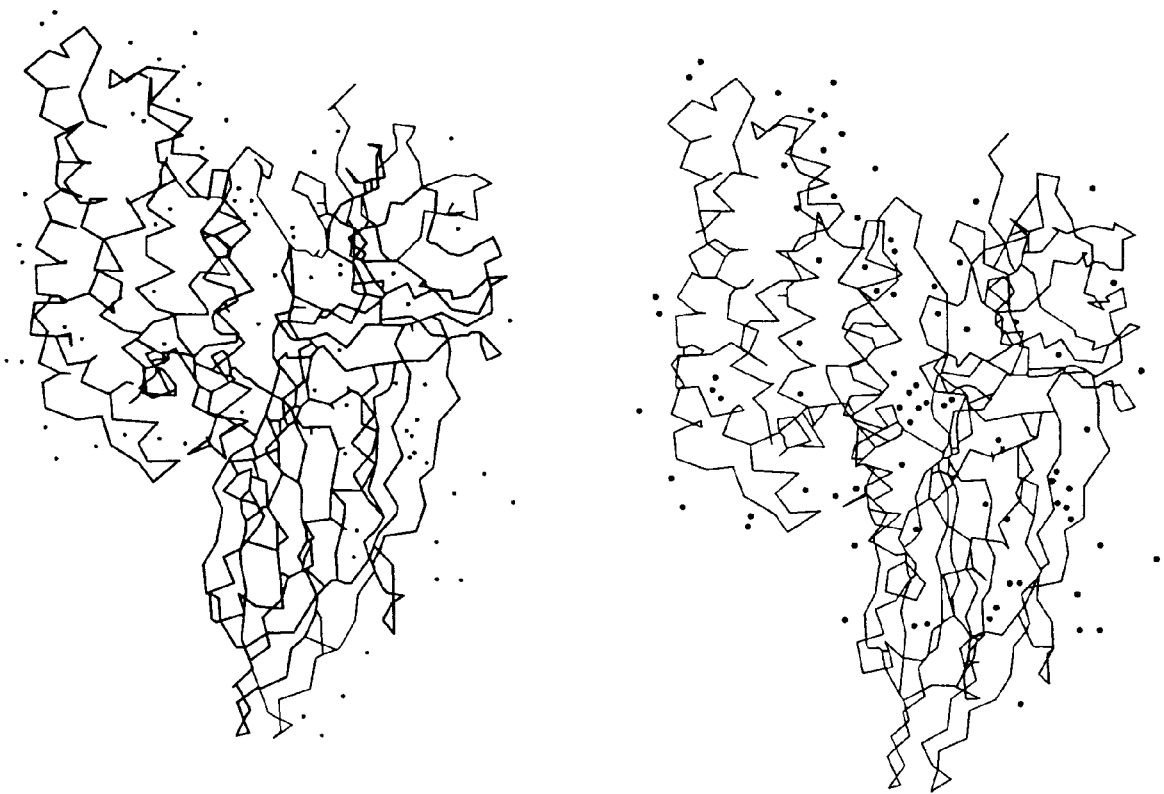
Figure 3A:
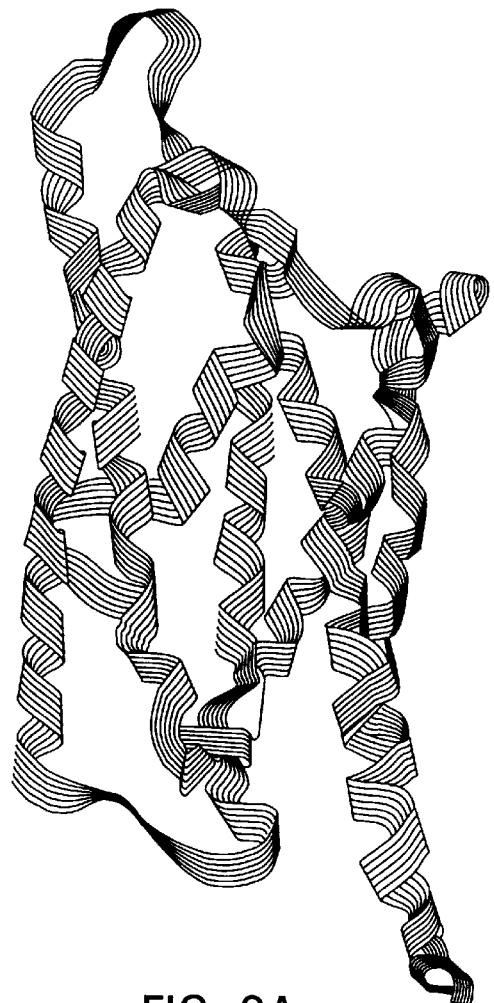
Figure 3B:
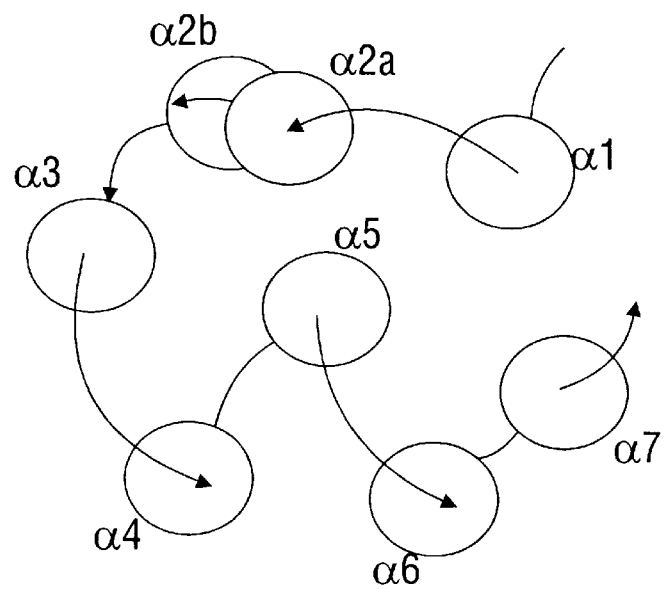
Figure 5A:
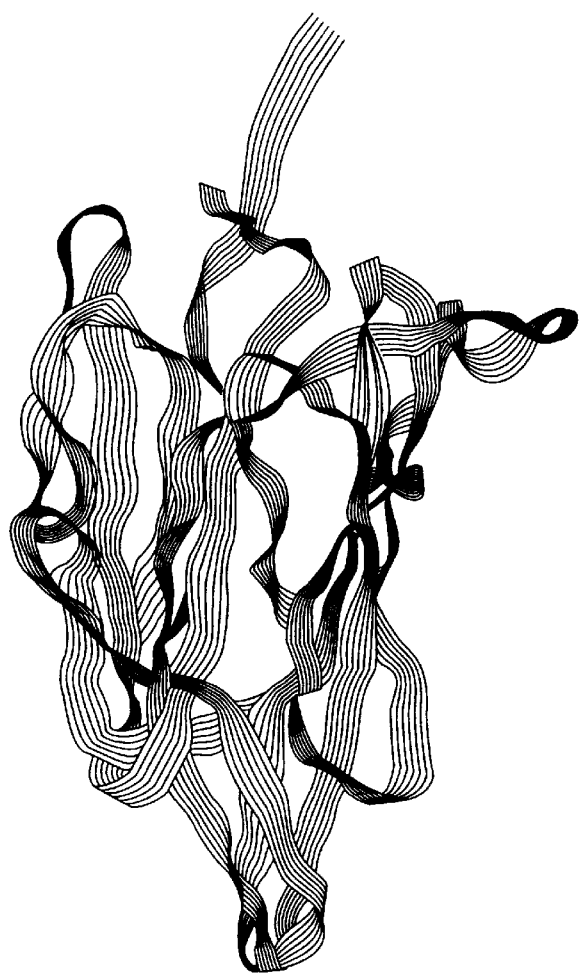
Figure 5B:
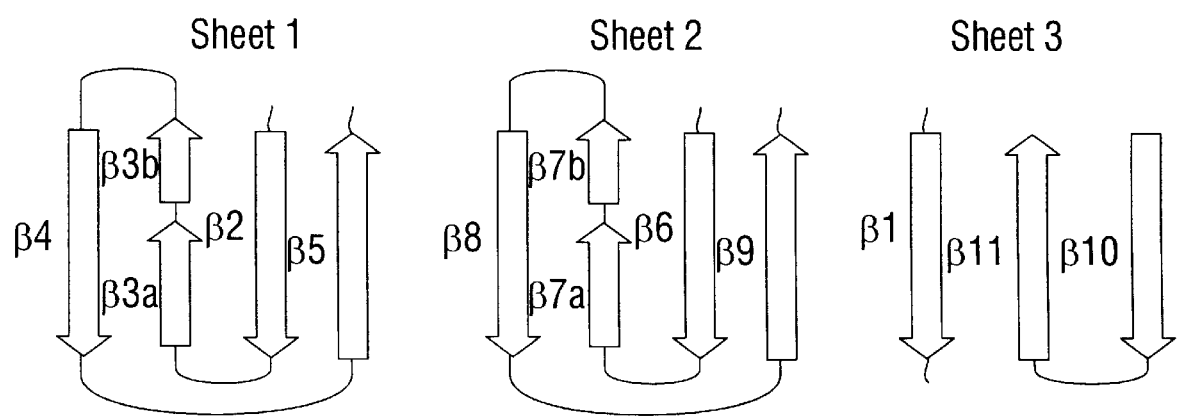
Figure 7A:
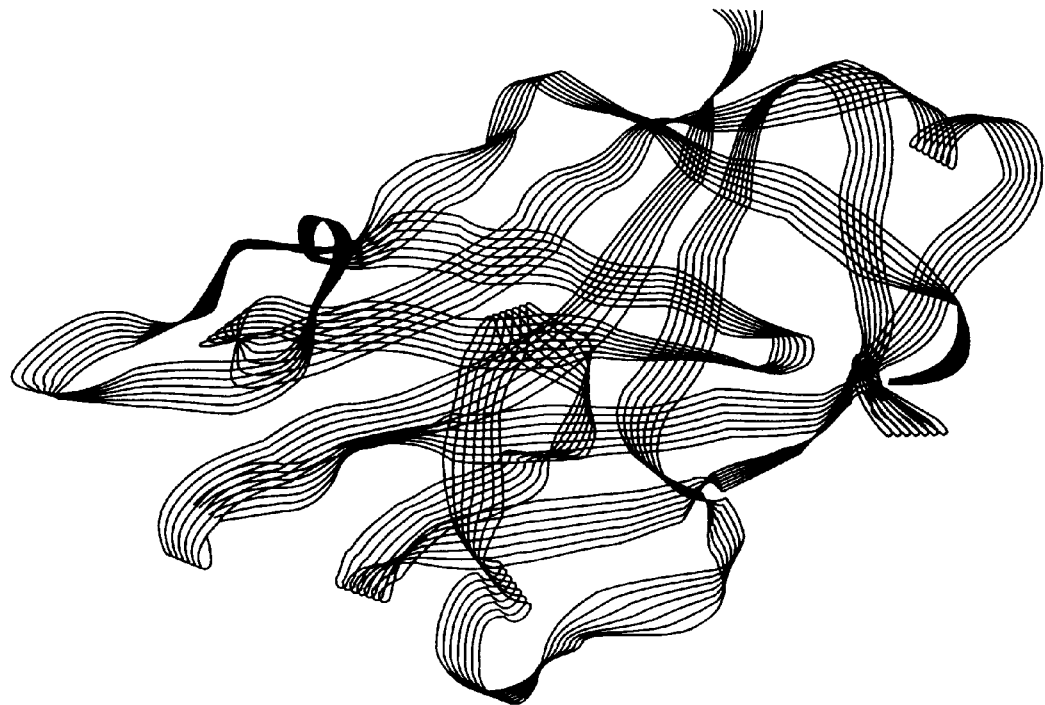
Figure 7B:
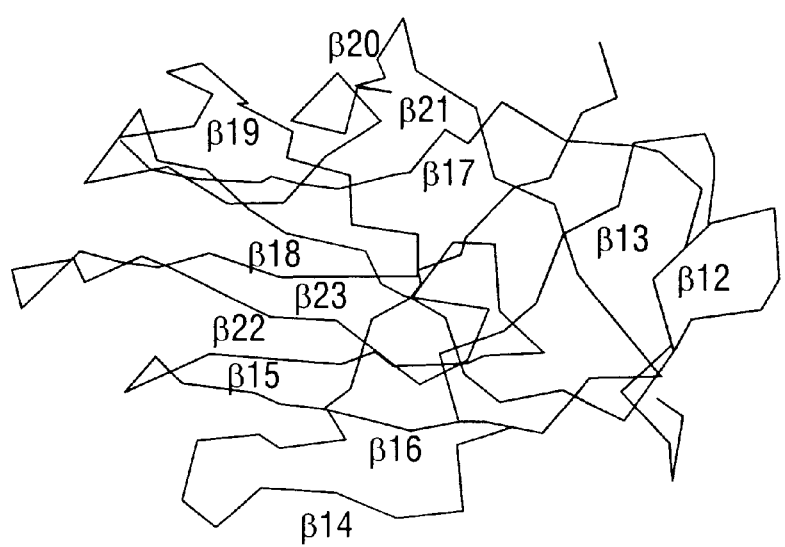

The structure of Cry3Bb is similar to that of Cry3A (Li et al., 1991). It consists of 5825 protein atoms from 588 residues (amino acids 64–652) forming three discrete domains (FIG. 1). A total of 251 water molecules have been identified in the Cry3Bb structure (FIG. 2). Domain 1 (residues 64–294) is a seven helical bundle formed by six helices twisted around the central helix, α5 (FIG. 3). The amino acids forming each helix are listed in FIG. 4. Domain 2 (residues 295–502) contains three antiparallel β-sheets (FIG. 5A and FIG. 5B). Sheets 1 and 2, each composed of 4 β strands, form the distinctive "Greek key" motif. The outer surface of sheet 3, composed of 3 β strands, makes contact with helix α7 of domain 1. FIG. 6 lists the amino acids comprising each β strand in domain 2. A small α helix, α8 which follows β strand 1, is also included in domain 2. Domain 3 (residues 503–652) has a "jelly roll" β-barrel topology which has a hydrophobic core and is nearly parallel to the a and perpendicular to the c axes of the lattice (FIG. 7A and FIG. 7B). The amino acids comprising each β strand of domain 3 are listed in FIG. 8.

Figure 9A:
Figure 9B:
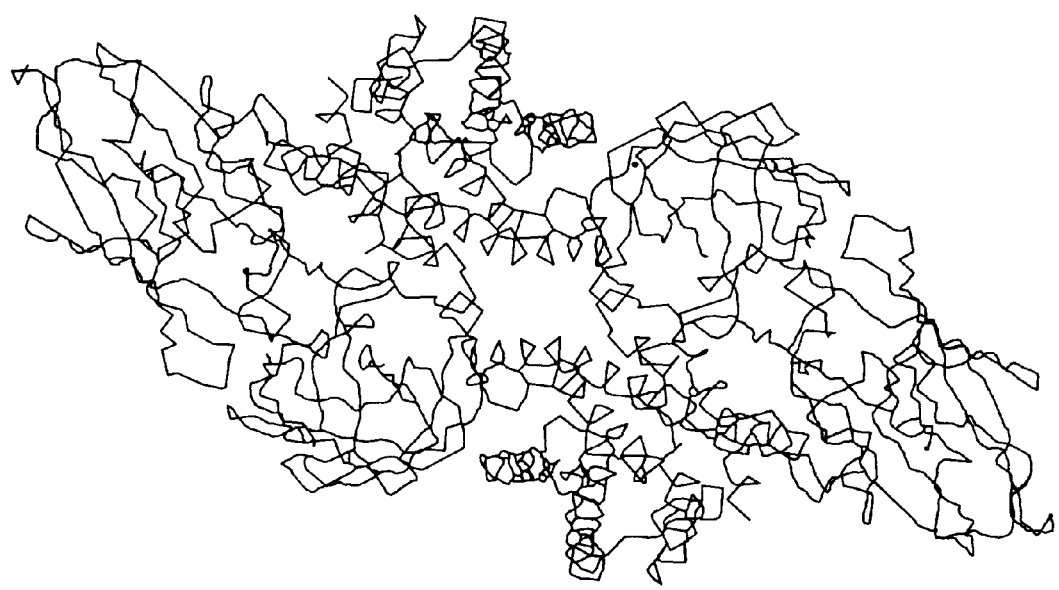

The monomers of Cry3Bb in the crystal form a dimeric quaternary structure along a two-fold axis parallel to the a axis (FIG. 9A and FIG. 9B). Helix α6 lies in a cleft formed by the interface of domain 1 and domains 1 and 3 of its symmetry related molecule. There are numerous close hydrogen bonding contacts along this surface, confirming the structural stability of the dimer.

5.2 EXAMPLE 2—PREPARATION OF CRY3BB.60

*B. thuringiensis* EG7231 was grown through sporulation in C2 medium with chloramphenicol (Cml) selection. The solids from this culture were recovered by centrifugation and washed with water. The toxin was purified by recrystallization from 4.0 M NaBr (Cody et al., 1992). The purified Cry3Bb was solubilized in 10 ml of 50 mM KOH/100 mg Cry3Bb and buffered to pH 9.0 with 100 mM CAPS (pH 9.0). The soluble toxin was treated with trypsin at a weight ratio of 50 mg toxin to 1 mg trypsin. After 20 min of trypsin digestion the predominant protein visualized by SDS-polyacrylamide gel electrophoresis (SDS-PAGE) was 60 kDa. Further digestion of the 60-kDa toxin was not observed. FIG. 4 illustrates the Coomassie-stained Cry3Bb and Cry3Bb.60 following SDS-PAGE.

5.3 EXAMPLE 3—PURIFICATION AND SEQUENCING OF CRY3BB.60

Cry3Bb.60 was electrophoretically purified by SDS-PAGE and electroblotted to Immobilon-P® (Millipore) membrane by semi-dry transfer at 15 V for 30 min. The membrane was then washed twice with water and stained with 0.025% R-250, 40% methanol. To reduce the background, the blot was destained with 50% methanol until the stained protein bands were visible. The blot was then air dried, and the stained Cry3Bb.60 band was cut out of the membrane. This band was sent to the Tufts University Sequencing Laboratory (Boston, Mass.) for N-terminal sequencing. The experimentally-determined N-terminal amino acid sequence is shown in Table 7 beside the known amino acid sequence starting at amino acid residue 160.

TABLE 7

AMINO ACID SEQUENCE OF THE N-TERMINUS OF CRY3BB.60 AND COMPARISON TO THE KNOWN SEQUENCE OF CRY3BB

| Deduced Sequence | Known Sequence | Residue # |
| --- | --- | --- |
| S | S | 160 |
| K | K | 161 |
| R | R | 162 |
| S | S | 163 |
| Q | Q | 164 |
| D | D | 165 |
| R | R | 166 |

5.4 EXAMPLE 4—BIOACTIVITY OF CRY3BB.60

Cry3Bb was prepared for bioassay by solubilization in a minimal amount of 50 mM KOH, 10 ml per 100 mg toxin, and buffered to pH 9.0 with 100 mM CAPS, pH 9.0. Cry3Bb.60 was prepared as described in Example 1. Both preparations were kept at room temperature 12 to 16 hours prior to bioassay. After seven days the mortality of the population was determined and analyzed to determine the lethal concentration of each toxin. These results are numerized in Table 8.

TABLE 8

BIOACTIVITY OF CRY3BB AND CRY3BB.60 AGAINST THE SOUTHERN CORN ROOTWORM (*DIBIOTICA UNDECIMPUNCTATA*)

| | LC$_{50}$ mg/well | 95% C.I. |
| --- | --- | --- |
| Cry3Bb | 24.09 | 15–39 |
| Cry3Bb.60 | 6.72 | 5.25–8.4 |

5.5 EXAMPLE 5—ION-CHANNEL FORMATION BY CRY3BB AND CRYB2.60

Cry3Bb.60 and Cry3Bb were evaluated for their ability to form ion channels in planar lipid bilayers. Bilayers of phosphatidylcholine were formed on Teflon® supports over a 0.7-mm hole. A bathing solution of 3.5 ml 100 mM KOH, 10 mM CaCl$_2$, 100 mM CAPS (pH 9.5) was placed on either side of the Teflon® partition. The toxin was added to one side of the partition and a voltage of 60 mV was imposed across the phosphatidylcholine bilayer. Any leakage of ions through the membrane was amplified and recorded. An analysis of the frequency of the conductances created by either Cry3Bb or Cry3Bb.60 are illustrated in FIG. 5A and FIG. 5B. Cry3Bb.60 readily formed ion channels whereas Cry3Bb rarely formed channels.

5.6 EXAMPLE 6—FORMATION OF HIGH MOLECULAR-WEIGHT OLIGOMERS

Individual molecules of Cry3Bb or Cry3Bb.60 form a complex with another like molecule. The ability of Cry3Bb to form an oligomer is not reproducibly apparent. The complex cannot be repeatedly observed to form under nondenaturing conditions. Cry3Bb.60 formed a significantly greater amount of a higher molecular-weight complex ($\geq 120$ kDa) with other Cry3Bb.60 molecules. Oligomers of Cry3Bb are demonstrated by the intensity of the Coomassie-stained SDS polyacrylamide gel. Oligomerization is visualized on SDS-PAGE by not heating samples prior to loading on the gel to retain some nondenatured toxin. These data suggest that Cry3Bb.60 more readily forms the higher order complex than Cry3Bb alone. Oligomerization is also observed by studying the conductance produced by these molecules and the time-dependent increase in conductance. This change in conductance can be attributed to oligomerization of the toxin.

5.7 EXAMPLE 7—DESIGN METHOD 1: IDENTIFICATION AND ALTERATION OF PROTEASE-SENSITIVE SITES AND PROTEOLYTIC PROCESSING

It has been reported in the literature that treatment of Cry3A toxin protein with trypsin, an enzyme that cleaves proteins on the carboxyl side of available lysine and arginine residues, yields a stable cleavage product of 55 kDa from the 67 kDa native protein (Carroll et al., 1989). N-terminal sequencing of the 55 kDa product showed cleavage occurs at amino acid residue R158. The truncated Cry3A protein was found to retain the same level of insecticidal activity as the native protein. Cry3Bb toxin protein was also treated with trypsin. After digestion, the protein size decreased from 68 kDa, the molecular weight of the native Cry3Bb toxin, to 60 kDa. No further digestion was observed. N-terminal sequencing revealed the trypsin cleavage site of the truncated toxin (Cry3Bb.60) to be amino acid R159 in l$\alpha$3,4 of Cry3Bb. Unexpectedly, the bioactivity of the truncated Cry3Bb toxin was found to increase.

Using this method, protease digestion of a *B. thuringiensis* toxin protein, a proteolytically sensitive site was identified on Cry3Bb, and a more highly active form of the protein (Cry3Bb.60) was identified. Modifications to this proteolytically-sensitive site by introducing an additional protease recognition site also resulted in the isolation of a biologically more active protein. It is also possible that removal of other protease-sensitive site(s) may improve activity. Proteolytically sensitive regions, once identified, may be modified or utilized to produce biologically more active toxins.

5.7.1 CRY3BB.60

Treatment of solubilized Cry3Bb toxin protein with trypsin results in the isolation of a stable, truncated Cry3Bb toxin protein with a molecular weight of 60 kDa (Cry3Bb.60). N-terminal sequencing of Cry3Bb.60 shows the trypsin-sensitive site to be R159 in l$\alpha$3,4 of the native toxin. Trypsin digestion results in the removal of helices 1–3 from the native Cry3Bb but also increases the activity of the toxin against SCRW larvae approximately four-fold.

Cry3Bb.60 is a unique toxin with enhanced insecticidal use over the parent Cry3Bb. Improved biological activity, is only one parameter that distinguishes it as a new toxin. Aside from the reduced size, Cry3Bb.60 is also a more soluble protein. Cry3Bb precipitates from solution at pH 6.5 while Cry3Bb.60 remains in solution from pH 4.5 to pH 12. Cry3Bb.60 also forms ion channels with greater frequency than Cry3Bb.

Cry3Bb.60 is produced by either the proteolytic removal of the first 159 amino acid residues, or the in vivo production of this toxin, by bacteria or plants expressing the gene for Cry3Bb.60, that is, the Cry3Bb gene without the first 483 nucleotides.

In conclusion, Cry3Bb.60 is distinct from Cry3Bb in several important ways: enhanced insecticidal activity; enhanced range of solubility; enhanced ability to form channels; and reduced size.

5.7.2 EG11221

Semi-random mutagenesis of the trypsin-sensitive l$\alpha$3,4 region of Cry3Bb resulted in the isolation of Cry3Bb.11221, a designed Cry3Bb protein that exhibits over a 6-fold increase in activity against SCRW larvae compared to WT. Cry3Bb.11221 has 4 amino acid changes in the l$\alpha$3,4 region. One of these changes, L158R, introduces an additional trypsin site adjacent to R159, the proteolytically sensitive site used to produce Cry3Bb.60 (example 4.1.1). Cry3Bb.11221 is produced by *B. thuringiensis* as a full length toxin protein but is presumably digested by insect gut proteases to the same size as Cry3Bb.60 (see Cry3A results from Carroll et al., 1989). The additional protease recognition site may make the l$\alpha$3,4 region even more sensitive to digestion, thereby increasing activity.

5.8 EXAMPLE 8—DESIGN METHOD 2: DETERMINATION AND MANIPULATION OF BOUND WATER

There are several ways that water molecules can associate with a protein, including surface water that is easily removed and bound water that is more difficult to extract (Dunitz, 1994; Zhang and Matthews, 1994). The function of bound water has been the subject of significant academic extrapolation, but the precise function has little experimental validation. Some of the most interesting bound or structural water is the water that participates in the protein structure from inside the protein itself.

The occupation of a site by a water molecule can indicate a stable pocket within a protein or a looseness of packing created by water-mediated salt bridges and hydrogen bonding to water. This can reduce the degree of bonding between amino acids, possibly making the region more flexible. A different amino acid sequence around that same site could result in better packing, collapsing the pocket around polar or charged amino acids. This may result in decreased flexibility. Therefore, the degree of hydration of a region of a protein may determine the flexibility or mobility of that region, and manipulation of the hydration may alter the flexibility. Methods of increasing the hydration of a water-exposed region include increasing the number of hydrophobic residues along that surface. It is taught in the art that exposed hydrophobic residues require significantly more water to hydrate than hydrophilic residues (CRC Handbook of Chemistry and Physics, CRC Press, Inc.). It is not taught, however, that by doing this, improvements to the biological activity of a protein can be achieved.

Structural water has not previously been identified in *B. thuringiensis* δ-endotoxins including Cry3Bb. Furthermore, there are no reports of the function of this structural water in δ-endotoxins or bacterial toxins. In the analysis of Cry3Bb, it was observed that a collection of water molecules are located around l$\alpha$3,4, a site defined by the inventors as important for improvement of bioactivity. The loop $\alpha$3,4 region is surface exposed and may define a hinge in the protein permitting either removal or movement of the first three helices of domain 1. The hydration found around this region may impart flexibility and mobility to this loop. The observation of structural water at the lα3,4 site provided an analytical tool for further structure analysis. If this important site is surrounded by water, then other important sites may also be completely or partially surrounded by water. Using this insight, structural water surrounding helices 5 and 6 was then identified. This structural water forms a column through the protein, effectively separating helices 5 and 6 from the rest of the molecule. The structures of Cry3A and Cry3Bb suggest that helices 5 and 6 are tightly associated, bound together by Van der Waals interactions. Alone, helix 5 from Cry3A, although insufficient for biological activity, has been demonstrated to have the ability to form ion channels in an artificial membrane (Gazit and Shai, 1993). The ion channels formed by helix 5 are 10-fold smaller than the channels of the full length toxin suggesting that significantly more toxin structure is required for the full-sized ion channels. In Cry3Bb, helix 5 as part of a cluster of α helices (domain 1) has been found to form ion channels (Von Tersch et al., 1994). Unpublished experimental observations by the inventors demonstrate that helix 6 also crossed the biological membrane. Helices 5 and 6, therefore, are the putative channel-forming helices necessary for toxicity.

The hydration around these helices may indicate that flexibility of this region is necessary for toxicity. It is conceivable, therefore, that if it were possible to improve the hydration around helices 5 and 6, one could create a better toxin protein. Care must be taken, however, to avoid creating continuous hydrophobic surfaces between helices 5–6 and any other part of the protein which could, by hydrophobic interactions, act to restrict movement of the mobile helices. The mobility of helices 5 and 6 may also depend on the flexibility of the loops attached to them as well as on other regions of the Cry3Bb molecule, particularly in domain 1, which may undergo conformational changes to allow insertion of the 2 helices into the membrane. Altering the hydration of these regions of the protein may also affect its bioactivity.

5.8.1 CRY3BB.11032

A collection of bound water residues indicated the relative flexibility of the lα3,4 region. The flexibility of this loop can be increased by increasing the hydration of the region by substituting relatively hydrophobic residues for the exposed hydrophilic residues. An example of an improved, designed protein having this type of substitution is Cry3Bb.11032. Cry3Bb.11032 has the amino acid change D165G; glycine is more hydrophobic than aspartate (Kyte and Doolittle hydrophobicity score of −0.4 vs. −3.5 for aspartate). Cry3Bb.11032 is approximately 3 times more active than WT Cry3Bb.

5.8.2 CRY3BB.11051

To increase the hydration of the lα4,5 region of Cry3Bb, glycine was substituted for the surface exposed residue K189. Glycine is more hydrophobic than lysine (Kyte and Doolittle hydrophobicity score of −0.4 vs. −3.9 for lysine) and may result in an increase in bound water. The increase in bound water may impart greater flexibility to the loop region which precedes the channel-forming helix, α5. The designed Cry3Bb protein with the K189G change, Cry3Bb.11051, exhibits a 3-fold increase in activity compared to WT Cry3Bb.

5.8.3 ALTERATIONS TO Lα7,β1 (CRY3BB.11241 AND 11242)

Amino acid changes made in the surface-exposed loop connecting α-helix 7 and β-strand 1 (lα7,β1) resulted in the identification of 2 altered Cry3Bb proteins with increased bioactivities, Cry3Bb.11241 and Cry3Bb.11242. Analysis of the hydropathy index of 2 of these proteins over the 20 amino acid sequence 281–300, inclusive of the lα7,β1 region, reveal that the amino acid substitutions in these proteins have made the lα7,β1 region much more hydrophobic. The grand average of hydropathy value (GRAVY) was determined for each protein sequence using the PC\GENE® (IntelliGenetics, Inc., Mountain View, Calif., release 6.85) protein sequence analysis computer program, SOAP, and a 7 amino acid interval. The SOAP program is based on the method of Kyte and Doolittle (1982). The increase in hydrophobicity of the lα7,β1 region for each protein may increase the hydration of the loop and, therefore, the flexibility. The altered proteins, their respective amino acid changes, fold-increases over WT bioactivity, and GRAVY values are listed in Table 9.

TABLE 9

HYDROPATHY VALUES FOR THE Lα7,β1 REGION OF CRY3BB AND 2 DESIGNED CRY3BB PROTEINS SHOWING INCREASED SCRW BIOACTIVITY

| Cry3Bb* Protein | Amino Acid Changes | Fold Increase in Bioactivity Over WT | GRAVY (Amino Acids 281–300) |
|---|---|---|---|
| wildtype | — | — | 4.50 |
| Cry3Bb.11241 | Y287F,D288N,R290L | 2.6x | 10.70 |
| Cry3Bb.11242 | R290V | 2.5x | 8.85 |

5.8.4 ALTERATIONS TO Lβ1,α8 (CRY3BB.11228, CRY3BB.11229, CRY3BB.11230, CRY3BB.11233, CRY3BB.11236, CRY3BB.11237, CRY3BB.11238 AND CRY3BB.11239)

The surface-exposed loop between β-strand 1 and α-helix 8 (lβ1,α8) defines the boundary between domains 1 and 2 of Cry3Bb. The introduction of semi-random amino acid changes to this region resulted in the identification of several altered Cry3Bb proteins with increased bioactivity. Hydropathy index analysis of the amino acid substitutions found in the altered proteins shows that the changes have made the exposed region more hydrophobic which may result in increased hydration and flexibility. Table 10 lists the altered proteins, their respective amino acid changes and fold increases over WT Cry3Bb and the grand average of hydropathy value (GRAVY) determined using the PC\GENE® (IntelliGenetics, Inc., Mountain View, Calif., release 6.85) protein sequence analysis program, SOAP, over the 20 amino acid sequence 305–324 inclusive of lβ1,α8, using a 7 amino acid interval.

TABLE 10

HYDROPATHY VALUES FOR THE Lβ1, α8 REGION OF CRY3BB AND 8 DESIGNED CRY3BB* PROTEINS SHOWING INCREASED SCRW BIOACTIVITY

| Cry3Bb* Protein | Amino Acid Changes | Fold Increase in Bioactivity Over Wild Type | GRAVY (Amino Acids 305–324) |
|---|---|---|---|
| wildtype | — | — | 0.85 |
| Cry3Bb.11228 | S311L, N313T, E317K | 4.1x | 4.35 |
| Cry3Bb.11229 | S311T, B317K, Y318C | 2.5x | 2.60 |
| Cry3Bb.11230 | S311A, L312V, Q316W | 4.7x | 3.65 |
| Cry3Bb.11233 | S311A, Q316D | 2.2x | 2.15 |
| Cry3Bb.11236 | S311I | 3.1x | 3.50 |
| Cry3Bb.11237 | S311I, N313H | 5.4x | 3.65 |
| Cry3Bb.11238 | N313V, T314N, Q316M, E317V | 2.6x | 9.85 |

TABLE 10-continued

HYDROPATHY VALUES FOR THE Lβ1, α8 REGION OF CRY3BB AND 8 DESIGNED CRY3BB* PROTEINS SHOWING INCREASED SCRW BIOACTIVITY

| Cry3Bb*<br>Protein | Amino Acid<br>Changes | Fold Increase in<br>Bioactivity Over<br>Wild Type | GRAVY<br>(Amino Acids<br>305–324) |
| --- | --- | --- | --- |
| Cry3Bb.11239 | N313R, L315P,<br>Q316L, E317A | 2.8× | 3.95 |

5.8.5 CRY3BB.11227, CRY3BB.11241 AND CRY3BB.11242

Amino acid Q238, located in helix 6 of Cry3Bb, has been identified as a residue that, by its large size and hydrogen bonding to R290, blocks complete hydration of the space between helix 6 and helix 4. Substitution of R290 with amino acids that do not form hydrogen bonds or that have side chains that can not span the physical distance to hydrogen bond with Q238 may result in increased hydration around Q238. Q238, unable to hydrogen bond to R290, may now bind water. This may increase the flexibility of the channel-forming region. Designed proteins Cry3Bb.11227 (R290N), Cry3Bb.11241 (R290L) and Cry3Bb.11242 (R290V) show increased activities of approximately 2-fold, 2.6-fold and 2.5-fold, respectively, against SCRW larvae compared to WT.

5.9 EXAMPLE 9—DESIGN METHOD 3: MANIPULATION OF HYDROGEN BONDS AROUND MOBILE REGIONS

Mobility of regions of a protein may be required for activity. The mobility of the αα5,6 region, the putative channel-forming region of Cry3Bb, may be improved by decreasing the number of hydrogen bonds, including salt bridges (hydrogen bonds between oppositely charged amino acid side chains), between helices 5–6 and any other part of the molecule or dimer structure. These hydrogen bonds may impede the movement of the two helices. Decreasing the number of hydrogen bonds and salt bridges may improve biological activity. Replacement of hydrogen-bonding amino acids with hydrophobic residues must be done with caution to avoid creating continuous hydrophobic surfaces between helices 5–6 and any other part of the dimer. This may decrease mobility by increasing hydrophobic surface interactions.

5.9.1 CRY3BB.11222 AND CRY3BB.11223

Tyr230 is located on helix 6 and, in the quaternary dimer structure of Cry3Bb, this amino acid is coordinated with Tyr230 from the adjacent molecule. Three hydrogen bonds are formed between the two helices 6 in the two monomers because of this single amino acid. In order to improve the flexibility of helices 5–6, the helices theoretically capable of penetrating the membrane and forming an ion channel, the hydrogen bonds across the dimer were removed by changing this amino acid and a corresponding increase in biological activity was observed. The designed Cry3Bb proteins, Cry3Bb.11222 and Cry3Bb.EG11223, show a 4-fold and 2.8-fold increase in SCRW activity, respectively, compared to WT.

5.9.2 CRY3BB.11051

Designed Cry3Bb protein Cry3Bb.11051 has amino acid change K189G in lα4,5 of domain 1. In the WT Cry3Bb structure, the exposed side chain of K189 is close enough to the exposed side change of E123, located in lα2b,3, to form hydrogen bonds. Substitution of K189 with glycine, as found in this position in Cry3A, removes the possibility of hydrogen bond formation at this site and results in a protein with a bioactivity three-fold greater than WT Cry3Bb.

5.9.3 CRY3BB.11227, CRY3BB.11241 AND CRY3BB.11242

Amino acid Q238, located in helix 6 of Cry3Bb, has been identified as a residue that, by its large size and hydrogen bonding to R290, blocks complete hydration of the space between helix 6 and helix 4. Substitution of R290 with amino acids that do not form hydrogen bonds or that have side chains that can not span the physical distance to hydrogen bond with Q238 may increase the flexibility of the channel-forming region. Designed proteins Cry3Bb.11227 (R290N), Cry3Bb.11241 (R290L) and Cry3Bb.11242 (R290V) show increased activities of approximately 2-fold, 2.6-fold and 2.5-fold, respectively, against SCRW larvae compared to WT

5.10 EXAMPLE 10—DESIGN METHOD 4: LOOP ANALYSIS AND LOOP DESIGN AROUND FLEXIBLE HELICES

Loop regions of a protein structure may be involved in numerous functions of the protein including, but not limited to, channel formation, quaternary structure formation and maintenance, and receptor binding. Cry3Bb is a channel-forming protein. The availability of the ion channel-forming helices of δ-endotoxins to move into the bilayer depend upon the absence of forces that hinder the process. One of the forces possibly limiting this process is the steric hindrance of amino acid side chains in loop regions around the critical helices. The literature suggests that in at least one other bacterial toxin, not a B. thuringiensis toxin, the toxin molecule opens up or, in scientific terms, loses some of the quaternary structure to expose a membrane-active region (Cramer et al., 1990). This literature does not teach how to improve the probability of this event occurring and it is not known if B. thuringiensis toxins use this same process to penetrate the membrane. Reducing the steric hindrance of the amino acid side chains in these critical regions by reducing size or altering side chain positioning with the corresponding increase in biological activity was the inventive step.

5.10.1 ANALYSIS OF THE LOOP BETWEEN HELICES 3 AND 4 (CRY3BB.11032)

The inventors have discovered that the first three helices of domain one could be cleaved from the rest of the toxin by proteolytic digestion of the loop between helices α3 and α4 (Cry3Bb.60). Initial efforts to truncate the cry3Bb gene to produce this shortened, though more active Cry3Bb molecule, failed. For unknown reasons, B. thuringiensis failed to synthesize this 60-kDa molecule. It was then reasoned that perhaps the first three helices of domain 1 did not have to be proteolytically removed, or equivalently, the protein did not have to be synthesized in this truncated form to take advantage of the Cry3Bb.60 design. It was observed that the protein Cry3A had a small amino acid near the lα3,4 that might impart greater flexibility in the loop region thereby permitting the first three helices of domain 1 to move out of the way, exposing the membrane-active region. By designing a Cry3Bb molecule with a glycine residue near this loop, the steric hindrance of residues in the loop might be lessened. The redesigned protein, Cry3Bb.11032, has the amino acid change D165G, which replaces the larger aspartate residue (average mass of 115.09) with the smallest amino acid, glycine (average mass of 57.05). The activity of Cry3Bb.11032 is approximately 3-fold greater than that of the WT protein. In this way, the loop between helices α3 and α4 was rationally redesigned with a corresponding increase in the biological activity.

5.10.2 CRY3BB.11051

The loop region connecting helices α4 and α5 in Cry3Bb must be flexible so that the channel-forming helices α5–α6 can penetrate into the membrane. It was noticed that Cry3A has a glycine residue in the middle of this loop that may impart greater flexibility. The corresponding change, K189G, was made in Cry3Bb and the resulting, designed protein, Cry3Bb.11051, exhibits a 3-fold increase in activity against SCRW larvae compare to WT Cry3Bb.

5.10.3 ANALYSIS OF THE LOOP BETWEEN β-STRAND 1 AND HELIX 8 (CRY3BB.11228, CRY3BB.11229, CRY3BB.11230, CRY3BB.11232, CRY3BB.11233, CRY3BB.11236, CRY3BB.11237, CRY3BB.11238, AND CRY3BB.11239)

The loop region located between β strand 1 of domain 2 and α helix 8 in domain 2 is very close to the loop between α helices 6 and 7 in domain 1. Some of the amino acids side chains of lβ1,α8 appear as though they may sterically impede movement of lα6,7. Since lα6,7 must be flexible for the channel-forming helices α5–=6 to insert into the membrane, it was thought that re-engineering this loop may change the positioning of the side chains resulting in less steric hindrance. This was accomplished creating proteins with increased biological activities ranging from 2.2 to 5.4 times greater than WT. These designed toxin proteins and their amino acid changes are listed in Table 2 as Cry3Bb.11228, Cry3Bb.11229, Cry3Bb.11230, Cry3Bb.11232, Cry3Bb.11233, Cry3Bb.11236, Cry3Bb.11237, Cry3Bb.11238, and Cry3Bb.11239.

5.10.4 ANALYSIS OF THE LOOP BETWEEN HELIX 7 AND β-STRAND 1 (CRY3BB.11227, CRY3BB.11234, CRY3BB.11241, CRY3BB.11242, AND CRY3BB.11036)

If Cry3Bb is similar to a bacterial toxin which must open up to expose a membrane active region for toxicity, it is possible that other helices in addition to the channel-forming helices must also change positions. It was reasoned that, if helices α5–α6 insert into the membrane, than helix α7 may have to change positions also. It was shown in example 4.4.3 that increasing flexibility between helix α6 and α7 can increase activity, greater flexibility in the loop following helix α7, lα7,β1 may also increase bioactivity. Alterations to the lα7,β1 region of Cry3Bb resulted in the isolation of several proteins with increased activities ranging from 1.9 to 4.3 times greater than WT. These designed proteins are listed in Table 7 as Cry3Bb.11227, Cry3Bb.11234, Cry3Bb.11241, Cry3Bb.11242, and Cry3Bb.11036.

5.11 EXAMPLE 11—DESIGN METHOD 5: LOOP DESIGN AROUND β STRANDS AND β SHEETS

Loop regions of a protein structure may be involved in numerous functions of the protein including, but not limited to, channel formation, quaternary structure formation and maintenance, and receptor binding. A binding surface is often defined by a number of loops, as is the case with immunoglobulin G (IgG) (see Branden and Tooze, 1991, for review). What can not be determined at this point, however, is what loops will be important for receptor interactions just by looking at the structure of the protein in question. Since a receptor has not been identified for Cry3Bb, it is not even possible to compare the structure of Cry3Bb with other proteins that have the same receptor for structural similarities. To identify Cry3Bb loops that contribute to receptor interactions, random mutagenesis was performed on surface-exposed loops.

As each loop was altered, the profile of the overall bioactivities of the resultant proteins were examined and compared. The loops, especially in domain 2 which appears to be unnecessary for channel activity, fall into two categories: (1) loops that could be altered without much change in the level of bioactivity of the resultant proteins and (2) loops where alterations resulted in overall loss of resultant protein bioactivity. Using this design method, it is possible to identify several loops important for activity.

5.11.1 ANALYSIS OF LOOP β2,3

Semi-random mutagenesis of the loop region between β strands 2 and 3 resulted in the production of structurally stable toxin proteins with significantly reduced activities against SCRW larvae. The lβ2,3 region is highly sensitive to amino acid changes indicating that specific amino acids or amino acid sequences are necessary for toxin protein activity. It is conceivable, therefore, that specific changes in the lβ2,3 region will increase the binding and, therefore, the activity of the redesigned toxin protein.

5.11.2 ANALYSIS OF LOOP β6,7

Semi-random mutations introduced to the loop region between β strands 6 and 7 resulted in structurally stable proteins with an overall loss of SCRW bioactivity. The lβ6,7 region is highly sensitive to amino acid changes indicating that specific amino acids or amino acid sequences are necessary for toxin protein activity. It is conceivable, therefore, that specific changes in the lβ6,7 region will increase the binding and, therefore, the activity of the redesigned toxin protein.

5.11.3 ANALYSIS OF LOOP lβ10,11

Random mutations to the loop region between β strands 10 and 11 resulted in proteins having an overall loss of SCRW bioactivity. Loop β10,11 is structurally close to and interacts with loops β2,3 and β6,7. Specific changes to individual residues within the lβ10,11 region may also result in increased interaction with the insect membrane, increasing the bioactivity of the toxin protein.

5.11.4 CRY3BB.11095

Loops β2,3, β6,7 and β10,11 have been identified as important for bioactivity of Cry3Bb. The 3 loops are surface-exposed and structurally close together. Amino acid Q348 in the WT structure, located in β-strand 2 just prior to lβ2,3, does not form any intramolecular contacts. However, replacing Q348 with arginine (Q348R) results in the formation of 2 new hydrogen-bonds between R348 and the backbone carbonyls of R487 and R488, both located in lβ10,11. The new hydrogen bonds may act to stabilize the structure formed by the 3 loops. The designed protein carrying this change, Cry3Bb.11095, is 4.6-fold more active than WT Cry3Bb.

5.12 EXAMPLE 12—DESIGN METHOD 6: IDENTIFICATION AND RE-DESIGN OF COMPLEX ELECTROSTATIC SURFACES

Interactions of proteins include hydrophobic interactions (e.g., Van der Waals forces), hydrophilic interactions, including those between opposing charges on amino acid side chains (salt bridges), and hydrogen bonding. Very little is known about δ-endotoxin and receptor interactions. Currently, there are no literature reports identifying the types of interactions that predominate between *B. thuringiensis* toxins and receptors.

Experimentally, however, it is important to increase the strength of the *B. thuringiensis* toxin-receptor interaction and not permit the precise determination of the chemical interaction to stand in the way of improving it. To accomplish this, the electrostatic surface of Cry3Bb was defined by solving the Poisson-Boltzman distribution around the molecule. Once this electrically defined surface was solved, it could then be inspected for regions of greatest diversity. It was reasoned that these electrostatically diverse regions would have the greatest probability of participating in the specific interactions between the *B. thuringiensis* toxin proteins and the receptor, rather than more general and non-specific interactions. Therefore, these regions were chosen for redesign, continuing to increase the electrostatic diversity of the regions. In addition, examination of the electrostatic interaction around the putative channel forming region of the toxin created insights for redesign. This includes identification of an electropositive residue in an otherwise negatively charged conduit (see example 4.6.1).

5.12.1 R290 (CRY3BB.11227, CRY3BB.11241, AND CRY3BB.11242)

Examination of the Cry3Bb dimer interface along the domain 1 axis suggested that a pore or conduit for cations might be formed between the monomers. Electrostatic examination of this axis lent additional credibility to this suggestion. In fact, the hypothetical conduit is primarily negatively charged, an observation consistent with the biophysical analysis of cation-selective, δ-endotoxin channels. If a cation channel were formed along the axis of the dimer, then the cation could move between the monomers relatively easily with only one significant hurdle. A positively charged arginine residue (R290) lies in the otherwise negatively charged conduit. This residue could impede the cation movement through the channel. Based on this analysis, R290 was changed to uncharged residues. The bioactivity of redesigned proteins Cry3Bb.11227 (R290N), Cry3Bb.11241 (R290L) and Cry3Bb.11242 (R290V) was improved approximately 2-fold, 2.6-fold and 2.5-fold, respectively.

5.12.2 CRY3BB.60

Trypsin digestion of solubilized Cry3Bb yields a stable, truncated protein with a molecular weight of 60 kDa (Cry3Bb.60). Trypsin digestion occurs on the carboxyl side of residue R159, effectively removing helices 1 through 3 from the native Cry3Bb structure. The cleavage of the first 3 helices exposes an electrostatic surface different than those found in the native structure. The new surface has a combination of hydrophobic, polar and charged characteristics that may play a role in membrane interactions. The bioactivity of Cry3Bb.60 is 3.6-fold greater than that of WT Cry3Bb.

5.13 EXAMPLE 13—DESIGN METHOD 7: IDENTIFICATION AND REMOVAL OF METAL BINDING SITES

The literature teaches that the in vitro behavior of *B. thuringiensis* toxins can be increased by chelating divalent cations from the experimental system (Crawford and Harvey 1988). It was not known, however, how these divalent cations inhibited the in vitro activity. Crawford and Harvey (1988) demonstrated that the short circuit current across the midgut was more severely inhibited by *B. thuringiensis* in the presence of EDTA, a chelator of divalent ions, than in the absence of this agent, thus suggesting that this step in the mode of action of *B. thuringiensis* could be potentiated by removing divalent ions. Similar observations were made using black-lipid membranes and measuring an increase in the current created by the δ-endotoxins in the presence of EDTA to chelate divalent ions. There were at least three possible explanations for these observations. The first explanation could be that the divalent ions are too large to move through a ion channel more suitable for monovalent ions, thereby blocking the channel. Second, the divalent ions may cover the protein in the very general way, thereby buffering the charge interactions required for toxin membrane interaction and limiting ion channel activity. The third possibility is that a specific metal binding site exists on the protein and, when occupied by divalent ions, the performance of the ion channel is impaired. Although the literature could not differentiate the value of one possibility over another, the third possibility led to an analysis of the Cry3Bb structure searching for a specific metal binding site that might alter the probability that a toxin could form an ion channel.

5.13.1 H231 (CRY3BB.11222, CRY3BB.11224, CRY3BB.11225, AND CRY3BB.11226)

A putative metal binding site is formed in the Cry3Bb dimer structure by the H231 residues of each monomer. The H231 residues, located in helix α6, lie adjacent to each other and close to the axis of symmetry of the dimer. Removal of this site by replacement of histidine with other amino acids was evaluated by the absence of EDTA-dependent ion channel activity. The bioactivities of the designed toxin proteins, Cry3Bb.11222, Cry3Bb.11224, Cry3Bb.11225 and Cry3Bb.11226, are increased 4-, 5-, 3.6- and 3-fold, respectively, over that of WT Cry3Bb. Their respective amino acid changes are listed in Table 2.

5.14 EXAMPLE 14—DESIGN METHOD 8: ALTERATION OF QUATERNARY STRUCTURE

Figure 10:
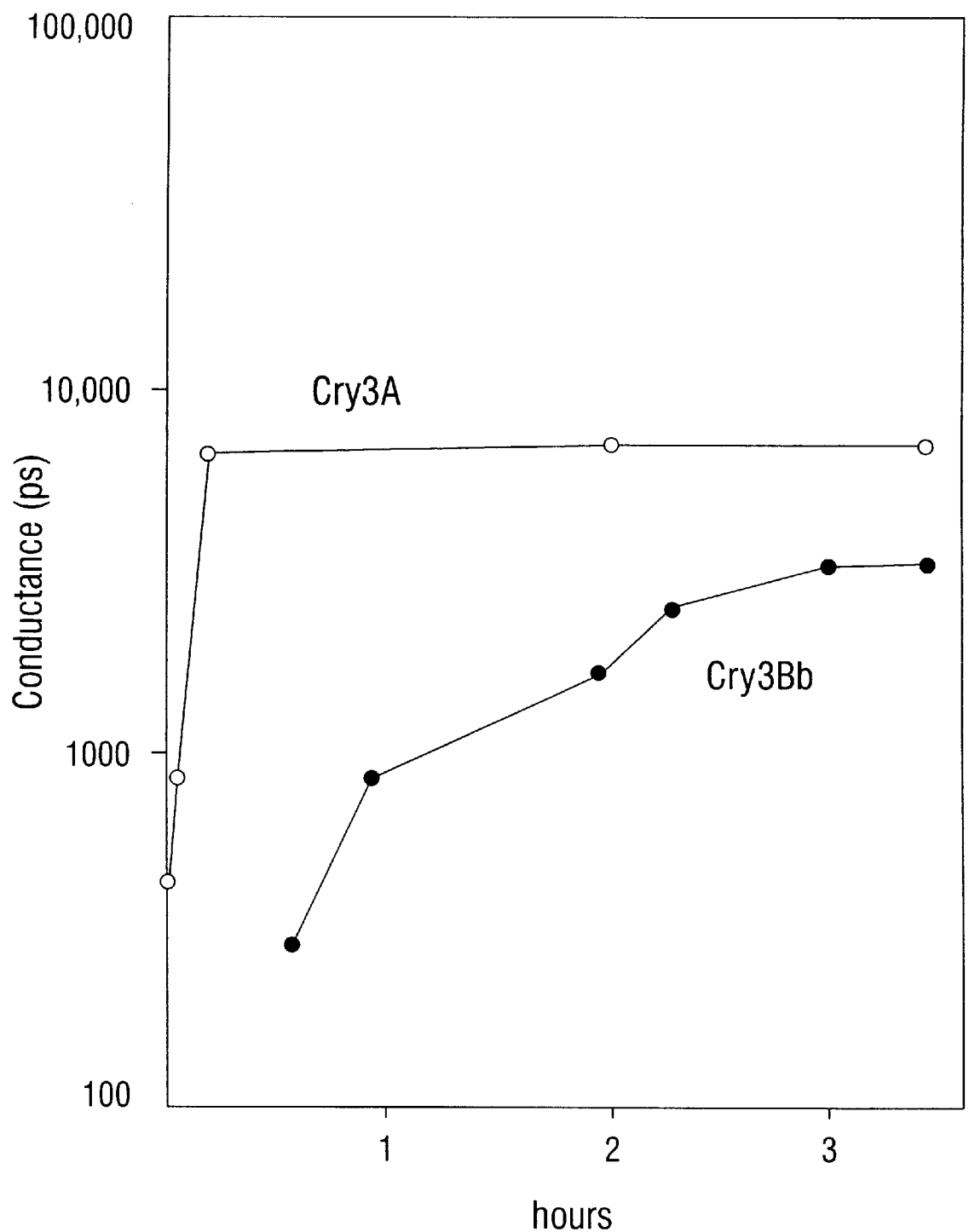

Cry3Bb can exist in solution as a dimer similar to a related protein, Cry3A (Walters et al., 1992). However, the importance of the dimer to biological activity is not known because the toxin as a monomer or as a higher order structure has not been seriously evaluated. It is assumed that specific amino acid residues contribute to the formation and stability of the quaternary structure. Once a contributing residue is identified, alterations can be made to diminish or enhance the effect of that residue thereby affecting the interaction between monomers. Channel activity is a useful way, but by no means the only way, to assess quaternary structure of Cry3Bb and its derivatives. It has been observed that Cry3Bb creates gated conductances in membranes that grow in size with time, ultimately resulting in large pores in the membrane (the channel activity of WT Cry3Bb is described in Section 12.1). It also has been observed that Cry3A forms a more stable dimer than Cry3Bb and coincidentally forms higher level conductances faster (FIG. 10). This observation led the inventors to propose that oligomerization and ion channel formation (conductance size and speed of channel formation) were related. Based on this observation Cry3Bb was re-engineered to make larger and more stable oligomers at a faster rate. It is assumed in this analysis that the rate of ion channel formation and growth mirrors this process. It is also possible that changes in quaternary structure may not affect channel activity alone or at all. Alterations to quaternary structure may also affect receptor interactions, protein processing in the insect gut environment, as well as other aspects of bioactivity unknown.

5.14.1 CRY3BB.11048

Comparative structural analysis of Cry3A and Cry3Bb led to the identification of structural differences between the two toxins in the ion channel-forming domain; specifically, an insertion of one amino acid between helix 2a and helix 2b in Cry3Bb. Removal of this additional amino acid in Cry 3B2, A104, and a D103E substitution, as in Cry3A, resulted in loss of channel gating and the formation of symmetrical pores. Once the pores are formed they remain open and allow a steady conductance ranging from 25–130 pS. This designed protein, Cry3Bb.11048, is 4.3 times more active than WT Cry3Bb against SCRW larvae.

5.14.2 OLIGOMERIZATION OF CRY3BB.60

Individual molecules of Cry3Bb or Cry3Bb.60 can form a complex with another like molecule. Oligomerization of Cry3Bb is demonstrated by SDS-PAGE, where samples are not heated in sample buffer prior to loading on the gel. The lack of heat treatment allows some nondenatured toxin to remain. Oligomerization is visualized following Coomassie staining by the appearance of a band at 2 times the molecular weight of the monomer. The intensity of the higher molecular weight band reflects the degree of oligomerization. The ability of Cry3Bb to form an oligomer is not reproducibly apparent. The complex cannot be repeatedly observed to form. Cry3Bb.60, however, forms a significantly greater amount of a higher molecular weight complex (120 kDa). These data suggest that Cry3Bb.60 more readily forms the higher order complex than Cry3Bb alone. Cry3Bb.60 also forms ion channels with greater frequency than WT Cry3Bb (see Section 5.12.9).

5.14.3 CRY3BB.11035

Changes were made in Cry3Bb to reflect the amino acid sequence in Cry3A at the end of $l\alpha 3,4$ and in the beginning of helix 4. These changes resulted in the designed protein, Cry3Bb.11035, that, unlike wild type Cry3Bb, forms spontaneous channels with large conductances. Cry3Bb.11035 is also approximately three times more active against SCRW larvae than WT Cry3Bb. Cry3Bb.11035 and its amino acid changes are listed in Table 10.

5.14.4 CRY3BB.11032

Cry3Bb.11032 was altered at residue 165 in helix $\alpha 4$, changing an asparate to glycine, as found in Cry3A. Cry3Bb.11032 is three-fold more active than WT Cry3Bb. The channel activity of Cry3Bb.11032 is much like Cry3Bb except when the designed protein is artificially incorporated into the membrane. A 16-fold increase in the initial channel conductances is observed compared to WT Cry3Bb (see Section 5.12.2). This increase in initial conductance presumably is due to enhanced quaternary structure, stability or higher-order structure.

5.14.5 EG11224

In the WT Cry3Bb dimer structure, histidine, at position 231 in domain 1, makes hydrogen bond contacts with D288 (domain 1), Y230 (domain 1), and, through a network of water molecules, also makes contacts to D610 (domain 3), all of the opposite monomer. D610 and K235 (domain 1) also make contact. Replacing the histidine with an arginine, H231R, results, in one orientation, in the formation of a salt bridge to D610 of the neighboring monomer. In a second orientation, the contacts with D288 of the neighboring monomer, as appear in the WT structure, are retained. In either orientation, R231 does not hydrogen bond to Y230 of the opposite monomer but does make contact with K235 which retains is contacts to K610 (V. Cody, research communication). The shifting hydrogen bonds have changed the interactions between the different domains of the protein in the quaternary structure. Overall, fewer hydrogen bonds exist between domains 1 of the neighboring monomers and a much stronger bond has been formed between domains 1 and 3. Channel activity was found to be altered. Cry3Bb.11224 produces small, quickly gating channels like Cry3Bb. However, unlike WT Cry3Bb, Cry3Bb.11224 does not exhibit β-mercaptoethanol-dependent activation. Replacing H231 with arginine resulted in a designed Cry3Bb protein, Cry3Bb.11224, exhibiting a 5-fold increase in bioactivity.

5.14.6 CRY3BB.11226

Cry3Bb.11226 is similar to Cry3Bb.11224, discussed in Section 4.8.5, in that the histidine at position 231 has been replaced. The amino acid change, H231T, results in the loss of β-mercaptoethanol dependent activation seen with WT Cry3Bb (see Section 5.12.1). The replacement of H231, a putative metal binding site, changes the interaction of regions in the quaternary structure resulting in a different type of channel activity. Cry3Bb.11226 is three-fold more active than WT Cry3Bb.

5.14.7 CRY3BB.11221

Cry3Bb.11221 has been re-designed in the $l\alpha 3,4$ region of Cry3Bb. The channels formed by Cry3Bb.11221 are much more well resolved than the conductances formed by WT Cry3Bb (see Section 5.12.6). Cry3Bb.11221 exhibits a 6.4-fold increase in bioactivity over that of WT Cry3Bb. The amino acid changes found in Cry3Bb.11221 are listed in Table 2.

5.14.8 CRY3BB.11242

The designed protein, Cry3Bb.11242, carrying the alteration R290V, forms small conductances immediately which grow rapidly and steadily to large conductances in about 3 min (see Section 5.12.7). This is contrast to WT Cry3Bb channels which take 30–45 min to appear and grow slowly over hours to large conductances. Cry3Bb.11242 also exhibits a 2.5-fold increase in bioactivity compared to WT Cry3Bb.

5.14.9 CRY3BB.11230

Cry3Bb.11230, unlike WT Cry3Bb, forms well resolved channels with long open states. These channels reach a maximum conductance of 3000 pS but do not continue to grow with time. Cry3Bb.11230 has been re-designed in the $l\beta 1,\alpha 8$ region of Cry3Bb and exhibits almost a 5-fold increase in activity against SCRW larvae (Table 9) and a 5.4-fold increase against WCRW larvae (Table 10) compared to WT Cry3Bb. The amino acid changes found in Cry3Bb.11230 are listed in Table 2.

5.15 EXAMPLE 15—DESIGN METHOD 9: DESIGN OF STRUCTURAL RESIDUES

The specific three-dimensional structure of a protein is held in place by amino acids that may be buried or otherwise removed from the surface of the protein. These structural determinants can be identified by inspection of forces responsible for the surface structure positioning. The impact of these structural residues can then be enhanced to restrict molecular motion or diminished to enhance molecular flexibility.

5.15.1 CRY3BB.11095

Loops $\beta 2,3$, $\beta 6,7$ and $\beta 10,11$, located in domain 2 of Cry3Bb, have been identified as important for bioactivity. The three loops are surface-exposed and structurally close together. Amino acid Q348 in the WT structure, located in β-strand 2 just prior to $l\beta 2,3$, does not form any intramolecular contacts. However, replacing Q348 with arginine (Q348R) results in the formation of 2 new hydrogen-bonds between R348 and the backbone carbonyls of R487 and R488, both located in $l\beta 10,11$. The new hydrogen bonds may act to stabilize the structure formed by the three loops. Certainly, the structure around R348 is more tightly packed as determined by X-ray crystallography. The designed protein carrying this change, Cry3Bb.11095, is 4.6-fold more active than WT Cry3Bb.

5.16 EXAMPLE 16—DESIGN METHOD 10: COMBINATORIAL ANALYSIS AND MUTAGENESIS

Individual sites in the engineered Cry3Bb molecule can be used together to create a Cry3Bb molecule with activity even greater than the activity of any one site. This method has not been precisely applied to any δ-endotoxin. It is also not obvious that improvements in two sites can be pulled together to improve the biological activity of the protein. In fact, data demonstrates that improvements to 2 sites, when pulled together into a single construct, do not necessarily further improve the biological activity of Cry3Bb. In some cases, the combination resulted in decreased protein stability and/or activity. Examples of proteins with site combinations that resulted in improved activity compared to WT Cry3Bb but decreased activity compared to 1 or more of the "parental" proteins are Cry3Bb.11235, 11046, 11057 and 11058. Cry3Bb.11082, which contains designed regions from 4 parental proteins, retains the level of activity from the most active parental strain (Cry3Bb.11230) but does not show an increase in activity. These proteins are listed in Table 7. The following are examples of instances where combined mutations have significantly improved biological activity.

5.16.1 CRY3BB.11231

Designed protein Cry3Bb.11231 contains the alterations found in Cry3Bb.11224 (H231R) and Cry3Bb.11228 (changes in lβ1,α8). The combination of amino acid changes found in Cry3Bb.11231 results in an increase in bioactivity against SCRW larvae of approximately 8-fold over that of WT Cry3Bb (Table 2). This increase is greater than exhibited by either Cry3Bb.11224 (5.0×) or Cry3Bb.11228 (4.1×) alone. Cry3Bb.11231 was also exhibits an 12.9-fold increase in activity compared to WT Cry3Bb against WCRW larvae (Table 10).

5.16.2 CRY3BB.11081

Designed Cry3Bb protein Cry3Bb.11081 was constructed by combining the changes found in Cry3Bb.11032 and Cry3Bb.11229 (with the exception of Y318C). Cry3Bb.11081 a 6.1-fold increase in activity over WT Cry3Bb; a greater increase in activity than either of the individual parental proteins, Cry3Bb.11032 (3.1-fold) and Cry3Bb.11229 (2.5-fold).

5.16.3 CRY3BB.11083

Designed Cry3Bb protein Cry3Bb.11083 was constructed by combining the changes found in Cry3Bb.11036 and Cry3Bb.11095. Cry3Bb.11083 exhibits a 7.4-fold increase in activity against SCRW larvae compared to WT Cry3Bb; a greater increase than either Cry3Bb.11036 (4.3 ×) or Cry3Bb.11095 (4.6×). Cry3Bb.11083 also exhibits a 5.4-fold increase in activity against WCRW larvae compared to WT Cry3Bb (Table 10).

5.16.4 CRY3BB.11084

Designed Cry3Bb protein Cry3Bb.11084 was constructed by combining the changes found in Cry3Bb.11032 and the S311L change found in Cry3Bb.11228. Cry3Bb.11084 exhibits a 7.2-fold increase in activity over that of WT Cry3Bb; a greater than either Cry3Bb.11032 (3.1×) or Cry3Bb.11228 (4.1×).

5.16.5 CRY3BB.11098

Designed Cry3Bb protein Cry3Bb.11098 was constructed to contain the following amino acid changes: D165G, H231R, S311L, N313T, and E317K. The nucleic acid sequence is given in SEQ ID NO:107, and the encoded amino acid sequence is given in SEQ ID NO:108.

5.17 EXAMPLE 17—DESIGN STRATEGY 11: ALTERATION OF BINDING TO GLYCOPROTEINS AND TO WCRW BRUSH BORDER MEMBRANES

While the identity of receptor(s) for Cry3Bb is unknown, it is nonetheless important to increase the interaction of the toxin with its receptor. One way to improve the toxin-receptor interaction with knowing the identity of the receptor is to reduce or eliminate non-productive binding to other biomolecules. The inventors have observed that Cry3Bb binds non-specifically to bovine serum albumin (BSA) that has been glycosylated with a variety of sugar groups, but not to non-glycosylated BSA. Cry3A, which is not active on Diabrotica species, shows similar but even greater binding to glycosylated-BSA. Similarly, Cry3A shows greater binding to immobolized WCRW brush border membrane (BBM) than does WT Cry3Bb, suggesting that much of the observed binding is non-productive. It was reasoned that the non-specific binding to WCRW BBM occurs via glycosylated proteins, and that binding to both glycosylated-BSA and WCRW BBM is non-productive in reaction pathway to toxicity. Therefore reduction or elimination of that binding would lead to enhanced binding to the productive receptor and to enhanced toxicity. Potential binding sites for sugar groups were targeted for redesign to reduce the non-specific binding of Cry3Bb to glycoproteins and to immobilized WCRW BBM.

5.17.1 CRY3BB.60

Cry3Bb-60, in which Cry3Bb has been cleaved at R159 in lα3,4, shows decreased binding to glycosylated-BSA and decreased binding to immobilized WCRW BBM. Cry3Bb-60 shows a 3.6-fold increase in bioactivity relative to WT Cry3Bb.

5.17.2 ALTERATIONS TO 1α3,4 (CRY3BB.11221)

Cry3Bb.11221 has been redesigned in the lα3,4 region of domain 1, which is the region in which Cry3Bb is cleaved to produce Cry3Bb-60. Cry3Bb.11221 also shows decreased binding to both glycosylated-BSA and immobilized WCRW BBM, and exhibits a 6.4-fold increase in bioactivity over that of WT Cry3Bb. Together with data for Cry3Bb.60 (section 5.17.1) these data suggest that this loop region contributes substantially to non-productive binding of the toxin.

5.17.3 ALTERATION TO 1β1,α8 (CRY3BB.11228,11230, 11237 AND 11231)

The lβ1,α8 region of Cry3Bb has been re-engineered to increase hydration (section 4.2.4) and enhance flexibility (section 4.4.3). Several proteins altered in this region, Cry3Bb.11228,11230, and 11237 demonstrate substantially lower levels of binding both glycosylated-BSA and immobilized WCRW BBM, and also show between 4.1- and 4.5-fold increases in bioactivity relative to WT Cry3Bb.

5.17.4 BINDING ACTIVITY

The tendencies of Cry3Bb and some of its derivatives to bind to glycosylated-BSA and to WCRW BBM were determined using a BIAcore™ surface plasmon resonance biosensor. For glycosylated-BSA binding, the glycosylated protein was immobilized using standard NHS chemistry to a CM5 chip (BIAcore), and the solubilized toxin was injected over the glycosylated-BSA surface. To measure binding to WCRW BBM, brush border membrane vesicles (BBMV) purified from WCRW midguts (English et al., 1991) were immobilized on an HPA chip (BIAcore) then washed with either 10 mM KOH or with 40 mM β-octylglucoside. The solubilized toxin was then injected over the resulting hybrid bilayer surface to detect binding. Protein concentration were determined by Protein Dye Reagent assay (BioRad) or BCA Protein Assay (Pierce).

Other methods may also be used to determine the same binding information. These include, but are not limited to, ligand blot experiments using labeled toxin, labeled glycosylated protein, or anti-toxin antibodies, affinity chromatography, and in vitro binding of toxin to intact BBMV.

5.18 EXAMPLE 18—CONSTRUCTION OF PLASMIDS WITH WT CRY3BB SEQUENCES

Standard recombinant DNA procedures were performed essentially as described by Sambrook et al., (1989).

5.18.1 PEG1701 pEG1701 (FIG. 11), contained in EG11204 and EG11037, was constructed by inserting the SphI-PstI fragment containing the cry3Bb gene and the cry1F terminator from pEG911 (Baum, 1994) into the SphI-PstI site of pEG854.9 (Baum et al., 1996), a high copy number *B. thuringiensis*—*E. coli* shuttle vector.

5.18.2 PEG1028 pEG1028 contains the HindIII fragment of cry3Bb from pEG1701 cloned into the multiple cloning site of pTZ18U at HindIII.

5.19 EXAMPLE 19—CONSTRUCTION OF PLASMIDS WITH ALTERED CRY3BB GENES

Plasmid DNA from *E. coli* was prepared by the alkaline lysis method (Maniatis et al., 1982) or by commercial plasmid preparation kits (examples: PERFECTprep™ kit, 5 Prime—3 Prime, Inc., Boulder Colo.; QIAGEN plasmid prep kit, QIAGEN Inc.). *B thuringiensis* plasmids were prepared from cultures grown in brain heart infusion plus 0.5% glycerol (BHIG) to mid logarithmic phase by the alkaline lysis method. When necessary for purification, DNA fragments were excised from an agarose gel following electrophoresis and recovered by glass milk using a Geneclean II® kit (BIO 101 Inc., La Jolla, Calif.). Alteration of the cry3Bb gene was accomplished using several techniques including site-directed mutagenesis, triplex PCR™, quasi-random PCR™ mutagenesis, DNA shuffling and standard recombinant techniques. These techniques are described in Sections 6.1, 6.2, 6.3, 6.4 and 6.5, respectively. The DNA sequences of primers used are listed in Section 7.

5.20 EXAMPLE 20—SITE-DIRECTED MUTAGENESIS

Site-directed mutagenesis was conducted by the protocols established by Kunkle (1985) and Kunkle et al. (1987) using the Muta-Gene™ M13 in vitro mutagenesis kit (BioRad, Richmond, Calif.). Combinations of alterations to cry3Bb were accomplished by using the Muta-Gene™ kit and multiple mutagenic oligonucleotide primers.

5.20.1 PEG1041 pEG1041, contained in EG11032, was constructed using the Muta-Gene™ kit, primer C, and single-stranded pEG1028 as the DNA template. The resulting altered cry3Bb DNA sequence was excised as a PflMI DNA fragment and used to replace the corresponding DNA fragment in pEG1701.

5.20.2 PEG1046 pEG1046, contained in EG11035, was constructed using the Muta-Gene™ kit, primer D, and single-stranded pEG1028 as the DNA template. The resulting altered cry3Bb DNA sequence was excised as a PflMI DNA fragment and used to replace the corresponding DNA fragment in pEG1701.

5.20.3 PEG1047 pEG1047, contained in EG11036, was constructed using the Muta-Gene™ kit, primer E, and single-stranded pEG1028 as the DNA template. The resulting altered cry3Bb DNA sequence was excised as a PflMI DNA fragment and used to replace the corresponding DNA fragment in pEG1701.

5.20.4 PEG1052 pEG1052, contained in EG11046, was constructed using the Muta-Gene™ kit, primers D and E, and single-stranded pEG1028 as the DNA template. The resulting altered cry3Bb DNA sequence was excised as a PflMI DNA fragment and used to replace the corresponding DNA fragment in pEG1701.

5.20.5 PEG1054 pEG1054, contained in EG11048, was constructed using the Muta-Gene™ kit, primer F, and single-stranded pEG1028 as the DNA template. The resulting altered cry3Bb DNA sequence was excised as a PflMI DNA fragment and used to replace the corresponding DNA fragment in pEG1701.

5.20.6 PEG1057 pEG1057, contained in EG11051, was constructed using the Muta-Gene™ kit, primer G, and single-stranded pEG1028 as the DNA template. The resulting altered cry3Bb DNA sequence was excised as a PflMI DNA fragment and used to replace the corresponding DNA fragment in pEG1701.

5.21 EXAMPLE 21—TRIPLEX PCR™

Triplex PCR™ is described by Michael (1994). This method makes use of a thermostable ligase to incorporate a phosphorylated mutagenic primer into an amplified DNA fragment during PCR™. PCR™ was performed on a Perkin Elmer Cetus DNA Thermal Cycler (Perkin-Elmer, Norwalk, Conn.) using a AmpliTaq™ DNA polymerase kit (Perkin-Elmer) and SphI-linearized pEG1701 as the template DNA. PCR™ products were cleaned using commercial kits such as Wizard™ PCR™ Preps (Promega, Madison, Wis.) and QIAquick PCR™ Purification kit (QIAGEN Inc., Chatsworth, Calif.).

5.21.1 PEG1708 AND PEG1709 pEG1708 and pEG1709, contained in EG11222 and EG11223, respectively, were constructed by replacing the PflMI—PflMI fragment of cry3Bb in pEG1701 with PflMI-digested and gel purified PCR™ fragment altered at cry3Bb nucleotide positions 688–690, encoding amino acid Y230. Random mutations were introduced into the Y230 codon by triplex PCR™. Mutagenic primer MVTO95 was phosphorylated and used together with outside primer pair FW001 and FW006. Primer MVT095 also contains a silent mutation at position 687, changing T to C, which, upon incorporation, introduces an additional EcoRI site into pEG1701.

5.21.2 PEG1710, PEG1711 AND PEG1712

Plasmids pEG1710, pEG1711 and pEG1712, contained in EG11224, EG11225 and EG11226, respectively, were created by replacing the PflMI—PflMI fragment of the cry3Bb gene in pEG1701 with PflMI-digested and gel purified PCR™ fragment altered at cry3Bb nucleotide positions 690–692, encoding H231. Random mutations were introduced into the H231 codon by triplex PCR™. Mutagenic primer MVT097 was phosphorylated and used together with outside primer pair FW001 and FW006. Primer MVT097 also contains a T to C sequence change at position 687 which, upon incorporation, results in an additional EcoRI site by silent mutation.

5.21.3 PEG1713 AND PEG1727 pEG1713 and pEG1727, contained in EG11227 and EG11242, respectively, were constructed by replacing the PflMI—PflMI fragment of the cry3Bb gene in pEG1701 with PflMI-digested and gel purified PCR™ fragment altered at cry3Bb nucleotide positions 868–870, encoding amino acid R290. Triplex PCR™ was used to introduce random changes into the R290 codon. The mutagenic primer, MVT091, was designed so that the nucleotide substitutions would result in approximately 36% of the sequences encoding amino acids D or E. MVT091 was phosphorylated and used together with outside primer pair FW001 and FW006.

5.22 EXAMPLE 22—QUASI-RANDOM PCR™ MUTAGENESIS

Quasi-random mutagenesis combines the mutagenic PCR™ techniques described by Vallette et al. (1989), Tomic et al. (1990) and LaBean and Kauffman (1993). Mutagenic primers, sometimes over 70 nucleotides in length, were designed to introduce changes over nucleotide positions encoding for an entire structural region, such as a loop. Degenerate codons typically consisted of a ratio of 82% WT nucleotide plus 6% each of the other 3 nucleotides per position to semi-randomly introduce changes over the target region (LaBean and Kauffman, 1993). When possible, natural restriction sites were utilized; class 2s enzymes were used when natural sites were not convenient (Stemmer and Morris, 1992, list additional restriction enzymes useful to this technique). PCR™ was performed on a Perkin Elmer Cetus DNA Thermal Cycler (Perkin-Elmer, Norwalk, Conn.) using a AmpliTaq™ DNA polymerase kit (Perkin-Elmer) and SphI-linearized pEG1701 as the template DNA. Quasirandom PCR™ amplification was performed using the following conditions: denaturation at 94° C. for 1.5 min.; annealing at 50° C. for 2 min. and extension at 72° C. for 3 min., for 30 cycles. The final 14 extension cycles were extended an additional 25 s per cycle. Primers concentration was 20 μM per reaction or 40 μM for long, mutagenic primers. PCR™ products were cleaned using commercial kits such as Wizard™ PCR™ Preps (Promega, Madison, Wis.) and QIAquick PCR™ Purification kit (QIAGEN Inc., Chatsworth, Calif.). In some instances PCR™ products were treated with Klenow Fragment (Promega) following the manufacturer's instructions to fill in any single base overhangs prior to restriction digestion.

5.22.1 pEG1707

EG1707, contained in EG11221, was constructed by replacing the PflAM—PflMI fragment of the cry3Bb gene in pEG1701 with PflMI-digested and gel purified PCR™ fragment altered at cry3Bb nucleotide positions 460–480, encoding lα3,4 amino acids 154–160. Primer MVT075, which includes a recognition site for the class 2s restriction enzyme BsaI, and primer FW006 were used to introduce changes into this region by quasi-random mutagenesis. Primers MVT076, also containing a BsaI site, and primer FW001 were used to PCR™ amplify a "linker" fragment. Following PCR™ amplification, both products were cleaned, end-filled, digested with BsaI and ligated to each other. Ligated fragment was gel purified and used as template for PCR™ amplification using primer pair FW001 and FW006. PCR™ product was cleaned, digested with PflMI, gel purified and ligated into PflMI-digested and purified pEG1701 vector DNA.

5.22.2 pEG1720 AND pEG1726 pEG1720 and pEG1726, contained in EG11234 and EG11241, respectively, were constructed by replacing the PflMI—PflMI fragment of the cry3Bb gene in pEG1701 with PflMI-digested and gel purified PCR™ fragment altered at cry3Bb nucleotide positions 859–885, encoding lα7,β1 amino acids 287–295. Quasi-random PCR™ mutagenesis was used to introduce changes into this region. Mutagenic primer MVT111, designed with a BsaI site, and primer FW006 were used to introduce the changes. Primer pair MVT094, also containing a BsaI site, and FW001 were used to amplify the linker fragment. The PCR™ products were digested with BsaI, gel purified then ligated to each other. Ligated product was PCR™ amplified using primer pair FW001 and FW006, digested with PflMI.

5.22.3 pEG1714, pEG1715, pEG1716, pEG1718, pEG1719, EG1722, pEG1723, pEG1724 AND pEG1725 pEG1714, pEG1715, pEG1716, pEG1718, pEG1719, pEG1722, pEG1723, pEG1724 and pEG1725, contained in EG11228, EG11229, EG11230, EG11232, EG11233, EG11236, EG11237, EG11238 and EG11239, respectively, were constructed by replacing the PflMI—PflMI fragment of the cry3Bb gene in pEG1701 with PflMI-digested and gel purified PCR™ fragment altered at cry3Bb nucleotide positions 931–954, encoding lβ1,α8 amino acids 311–318. Quasi-random PCR™ mutagenesis was used to introduce changes into this region using mutagenic primer MVT103 and primer FW006. Primers FW001 and FW006 were used to amplify a linker fragment. The PCR™ products were end-filled using Klenow and digested with BamHI. The larger fragment from the FW001–FW006 digest was gel purified then ligated to the digested MVT103-FW006 fragment. Ligated product was gel purified and amplified by PCR™ using primer pair FW001 and FW006. The amplified product was digested with PflMI and gel purified prior to ligation into PflMI-digested and purified pEG1701 vector DNA.

5.22.4 pEG1701.Lβ2.3

Plasmids carrying alterations of cry3Bb WT sequence at nucleotides 1051–1065, encoding structural region lβ2,3 of Cry3Bb, were constructed by replacing the MluI-SpeI fragment of pEG1701 with isolated MluI- and SpeI-digested PCR™ product. The PCR™ product was generated by quasi-random PCR™ mutagenesis were mutagenic primer MVT081 was paired with FW006. These plasmids as a group are designated pEG11701.lβ2,3.

5.22.5 pEG1701.lβ6,7

Plasmids containing mutations of the cry3Bb WT sequence at nucleotides 1234–1248, encoding structural region lβ6,7 of Cry3Bb, were constructed by replacing the MluI-SpeI fragment of pEG1701 with isolated MluI- and SpeI-digested PCR™ product. The PCR™ product was generated by quasi-random PCR™ mutagenesis where mutagenic primer MVT085 was paired with primer WD115. Primer pair MVT089 and WDI 12 were used to amplify a linker fragment. Both PCR™ products were digested with TaqI and ligated to each other. The ligation product was gel purified and PCR™ amplified using primer pair MVT089 and FW006. The amplified product was digested with MluI and SpeI and ligated into MluI and SpeI digested and purified pEG1701 vector DNA. These plasmids as a group are designated pEG1701.lβ6,7.

5.22.6 pEG1701.lβ10,11

Plasmids containing mutated cry3Bb sequences at nucleotides 1450–1467, encoding structural region lβ10,11 of Cry3Bb, were constructed by replacing the SpeI-PstI fragment of pEG1701 with isolated SpeI- and PstI-digested PCR™ product. The PCR™ product was generated by quasi-random PCR™ mutagenesis where mutagenic primer MVT105 was paired with primer MVT070. Primer pair MVT092 and MVT083 were used to generate a linker fragment. (MVT083 is a mutagenic oligo designed for another region. The sequence changes introduced by MVT083 are removed following restriction digestion and do not impact the alteration of cry3Bb in the lβ10,11 region.) Both PCR™ products were digested with BsaI, ligated together, and the ligation product PCR™ amplified with primer pair MVT083 and MVT070. The resulting PCR™ product was digested with SpeI and PstI, and gel purified. These plasmids as a group are designated pEG1701.lβ10,1.

5.23 EXAMPLE 23—DNA SHUFFLING

DNA-shuffling, as described by Stemmer (1994), was used to combine individual alterations in the cry3Bb gene.

5.23.1 pEG1084, pEG1085, pEG1086 AND pEG1087 pEG1084, pEG1085, pEG1086, and pEG1087, contained in EG11081, EG11082, EG11083, and EG11084, respectively, were recovered from DNA-shuffling. Briefly, PflMI DNA fragments were generated using primer set A and B and each of the plasmids pEG1707, pEG1714, pEG1715, pEG1716, pEG1041, pEG1046, pEG1047, and pEG1054 as DNA templates. The resulting DNA fragments were pooled in equal-molar amounts and digested with DNaseI and 50–100 bp DNA fragments were recovered from an agarose gel by three successive freeze-thaw cycles: three min in a dry-ice ethanol bath followed by complete thawing at 50° C. The recovered DNA fragments were assembled by primerless-PCR™ and PCR™-amplified using the primer set A and B as described by Stemmer (1994). The final PCR™-amplified DNA fragments were cut with PflMI and used to replace the corresponding cry3Bb PflMI DNA fragment in pEG1701.

5.24 EXAMPLE 24—RECOMBINANT DNA TECHNIQUES

Standard recombinant DNA procedures were performed essentially as described by Sambrook et al. (1989).

5.24.1 pEG1717 pEG1717, contained in EG11231, was constructed by replacing the small BglII fragment of pEG1710 with the small BglII fragment from pEG1714.

5.24.2 pEG1721 pEG1721, contained in EG11235, was constructed by replacing the small BglII fragment from pEG1710 with the small BglII fragment from pEG1087.

5.24.3 pEG1063 pEG1062, contained in EG11057, was constructed by replacing the NcoI DNA fragment containing ori 43 from pEG1054 with the isolated NcoI DNA fragment containing ori 43 and the alterations in cry3Bb from pEG1046.

5.24.4 pEG1063 pEG1063, contained in EG11058, was constructed by replacing the NcoI DNA fragment containing ori 43 from pEG1054 with the isolated NcoI DNA fragment containing ori 43 and the alterations in cry3Bb from pEG1707.

5.24.5 pEG1095 pEG1095, contained in EG11095, was constructed by replacing the MluI-SpeI DNA fragment in pEG1701 with the corresponding MluI-SpeI DNA fragment from pEG1086.

5.25 EXAMPLE 25—PRIMERS UTILIZED IN CONSTRUCTING CRY3BB* VARIANTS

Shown below are the primers used for site-directed mutagenesis, triplex PCR™ and quasi-random PCR™ to prepare the cry3Bb* variants as described above. Primers were obtained from Ransom Hill Bioscience, Inc. (Ramona, Calif.) and Integrated DNA Technologies, Inc. (Coralville, Iowa.). The specific composition of the primers containing particular degeneracies at one or more residues is given in Section 5.30, Example 30.

5.25.1 PRIMER FW001 (SEQ ID NO:71):
5'-AGACAACTCTACAGTAAAAGATG-3'

5.25.2 PRIMER FW006 (SEQ ID NO:72):
5'-GGTAATTGGTCAATAGAATC-3'

5.25.3 PRIMER MVT095 (SEQ ID NO:73):
5'-CAGAAGATGTTGCTGAATTCNNNCATAGAC AATTAAAAC-3'

5.25.4 PRIMER MVT097 (SEQ ID NO:74):
5'-GATGTTGCTGAATTCTATNNNAGACAATTAAAAC-3'

5.25.5 PRIMER MVT091 (SEQ ID NO:75):
5'-CCCATTTTATGATATTBDNTTATACTCAAAAGG-3'

5.25.6 PRIMER MVT075 (SEQ ID NO:76):
5'-AGCTATGCTGGTCTCGGAAGAAAEFNFFNJF JNFJFJNFINJFJAAAAGAAGCCAAGATCGAAT-3'

5.25.7 PRIMER MVT076 (SEQ ID NO:77):
5'-GGTCACCTAGGTCTCTCTTCCAGGAATTTAACG CATTAAC-3'

5.25.8 PRIMER MVT111 (SEQ ID NO:78):
5'-AGCTATGCTGGTCTCCCATTTJEHIEJEJJEIIKRR JEHEIJEENIIIGTTAAAACAGAACTAAC-3'

5.25.9 PRIMER MVT094 (SEQ ID NO:79):
5'-ATCCAGTGGGGTCTCAAATGGGAAAAGTACA ATTAG-3'

5.25.10 PRIMER MVT103 (SEQ ID NO:80):
5'-CATTTTTACGGATCCAATTTTTJFFFJNEEJEFNF JNFEILEIJEOGGACCAACTTTTTTGAG-3'

5.25.11 PRIMER MVT081 (SEQ ID NO:81):
5'-GAATTTCATACGCGTCTTCAACCTGGTJEHJJJ IINMEEIEJTCTTTCAATTATTGGTCTGG-3'

5.25.12 PRIMER MVT085 (SEQ ID NO:82):
5'-AAAAGTTTATCGAACTATAGCTAATACAGAC GTAGCGGCTJQQFFNEEJIIJEE IGTATATTTAGGTGTTACG-"

5.25.13 PRIMER A (SEQ ID NO:83) 3B2PFLM1:
5'-GGAGTTCCATTTGCTGGGGC-3'

5.25.14 PRIMER B (SEQ ID NO:84) 3B2PFLM2:
5'-ATCTCCATAAAATGGGG-3'

5.25.15 PRIMER C (SEQ ID NO:85) 3B2165DG:
5'-GCGAAGTAAAAGAAGCCAAGGTCGAATAAGGG-3'

5.25.16 PRIMER D (SEQ ID NO:86) 3B2160SKRD:
5'-CCTTTAAGTTTGCGAAATCCACACAGCCAAG GTCGAATAAGGG-3'

5.25.17 PRIMER E (SEQ ID NO:87) 3B2290VP:
5'-CCCATTTTATGATGTTCGGTTATACCCAAAAG GGG-3'

5.25.18 PRIMER F (SEQ ID NO:88) 3B2EDA104:
5'-GGCCAAGTGAAGACCCATGGAAGGC-3'

5.25.19 PRIMER G (SEQ ID NO:89) 3B2KG189:
5'-GCAGTTTCCGGATTCGAAGTGC-3'

5.25.20 PRIMER WD112 (SEQ ID NO:90):
5'-CCGCTACGTCTGTATTA-3'

5.25.21 PRIMER WD115 (SEQ ID NO:91):
5'-ATAATGGAAGCACCTGA-3'

5.25.22 PRIMER MVT105 (SEQ ID NO:92):
5'-AGCTATGCTGGTCTTCTTAEJIFEIIEFFIJFIJII NACAATTCCATTTTTTACTTGG-3'

5.25.23 PRIMER MVT092 (SEQ ID NO:93):
5'-ATCCAGTTGGGTCTCTAAGAAACAAACCGCG TAATTAAGC-3'

5.25.24 PRIMER MVT070 (SEQ ID NO:94):
5'-CCTCAAGGGTTATAACATCC-3'

5.25.25 PRIMER MVT083 (SEQ ID NO:95):
5'-GTACAAAAGCTAAGCTTTIEJIINPEEMEEIJNJESCG AACTATAGCTAATACAG-3'

5.26 EXAMPLE 26—SEQUENCE ANALYSIS OF ALTERED CRY3BB GENES

*E. coli* DH5α™ (GIBCO BRL, Gaithersburg, Md.), JM110 and Sure™ (Stratagene, La Jolla, Calif.) cells were sometimes used amplify plasmid DNA for sequencing. Plasmids were transformed into these cells using the manufacturers' procedures. DNA was sequenced using the Sequenase® 2.0 DNA sequencing kit purchased from U.S. Biochemical Corporation (Cleveland, Ohio). The plasmids described in Section 6, their respective divergence from WT cry3Bb sequence, the resulting amino acid changes and the protein structure site of the changes are listed in Table 11.

TABLE 11

DNA SEQUENCE CHANGES OF CRY3BB* GENES AND RESULTING AMINO ACID SUBSTITUTIONS OF THE CRY3BB* PROTEINS

| Plasmid | cry3Bb* DNA Sequence | Cry3Bb* Amino Acid Sequence | Structual Site of Alteration |
|---|---|---|---|
| pEG1707 | A460T, C461T, A462T, C464A, T465C, T466C, T467A, A468T, A469T, G470C, T472C, T473G, G474T, A477T, A478T, G479C | T154F, P155H, L156H, L158R | 1α3, 4 |
| pEG1708 | T687C, T688C, A689T, C691A, A692G | Y230L, H231S | α6 |
| pEG1709 | T667C, T687C, T688A, A689G, C691A, A692G | S223P, Y230S | α6 |
| pEG1710 | T687C, A692G | H231R | α6 |
| pEG1711 | T687C, C691A | H231N, T241S | α6 |
| pEG1712 | T687C, C691A, A692C, T693C | H231T | α6 |
| pEG1713 | C868A, G869A, G870T | R290N | 1α7, β1 |
| pEG1714 | C932T, A938C, T942G, G949A, T954C | S311L, N313T, E317K | 1β1, α8 |
| pEG1715 | T931A, A933C, T942A, T945A, G949A, A953G, T954C | S311T, E317K, Y318C | 1β1, α8 |
| pEG1716 | T931G, A933C, C934G, T945G, C946T, A947G, G951A, T954C | S311A, L312V, Q316W | 1β1, α8 |
| pEG1717 | T687C, A692G, C932T, A938C, T942G, G949A, T954C | H231R, S311L, N313T, E317K | α6, 1β1, α8 |
| pEG1718 | T931A, A933G, T935C, T936A, A938C, T939C, T942C, T945A, G951T, T954C | S311T, L312P, N313T, E317N | 1β1, α8 |
| pEG1719 | T931G, A933C, T936G, T942C, C943T, T945A, C946G, G948C, T954C | S311A, Q316D | 1β1, α8 |
| pEG1720 | T861C, T866C, C868A, T871C, T872G, A875T, T877A, C878G, A882G | I289T, L291R, Y292F, S293R | 1α7, β1 |
| pEG1721 | T687C, A692G, C932T | H231R, S311L | α6, 1β1, α8 |
| pEG1722 | T931A, C932T, A933C, T936C, T942G, T945A, T954C | S311I | 1β1, α8 |
| pEG1723 | T931A, C932T, A933C, T936C, A937G, A938T, C941A, T942C, T945A, C946A, A947T, A950T, T954C | S311I, N313H | 1β1, α8 |
| pEG1724 | A933C, T936C, A937G, A938T, C941A, T942C, T945A, C946A, A947T, A950T, T954C | N313V, T314N, Q316M, E317V | 1β, α8 |
| pEG1725 | A933T, A938G, T939G, T942A, T944C, T945A, A947T, G948T, A950C, T954C | N313R, L315P, Q316L, E317A | 1β1, α8 |
| pEG1726 | A860T, T861C, G862A, C868T, G869T, T871C, A873T, T877A, C878G, A879T | Y287F, D288N, R290L | 1α7, β1 |
| pEG1727 | C868G, G869T | R290V | 1α7, β1 |
| pEG1041 | A494G | D165G | α4 |
| pEG1046 | G479A, A481C, A482C, A484C, G485A, A486C, A494G | S160N, K161P, P162H, D165G | α4 |
| pEG1047 | A865G, T877C | I289V, S293P | 1α7, β1 |
| pEG1052 | G479A, A481C, A482C, A484C, G485A, A486C, A494G, A865G, T877C | S160N, K161P, P162H, D165G, I289V, S293P | α4, 1α7, β1 |
| pEG1054 | T309A, Δ310, Δ311, Δ312 | D103E, ΔA104 | 1α2α, 2b |
| pEG1057 | A565G, A566G | K189G | 1α4, 5 |
| pEG1062 | T309A, Δ310, Δ311, Δ312, G479A, A481C, A482C, A484C, G485A, A486C, A494G | D103E, ΔA104, S160N, K161P, P162H, D165G | 1α2a, 2b α4 |
| pEG1063 | T309A, Δ310, Δ311, Δ312, A460T, C461T, A462T, C464A, T465C, T466C, T467A, A468T, A469T, G470C, T472C, T473G, G474T, A477T, A478T, G479C | D103E, ΔA104, T154F, P155H, L156H, L158R | 1α2a, 2b 1α3, 4 |
| pEG1084 | A494G, T931A, A933C, T942A, T945A, G949A, T954C | D165G, S311T, E317K | α4, 1β1, α8 |
| pEG1085 | A494G, A865G, T877C, T914C, T931G, A933C, C934G, T945G, C946T, A947G, G951A, T954C, A1043G, T1094C | D165G, I289V, S293P, F305S, S311A, L312V, Q316W, Q348R, V365A | α4, 1α7, β1 β1, 1β1, α8 β2, β3b |
| pEG1086 | A865G, T877C, A1043G | I289V, S293P, Q348R | 1α7, β1, β2 |
| pEG1087 | A494G, C932T | D165G, S311L | α4, 1β1, α8 |
| pEG1095 | A1043G | Q348R | β2 |

5.27 EXAMPLE 27—EXPRESSION OF CRY3BB* PROTEINS 5.27.1 CULTURE CONDITIONS

LB agar was prepared using a standard formula (Maniatis et al., 1982). Starch agar was obtained from Difco Laboratories (Detroit, Mich.) and supplemented with an additional 5 g/l of agar. C2 liquid medium is described by Donovan et al. (1988). C2 medium was sometimes prepared without the phosphate buffer (C2-P). All cultures were incubated at 25° C. to 30° C.; liquid cultures were also shaken at 250 rpm, until sporulation and lysis had occurred.

5.27.2 TRANSFORMATION CONDITIONS pEG1701 and derivatives thereof were introduced into acrystalliferious *B. thuringiensis* var. *kurstaki* EG7566 (Baum, 1994) or EG10368 (U.S. Pat. No. 5,322,687) by the electroporation method of Macaluso and Mettus (1991). In some cases, the method was modified as follows to maximize the number of transformants. The recipient *B. thuringiensis* strain was inoculated from overnight growth at 30° C. on LB agar into brain heart infusion plus 0.5% glycerol, grown to an optical density of approximately 0.5 at 600 nm, chilled on ice for 10 min, washed 2× with EB and resuspended in a 1/50 volume of EB. Transformed cells were selected on LB agar or starch agar plus 5 μg/ml chloramphenicol. Visual screening of colonies was used to identify transformants producing crystalline protein; those colonies were generally more opaque than colonies that did not produce crystalline protein.

5.27.3 STRAIN AND PROTEIN DESIGNATIONS

A transformant containing an altered cry3Bb* gene encoding an altered Cry3Bb* protein is designated by an "EG" number, e.g., EG11231. The altered Cry3Bb* protein is designated Cry3Bb followed by the strain number, e.g., Cry3Bb.11231. Collections of proteins with alterations at a structural site are designated Cry3Bb followed by the structural site, e.g., Cry3Bb.1β2,3. Table 12 lists the plasmids pertinent to this invention, the new B. thuringiensis strains containing the plasmids, the acrystalliferous B. thuringiensis recipient strain used, and the proteins produced by the new strains.

5.28 EXAMPLE 28—GENERATION AND CHARACTERIZATION OF CRY3BB-60

5.28.1 GENERATION OF CRY3BB-60

Cry3Bb-producing strain EG7231 (U.S. Pat. No. 5,187, 091) was grown in C2 medium plus 3 mg/ml chloramphenicol. Following sporulation and lysis, the culture was washed with water and Cry3Bb protein purified by the NaBr solubilization and recrystallization method of Cody et al. (1992). Protein concentration was determined by BCA Protein Assay (Pierce, Rockford, Ill.). Recrystallized protein was solubilized in 10 ml of 50 mM KOH per 100 mg of Cry3Bb protein and buffered to pH 9.0 with 100 mM CAPS (3-[cyclohexylamino]-1-propanesulfonic acid), pH 9.0. The soluble toxin was treated with trypsin at a weight ratio of 50 mg toxin to 1 mg trypsin for 20 min to overnight at room temperature. Trypsin cleaves proteins on the carboxyl side of available arginine and lysine residues. For 8-dose bioassay, the solubilization conditions were altered slightly to increase the concentration of protein: 50 mM KOH was added dropwise to 2.7 ml of a 12.77 mg/ml suspension of purified Cry3Bb* until crystal solubilization occurred. The volume was then adjusted to 7 ml with 100 mM CAPS, pH 9.0.

TABLE 12

PLASMIDS CARRYING ALTERED CRY3BB* GENE TRANSFORMED INTO B. THURINGIENSIS FOR EXPRESSION OF ALTERED CRY3BB* PROTEINS

| Plasmid Designation | New BT Strain | Expressed Protein |
|---|---|---|
| pEG1701 | EG11204 | WT Cry3Bb |
| pEG1701 | EG11037 | WT Cry3Bb |
| pEG1707 | EG11221 | Cry3Bb.11221 |
| pEG1708 | EG11222 | Cry3Bb.11222 |
| pEG1709 | EG11223 | Cry3Bb.11223 |
| pEG1710 | EG11224 | Cry3Bb.11224 |
| pEG1711 | EG11225 | Cry3Bb.11225 |
| pEG1712 | EG11226 | Cry3Bb.11226 |
| pEG1713 | EG11227 | Cry3Bb.11227 |
| pEG1714 | EG11228 | Cry3Bb.11228 |
| pEG1715 | EG11229 | Cry3Bb.11229 |
| pEG1716 | EG11230 | Cry3Bb.11230 |
| pEG1717 | EG11231 | Cry3Bb.11231 |
| pEG1718 | EG11232 | Cry3Bb.11232 |
| pEG1719 | EG11233 | Cry3Bb.11233 |
| pEG1720 | EG11234 | Cry3Bb.11234 |
| pEG1721 | EG11235 | Cry3Bb.11235 |
| pEG1722 | EG11236 | Cry3Bb.11236 |
| pEG1723 | EG11237 | Cry3Bb.11237 |
| pEG1724 | EG11238 | Cry3Bb.11238 |
| pEG1725 | EG11239 | Cry3Bb.11239 |
| pEG1726 | EG11241 | Cry3Bb.11241 |
| pEG1727 | EG11242 | Cry3Bb.11242 |
| pEG1041 | EG11032 | Cry3Bb.11032 |
| pEG1046 | EG11035 | Cry3Bb.11035 |
| pEG1047 | EG11036 | Cry3Bb.11036 |
| pEG1052 | EG11046 | Cry3Bb.11046 |
| pEG1054 | EG11048 | Cry3Bb.11048 |
| pEG1057 | EG11051 | Cry3Bb.11051 |
| pEG1062 | EG11057 | Cry3Bb.11057 |
| pEG1063 | EG11058 | Cry3Bb.11058 |
| pEG1084 | EG11081 | Cry3Bb.11081 |
| pEG1085 | EG11082 | Cry3Bb.11082 |
| pEG1086 | EG11083 | Cry3Bb.11083 |
| pEG1087 | EG11084 | Cry3Bb.11084 |
| pEG1095 | EG11095 | Cry3Bb.11095 |
| pEG1098 | EG11098 | Cry3Bb.11098 |
| pEG1701.1β2, 3 | collection of unnamed strains | Cry3Bb.1β2, 3 |
| pEG1701.1β6, 7 | collection of unnamed strains | Cry3Bb.1β6, 7 |
| pEG1701.1β10, 11 | collection of unnamed strains | Cry3Bb.1β10, 11 |

5.28.2 DETERMINATION OF MOLECULAR WEIGHT OF CRY3BB-60

The molecular weight of the predominant trypsin digestion fragment of Cry3Bb was determined to be 60 kDa by SDS-polyacrylamide gel electrophoresis (SDS-PAGE) analysis using commercial molecular weight markers. This digestion fragment is designated Cry3Bb-60. No further digestion of the 60 kDa cleavage product was observed.

5.28.3 DETERMINATION OF NH$_2$-TERMINUS OF CRY3BB-60

To determine the NH$_2$-terminal sequence of Cry3Bb-60, the trypsin digest was fractionated by SDS-PAGE and transferred to Immobilon™-P membrane (Millipore Corporation, Bedford, Mass.) following standard western blotting procedures. After transfer, the membrane was rinsed twice with water then stained with 0.025% Coomassie Brilliant Blue R-250 plus 40% methanol for 5 min, destained with 50% methanol and rinsed in water. The Cry3Bb.60 band was excised with a razor blade. NH$_2$-terminal sequencing was performed at the Tufts Medical School, Department of Physiology (Boston, Mass.) using standard automated Edman degradation procedures. The NH$_2$-terminal amino acid sequence was determined to be SKRSQDR (SEQ ID NO:96), corresponding to amino acids 160–166 of Cry3Bb. Trypsin digestion occurred on the carboxyl side of amino acid R159 resulting in the removal of helices 1–3.

5.29 EXAMPLE 29—BIOACTIVITY OF CRY3BB* PROTEINS

5.29.1 CULTURE CONDITIONS AND PROTEIN CONCENTRATION DETERMINATION

Cultures for 1-dose bioassays were grown in C2-P plus 5 μg/ml chloramphenicol (C2-P/cm5) then diluted with 3 volumes of 0.005% Triton X-100®. The protein concentrations of these cultures were not determined. Cultures for 8-dose bioassays were grown in C2/cm5, washed 1–2 times with 1–2 volumes of sterile water and resuspended in 1/10 volume of sterile 0.005% Triton X-100®. The toxin protein concentration of each concentrate was determined as described by Brussock and Currier (1990), omitting the treatment with 3 M HEPES. The protein concentration was adjusted to 3.2 mg/ml in 0.005% Triton X-100® for the top dose of the assay. Cry3Bb.60 was produced and quantified for 8-dose assay as described in Section 9.1.

5.29.2 INSECT BIOASSAYS

*Diabrotica undecimpunctata howardi* Barber (southern corn rootworm or SCRW) and *Diabrotica virgifera virgifera* LeConte (western corn rootworm or WCRW) larvae were reared as described by Slaney et al. (1992). Eight-dose assays and probit analyses were performed as described by Slaney et al. (1992). Thirty-two larvae were tested per dose at 50 μl of sample per well of diet (surface area of 175 mm²). Positive controls were WT Cry3Bb-producing strains EG11037 or EG11204. All bioassays were performed using 128-well trays containing approximately 1 ml of diet per well with perforated mylar sheet covers (C-D International Inc., Pitman, N.J.). One-dose assays were performed essentially the same except only 1 dose was tested per strain. All assay were replicated at least twice.

5.29.3 INSECT BIOASSAY RESULTS: 1-DOSE ASSAYS AGAINST SCRW

Results from 1-dose assays are expressed as the relative mortality (RM) of the experimental strain compared to WT (% mortality of experimental culture divided by % mortality of WT culture). Altered and improved Cry3Bb proteins derived from plasmids constructed using PCR™ methods introducing random or semi-random changes into the cry3Bb gene sequence were distinguished from other altered but not improved Cry3Bb proteins by replicated, 1-dose assay against SCRW larvae. Those proteins showing increased activity (defined as RM≧1.5) compared to WT Cry3Bb or, in the case of proteins with combinations of altered sites, compared to a "parental" altered Cry3Bb protein were further characterized by 8-dose assay. The overall RM "pattern" produced by 1-dose assay results from a collection of proteins carrying random or semi-random alterations within a single structural region, e.g., in 1β2,3, can be used to determine if that structural region is important for bioactivity. Retention of WT levels of activity (RM≈1) indicate changes are tolerated in that region. Overall loss of activity (RM<1) distinguishes the region as important for bioactivity.

5.29.4 CRY3BB.1β2,3: RESULTS OF 1-DOSE BIOASSAYS AGAINST SCRW

Cry3Bb.1β2.3 protein are a collection of proteins altered in the 1β2,3 region of Cry3Bb (see Section 5.3.4). Typical results of 1-dose assays of these altered proteins are shown in FIG. 12. The RM values for Cry3Bb.1β2,3 proteins are less than 1, with a few exceptions of values close to 1, indicating that this region is important for toxicity.

5.29.5 CRY3BB.1β6,7: RESULTS OF 1-DOSE BIOASSAYS AGAINST SCRW

Cry3Bb.1β6,7 proteins are a collection of proteins altered in the 1β6,7 region of Cry3Bb (see Section 5.3.5). Typical results of 1-dose assays of these altered proteins are shown in FIG. 13. With a few exceptions of values close to 1, the RM values for Cry3Bb.1β6,7 proteins are less than 1, indicating that this region is important for toxicity.

5.29.6 CRY3BB.1β10,11: RESULTS OF 1-DOSE BIOASSAYS AGAINST SCRW

Cry3Bb.1β10,11 proteins are a collection of proteins altered in the 1β10,11 region of Cry3Bb (see Section 5.3.6). Typical results of 1-dose assays of these altered proteins are shown in FIG. 14. With a few exceptions of values close to 1, the RM values for Cry3Bb.1β10,11 proteins are less than 1, indicating that this region is important for bioactivity.

5.29.7 INSECT BIOASSAY RESULTS: RESULTS OF 8-DOSE ASSAYS AGAINST SCRW

Results from 8-dose assays are expressed as an $LC_{50}$ value (protein concentration giving 50% mortality) with 95% confidence intervals. The $LC_{50}$ values with 95% confidence intervals of altered Cry3Bb proteins showing improved activities against SCRW larvae and $LC_{50}$ values of the WT Cry3Bb control determined at the same time are listed in Table 13 along with the fold increase over WT activity for each improved protein.

TABLE 13

DESIGNED CRY3BB PROTEINS WERE TESTED AGAINST SCRW LARVAE IN REPLICATED, 8-DOSE ASSAYS TO DETERMINE THE $LC_{50}$ VALUES

| | $LC_{50}$ μg/well (95% C.I.) | | Fold |
|---|---|---|---|
| Improved Protein | Improved Protein | WT Cry3Bb Control | Increase Over WT Activity |
| Cry3Bb.60 | 6.7 (5.3–8.4) | 24.1 (15–39) | 3.6× |
| Cry3Bb.11221 | 3.2 (2.5–4) | 20.5 (14.5–29) | 6.4× |
| Cry3Bb.11222 | 7.3 (6–9) | 29.4 (23–37) | 4.0× |
| Cry3Bb.11223 | 10.5 (9–12) | 29.4 (23–37) | 2.8× |
| Cry3Bb.11224 | 6.5 (5.1–8.2) | 32.5 (25–43) | 5.0× |
| Cry3Bb.11225 | 13.7 (11–16.8) | 49.5 (39–65) | 3.6× |
| Cry3Bb.11226 | 16.7 (10.6–24.2) | 49.5 (39–65) | 3.0× |
| Cry3Bb.11227 | 11.1 (9.1–13.5) | 21.3 (16–28) | 1.9× |
| Cry3Bb.11228 | 8.0 (6.6–9.8) | 32.9 (25–45) | 4.1× |
| Cry3Bb.11229 | 7.2 (5.8–8.8) | 18.2 (15–22) | 2.5× |
| Cry3Bb.11230 | 7.0 (5.8–8.6) | 32.9 (25–45) | 4.7× |
| Cry3Bb.11231 | 3.3 (3.0–3.7) | 26.1 (22–31) | 7.9× |
| Cry3Bb.11232 | 6.4 (5.4–7.7) | 32.9 (25–45) | 5.1× |
| Cry3Bb.11233 | 15.7 (12–20) | 32.9 (25–45) | 2.2× |
| Cry3Bb.11234 | 7 (6–9) | 29 (22–39) | 4.1× |
| Cry3Bb.11235 | 4.2 (3.6–4.9) | 13.3 (10–17) | 3.2× |
| Cry3Bb.11236 | 11.6 (9–15) | 36.4 (27–49) | 3.1× |
| Cry3Bb.11237 | 6.8 (4–11) | 36.4 (27–49) | 5.4× |
| Cry3Bb.11238 | 13.9 (11–17) | 36.4 (27–49) | 2.6× |
| Cry3Bb.11239 | 13.0 (10–16) | 36.4 (27–49) | 2.8× |
| Cry3Bb.11241 | 11 (7–16) | 29 (22–39) | 2.6× |
| Cry3Bb.11242 | 11.9 (9.2–16) | 30 (23–38) | 2.5× |
| Cry3Bb.11032 | 4.2 (3.6–4.9) | 13.3 (10–17) | 3.1× |
| Cry3Bb.11035 | 10.3 (8–13) | 27.9 (23–34) | 2.7× |
| Cry3Bb.11036 | 6.5 (5.1–7.9) | 27.9 (23–34) | 4.3× |
| Cry3Bb.11046 | 12.1 (8–19) | 31.2 (25–39) | 2.6× |
| Cry3Bb.11048 | 8.3 (6–11) | 35.4 (24–53) | 4.3× |
| Cry3Bb.11051 | 11.8 (8–16) | 35.4 (24–53) | 3.0× |
| Cry3Bb.11057 | 8.8 (7–11) | 29.5 (24–36) | 3.4× |
| Cry3Bb.11058 | 9.6 (6–14) | 33.4 (27–43) | 3.5× |
| Cry3Bb.11081 | 8.5 (7–11) | 51.5 (37–79) | 6.1× |
| Cry3Bb.11082 | 10.6 (8–13) | 51.5 (37–79) | 4.9× |
| Cry3Bb.11083 | 7.0 (5–10) | 51.5 (37–79) | 7.4× |
| Cry3Bb.11084 | 7.2 (4–12) | 51.5 (37–79) | 7.2× |
| Cry3Bb.11095 | 11.1 (9–14) | 51.5 (37–79) | 4.6× |
| Cry3Bb.11098 | | | |

5.29.8 INSECT BIOASSAY RESULTS: 8-DOSE ASSAYS AGAINST WCRW

WCRW larvae are delicate and difficult to work with. Therefore, only some of the designed Cry3Bb showing improved activity against SCRW larvae were also tested against WCRW larvae in 8-dose assays. The $LC_{50}$ determinations for the designed Cry3Bb proteins are shown in Table 14 along with the $LC_{50}$ values of the WT Cry3Bb control determined at the same time.

TABLE 14

CRY3BB* PROTEINS SHOWING IMPROVED ACTIVITY AGAINST SCRW LARVAE ALSO SHOW IMPROVED ACTIVITY AGAINST WCRW LARVAE

| | LC$_{50}$ µg/well (95% C.I.) | | |
|---|---|---|---|
| Improved Protein | Improved Protein | WT Cry3Bb Control | Fold Increase Over WT Activity |
| EG11083 | 6.3 (4.7–8.2) | 63.5 (46–91) | 10.1× |
| EG11230 | 4.5 (2.1–7.4) | 24.2 (13–14) | 5.4× |
| EG11231 | 2.5 (1.7–3.6) | 32.2 (14–67) | 12.9× |

5.30 EXAMPLE 30—CHANNEL ACTIVITY

Ion channels produced by Cry3Bb and some of its derivatives were measured by the methods described by Slatin et al. (1990). In some instances, lipid bilayers were prepared from a mixture of 4:1 phophatidylethanolamine (PE) : phosphatidylcholine (PC). Toxin protein was solubilized from washed, C2 medium, *B. thuringiensis* cultures with 12 mM KOH. Following centrifugation to remove spores and other debris, 10 µg of soluble toxin protein was added to the cis compartment (4.5 ml volume) of the membrane chamber. Protein concentration was determined using the BCA Protein Assay (Pierce).

5.30.1 CHANNEL ACTIVITY OF WT CRY3BB.

Upon exposure to black lipid membranes, Cry3Bb forms ion channels with various conductance states. The channels formed by Cry3Bb are rarely discrete channels with well resolved open and closed states and usually require incubation of the toxin with the membrane for 30–45 min before any channel-like events are observed. After formation of the initial conductances, the size increases from approximately 200 pS to over 10,000 pS over 2–3 h. Only the small conductances ($\leq$200 pS) are voltage dependent. Over 200 pS, the conductances are completely symmetric. Cry3Bb channels also exhibit β-mercaptoethanol-dependent activation, growing from small channel conductances of ~200 pS to several thousand pS within 2 min of the addition of β-mercaptoethanol to the cis compartment of the membrane chamber.

5.30.2 CRY3BB.11032

The channel activity of Cry3Bb.11032 is much like WT Cry3Bb when the solubilized toxin protein is added to the cis compartment of the membrane chamber. However, when this protein is artificially incorporated into the membrane by forming or "painting" the membrane in the presence of the Cry3Bb.11032 protein, a 16-fold increase in the initial channel conductances is observed (~4000 pS). This phenomenon is not observed with WT Cry3Bb.

5.30.3 CRY3BB.11035

Upon exposure to artificial membranes, the Cry3Bb.11035 protein spontaneously forms channels that grow to large conductances within a relatively short time span (~5 min). Conductance values ranges from 3000–6000 pS and, like WT Cry3Bb, are voltage dependent at low conductance values.

5.30.4 CRY3BB.11048

The Cry3Bb.11048 protein is quite different than WT Cry3Bb in that it appears not to form channels at all, but, rather, forms symmetrical pores with respect to voltage. Once the pore is formed, it remains open and allows a steady conductance ranging from 25 to 130 pS.

5.30.5 CRY3BB.11224 AND CRY3BB.11226

The metal binding site of WT Cry3Bb formed by H231 in the dimer structure was removed in proteins Cry3Bb.11224 and Cry3Bb.11226. The conductances formed by both designed proteins are identical to that of WT Cry3Bb with the exception that neither of the designed proteins exhibits β-mercaptoethanol-dependent activation.

5.30.6 CRY3BB.11221

Cry3Bb.11221 protein has been observed to immediately form small channels of 100–200 pS with limited voltage dependence. Some higher conductances were observed at the negative potential. In other studies, the onset of activity was delayed by 27 min, which is more typical for WT Cry3Bb. Unlike WT Cry3Bb, however, Cry3Bb.11221 forms well resolved, 600 pS channels with long open states. The protein eventually reaches conductances of 7000 pS.

5.30.7 CRY3BB.11242

Cry3Bb.11242 protein forms small conductances immediately upon exposure to an artificial membrane. The conductances grow steadily and rapidly to 6000 pS in approximately 3 min. Some voltage dependence was noted with a preference for a negative imposed voltage.

5.30.8 CRY3BB.11230

Unlike WT Cry3Bb, Cry3Bb.11230 forms well resolved channels with long open states that do not continue to grow in conductance with time. The maximum observed channel conductances reached 3000 pS. FIG. 15 illustrates the difference between the channels formed by Cry3Bb and Cry3Bb.11230.

5.30.9 CRY3BB.60

Cry3Bb.60 forms well resolved ion channels within 20 min of exposure to an artificial membrane. These channels grow in conductance and frequency with time. The behavior of Cry3Bb.60 in a planar lipid bilayer differs from Cry3Bb in two significant ways. The conductances created by Cry3Bb.60 form more quickly than Cry3Bb and, unlike Cry3Bb, the conductances are stable, having well resolved open and closed states definitive of stable ion channels (FIG. 16).

5.31 EXAMPLE 31—PRIMER COMPOSITIONS

TABLE 15

| SEQ ID NO: 83 | % of Nucleotide in mixture | | | |
|---|---|---|---|---|
| Code | A | T | G | C |
| N | 25 | 25 | 25 | 25 |

TABLE 16

| SEQ ID NO: 84 | % of Nucleotide in mixture | | | |
|---|---|---|---|---|
| Code | A | T | G | C |
| N | 25 | 25 | 25 | 25 |

TABLE 17

| SEQ ID NO: 85 | % of Nucleotide in mixture | | | |
|---|---|---|---|---|
| Code | A | T | G | C |
| B | 16 | 16 | 52 | 16 |
| D | 70 | 10 | 10 | 10 |
| N | 25 | 25 | 25 | 25 |

TABLE 18

| SEQ ID NO: 86 | % of Nucleotide in mixture | | | |
|---|---|---|---|---|
| Code | A | T | G | C |
| E | 82 | 6 | 6 | 6 |
| F | 6 | 6 | 6 | 82 |
| J | 6 | 82 | 6 | 6 |
| I | 6 | 6 | 82 | 6 |
| N | 25 | 25 | 25 | 25 |

TABLE 19

| SEQ ID NO: 88 | % of Nucleotide in mixture | | | |
|---|---|---|---|---|
| Code | A | T | G | C |
| J | 6 | 82 | 6 | 6 |
| E | 82 | 6 | 6 | 6 |
| H | 1 | 1 | 1 | 97 |
| I | 6 | 6 | 82 | 6 |
| K | 15 | 15 | 15 | 55 |
| R | 15 | 55 | 15 | 15 |

TABLE 20

| SEQ ID NO: 90 | % of Nucleotide in mixture | | | |
|---|---|---|---|---|
| Code | A | T | G | C |
| J | 6 | 82 | 6 | 6 |
| F | 6 | 6 | 6 | 82 |
| N | 25 | 25 | 25 | 25 |
| E | 82 | 6 | 6 | 6 |
| I | 6 | 6 | 82 | 6 |
| L | 8 | 1 | 83 | 8 |
| O | 1 | 1 | 1 | 97 |

TABLE 21

| SEQ ID NO: 91 | % of Nucleotide in mixture | | | |
|---|---|---|---|---|
| Code | A | T | G | C |
| J | 6 | 82 | 6 | 6 |
| E | 82 | 6 | 6 | 6 |
| H | 1 | 1 | 1 | 97 |
| I | 6 | 6 | 82 | 6 |
| N | 25 | 25 | 25 | 25 |
| M | 82 | 2 | 8 | 8 |

TABLE 22

| SEQ ID NO: 92 | % of Nucleotide in mixture | | | |
|---|---|---|---|---|
| Code | A | T | G | C |
| J | 6 | 82 | 6 | 6 |
| Q | 0 | 9 | 82 | 9 |
| F | 6 | 6 | 6 | 82 |
| N | 25 | 25 | 25 | 25 |
| E | 82 | 6 | 6 | 6 |
| J | 6 | 6 | 82 | 6 |

TABLE 23

| SEQ ID NO: 92 | % of Nucleotide in mixture | | | |
|---|---|---|---|---|
| Code | A | T | G | C |
| J | 6 | 82 | 6 | 6 |
| F | 6 | 6 | 6 | 82 |
| N | 25 | 25 | 25 | 25 |
| E | 82 | 6 | 6 | 6 |
| I | 6 | 6 | 82 | 6 |

TABLE 24

| SEQ ID NO: 92 | % of Nucleotide in mixture | | | |
|---|---|---|---|---|
| Code | A | T | G | C |
| J | 6 | 82 | 6 | 6 |
| N | 25 | 25 | 25 | 25 |
| E | 82 | 6 | 6 | 6 |
| I | 6 | 6 | 82 | 6 |
| M | 82 | 2 | 8 | 8 |
| P | 8 | 2 | 8 | 82 |
| S | 1 | 97 | 1 | 1 |

5.32 EXAMPLE 32—ATOMIC COORDINATES FOR CRY3BB

The atomic coordinates of the Cry3Bb protein are given in the Appendix included in Section 9.1

5.33 EXAMPLE 33—ATOMIC COORDINATES FOR CRY3A

The atomic coordinates of the Cry3A protein are given in the Appendix included in Section 9.2

5.34 EXAMPLE-34—MODIFICATION OF CRY GENES FOR EXPRESSION IN PLANTS

Wild-type cry genes are known to be expressed poorly in plants as a full length gene or as a truncated gene. Typically, the G+C content of a cry gene is low (37%) and often contains many A+T rich regions, potential polyadenylation sites and numerous ATTTA sequences. Table 25 shows a list of potential polyadenylation sequences which should be avoided when preparing the "plantized" gene construct.

TABLE 25

LIST OF SEQUENCES OF THE POTENTIAL POLYADENYLATION SIGNALS

| | |
|---|---|
| AATAAA* | AAGCAT |
| AATAAT* | ATTAAT |
| AACCAA | ATACAT |
| ATATAA | AAAATA |
| AATCAA | ATTAAA** |
| ATACTA | AATTAA** |
| ATAAAA | AATACA** |
| ATGAAA | CATAAA** |

*indicates a potential major plant polyadenylation site.
**indicates a potential minor animal polyadenylation site.
All others are potential minor plant polyadenylation sites.

The regions for mutagenesis may be selected in the following manner. All regions of the DNA sequence of the cry gene are identified which contained five or more consecutive base pairs which were A or T. These were ranked in terms of length and highest percentage of A+T in the surrounding sequence over a 20–30 base pair region. The DNA is analysed for regions which might contain polyadenylation sites or ATTTA sequences. Oligonucleotides are then designed which maximize the elimination of A+T consecutive regions which contained one or more polyadenylation sites or ATTTA sequences. Two potential plant polyadenylation sites have been shown to be more critical based on published reports. Codons are selected which increase G+C content, but do not generate restriction sites for enzymes useful for cloning and assembly of the modified gene (e.g., BamHI, BglII, SacI, NcoI, EcoRV, etc.). Likewise condons are avoided which contain the doublets TA or GC which have been reported to be infrequently-found codons in plants.

Although the CaMV35S promoter is generally a high level constitutive promoter in most plant tissues, the expression level of genes driven the CaMV35S promoter is low in floral tissue relative to the levels seen in leaf tissue. Because the economically important targets damaged by some insects are the floral parts or derived from floral parts (e.g., cotton squares and bolls, tobacco buds, tomato buds and fruit), it is often advantageous to increase the expression of crystal proteins in these tissues over that obtained with the CaMV35S promoter.

The 35S promoter of Figwort Mosaic Virus (FMV) is analogous to the CaMV35S promoter. This promoter has been isolated and engineered into a plant transformation vector. Relative to the CaMV promoter, the FMV 35S promoter is highly expressed in the floral tissue, while still providing similar high levels of gene expression in other tissues such as leaf. A plant transformation vector, may be constructed in which the full length synthetic cry gene is driven by the FMV 35S promoter. Tobacco plants may be transformed with the vector and compared for expression of the crystal protein by Western blot or ELISA immunoassay in leaf and floral tissue. The FMV promoter has been used to produce relatively high levels of crystal protein in floral tissue compared to the CaMV promoter.

5.35 EXAMPLE 35—EXPRESSION OF SYNTHETIC CRY GENES WITH ssRUBISCO PROMOTERS AND CHLOROPLAST TRANSIT PEPTIDES

The genes in plants encoding the small subunit of RUBISCO (SSU) are often highly expressed, light regulated and sometimes show tissue specificity. These expression properties are largely due to the promoter sequences of these genes. It has been possible to use SSU promoters to express heterologous genes in transformed plants. Typically a plant will contain multiple SSU genes, and the expression levels and tissue specificity of different SSU genes will be different. The SSU proteins are encoded in the nucleus and synthesized in the cytoplasm as precursors that contain an N-terminal extension known as the chloroplast transit peptide (CTP). The CTP directs the precursor to the chloroplast and promotes the uptake of the SSU protein into the chloroplast. In this process, the CTP is cleaved from the SSU protein. These CTP sequences have been used to direct heterologous proteins into chloroplasts of transformed plants.

The SSU promoters might have several advantages for expression of heterologous genes in plants. Some SSU promoters are very highly expressed and could give rise to expression levels as high or higher than those observed with the CaMV35S promoter. The tissue distribution of expression from SSU promoters is different from that of the CaMV35S promoter, so for control of some insect pests, it may be advantageous to direct the expression of crystal proteins to those cells in which SSU is most highly expressed. For example, although relatively constitutive, in the leaf the CaMV35S promoter is more highly expressed in vascular tissue than in some other parts of the leaf, while most SSU promoters are most highly expressed in the mesophyll cells of the leaf. Some SSU promoters also are more highly tissue specific, so it could be possible to utilize a specific SSU promoter to express the protein of the present invention in only a subset of plant tissues, if for example expression of such a protein in certain cells was found to be deleterious to those cells. For example, for control of Colorado potato beetle in potato, it may be advantageous to use SSU promoters to direct crystal protein expression to the leaves but not to the edible tubers.

Utilizing SSU CTP sequences to localize crystal proteins to the chloroplast might also be advantageous. Localization of the *B. thuringiensis* crystal proteins to the chloroplast could protect these from proteases found in the cytoplasm. This could stabilize the proteins and lead to higher levels of accumulation of active toxin. cry genes containing the CTP could be used in combination with the SSU promoter or with other promoters such as CaMV35S.

5.36 EXAMPLE 36—TARGETING OF CRY* PROTEINS TO THE EXTRACELLULAR SPACE OR VACUOLE THROUGH THE USE OF SIGNAL PEPTIDES

The *B. thuringiensis* proteins produced from the synthetic genes described here are localized to the cytoplasm of the plant cell, and this cytoplasmic localization results in plants that are insecticidally effective. It may be advantageous for some purposes to direct the *B. thuringiensis* proteins to other compartments of the plant cell. Localizing *B. thuringiensis* proteins in compartments other than the cytoplasm may result in less exposure of the *B. thuringiensis* proteins to cytoplasmic proteases leading to greater accumulation of the protein yielding enhanced insecticidal activity. Extracellular localization could lead to more efficient exposure of certain insects to the *B. thuringiensis* proteins leading to greater efficacy. If a *B. thuringiensis* protein were found to be deleterious to plant cell function, then localization to a noncytoplasmic compartment could protect these cells from the protein.

In plants as well as other eukaryotes, proteins that are destined to be localized either extracellularly or in several specific compartments are typically synthesized with an N-terminal amino acid extension known as the signal peptide. This signal peptide directs the protein to enter the compartmentalization pathway, and it is typically cleaved from the mature protein as an early step in compartmentalization. For an extracellular protein, the secretory pathway typically involves cotranslational insertion into the endoplasmic reticulum with cleavage of the signal peptide occurring at this stage. The mature protein then passes through the Golgi body into vesicles that fuse with the plasma membrane thus releasing the protein into the extracellular space. Proteins destined for other compartments follow a similar pathway. For example, proteins that are destined for the endoplasmic reticulum or the Golgi body follow this scheme, but they are specifically retained in the appropriate compartment. In plants, some proteins are also targeted to the vacuole, another membrane bound compartment in the cytoplasm of many plant cells. Vacuole targeted proteins diverge from the above pathway at the Golgi body where they enter vesicles that fuse with the vacuole.

A common feature of this protein targeting is the signal peptide that initiates the compartmentalization process. Fusing a signal peptide to a protein will in many cases lead to the targeting of that protein to the endoplasmic reticulum. The efficiency of this step may depend on the sequence of the mature protein itself as well. The signals that direct a protein to a specific compartment rather than to the extracellular space are not as clearly defined. It appears that many of the signals that direct the protein to specific compartments are contained within the amino acid sequence of the mature protein. This has been shown for some vacuole targeted proteins, but it is not yet possible to define these sequences precisely. It appears that secretion into the extracellular space is the "default" pathway for a protein that contains a signal sequence but no other compartmentalization signals. Thus, a strategy to direct B. thuringiensis proteins out of the cytoplasm is to fuse the genes for synthetic B. thuringiensis genes to DNA sequences encoding known plant signal peptides. These fusion genes will give rise to B. thuringiensis proteins that enter the secretory pathway, and lead to extracellular secretion or targeting to the vacuole or other compartments. Signal sequences for several plant genes have been described. One such sequence is for the tobacco pathogenesis related protein PRIb has been previously described (Cornelissen et al., 1986). The PRIb protein is normally localized to the extracellular space. Another type of signal peptide is contained on seed storage proteins of legumes. These proteins are localized to the protein body of seeds, which is a vacuole like compartment found in seeds. A signal peptide DNA sequence for the β-subunit of the 7S storage protein of common bean (*Phaseolus vulgaris*), PvuB has been described (Doyle et al., 1986). Based on the published these published sequences, genes may be synthesized chemically using oligonucleotides that encode the signal peptides for PR1b and PvuB. In some cases to achieve secretion or compartmentalization of heterologous proteins, it may be necessary to include some amino acid sequence beyond the normal cleavage site of the signal peptide. This may be necessary to insure proper cleavage of the signal peptide.

5.37 EXAMPLE 37—ISOLATION OF TRANSGENIC MAIZE RESISTANT TO DIABROTICA SPP. USING CRY3BB VARIANTS

5.37.1 PLANT GENE CONSTRUCTION

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter". The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. Such promoters may be obtained from plants or plant viruses and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), and the Figwort Mosaic Virus (FMV) 35S promoter. All of these promoters have been used to create various types of DNA constructs which have been expressed in plants (see e.g., U.S. Pat. No. 5,463,175, specifically incorporated herein by reference).

The particular promoter selected should be capable of causing sufficient expression of the enzyme coding sequence to result in the production of an effective amount of protein. One set of preferred promoters are constitutive promoters such as the CaMV35S or FMV35S promoters that yield high levels of expression in most plant organs (U.S. Pat. No. 5,378,619, specifically incorporated herein by reference). Another set of preferred promoters are root enhanced or specific promoters such as the CaMV derived 4 as-1 promoter or the wheat POX1 promoter (U.S. Pat. No. 5,023,179, specifically incorporated herein by reference; Hertig et al., 1991). The root enhanced or specific promoters would be particularly preferred for the control of corn rootworm (Diabroticus spp.) in transgenic corn plants.

The promoters used in the DNA constructs (i.e. chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eucaryotic genes, or from a synthetic gene sequence. The present invention is not limited to constructs wherein the non-translated region is derived from the 5' non-translated sequence that accompanies the promoter sequence.

For optimized expression in monocotyledenous plants such as maize, an intron should also be included in the DNA expression construct. This intron would typically be placed near the 5' end of the mRNA in untranslated sequence. This intron could be obtained from, but not limited to, a set of introns consisting of the maize hsp70 intron (U.S. Pat. No. 5,424,412; specifically incorporated herein by reference) or the rice Act1 intron (McElroy et al., 1990). As shown below, the maize hsp70 intron is useful in the present invention.

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of Agrobacterium tumor-inducing (Ti) plasmid genes, such as the nopaline synthase (NOS) gene and (2) plant genes such as the pea ssRUBISCO E9 gene (Fischhoff et al., 1987).

5.37.2 PLANT TRANSFORMATION AND EXPRESSION

A chimeric plant gene containing a structural coding sequence of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella (1983), Bevan (1983), Klee (1985) and Eur. Pat. Appl. Publ. No. EP0120516. In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen (Fromm et al., 1986; Armstrong et al., 1990; Fromm et al., 1990).

5.37.3 CONSTRUCTION OF MONOCOT PLANT EXPRESSION VECTORS FOR cry3Bb VARIANTS

5.37.3.1 DESIGN OF Cry3Bb VARIANT GENES FOR PLANT EXPRESSION

For efficient expression of the cry3Bb variants in transgenic plants, the gene encoding the variants must have a suitable sequence composition (Diehn et al., 1996). One example of such a sequence is shown for the v11231 gene (SEQ ID NO:99) which encodes the Cry3Bb11231 variant protein (SEQ ID NO:100) with Diabrotica activity. This gene was derived via mutagenesis (Kunkel, 1985) of a cry3Bb synthetic gene (SEQ ID NO:101) encoding a protein essentially homologous to the protein encoded by the native cry3Bb gene (Gen Bank Accession Number m89794, SEQ ID NO:102). The following oligonucleotides were used in the mutagenesis of the original cry3Bb synthetic gene (SEQ ID NO:101) to create the v11231 gene (SEQ ID NO:99):

control of the enhanced CaMV35S promoter was isolated by gel electrophoresis and purification. This fragment was ligated with pMON30460 treated with NotI and calf intestinal alkaline phosphatase (pMON30460 contains the neomycin phosphotransferase coding sequence under control of the CaMV35S promoter). Kanamycin resistant colonies were obtained by transformation of this ligation mix into *E. coli* and colonies containing pMON33710 identified by restriction endonuclease digestion of plasmid miniprep DNAs. Restriction enzymes such as NotI, EcoRV, HindII, NcoI, EcoRI, and BglII can be used to identify the appropriate clones containing the NotI fragment of pMON33708 in the NotI site of pMON30460 (i.e. pMON33710) in the orientation such that both genes are in tandem (i.e. the 3' end of the v11231 expression cassette is linked to the 5' end of the nptII expression cassette). Expression of the v11231 protein by pMON33710 in corn protoplasts was confirmed by electroporation of pMON33710 DNA into protoplasts followed by protein blot and ELISA analysis. This vector can be introduced into the genomic DNA of corn embryos by particle gun bombardment followed by paromomycin selection to obtain corn plants expressing the v11231 gene essentially as described in U.S. Pat. No. 5,424,412, specifically incorporated herein by reference.

In this example, the vector was introduced via cobombardment with a hygromycin resistance conferring plasmid into immature embryo scutella (IES) of maize, followed by hygromycin selection, and regeneration. Transgenic corn lines expressing the v11231 protein were identified by ELISA analysis. Progeny seed from these events were subsequently tested for protection from Diabrotica feeding.

Oligo #1:
5'-TAGGCCTCCATCCATGGCAAACCCTAACAATC-3' (SEQ ID NO:103)
Oligo #2:
5'-TCCCATCTTCCTACTTACGACCCTGCAGAAATACGGTCCAAC-3' (SEQ ID NO:104)
Oligo #3:
5'-GACCTCACCTACCAAACATTCGATCTTG-3' (SEQ ID NO:105)
Oligo #4:
5'-CGAGTTCTACCGTAGGCAGCTCAAG-3' (SEQ ID NO:106)

5.37.3.2 CONSTRUCTION OF Cry3Bb MONOCOT PLANT EXPRESSION VECTOR

To place the cry3Bb variant gene v11231 in a vector suitable for expression in monocotyledonous plants (i.e. under control of the enhanced Cauliflower Mosaic Virus 35S promoter and link to the hsp70 intron followed by a nopaline synthase polyadenylation site as in U.S. Pat. No. 5,424,412, specifically incorporated herein by reference), the vector pMON19469 was digested with NcoI and EcoRI. The larger vector band of approximately 4.6 kb was electrophoresed, purified, and ligated with T4 DNA ligase to the NcoI-EcoRI fragment of approximately 2 kb containing the vl 1231 gene (SEQ ID NO:99). The ligation mix was transformed into *E. coli*, carbenicillin resistant colonies recovered and plasmid DNA recovered by DNA miniprep procedures. This DNA was subjected to restriction endonuclease analysis with enzymes such as NcoI and EcoRi (together), NotI, and PstI to identify clones containing pMON33708 (the v11231 coding sequence fused to the hsp70 intron under control of the enhanced CaMV35S promoter).

To place the v11231 gene in a vector suitable for recovery of stably transformed and insect resistant plants, the 3.75-kb NotI restriction fragment from pMON33708 containing the v11231 coding sequence fused to the hsp70 intron under

5.37.3.3 IN PLANTA PERFORMANCE OF Cry3Bb.11231

Transformed corn plants expressing Cry3Bb.11231 protein were challenged with western corn rootworm (WCR) larvae in both a seedling and 10 inch pot assay. The transformed genotype was A634, where the progeny of the R0 cross by A634 was evaluated. Observations included effect on larval development (weight), root damage rating (RDR), and protein expression. The transformation vector containing the cry3Bb gene was pMON33710. Treatments included the positive and negative iso-populations for each event and an A634 check.

The seedling assay consisted of the following steps: (i) single seeds were placed in 1 oz cups containing potting soil; (ii) at spiking, each seedling was infested with 4 neonate larvae; and (iii) after infestation, seedlings were incubated for 7 days at 25° C., 50% RH, and 14:10 (L:D) photo period. Adequate moisture was added to the potting soil during the incubation period to maintain seedling vigor.

The 10 inch pot assay consisted of the following steps: (i) single seeds were placed in 10 inch pots containing potting soil; (ii) at 14 days post planting, each pot was infested with 800 eggs which have been pre-incubated such that hatch would occur 5–7 days post infestation; and (iii) after infestation, plants were incubated for 4 weeks under the same environmental conditions as the seedling assay. Pots were both sub and top irrigated daily.

For the seedling assay, on day 7 plants were given a root damage rating, and surviving larvae were weighed. Also at this time, Cry3Bb protein concentrations in the roots were determined by ELISA. The scale used for the seedling assay to assess root damage is as follows: RDR (root damage rating) 0=no visible feeding; RDR 1=very light feeding; RDR 2=light feeding; RDR 3=moderate feeding; RDR 4=heavy feeding; and RDR 5=very heavy feeding.

Results of the seedling assay are shown in Table 26. Plants expressing Cry3Bb protein were completely protected by WCR feeding, where surviving larvae within this treatment had not grown. Mean larval weights ranged from 2.03–2.73 mg for the nonexpressing treatments, where the surviving larval average weight was 0.11 mg on the expressing cry3Bb treatment. Root damage ratings were 3.86 and 0.33 for the nonexpressing and expressing isopopulations respectively. Larval survival ranged from 75–85% for the negative and check treatments, where only 25% of the larvae survived on the Cry3Bb treatment.

TABLE 26

EFFECT OF CRY3BB EXPRESSING PLANTS ON WCR LARVAE IN A SEEDLING ASSAY

| | | | Plants | | Larvae | | |
|---|---|---|---|---|---|---|---|
| Event | Treatment | N | Root (ppm) | RDR ± SD | N | % Surv | Mean ± SD Wt. (mg) |
| 16 | Negative | 7 | 0.0 | 3.86 ± 0.65 | 21 | 75 | 2.73 ± 1.67 |
| 16 | Positive | 3 | 29.01 | 0.33 ± 0.45 | 3 | 25 | 0.11 ± 0.07 |
| A634 | Check | 4 | 0.0 | — | 13 | 81 | 2.03 ± 0.83 |

For the 10 inch pot assay, at 4 weeks post infestation plant height was recorded and a root damage rating (Iowa 1–6 scale; Hills and Peters, 1971) was given.

Results of the 10 inch pot assay are shown in Table 27. Plants expressing Cry3Bb protein had significantly less feeding damage and were taller than the non-expressing plants. Event 16, the higher of the two expressing events provided nearly complete control. The negative treatments had very high root damage ratings indicating very high insect pressure. The positive mean root damage ratings were 3.4 and 2.2 for event 6 and 16, respectively. Mean RDR for the negative treatment was 5.0 and 5.6.

TABLE 27

EFFECT OF CRY3BB EXPRESSING CORN IN CONTROLLING WCR LARVAL FEEDING IN A 10 INCH POT ASSAY

| Event | Treatment | N | Root (ppm) | RDR ± SD | Plant Height (cm) |
|---|---|---|---|---|---|
| 6 | Negative | 7 | 0.0 | 5.0 ± 1.41 | 49.7 ± 18.72 |
| 6 | Positive | 5 | 7.0 | 3.4 ± 1.14 | 73.9 ± 8.67 |
| 16 | Negative | 5 | 0.0 | 5.6 ± 0.89 | 61.2 ± 7.75 |
| 16 | Negative | 5 | 55.0 | 2.2 ± 0.84 | 83.8 ± 7.15 |

In summary, corn plants expressing Cry3Bb protein have a significant biological effect on WCR larval development as seen in the seedling assay. When challenged with very high infestation levels, plants expressing the Cry3Bb protein were protected from WCR larval feeding damage as illustrated in the 10 inch pot assay.

6.0 BRIEF DESCRIPTION OF THE SEQUENCE IDENTIFIERS

SEQ ID NO:1 DNA sequence of cry3Bb.11221 gene.
SEQ ID NO:2 Amino acid sequence of Cry3Bb.11221 polypeptide.
SEQ ID NO:3 DNA sequence of cry3Bb.11222 gene.
SEQ ID NO:4 Amino acid sequence of Cry3Bb.11222 polypeptide.
SEQ ID NO:5 DNA sequence of cry3Bb.11223 gene.
SEQ ID NO:6 Amino acid sequence of Cry3Bb.11223 polypeptide.
SEQ ID NO:7 DNA sequence of cry3Bb.11224 gene.
SEQ ID NO:8 Amino acid sequence of Cry3Bb.11224 polypeptide.
SEQ ID NO:9 DNA sequence of cry3Bb.11225 gene.
SEQ ID NO:10 Amino acid sequence of Cry3Bb.11225 polypeptide.
SEQ ID NO:11 DNA sequence of cry3Bb.11226 gene.
SEQ ID NO:12 Amino acid sequence of Cry3Bb.11226 polypeptide.
SEQ ID NO:13 DNA sequence of cry3Bb.11227 gene.
SEQ ID NO:14 Amino acid sequence of Cry3Bb.11227 polypeptide.
SEQ ID NO:15 DNA sequence of cry3Bb.11228 gene.
SEQ ID NO:16 Amino acid sequence of Cry3Bb.11228 polypeptide.
SEQ ID NO:17 DNA sequence of cry3Bb.11229 gene.
SEQ ID NO:18 Amino acid sequence of Cry3Bb.11229 polypeptide.
SEQ ID NO:19 DNA sequence of cry3Bb.11230 gene.
SEQ ID NO:20 Amino acid sequence of Cry3Bb.11230 polypeptide.
SEQ ID NO:21 DNA sequence of cry3Bb.11231 gene.
SEQ ID NO:22 Amino acid sequence of Cry3Bb.11231 polypeptide.
SEQ ID NO:23 DNA sequence of cry3Bb.11232 gene.
SEQ ID NO:24 Amino acid sequence of Cry3Bb.11232 polypeptide.
SEQ ID NO:25 DNA sequence of cry3Bb.11233 gene.
SEQ ID NO:26 Amino acid sequence of Cry3Bb.11233 polypeptide.
SEQ ID NO:27 DNA sequence of cry3Bb.11234gene.
SEQ ID NO:28 Amino acid sequence of Cry3Bb.11234 polypeptide.
SEQ ID NO:29 DNA sequence of cry3Bb.11235 gene.
SEQ ID NO:30 Amino acid sequence of Cry3Bb.11235 polypeptide.
SEQ ID NO:31 DNA sequence of cry3Bb.11236 gene.
SEQ ID NO:32 Amino acid sequence of Cry3Bb.11236 polypeptide.
SEQ ID NO:33 DNA sequence of cry3Bb.11237 gene.
SEQ ID NO:34 Amino acid sequence of Cry3Bb.11237 polypeptide.
SEQ ID NO:35 DNA sequence of cry3Bb.11238 gene.
SEQ ID NO:36 Amino acid sequence of Cry3Bb.11238 polypeptide.
SEQ ID NO:37 DNA sequence of cry3Bb.11239 gene.
SEQ ID NO:38 Amino acid sequence of Cry3Bb.11239 polypeptide.
SEQ ID NO:39 DNA sequence of cry3Bb.11241 gene.
SEQ ID NO:40 Amino acid sequence of Cry3Bb.11241 polypeptide.
SEQ ID NO:41 DNA sequence of cry3Bb.11242 gene.
SEQ ID NO:42 Amino acid sequence of Cry3Bb.11242 polypeptide.
SEQ ID NO:43 DNA sequence of cry3Bb.11032 gene.
SEQ ID NO:44 Amino acid sequence of Cry3Bb.11032 polypeptide.
SEQ ID NO:45 DNA sequence of cry3Bb.11035 gene.
SEQ ID NO:46 Amino acid sequence of Cry3Bb.11035 polypeptide.

SEQ ID NO:47 DNA sequence of cry3Bb.11036 gene.
SEQ ID NO:48 Amino acid sequence of Cry3Bb.11036 polypeptide.
SEQ ID NO:49 DNA sequence of cry3Bb.11046 gene.
SEQ ID NO:50 Amino acid sequence of Cry3Bb.11046 polypeptide.
SEQ ID NO:51 DNA sequence of cry3Bb.11048 gene.
SEQ ID NO:52 Amino acid sequence of Cry3Bb.11048 polypeptide.
SEQ ID NO:53 DNA sequence of cry3Bb.11051 gene.
SEQ ID NO:54 Amino acid sequence of Cry3Bb.11051 polypeptide.
SEQ ID NO:55 DNA sequence of cry3Bb.11057 gene.
SEQ ID NO:56 Amino acid sequence of Cry3Bb.11057 polypeptide.
SEQ ID NO:57 DNA sequence of cry3Bb.11058 gene.
SEQ ID NO:58 Amino acid sequence of Cry3Bb.11058 polypeptide.
SEQ ID NO:59 DNA sequence of cry3Bb.11081 gene.
SEQ ID NO:60 Amino acid sequence of Cry3Bb.11081 polypeptide.
SEQ ID NO:61 DNA sequence of cry3Bb.11082 gene.
SEQ ID NO:62 Amino acid sequence of Cry3Bb.11082 polypeptide.
SEQ ID NO:63 DNA sequence of cry3Bb.11083 gene.
SEQ ID NO:64 Amino acid sequence of Cry3Bb.11083 polypeptide.
SEQ ID NO:65 DNA sequence of cry3Bb.11084 gene.
SEQ ID NO:66 Amino acid sequence of Cry3Bb.11084 polypeptide.
SEQ ID NO:67 DNA sequence of cry3Bb.11095 gene.
SEQ ID NO:68 Amino acid sequence of Cry3Bb.11095 polypeptide.
SEQ ID NO:69 DNA sequence of cry3Bb.60 gene.
SEQ ID NO:70 Amino acid sequence of Cry3Bb.60 polypeptide.
SEQ ID NO:71 Primer FW001.
SEQ ID NO:72 Primer FW006.
SEQ ID NO:73 Primer MVT095.
SEQ ID NO:74 Primer MVT097.
SEQ ID NO:75 Primer MVT091.
SEQ ID NO:76 Primer MVT075.
SEQ ID NO:77 Primer MVT076.
SEQ ID NO:78 Primer MVT111.
SEQ ID NO:79 Primer MVT094.
SEQ ID NO:80 Primer MVT103.
SEQ ID NO:81 Primer MVT081.
SEQ ID NO:82 Primer MVT085.
SEQ ID NO:83 Primer A.
SEQ ID NO:84 Primer B.
SEQ ID NO:85 Primer C.
SEQ ID NO:86 Primer D.
SEQ ID NO:87 Primer E.
SEQ ID NO:88 Primer F.
SEQ ID NO:89 Primer G.
SEQ ID NO:90 Primer WD112.
SEQ ID NO:91 Primer WD115.
SEQ ID NO:92 Primer MVT105.
SEQ ID NO:93 Primer MVT092.
SEQ ID NO:94 Primer MVT070.
SEQ ID NO:95 Primer MVT083.
SEQ ID NO:96 N-terminal amino acid of Cry3Bb polypeptide.
SEQ ID NO:97 DNA sequence of wild-type cry3Bb gene.
SEQ ID NO:98 Amino acid sequence of wild-type Cry3Bb polypeptide.
SEQ ID NO:99 Plantized DNA sequence for cry3Bb.11231 gene.
SEQ ID NO:100 Amino acid sequence of plantized Cry3Bb.11231 polypeptide.
SEQ ID NO:101 DNA sequence of cry3Bb gene used to prepareSEQ ID NO:99.
SEQ ID NO:102 DNA sequence of wild-type cry3Bb gene, Genbank #M89794.
SEQ ID NO:103 DNA sequence of Oligo #1.
SEQ ID NO:104 DNA sequence of Oligo #2.
SEQ ID NO:105 DNA sequence of Oligo #3.
SEQ ID NO:106 DNA sequence of Oligo #4.
SEQ ID NO:107 DNA sequence of cry3Bb.11098 gene.
SEQ ID NO:108 Amino acid sequence of Cry3Bb.11098 polypeptide.

7.0 REFERENCES

The following references, to the extent that they provide exemplary procedural or other details supplementary to those set forth herein, are specifically incorporated herein by reference.

U.S. Pat. No. 4,237,224, issued Dec. 2, 1980.
U.S. Pat. No. 4,332,898, issued Jun. 1, 1982.
U.S. Pat. No. 4,342,832, issued Aug. 3, 1982.
U.S. Pat. No. 4,356,270, issued Oct. 26, 1982.
U.S. Pat. No. 4,362,817, issued Dec. 7, 1982.
U.S. Pat. No. 4,371,625, issued Feb. 1, 1983.
U.S. Pat. No. 4,448,885, issued May 15, 1984.
U.S. Pat. No. 4,467,036, issued Aug. 21, 1984.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,757,011, issued Jul. 12, 1988.
U.S. Pat. No. 4,766,203, issued Aug. 23, 1988.
U.S. Pat. No. 4,769,061, issued Sep. 6, 1988.
U.S. Pat. No. 4,797,279, issued Jan. 10, 1989.
U.S. Pat. No. 4,800,159, issued Jan. 24, 1989.
U.S. Pat. No. 4,883,750, issued Nov. 28, 1989.
U.S. Pat. No. 4,910,016, issued Mar. 20, 1990.
U.S. Pat. No. 4,940,835, issued Feb. 23, 1990.
U.S. Pat. No. 4,965,188, issued Oct. 23, 1990.
U.S. Pat. No. 4,971,908, issued Nov. 20, 1990.
U.S. Pat. No. 4,987,071, issued Jan. 22, 1991.
U.S. Pat. No. 5,380,831, issued Jan. 10, 1995.
U.S. Pat. No. 5,023,179, issued Jun. 11, 1991.
U.S. Pat. No. 5,024,837, issued Jun. 18, 1991.
U.S. Pat. No. 5,126,133, issued Jun. 30, 1992.
U.S. Pat. No. 5,176,995, issued Oct. 15, 1991.
U.S. Pat. No. 5,187,091, issued Feb. 16, 1993.
U.S. Pat. No. 5,322,687, issued Jun. 21, 1994.
U.S. Pat. No. 5,334,711, issued Aug. 2, 1994.
U.S. Pat. No. 5,378,619, issued Jan. 3, 1995.
U.S. Pat. No. 5,424,412, issued Jun. 13, 1995.
U.S. Pat. No. 5,441,884, issued Aug. 15, 1995.
U.S. Pat. No. 5,463,175, issued Oct. 31, 1995.
U.S. Pat. No. 5,500,365, issued Mar 19, 1996.
U.S. Pat. No. 5,591,616, issued Jan. 7, 1997.
U.S. Pat. No. 5,631,359, issued May 20, 1997.
U.S. Pat. No. 5,659,123, issued Aug. 19, 1997.
Eur. Pat. No. EP 0120516.
Eur. Pat. No. EP 0360257.
Eur. Pat. Appl. No. 92110298.4.
Eur. Pat. Appl. No. 295156A1.
Great Britain Patent 2202328.
Int. Pat. Appl. Publ. No. WO 91/03162.
Int. Pat. Appl. Pubi. No. WO 92/07065.
Int. Pat. Appl. Publ. No. WO 93/15187.
Int. Pat. Appl. Publ. No. WO 93/23569.
Int. Pat. Appl. Publ. No. WO 94/02595.

Int. Pat. Appl. Publ. No. WO 94/13688.
Intl. Pat. Appl. Publ. No. PCT/US87/00880.
Intl. Pat. Appl. Publ. No. PCT/US89/01025.
Intl. Pat. Appl. Publ. No. WO 88/09812.
Intl. Pat. Appl. Publ. No. WO 88/10315.
Intl. Pat. Appl. Publ. No. WO 89/06700.
Intl. Pat. Appl. Publ. No. WO 93/07278.
Abbott, "A method for computing the effectiveness of an insecticide," *J. Econ. Entomol.*, 18:265–267, 1925.
Abdullah et al., *Biotechnology*, 4:1087, 1986.
Almond and Dean, *Biochemistry*, 32:1040–1046, 1993.
An et al., *EMBO J.*, 4:277–287, 1985.
Angsuthanasamnbat et al., *FEMS Microbiol. Lett.*, 111:255–262, 1993.
Armstrong et al., *Plant Cell Rep.*, 9:335–339, 1990.
Aronson, Wu, Zhang, "Mutagenesis of specificity and toxicity regions of a *Bacillus thuringiensis* protoxin gene." *J. Bacteriol.*, 177:4059–4065, 1995.
Bagdasarian et al., *Gene*, 16:237, 1981.
Baum et al., *Appl. Environ. Microbiol.*, 56:3420–3428, 1990.
Baum, "Tn5401, a new class II transposable element from *Bacillus thuringiensis*," *J. Bacteriol.*, 176:2835–2845, 1994.
Baum, *J. Bacteriol.*, 177:4036–4042, 1995.
Baum, Kakefuda, Gawron-Burke, "Engineering *Bacillus thuringiensis* Bioinsecticides with an Indigenous Site-Specific Recombination System," *Appl. Environ. Microbiol.*, 62(12):4367–4373, 1996.
Benbrook et al., In: *Proceedings Bio Expo 1986*, Butterworth, Stoneham, Mass., pp. 27–54, 1986.
Bevan et al., *Nature*, 304:184, 1983.
Bolivar et al., *Gene*, 2:95, 1977.
Branden and Tooze, *"Introduction to Protein Structure,"* Garland Publishing, Inc., New York, N.Y., 1991.
Brussock and Currier, "Use of sodium dodecyl sulfate-polacryamide gel electrophoresis to quantify *Bacillus thuringiensis* δ-endotoxins," In: "Analytical Chemistry of *Bacillus thuringiensis*," L. A. Hickle and W. L. Fitch, (Eds), American Chemical Society, Washington D. C., pp. 78–87, 1990.
Capecchi, "High efficiency transformation by direct microinjection of DNA into cultured mammalian cells," *Cell*, 22(2):479–488, 1980.
Caramori, Albertini, Galizzi, "In vivo generation of hybrids between two *Bacillus thuringiensis* insect-toxin-encoding genes," *Gene*, 98:37–44, 1991.
Cashmore et al., *Gen. Eng. of Plants*, Plenum Press, New York, 29–38, 1983.
Chambers et al., *Appl. Environ. Microbiol.*, 173:3966–3976, 1991.
Chau et al., *Science*, 244:174–181, 1989.
Chen et al., *Nucl. Acids Res.*, 20:4581–9, 1992.
Chen, Curtiss, Alcantara, Dean, "Mutations in domain I of *Bacillus thuringiensis* δ-endotoxin CryIAb reduce the irreversible binding of toxin to *Manduca sexta* brush border membrane vesicles," *J. Biol. Chem.*, 270:6412–6419, 1995.
Chen, Lee, Dean, "Site-directed mutations in a highly conserved region of *Bacillus thuringiensis* δ-endotoxin affect inhibition of short circuit current across *Bombyx mori* midguts," *Proc. Natl. Acad. Sci. USA*, 90:9041–9045, 1993.
Chowrira and Burke, *Nucl. Acids Res.*, 20:2835–2840, 1992.
Clapp, "Somatic gene therapy into hematopoietic cells. Current status and future implications," *Clin. Perinatol.*, 20(1):155–168, 1993.
Cody, Luft, Jensen, Pangbom English, "Purification and crystallization of insecticidal δ-endotoxin CryIIIB2 from *Bacillus thuringiensis*," *Proteins. Struct. Funct. Genet.*, 14:324, 1992.
Collins and Olive, *Biochem.*, 32:2795–2799, 1993.
Conway and Wickens, In: *RNA Processing*, p. 40, Cold Spring Harbor Laboratory, Cold Spring Harbor, N.Y., 1988.
Cornelissen et al., "A tobacco mosaic virus-induced tobacco protein is homologous to the sweet-tasting protein thaumatin," *Nature*, 321(6069):531–532, 1986.
Cramer, Cohen, Merrill, Song, "Structure and dynamics of the colicin E1 channel," *Molec. Microbiol.*, 4:519–526, 1990.
CRC Handbook of Chemistry and Physics, $58^{th}$ edition, CRC Press, Inc., Cleveland, Ohio, p. C-769, 1977.
Cristou et al., *Plant Physiol*, 87:671–674, 1988.
Curiel, Agarwal, Wagner, Cotten, "Adenovirus enhancement of transferrin-polylysine-mediated gene delivery," *Proc. Natl. Acad. Sci. USA*, 88(19):8850–8854, 1991.
Curiel, Wagner, Cotten, Birnstiel, Agarwal, Li, Loechel, Hu, "High-efficiency gene transfer mediated by adenovirus coupled to DNA-polylysine complexes," *Hum. Gen. Ther.*, 3(2):147–154, 1992.
Daum, "Revision of two computer programs for probit analysis," *Bull. Entomol. Soc. Amer.*, 16:10–15, 1970.
De Maagd, Kwa, van der Klei, Yamamoto, Schipper, Vlak, Stiekema, Bosch, "Domain III substitution in *Bacillus thuringiensis* delta-endotoxin CryIA(b) results in superior toxicity for *Spodoptera exigua* and altered membrane protein recognition," *Appl. Environ. Microbiol.*, 62:1537–1543, 1996.
Dean et al., *Nucl. Acids Res.*, 14(5):2229, 1986.
Dhir et al., *Plant Cell Reports*, 10:97, 1991.
Diehn et al., *Genet. Engineer.*, 18:83–99, 1996.
Donovan, Dankocsik, Gilbert, Groat, Gawron-Burke, Carlton, "The P2 protein of *Bacillus thuringiensis* var. *kurstaki*: nucleotide sequence and entomocidal activity," *J. Biol. Chem.*, 263:561–567, 1988.
Doyle et al., *J. Biol. Chem.*, 261(20):9228–9236, 1986.
Dropulic et al., *J. Virol.*, 66:1432–41, 1992.
Dunitz, "The entropic cost of bound water in crystals and biomolecules," *Science*, 264:670-68x, 1994.
Earp and Ellar, *Nucl. Acids Res.*, 15:3619, 1987.
Eglitis and Anderson, "Retroviral vectors for introduction of genes into mammalian cells," *Biotechniques*, 6(7):608–614, 1988.
Eglitis, Kantoff, Kohn, Karson, Moen, Lothrop, Blaese, Anderson, "Retroviral-mediated gene transfer into hemopoietic cells," *Adv. Exp. Med. Biol.*, 241:19–27, 1988.
Elroy-Stein and Moss, *Proc. Natl. Acad. Sci. USA*, 87:6743–7, 1990.
English and Slatin, *Insect Biochem. Mol. Biol.*, 22:1–7, 1992.
English, Readdy, Bastian, "Delta-endotoxin-induced leakage of $^{86}Rb^{+K+}$ and $H_2O$ from phospholipid vesicles is catalyzed by reconstituted midgut membrane," *Insect Biochem.*, 21:177–184, 1991.
Fischhoff et al., *Bio/Technology*, 5:807–813, 1987.
Fraley et al., *Bio/Technology*, 3 :629–635, 1985.
Fraley et al., *Proc. Natl. Acad. Sci. USA*, 80:4803, 1983.
Frohman, PCR™ Protocols, a Guide to Methods and Applications XVIII Ed., Academic Press, New York, 1990.
Fromm et al., *Bio/Technology*, 8:833–839, 1990.
Fromm et al., *Nature*, 319:791–793, 1986.
Fromm, Taylor, Walbot, "Expression of genes transferred into monocot and dicot plant cells by electroporation," *Proc. Natl. Acad. Sci. USA*, 82(17):5824–5828, 1985.

Fujimura et al., *Plant Tissue Cult. Lett.*, 2:74, 1985.

Fynan, Webster, Fuller, Haynes, Santoro, Robinson, "DNA vaccines: protective immunizations by parenteral, mucosal, and gene gun inoculations," *Proc. Natl. Acad. Sci. USA*, 90(24):11478–11482, 1993.

Galitsky, Cody, Wojtczak, Ghosh, Luft, Pangbom, Wawrzak, English, "Crystal and Molecular Structure of the Insecticidal Bacterial δ-Endotoxin CryIIIB2 of *Bacillus thuringiensis*," Research Communication to Ecogen Inc., Langhorne, Pa., 1993.

Gao and Huang, *Nucl. Acids Res.*, 21:2867–72, 1993.

Gazit and Shai, "Structural and Functional Characterization of the α-5 segment of *Bacillus thuringiensis* δ-endotoxin," Biochemistry, 32:3429–3436, 1993.

Gazit and Shai, "The assembly and organization of the α5 and α7 helices from the pore-forming domain of *Bacillus thuringiensis* δ-endotoxin," *J. Biol. Chem.*, 270:2571–2578,1995.

Ge, Rivers, Milne, Dean, "Functional domains of *Bacillus thuringiensis* insecticidal crystal proteins: refinement of *Heliothis virescens* and *Trichoplusia ni* specificity domains on CryIA(c)," *J. Biol. Chem.*, 266:17954–17958, 1991.

Genovese and Milcarek, In: *RNA Processing*, p. 62, Cold Spring Harbor Laboratory, Cold Spring Harbor, N.Y., 1988.

Gil and Proudfoot, *Nature*, 312:473, 1984.

Gonzalez Jr. et al., *Proc. Natl. Acad. Sci USA*, 79:6951–6955, 1982.

Graham and van der Eb, "Transformation of rat cells by DNA of human adenovirus 5," *Virology*, 54(2):536–539, 1973.

Grochulski, Masson, Borisova, Pusztai-Carey, Schwartz, Brousseau, Cygler, "*Bacillus thuringiensis* CryIA(a) insecticidal toxin: crystal structure and channel formation," *J. Mol. Biol.*, 254:447–464, 1995.

Guerrier-Takada et al., *Cell*, 35:849, 1983.

Hampel and Tritz, *Biochem.*, 28:4929, 1989.

Hampel et al., *Nucl. Acids Res.*, 18:299, 1990.

Harlow and Lane, "Antibodies: A Laboratory Manual," Cold Spring Harbor Laboratory, Cold Spring Harbor, N.Y., 1988.

Herrera-Estrella et al., *Nature*, 303:209, 1983.

Hertel et al., *Nucl. Acids Res.*, 20:3252, 1992.

Hertig et al., *Plant Mol. Biol.*, 16:171–174, 1991.

Hess, *Intern Rev. Cytol.*, 107:367, 1987.

Hills and Peters, *J. Econ. Entomol.*, 64:764–765, 1971.

Hockema, In: *The Binary Plant Vector System*, Offsetdurkkerij, Kanters B. V., Alblasserdam, Chapter 5.

Höfte and Whitely, *Microbiol. Rev.*, 53:242–255, 1989.

Holland et al., *Biochemistry*, 17:4900, 1978.

Holsters et al., *Mol. Gen. Genet.*, 163:181–187, 1978.

Honee, van der Salm, Visser, *Nucl. Acids Res.*, 16:6240, 1988.

Horsch et al., *Science*, 227:1229–1231, 1985.

Humason, In: *Animal Tissue Techniques*, W. H. Freeman and Company, 1967.

Jaeger et al., *Proc. Natl. Acad. Sci. USA*, 86: 7706–7710, 1989.

Johnston and Tang, "Gene gun transfection of animal cells and genetic immunization," *Methods Cell. Biol.*, 43(A):353–365, 1994.

Jorgensen et al., *Mol. Gen. Genet.*, 207:471, 1987.

Kaiser and Kezdy, *Science*, 223:249–255, 1984.

Kashani-Saber et al., *Antisense Res. Dev.*, 2:3–15, 1992.

Keller et al., *EMBO J.*, 8:1309–14, 1989.

Klee et al., *Bio/Technology*, 3:637–642, 1985.

Klein et al., *Nature*, 327:70, 1987.

Klein et al., Proc. Natl. Acad. Sci. USA, 85:8502–8505, 1988.

Kozak, *Nature*, 308:241–246, 1984.

Krieg et al., Anzeigerfur Schadlingskunde Pflanzenschutz Umweltschutz, 57:145–150, 1984.

Krieg et al., *Z. ang Ent.*, 96:500–508, 1983.

Kuby, *Immunology 2nd Edition*, W. H. Freeman & Company, N.Y., 1994

Kunkle, "Rapid and efficient site-specific mutagenesis without phenotypic selection," *Proc. Natl. Acad. Sci. USA*, 82:488–492, 1985.

Kunkle, Roberts, Zabour, *Methods Enzymol.*, 154:367–382, 1987.

Kwak, Lu, Dean, "Exploration of receptor binding of *Bacillus thuringiensis* toxins," *Mem. Inst. Oswaldo*, 90:75–79, 1995.

Kwoh et al., *Proc. Natl. Acad. Sci. USA*, 86(4):1173–1177, 1989.

Kyte and Doolittle, *J. Mol. Biol.*, 157:105–132, 1982.

L'Huillier et al., *EMBO J.*, 11:4411–8, 1992.

LaBean and Kauffman, "Design of synthetic gene libraries encoding random sequence proteins with desired ensemble characteristics," *Prot. Sci.*, 2:1249–1254, 1993.

Lambert, Buysse, Decock, Jansens, Piens, Saey, Seurinck, Van Audenhove, Van Rie, Van Vliet, Peferoen, "A *Bacillus thuringiensis* insecticidal crystal protein with a high activity against members of the family Noctuidae," *Appl. Environ. Microbiol.*, 62:80–86, 1996.

Lee, Milne, Ge, Dean, "Location of a *Bombyx mori* receptor binding region on a *Bacillus thuringiensis* δ-endotoxin," *J. Biol. Chem.*, 267:3115–3121, 1992.

Lee, Young, Dean, "Domain III exchanges of *Bacillus thuringiensis* CryIA toxins affect binding to different gypsy moth midgut receptors," *Biochem. Biophys. Res. Commun.*, 216:306–312, 1995.

Li, Carroll, Ellar, "Crystal structure of insecticidal δ-endotoxin from *Bacillus thuringiensis* at 2.5 Å resolution," *Nature* (London), 353:815–821, 1991.

Lieber et al., *Methods Enzymol.*, 217:47–66, 1993.

Lindstrom et al., *Developmental Genetics*, 11:160, 1990.

Lisziewicz et al., *Proc. Natl. Acad. Sci. U.S.A.*, 90:8000–4, 1993.

Lorz et al., *Mol. Gen. Genet.*, 199:178, 1985.

Lu, Rajamohan, Dean, "Identification of amino acid residues of *Bacillus thuringiensis* δ-endotoxin CryIAa associated with membrane binding and toxicity to *Bombyx mori,*" *J. Bacteriol.*, 176:5554–5559, 1994.

Lu, Xiao, Clapp, Li, Broxmeyer, "High efficiency retroviral mediated gene transduction into single isolated immature and replatable CD34(3+) hematopoietic stem/progenitor cells from human umbilical cord blood," *J. Exp. Med.*, 178(6):2089–2096, 1993.

Macaluso and Mettus, *J. Bacteriol.*, 173:1353–1356, 1991.

Maddock et al., *Third International Congress of Plant Molecular Biology*, Abstract 372, 1991.

Maloy et al., "Microbial Genetics" 2nd Edition. Jones and Bartlett Publishers, Boston, Mass., 1994.

Maloy, "Experimental Techniques in Bacterial Genetics" Jones and Bartlett Publishers, Boston, Mass., 1990.

Maniatis, Fritsch, Sambrook, In: *Molecular Cloning: A Laboratory Manual*, Cold Spring Harbor Laboratory, Cold Spring Harbor, N.Y., 1982.

Marcotte et al., *Nature*, 335:454, 1988.

McDevitt et al., *Cell*, 37:993–999, 1984.

McElroy et al., *Plant Cell*, 2:163–171, 1990.

Mettus and Macaluso, *Appl. Environ. Microbiol.*, 56:1128–1134, 1990.

Michael, "Mutagenesis by Incorporation of a Phosphorylated Oligo During PCR™ Amplification," BioTechniques, 16(3):410–412, 1994.

Neuhaus et al., Theor. Appl. Genet., 75:30, 1987.

Odell et al., Nature, 313:810, 1985.

Ohara et al., Proc. Natl. Acad. Sci. USA, 86(15):5673–5677, 1989.

Ohkawa et al., Nucl. Acids Symp. Ser., 27:15–6, 1992.

Ojwang et al., Proc. Natl. Acad. Sci. USA, 89:10802–6, 1992.

Olson et al., J. Bacteriol., 150:6069, 1982.

Omirulleh et al., Plant Molecular Biology, 21:415–428, 1993.

Pandey and Marzluff, In "RNA Processing," p.133, Cold Spring Harbor Laboratory, Cold Spring Harbor, N.Y., 1987.

Pena et al., Nature, 325:274, 1987.

Perrault et al, Nature, 344:565, 1990.

Perrotta and Been, Biochem., 31:16, 1992.

Pieken et al., Science, 253:314, 1991.

Poszkowski et al., EMBO J, 3:2719, 1989.

Potrykus et al., Mol. Gen. Genet., 199:183, 1985.

Poulsen et al., Mol. Gen. Genet., 205:193–200, 1986.

Prokop and Bajpai, "Recombinant DNA Technology I," Ann. N.Y. Acad. Sci., 646:1–383, 1991.

Rajamohan, Alcantara, Lee, Chen, Curtiss, Dean, "Single amino acid changes in domain II of Bacillus thuringiensis CryIAb δ-endotoxin affect irreversible binding to Manduca sexta midgut membrane vesicles," J. Bacteriol., 177:2276–2282, 1995.

Rajamohan, Cotrill, Gould, Dean, "Role of domain II, loop 2 residues of Bacillus thuringiensis CryIAb δ-endotoxin in reversible and irreversible binding to Manduca sexta and Heliothis virescens," J. Biol. Chem., 271:2390–2397, 1996.

Rogers et al., In: Methods For Plant Molecular Biology, A. Weissbach and H. Weissbach, eds., Academic Press Inc., San Diego, Calif. 1988.

Rogers et al., Methods Enzymol., 153:253–277, 1987.

Rossi et al., Aids Res. Hum. Retrovir., 8:183, 1992.

Sadofsky and Alwine, Molec. Cell. Biol., 4(8):1460–1468, 1984.

Sambrook et al., "Molecular Cloning: A Laboratory Manual," Cold Spring Harbor Laboratory, Cold Spring Harbor, N.Y., 1989.

Sanchis, Lereclus, Menou, Chaufaux, Guo, Lecadet, Mol. Microbiol., 3:229–238, 1989.

Sanchis, Lereclus, Menou, Chaufaux, Lecadet, Mol. Microbiol., 2:393–404, 1988.

Sarver et al., Science, 247:1222–1225, 1990.

Saville and Collins, Cell, 61:685–696, 1990.

Saville and Collins, Proc. Natl. Acad. Sci. USA, 88:8826–8830, 1991.

Scanlon et al., Proc. Natl. Acad Sci. USA, 88:10591–5, 1991.

Scaringe et al., Nucl. Acids. Res., 18:5433–5441, 1990.

Schnepf and Whitely, Proc. Natl. Acad. Sci. USA, 78:2893–2897, 1981.

Schnepf et al., J. Biol. Chem., 260:6264–6272, 1985.

Segal, "Biochemical Calculations" 2nd Edition, John Wiley & Sons, New York, 1976.

Shaw and Kamen, Cell, 46:659–667, 1986.

Shaw and Kamen, In: "RNA Processing", p. 220, Cold Spring Harbor Laboratory, Cold Spring Harbor, N.Y., 1987.

Simpson, Science, 233:34, 1986.

Slaney, Robbins, English, "Mode of action of Bacillus thuringiensis toxin CryIIIA: An analysis of toxicity in Leptinotarsa decemlineata (Say) and Diabrotica undecimpunctata howardi Barber," Insect Biochem. Molec. Biol., 22:9–18, 1992.

Slatin, Abrams, English, "Delta-endotoxins form cation-selective channels in planar lipid bilayers," Biochem. Biophys. Res. Comm., 169(2):765–772, 1990.

Smedley and Ellar, "Mutagenesis of three surface-exposed loops of a Bacillus thuringiensis insecticidal toxin reveals residues important for toxicity, receptor recognition and possibly membrane insertion," Microbiology, 142:1617–1624, 1996.

Smith and Ellar, "Mutagenesis of two surface-exposed loops of the Bacillus thuringiensis CryIC δ-endotoxin affects insecticidal specificity," Biochem. J., 302:611–616, 1994.

Smith, Merrick, Bone, Ellar, Appl. Environ. Microbiol., 62:680–684, 1996.

Spielmann et al., Mol. Gen. Genet., 205:34, 1986.

Stemmer and Morris, "Enzymatic Inverse PCR™. A Restriction Site Independent, Single-Fragment Method for High-Efficiency, Site-Directed Mutagenesis," BioTechniques, 13(2):214–220, 1992.

Stemmer, Proc. Natl. Acad Sci. USA, 91:10747–1075, 1994.

Taira et al., Nucl. Acids Res., 19:5125–30, 1991.

Tomic et al., Nucl. Acids Res., 12:1656, 1990.

Tomic, Sunjevaric, Savtchenko, Blumenberg, "A rapid and simple method for introducing specific mutations into any position of DNA leaving all other positions unaltered," Nucleic Acids Res., 18(6): 1656, 1990.

Toriyama et al., Theor Appl. Genet., 73:16, 1986.

Uchimiya et al., Mol. Gen. Genet., 204:204, 1986.

Upender et al., Biotechniques, 18:29–31, 1995.

Usman and Cedergren, TIBS, 17:34, 1992.

Usman and Cedergren, Trends in Biochem. Sci., 17:334, 1992.

Usman et al., J. Am. Chem. Soc., 109:7845–7854, 1987.

Vallette, Merge, Reiss, Adesnik, "Construction of mutant and chimeric genes using the polymerase chain reaction," Nucl. Acids Res., 17:723–733, 1989.

Vasil et al., "Herbicide-resistant fertile transgenic wheat plants obtained by microprojectile bombardment of regenerable embryogenic callus," Biotechnology, 10:667–674, 1992.

Vasil, Biotechnology, 6:397, 1988.

Velten and Schell, Nucl. Acids Res., 13:6981–6998, 1985.

Velten et al., EMBO J, 3:2723–2730, 1984.

Ventura et al., Nucl. Acids Res., 21:3249–55, 1993.

Vodkin et al., Cell, 34:1023, 1983.

Vogel et al., J. Cell Biochem., Suppl. 13D:312, 1989.

Von Tersch, Slatin, Kulesza, English, "Membrane permeabilizing activity of Bacillus thuringiensis Coleopteran-active toxins CryIIIB2 and CryIIIB2 domain 1 peptides," Appl. Env Microbiol., 60:3711–3717, 1994.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," Proc. Natl. Acad. Sci. USA, 89(13):6099–6103, 1992.

Walker et al., Proc. Natl. Acad. Sci. USA, 89(1):392–396, 1992.

Walters et al., Biochem. Biophys. Res. Commun., 196:921–926, 1993.

Watson et al., Molecular Biology of the Gene, 4th Ed., W. A. Benjamin, Inc., Menlo Park, Calif., 1987.

Weerasinghe et al., J. Virol., 65:5531–4, 1991.

Weissbach and Weissbach, Methods for Plant Molecular Biology, (eds.), Academic Press, Inc., San Diego, Calif., 1988.

Wenzler et al., *Plant Mol. Biol.*, 12:41–50, 1989.
Wickens and Stephenson, *Science*, 226:1045, 1984.
Wickens et al., In: "RNA Processing," p. 9, Cold Spring Harbor Laboratory, Cold Spring Harbor, N.Y., 1987.
Wolfersberger et al., *Appl. Environ. Microbiol.*, 62:279–282, 1996.
Wong and Neumann, "Electric field mediated gene transfer," *Biochim. Biophys. Res. Commun.*, 107(2):584–587, 1982.
Woolf et al., *Proc. Natl. Acad Sci. USA*, 89:7305–7309, 1992.
Wu and Aronson, "Localized mutagenesis defines regions of the *Bacillus thuringiensis* δ-endotoxin involved in toxicity and specificity," *J. Biol. Chem.*, 267:2311–2317, 1992.
Wu and Dean, "Functional significance of loops in the receptor binding domain of *Bacillus thuringiensis* CryIIIA δ-endotoxin," *J. Mol. Biol.*, 255:628–640, 1996.
Yamada et al., *Plant Cell Rep.*, 4:85, 1986.
Yang et al., *Proc. Natl. Acad. Sci. USA*, 87:4144–48, 1990.
Yu et al., *Proc. Natl. Acad. Sci. USA*, 90:6340–4, 1993.
Zatloukal, Wagner, Cotten, Phillips, Plank, Steinlein, Curiel, Bimstiel, "Transferrinfection: a highly efficient way to express gene constructs in eukaryotic cells," *Ann. N. Y. Acad. Sci.*, 660:136–153, 1992.
Zhang and Matthews, "Conservations of solvent-binding sites in 10 crystal forms of T4 lysozyme," *Prot. Sci.*, 3:1031–1039, 1994.
Zhou et al., *Mol. Cell Biol.*, 10:4529–37, 1990.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

---

What is claimed is:

1. A modified polynucleotide that encodes a polypeptide comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:100, and SEQ ID NO:108.

2. The polynucleotide of claim 1, wherein said modified polynucleotide comprises a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:99, and SEQ ID NO:107.

3. The polynucleotide of claim 1, further characterized as DNA, cDNA, RNA, or mRNA.

4. The polynucleotide of claim 1, wherein said modified polynucleotide encodes a polypeptide comprising the amino acid sequence of SEQ ID NO:2.

5. The polynucleotide of claim 4, wherein said modified polynucleotide comprises the nucleic acid sequence of SEQ ID NO:1.

6. The polynucleotide of claim 1, wherein said modified polynucleotide encodes a polypeptide comprising the amino acid sequence of SEQ ID NO:4.

7. The polynucleotide of claim 6, wherein said modified polynucleotide comprises the nucleic acid sequence of SEQ ID NO:3.

8. The polynucleotide of claim 1, wherein said modified polynucleotide encodes a polypeptide comprising the amino acid sequence of SEQ ID NO:6.

9. The polynucleotide of claim 8, wherein said modified polynucleotide comprises the nucleic acid sequence of SEQ ID NO:5.

10. The polynucleotide of claim 1, wherein said modified polynucleotide encodes a polypeptide comprising the amino acid sequence of SEQ ID NO:8.

11. The polynucleotide of claim 10, wherein said modified polynucleotide comprises the nucleic acid sequence of SEQ ID NO:7.

12. The polynucleotide of claim 1, wherein said modified polynucleotide encodes a polypeptide comprising the amino acid sequence of SEQ ID NO:10.

13. The polynucleotide of claim 12, wherein said modified polynucleotide comprises the nucleic acid sequence of SEQ ID NO:9.

14. The polynucleotide of claim 1, wherein said modified polynucleotide encodes a polypeptide comprising the amino acid sequence of SEQ ID NO:12.

15. The polynucleotide of claim 14, wherein said modified polynucleotide comprises the nucleic acid sequence of SEQ ID NO:11.

16. The polynucleotide of claim 1, wherein said modified polynucleotide encodes a polypeptide comprising the amino acid sequence of SEQ ID NO:14.

17. The polynucleotide of claim 16, wherein said modified polynucleotide comprises the nucleic acid sequence of SEQ ID NO:13.

18. The polynucleotide of claim 1, wherein said modified polynucleotide encodes a polypeptide comprising the amino acid sequence of SEQ ID NO:16.

19. The polynucleotide of claim 18, wherein said modified polynucleotide comprises the nucleic acid sequence of SEQ ID NO:15.

20. The polynucleotide of claim 1, wherein said modified polynucleotide encodes a polypeptide comprising the amino acid sequence of SEQ ID NO:18.

21. The polynucleotide of claim 20, wherein said modified polynucleotide comprises the nucleic acid sequence of SEQ ID NO:17.

22. The polynucleotide of claim 1, wherein said modified polynucleotide encodes a polypeptide comprising the amino acid sequence of SEQ ID NO:20.

23. The polynucleotide of claim 22, wherein said modified polynucleotide comprises the nucleic acid sequence of SEQ ID NO:19.

24. The polynucleotide of claim 1, wherein said modified polynucleotide encodes a polypeptide comprising the amino acid sequence of SEQ ID NO:22.

25. The polynucleotide of claim 24, wherein said modified polynucleotide comprises the nucleic acid sequence of SEQ ID NO:21.

26. The polynucleotide of claim 1, wherein said modified polynucleotide encodes a polypeptide comprising the amino acid sequence of SEQ ID NO:24.

27. The polynucleotide of claim 26, wherein said modified polynucleotide comprises the nucleic acid sequence of SEQ ID NO:23.

28. The polynucleotide of claim 1, wherein said modified polynucleotide encodes a polypeptide comprising the amino acid sequence of SEQ ID NO:26.

29. The polynucleotide of claim 28, wherein said modified polynucleotide comprises the nucleic acid sequence of SEQ ID NO:25.

30. The polynucleotide of claim 1, wherein said modified polynucleotide encodes a polypeptide comprising the amino acid sequence of SEQ ID NO:28.

31. The polynucleotide of claim 30, wherein said modified polynucleotide comprises the nucleic acid sequence of SEQ ID NO:27.

32. The polynucleotide of claim 1, wherein said modified polynucleotide encodes a polypeptide comprising the amino acid sequence of SEQ ID NO:30.

33. The polynucleotide of claim 32, wherein said modified polynucleotide comprises the nucleic acid sequence of SEQ ID NO:29.

34. The polynucleotide of claim 1, wherein said modified polynucleotide encodes a polypeptide comprising the amino acid sequence of SEQ ID NO:32.

35. The polynucleotide of claim 34, wherein said modified polynucleotide comprises the nucleic acid sequence of SEQ ID NO:31.

36. The polynucleotide of claim 1, wherein said modified polynucleotide encodes a polypeptide comprising the amino acid sequence of SEQ ID NO:34.

37. The polynucleotide of claim 36, wherein said modified polynucleotide comprises the nucleic acid sequence of SEQ ID NO:33.

38. The polynucleotide of claim 1, wherein said modified polynucleotide encodes a polypeptide comprising the amino acid sequence of SEQ ID NO:36.

39. The polynucleotide of claim 38, wherein said modified polynucleotide comprises the nucleic acid sequence of SEQ ID NO:35.

40. The polynucleotide of claim 1, wherein said modified polynucleotide encodes a polypeptide comprising the amino acid sequence of SEQ ID NO:38.

41. The polynucleotide of claim 40, wherein said modified polynucleotide comprises the nucleic acid sequence of SEQ ID NO:37.

42. The polynucleotide of claim 1, wherein said modified polynucleotide encodes a polypeptide comprising the amino acid sequence of SEQ ID NO:40.

43. The polynucleotide of claim 42, wherein said modified polynucleotide comprises the nucleic acid sequence of SEQ ID NO:39.

44. The polynucleotide of claim 1, wherein said modified polynucleotide encodes a polypeptide comprising the amino acid sequence of SEQ ID NO:42.

45. The polynucleotide of claim 44, wherein said modified polynucleotide comprises the nucleic acid sequence of SEQ ID NO:41.

46. The polynucleotide of claim 1, wherein said modified polynucleotide encodes a polypeptide comprising the amino acid sequence of SEQ ID NO:44.

47. The polynucleotide of claim 46, wherein said modified polynucleotide comprises the nucleic acid sequence of SEQ ID NO:43.

48. The polynucleotide of claim 1, wherein said modified polynucleotide encodes a polypeptide comprising the amino acid sequence of SEQ ID NO:46.

49. The polynucleotide of claim 48, wherein said modified polynucleotide comprises the nucleic acid sequence of SEQ ID NO:45.

50. The polynucleotide of claim 1, wherein said modified polynucleotide encodes a polypeptide comprising the amino acid sequence of SEQ ID NO:48.

51. The polynucleotide of claim 50, wherein said modified polynucleotide comprises the nucleic acid sequence of SEQ ID NO:47.

52. The polynucleotide of claim 1, wherein said modified polynucleotide encodes a polypeptide comprising the amino acid sequence of SEQ ID NO:50.

53. The polynucleotide of claim 52, wherein said modified polynucleotide comprises the nucleic acid sequence of SEQ ID NO:49.

54. The polynucleotide of claim 1, wherein said modified polynucleotide encodes a polypeptide comprising the amino acid sequence of SEQ ID NO:52.

55. The polynucleotide of claim 54, wherein said modified polynucleotide comprises the nucleic acid sequence of SEQ ID NO:51.

56. The polynucleotide of claim 1, wherein said modified polynucleotide encodes a polypeptide comprising the amino acid sequence of SEQ ID NO:54.

57. The polynucleotide of claim 56, wherein said modified polynucleotide comprises the nucleic acid sequence of SEQ ID NO:53.

58. The polynucleotide of claim 1, wherein said modified polynucleotide encodes a polypeptide comprising the amino acid sequence of SEQ ID NO:56.

59. The polynucleotide of claim 58, wherein said modified polynucleotide comprises the nucleic acid sequence of SEQ ID NO:55.

60. The polynucleotide of claim 1, wherein said modified polynucleotide encodes a polypeptide comprising the amino acid sequence of SEQ ID NO:58.

61. The polynucleotide of claim 60, wherein said modified polynucleotide comprises the nucleic acid sequence of SEQ ID NO:57.

62. The polynucleotide of claim 1, wherein said modified polynucleotide encodes a polypeptide comprising the amino acid sequence of SEQ ID NO:60.

63. The polynucleotide of claim 62, wherein said modified polynucleotide comprises the nucleic acid sequence of SEQ ID NO:59.

64. The polynucleotide of claim 1, wherein said modified polynucleotide encodes a polypeptide comprising the amino acid sequence of SEQ ID NO:62.

65. The polynucleotide of claim 64, wherein said modified polynucleotide comprises the nucleic acid sequence of SEQ ID NO:61.

66. The polynucleotide of claim 1, wherein said modified polynucleotide encodes a polypeptide comprising the amino acid sequence of SEQ ID NO:64.

67. The polynucleotide of claim 66, wherein said modified polynucleotide comprises the nucleic acid sequence of SEQ ID NO:63.

68. The polynucleotide of claim 1, wherein said modified polynucleotide encodes a polypeptide comprising the amino acid sequence of SEQ ID NO:66.

69. The polynucleotide of claim 68, wherein said modified polynucleotide comprises the nucleic acid sequence of SEQ ID NO:65.

70. The polynucleotide of claim 1, wherein said modified polynucleotide encodes a polypeptide comprising the amino acid sequence of SEQ ID NO:68.

71. The polynucleotide of claim 70, wherein said modified polynucleotide comprises the nucleic acid sequence of SEQ ID NO:67.

72. The polynucleotide of claim 1, wherein said modified polynucleotide encodes a polypeptide comprising the amino acid sequence of SEQ ID NO:70.

73. The polynucleotide of claim 72, wherein said modified polynucleotide comprises the nucleic acid sequence of SEQ ID NO:69.

74. The polynucleotide of claim 1, wherein said modified polynucleotide encodes a polypeptide comprising the amino acid sequence of SEQ ID NO:100.

75. The polynucleotide of claim 74, wherein said modified polynucleotide comprises the nucleic acid sequence of SEQ ID NO:99.

76. The polynucleotide of claim 1, wherein said modified polynucleotide encodes a polypeptide comprising the amino acid sequence of SEQ ID NO:108.

77. The polynucleotide of claim 76, wherein said modified polynucleotide comprises the nucleic acid sequence of SEQ ID NO:107.

78. The polynucleotide of claim 1, wherein said modified polynucleotide is operably linked to a promoter that expresses said sequence region to produce said polypeptide.

79. The polynucleotide of claim 78, wherein said promoter is a heterologous promoter.

80. The polynucleotide of claim 79, wherein said promoter is a plant-expressible promoter.

81. The polynucleotide of claim 80, wherein said plant-expressible promoter is selected from the group consisting of a corn sucrose synthetase 1 promoter, corn alcohol dehydrogenase 1 promoter, corn light harvesting complex promoter, corn heat shock protein promoter, pea small subunit RuBP carboxylase promoter, Ti plasmid mannopine synthase promoter, Ti plasmid nopaline synthase promoter, petunia chalcone isomerase promoter, bean glycine rich protein 1 promoter, Potato patatin promoter, lectin promoter, CaMV 35S promoter, and S-E9 small subunit RuBP carboxylase promoter.

82. A vector comprising the polynucleotide of claim 1.

83. The vector of claim 82, further defined as a plasmid, cosmid, phagemid, artificial chromosome, phage or viral vector.

84. The vector of claim 82, wherein said modified polynucleotide encodes a polypeptide comprising the amino acid sequence of SEQ ID NO:2, SEQ ID NO:4, SEQ ID NO:6, SEQ ID NO:8, or SEQ ID NO:10.

85. The vector of claim 84, wherein said modified polynucleotide comprises the nucleic acid sequence of SEQ ID NO:1, SEQ ID NO:3, SEQ ID NO:5, SEQ ID NO:7, or SEQ ID NO:9.

86. The vector of claim 82, wherein said modified polynucleotide encodes a polypeptide comprising the amino acid sequence of SEQ ID NO:12, SEQ ID NO:14, SEQ ID NO:16, SEQ ID NO:18, or SEQ ID NO:20.

87. The vector of claim 86, wherein said modified polynucleotide comprises the nucleic acid sequence of SEQ ID NO:11, SEQ ID NO:13, SEQ ID NO:15, SEQ ID NO:17, or SEQ ID NO:19.

88. The vector of claim 82, wherein said modified polynucleotide encodes a polypeptide comprising the amino acid sequence of SEQ ID NO:22, SEQ ID NO:24, SEQ ID NO:26, SEQ ID NO:28, or SEQ ID NO:30.

89. The vector of claim 88, wherein said modified polynucleotide comprises the nucleic acid sequence of SEQ ID NO:21, SEQ ID NO:23, SEQ ID NO:25, SEQ ID NO:27, or SEQ ID NO:29.

90. The vector of claim 82, wherein said modified polynucleotide encodes a polypeptide comprising the amino acid sequence of SEQ ID NO:32, SEQ ID NO:34, SEQ ID NO:36, SEQ ID NO:38, or SEQ ID NO:40.

91. The vector of claim 90, wherein said modified polynucleotide comprises the nucleic acid sequence of SEQ ID NO:31, SEQ ID NO:33, SEQ ID NO:35, SEQ ID NO:37, or SEQ ID NO:39.

92. The vector of claim 82, wherein said modified polynucleotide encodes a polypeptide comprising the amino acid sequence of SEQ ID NO:42, SEQ ID NO:44, SEQ ID NO:46, SEQ ID NO:48, or SEQ ID NO:50.

93. The vector of claim 92, wherein said modified polynucleotide comprises the nucleic acid sequence of SEQ ID NO:41, SEQ ID NO:43, SEQ ID NO:45, SEQ ID NO:47, or SEQ ID NO:49.

94. The vector of claim 82, wherein said modified polynucleotide encodes a polypeptide comprising the amino acid sequence of SEQ ID NO:52, SEQ ID NO:54, SEQ ID NO:56, SEQ ID NO:58, or SEQ ID NO:60.

95. The vector of claim 94, wherein said modified polynucleotide comprises the nucleic acid sequence of SEQ ID NO:51, SEQ ID NO:53, SEQ ID NO:55, SEQ ID NO:57, or SEQ ID NO:59.

96. The vector of claim 82, wherein said modified polynucleotide encodes a polypeptide comprising the amino acid sequence of SEQ ID NO:62, SEQ ID NO:64, SEQ ID NO:66, SEQ ID NO:68, SEQ ID NO:70, SEQ ID NO:100, or SEQ ID NO:108.

97. The vector of claim 96, wherein said modified polynucleotide comprises the nucleic acid sequence of SEQ ID NO:61, SEQ ID NO:63, SEQ ID NO:65, SEQ ID NO:67, SEQ ID NO:69, SEQ ID NO:99, or SEQ ID NO:107.

* * * * *

UNITED STATES PATENT AND TRADEMARK OFFICE
CERTIFICATE OF CORRECTION

PATENT NO. : 6,060,594
DATED : May 9, 2000
INVENTOR(S) : Leigh H. English et al.

It is certified that error appears in the above-identified patent and that said Letters Patent is hereby corrected as shown below:

<u>Columns 9 and 10,</u>
Table 2, under "Cry3Bb* Amino Acid Changes", all three recitations of "P162H" should read -- R162H --.

<u>Columns 97 and 98,</u>
Table 11, under "Cry3Bb* Amino Acid Sequence", all three recitations of "P162H" should read -- R162H --.

Signed and Sealed this

Fourteenth Day of February, 2006

JON W. DUDAS
*Director of the United States Patent and Trademark Office*

SEQUENCE LISTING (1) GENERAL INFORMATION:

(iii) NUMBER OF SEQUENCES: 113

(2) INFORMATION FOR SEQ ID NO:1:

(i) SEQUENCE CHARACTERISTICS:
      (A) LENGTH: 1959 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..1956

(xi) SEQUENCE DESCRIPTION: SEQ ID NO:1:

```
ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
```

```
                115                 120                      125
AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
        130                 135                 140

GTT AAT GCG TTA AAT TCC TGG AAG AAA TTT CAC CAT TCT CGT CGT TCT     480
Val Asn Ala Leu Asn Ser Trp Lys Lys Phe His His Ser Arg Arg Ser
145                 150                 155                 160

AAA AGA AGC CAA GAT CGA ATA AGG GAA CTT TTT TCT CAA GCA GAA AGT     528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG     576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA     624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA     672
Leu Lys Asp Ala Gln Val Phe Gly Glu Glu Trp Gly Tyr Ser Ser Glu
210                 215                 220

GAT GTT GCT GAA TTT TAT CAT AGA CAA TTA AAA CTT ACA CAA CAA TAC     720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA     768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA     816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT     864
Met Thr Leu Thr Val Leu Asp Leu Ile Val Leu Phe Pro Phe Tyr Asp
        275                 280                 285

ATT CGG TTA TAC TCA AAA GGG GTT AAA ACA GAA CTA ACA AGA GAC ATT     912
Ile Arg Leu Tyr Ser Lys Gly Val Lys Thr Glu Leu Thr Arg Asp Ile
        290                 295                 300

TTT ACG GAT CCA ATT TTT TCA CTT AAT ACT CTT CAG GAG TAT GGA CCA     960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT    1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT    1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA    1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT    1152
Pro Ser Ile Gly Ser Ser Lys Thr Ile Thr Ser Pro Phe Tyr Gly Asp
        370                 375                 380

AAA TCT ACT GAA CCT GTA CAA AAG CTA AGC TTT GAT GGA CAA AAA GTT    1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG    1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA    1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC    1344
```

```
                              -continued

Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA    1392
His Val Ser Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCG GAA    1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG    1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT    1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC    1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA    1632
Ile Ile Glu Gly Pro Gly Phe Thr Gly Gly Asn Leu Leu Phe Leu Lys
530                 535                 540

GAA TCT AGT AAT TCA ATT GCT AAA TTT AAA GTT ACA TTA AAT TCA GCA    1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT    1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC    1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650

(2) INFORMATION FOR SEQ ID NO:2:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Pro Asn Asn Arg Ser Glu His Asp Thr Ile Lys Val Thr Pro
  1               5                  10                  15

Asn Ser Glu Leu Gln Thr Asn His Asn Gln Tyr Pro Leu Ala Asp Asn
                20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
        50                  55                  60
```

-continued

```
Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
                100                 105                 110

Gln Val Glu Val Leu Ile Asp Lys Lys Ile Glu Tyr Ala Lys Ser
            115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Phe His His Ser Arg Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
                180                 185                 190

Leu Phe Leu Pro Thr Tyr Ala Gln Ala Ala Asn Thr His Leu Leu Leu
                195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
                260                 265                 270

Met Thr Leu Thr Val Leu Asp Leu Ile Val Leu Phe Pro Phe Tyr Asp
                275                 280                 285

Ile Arg Leu Tyr Ser Lys Gly Val Lys Thr Glu Leu Thr Arg Asp Ile
                290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
                340                 345                 350

Gly Lys Asp Ser Phe Asn Tyr Trp Ser Gly Asn Tyr Val Glu Thr Arg
                355                 360                 365

Pro Ser Ile Gly Ser Ser Lys Thr Ile Thr Ser Pro Phe Tyr Gly Asp
370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
                435                 440                 445

His Val Ser Ala Gln Asp Ser Ile Asp Gln Leu Pro Pro Glu Thr Thr
                450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
```

```
                    485                 490                    495
Thr His Arg Ser Val Asp Phe Phe Asn Thr Ile Asp Ala Glu Lys Ile
            500                 505             510

Thr Gln Leu Pro Val Val Lys Ala Tyr Ala Leu Ser Ser Gly Ala Ser
        515                 520             525

Ile Ile Glu Gly Pro Gly Phe Thr Gly Gly Asn Leu Leu Phe Leu Lys
    530                 535             540

Glu Ser Ser Asn Ser Ile Ala Lys Phe Lys Val Thr Leu Asn Ser Ala
545                 550             555                 560

Ala Leu Leu Gln Arg Tyr Arg Val Arg Ile Arg Tyr Ala Ser Thr Thr
                565             570             575

Asn Leu Arg Leu Phe Val Gln Asn Ser Asn Asp Phe Leu Val Ile
            580             585             590

Tyr Ile Asn Lys Thr Met Asn Lys Asp Asp Leu Thr Tyr Gln Thr
        595             600             605

Phe Asp Leu Ala Thr Thr Asn Ser Asn Met Gly Phe Ser Gly Asp Lys
        610             615             620

Asn Glu Leu Ile Ile Gly Ala Glu Ser Phe Val Ser Asn Glu Lys Ile
625             630             635                 640

Tyr Ile Asp Lys Ile Glu Phe Ile Pro Val Gln Leu
            645             650
```

(2) INFORMATION FOR SEQ ID NO:3:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:3:

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA     240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT     288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA     336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125
```

```
AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT     480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT     528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG     576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA     624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA     672
Leu Lys Asp Ala Gln Val Phe Gly Glu Glu Trp Gly Tyr Ser Ser Glu
    210                 215                 220

GAT GTT GCT GAA TTC CTT AGT AGA CAA TTA AAA CTT ACA CAA CAA TAC     720
Asp Val Ala Glu Phe Leu Ser Arg Gln Leu Lys Leu Thr Gln Gln Tyr
225                 230                 235                 240

ACT GAC CAT TGT GTT AAT TGG TAT AAT GTT GGA TTA AAT GGT TTA AGA     768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA     816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT     864
Met Thr Leu Thr Val Leu Asp Leu Ile Val Leu Phe Pro Phe Tyr Asp
        275                 280                 285

ATT CGG TTA TAC TCA AAA GGG GTT AAA ACA GAA CTA ACA AGA GAC ATT     912
Ile Arg Leu Tyr Ser Lys Gly Val Lys Thr Glu Leu Thr Arg Asp Ile
    290                 295                 300

TTT ACG GAT CCA ATT TTT TCA CTT AAT ACT CTT CAG GAG TAT GGA CCA     960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT    1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT    1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA    1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT    1152
Pro Ser Ile Gly Ser Ser Lys Thr Ile Thr Ser Pro Phe Tyr Gly Asp
    370                 375                 380

AAA TCT ACT GAA CCT GTA CAA AAG CTA AGC TTT GAT GGA CAA AAA GTT    1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG    1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA    1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC    1344
Lys Asn Glu Thr Ser Thr Gln Thr Tyr Asp Ser Lys Arg Asn Asn Gly
        435                 440                 445
```

```
CAT GTA AGT GCA CAG GAT TCT ATT GAC CAA TTA CCG CCA GAA ACA ACA        1392
His Val Ser Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCG GAA        1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG        1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT        1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC        1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA        1632
Ile Ile Glu Gly Pro Gly Phe Thr Gly Gly Asn Leu Leu Phe Leu Lys
    530                 535                 540

GAA TCT AGT AAT TCA ATT GCT AAA TTT AAA GTT ACA TTA AAT TCA GCA        1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT        1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC        1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA        1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG        1872
Phe Asp Leu Ala Thr Thr Asn Ser Asn Met Gly Phe Ser Gly Asp Lys
    610                 615                 620

AAT GAA CTT ATA ATA GGA GCA GAA TCT TTC GTT TCT AAT GAA AAA ATC        1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                    1959
Tyr Ile Asp Lys Ile Glu Phe Ile Pro Val Gln Leu
                645                 650

(2) INFORMATION FOR SEQ ID NO:4:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:4:

Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80
```

-continued

```
Gly Val Pro Phe Ala Gly Ala Leu Thr Ser Phe Tyr Gln Ser Phe Leu
                85                  90                  95
Asn Thr Ile Trp Pro Ser Asp Ala Asp Pro Trp Lys Ala Phe Met Ala
            100                 105                 110
Gln Val Glu Val Leu Ile Asp Lys Lys Ile Glu Glu Tyr Ala Lys Ser
        115                 120                 125
Lys Ala Leu Ala Glu Leu Gln Gly Leu Gln Asn Asn Phe Glu Asp Tyr
    130                 135                 140
Val Asn Ala Leu Asn Ser Trp Lys Lys Thr Pro Leu Ser Leu Arg Ser
145                 150                 155                 160
Lys Arg Ser Gln Asp Arg Ile Arg Glu Leu Phe Ser Gln Ala Glu Ser
                165                 170                 175
His Phe Arg Asn Ser Met Pro Ser Phe Ala Val Ser Lys Phe Glu Val
            180                 185                 190
Leu Phe Leu Pro Thr Tyr Ala Gln Ala Ala Asn Thr His Leu Leu Leu
        195                 200                 205
Leu Lys Asp Ala Gln Val Phe Gly Glu Glu Trp Gly Tyr Ser Ser Glu
    210                 215                 220
Asp Val Ala Glu Phe Leu Ser Arg Gln Leu Lys Leu Thr Gln Gln Tyr
225                 230                 235                 240
Thr Asp His Cys Val Asn Trp Tyr Asn Val Gly Leu Asn Gly Leu Arg
                245                 250                 255
Gly Ser Thr Tyr Asp Ala Trp Val Lys Phe Asn Arg Phe Arg Arg Glu
            260                 265                 270
Met Thr Leu Thr Val Leu Asp Leu Ile Val Leu Phe Pro Phe Tyr Asp
        275                 280                 285
Ile Arg Leu Tyr Ser Lys Gly Val Lys Thr Glu Leu Thr Arg Asp Ile
    290                 295                 300
Phe Thr Asp Pro Ile Phe Ser Leu Asn Thr Leu Gln Glu Tyr Gly Pro
305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Gln Pro Gly Tyr Phe
            340                 345                 350
Gly Lys Asp Ser Phe Asn Tyr Trp Ser Gly Asn Tyr Val Glu Thr Arg
        355                 360                 365
Pro Ser Ile Gly Ser Ser Lys Thr Ile Thr Ser Pro Phe Tyr Gly Asp
    370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
            420                 425                 430
Lys Asn Glu Thr Ser Thr Gln Thr Tyr Asp Ser Lys Arg Asn Asn Gly
        435                 440                 445
His Val Ser Ala Gln Asp Ser Ile Asp Gln Leu Pro Pro Glu Thr Thr
    450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
```

-continued

```
Thr His Arg Ser Val Asp Phe Phe Asn Thr Ile Asp Ala Glu Lys Ile
        500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
        530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
        580                 585                 590

Tyr Ile Asn Lys Thr Met Asn Lys Asp Asp Leu Thr Tyr Gln Thr
        595                 600                 605

Phe Asp Leu Ala Thr Thr Asn Ser Asn Met Gly Phe Ser Gly Asp Lys
        610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650
```

(2) INFORMATION FOR SEQ ID NO:5:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:5:

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
1               5                   10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
            20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
        35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
    50                  55                  60

GCA GTT GGG ACA GGA ATT TCT GTT GTA GGG CAG ATT TTA GGT GTT GTA     240
Ala Val Gly Thr Gly Ile Ser Val Val Gly Gln Ile Leu Gly Val Val
65                  70                  75                  80

GGA GTT CCA TTT GCT GGG GCA CTC ACT TCA TTT TAT CAA TCA TTT CTT     288
Gly Val Pro Phe Ala Gly Ala Leu Thr Ser Phe Tyr Gln Ser Phe Leu
                85                  90                  95

AAC ACT ATA TGG CCA AGT GAT GCT GAC CCA TGG AAG GCT TTT ATG GCA     336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
```

-continued

```
           130                 135                 140
GTT AAT GCG TTA AAT TCC TGG AAG AAA ACA CCT TTA AGT TTG CGA AGT      480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT      528
Lys Arg Ser Gln Asp Arg Ile Arg Glu Leu Phe Ser Gln Ala Glu Ser
                    165                 170                 175

CAT TTT CGT AAT TCC ATG CCG TCA TTT GCA GTT TCC AAA TTC GAA GTG      576
His Phe Arg Asn Ser Met Pro Ser Phe Ala Val Ser Lys Phe Glu Val
                180                 185                 190

CTG TTT CTA CCA ACA TAT GCA CAA GCT GCA AAT ACA CAT TTA TTG CTA      624
Leu Phe Leu Pro Thr Tyr Ala Gln Ala Ala Asn Thr His Leu Leu Leu
            195                 200                 205

TTA AAA GAT GCT CAA GTT TTT GGA GAA GAA TGG GGA TAT TCT CCA GAA      672
Leu Lys Asp Ala Gln Val Phe Gly Glu Glu Trp Gly Tyr Ser Pro Glu
210                 215                 220

GAT GTT GCT GAA TTC AGT CAT AGA CAA TTA AAA CTT ACA CAA CAA TAC      720
Asp Val Ala Glu Phe Ser His Arg Gln Leu Lys Leu Thr Gln Gln Tyr
225                 230                 235                 240

ACT GAC CAT TGT GTT AAT TGG TAT AAT GTT GGA TTA AAT GGT TTA AGA      768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA      816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT      864
Met Thr Leu Thr Val Leu Asp Leu Ile Val Leu Phe Pro Phe Tyr Asp
        275                 280                 285

ATT CGG TTA TAC TCA AAA GGG GTT AAA ACA GAA CTA ACA AGA GAC ATT      912
Ile Arg Leu Tyr Ser Lys Gly Val Lys Thr Glu Leu Thr Arg Asp Ile
    290                 295                 300

TTT ACG GAT CCA ATT TTT TCA CTT AAT ACT CTT CAG GAG TAT GGA CCA      960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
    370                 375                 380

AAA TCT ACT GAA CCT GTA CAA AAG CTA AGC TTT GAT GGA CAA AAA GTT     1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG     1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA     1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC     1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA     1392
```

-continued

```
His Val Ser Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCG GAA     1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG     1488
Cys Phe Leu Met Gln Asp Arg Arg Gly Thr Ile Pro Phe Phe Thr Trp
                    485                 490                 495

ACA CAT AGA AGT GTA GAC TTT TTT AAT ACA ATT GAT GCT GAA AAG ATT     1536
Thr His Arg Ser Val Asp Phe Phe Asn Thr Ile Asp Ala Glu Lys Ile
                500                 505                 510

ACT CAA CTT CCA GTA GTG AAA GCA TAT GCC TTG TCT TCA GGT GCT TCC     1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA     1632
Ile Ile Glu Gly Pro Gly Phe Thr Gly Gly Asn Leu Leu Phe Leu Lys
530                 535                 540

GAA TCT AGT AAT TCA ATT GCT AAA TTT AAA GTT ACA TTA AAT TCA GCA     1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT     1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC     1776
Asn Leu Arg Leu Phe Val Gln Asn Ser Asn Asn Asp Phe Leu Val Ile
                580                 585                 590

TAC ATT AAT AAA ACT ATG AAT AAA GAT GAT GAT TTA ACA TAT CAA ACA     1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG     1872
Phe Asp Leu Ala Thr Thr Asn Ser Asn Met Gly Phe Ser Gly Asp Lys
610                 615                 620

AAT GAA CTT ATA ATA GGA GCA GAA TCT TTC GTT TCT AAT GAA AAA ATC     1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                 1959
Tyr Ile Asp Lys Ile Glu Phe Ile Pro Val Gln Leu
                645                 650

(2) INFORMATION FOR SEQ ID NO:6:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:6:

Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
                20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
        50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
```

-continued

```
                85                    90                    95
Asn Thr Ile Trp Pro Ser Asp Ala Asp Pro Trp Lys Ala Phe Met Ala
                    100                 105                 110
Gln Val Glu Val Leu Ile Asp Lys Lys Ile Glu Glu Tyr Ala Lys Ser
            115                 120                 125
Lys Ala Leu Ala Glu Leu Gln Gly Leu Gln Asn Asn Phe Glu Asp Tyr
        130                 135                 140
Val Asn Ala Leu Asn Ser Trp Lys Lys Thr Pro Leu Ser Leu Arg Ser
145                 150                 155                 160
Lys Arg Ser Gln Asp Arg Ile Arg Glu Leu Phe Ser Gln Ala Glu Ser
                165                 170                 175
His Phe Arg Asn Ser Met Pro Ser Phe Ala Val Ser Lys Phe Glu Val
            180                 185                 190
Leu Phe Leu Pro Thr Tyr Ala Gln Ala Ala Asn Thr His Leu Leu Leu
        195                 200                 205
Leu Lys Asp Ala Gln Val Phe Gly Glu Glu Trp Gly Tyr Ser Pro Glu
210                 215                 220
Asp Val Ala Glu Phe Ser His Arg Gln Leu Lys Leu Thr Gln Gln Tyr
225                 230                 235                 240
Thr Asp His Cys Val Asn Trp Tyr Asn Val Gly Leu Asn Gly Leu Arg
                245                 250                 255
Gly Ser Thr Tyr Asp Ala Trp Val Lys Phe Asn Arg Phe Arg Arg Glu
            260                 265                 270
Met Thr Leu Thr Val Leu Asp Leu Ile Val Leu Phe Pro Phe Tyr Asp
        275                 280                 285
Ile Arg Leu Tyr Ser Lys Gly Val Lys Thr Glu Leu Thr Arg Asp Ile
290                 295                 300
Phe Thr Asp Pro Ile Phe Ser Leu Asn Thr Leu Gln Glu Tyr Gly Pro
305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Gln Pro Gly Tyr Phe
            340                 345                 350
Gly Lys Asp Ser Phe Asn Tyr Trp Ser Gly Asn Tyr Val Glu Thr Arg
        355                 360                 365
Pro Ser Ile Gly Ser Ser Lys Thr Ile Thr Ser Pro Phe Tyr Gly Asp
370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
            420                 425                 430
Lys Asn Glu Thr Ser Thr Gln Thr Tyr Asp Ser Lys Arg Asn Asn Gly
        435                 440                 445
His Val Ser Ala Gln Asp Ser Ile Asp Gln Leu Pro Pro Glu Thr Thr
450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Phe Asn Thr Ile Asp Ala Glu Lys Ile
            500                 505                 510
```

```
Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
        530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asp Phe Leu Val Ile
                580                 585                 590

Tyr Ile Asn Lys Thr Met Asn Lys Asp Asp Leu Thr Tyr Gln Thr
        595                 600                 605

Phe Asp Leu Ala Thr Thr Asn Ser Asn Met Gly Phe Ser Gly Asp Lys
        610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:7:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:7:

ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
  1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
 50                  55                  60

GCA GTT GGG ACA GGA ATT TCT GTT GTA GGG CAG ATT TTA GGT GTT GTA     240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT     288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA     336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
    130                 135                 140
```

```
GTT AAT GCG TTA AAT TCC TGG AAG AAA ACA CCT TTA AGT TTG CGA AGT         480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT         528
Lys Arg Ser Gln Asp Arg Ile Arg Glu Leu Phe Ser Gln Ala Glu Ser
                    165                 170                 175

CAT TTT CGT AAT TCC ATG CCG TCA TTT GCA GTT TCC AAA TTC GAA GTG         576
His Phe Arg Asn Ser Met Pro Ser Phe Ala Val Ser Lys Phe Glu Val
                180                 185                 190

CTG TTT CTA CCA ACA TAT GCA CAA GCT GCA AAT ACA CAT TTA TTG CTA         624
Leu Phe Leu Pro Thr Tyr Ala Gln Ala Ala Asn Thr His Leu Leu Leu
                195                 200                 205

TTA AAA GAT GCT CAA GTT TTT GGA GAA GAA TGG GGA TAT TCT TCA GAA         672
Leu Lys Asp Ala Gln Val Phe Gly Glu Glu Trp Gly Tyr Ser Ser Glu
210                 215                 220

GAT GTT GCT GAA TTC TAT CGT AGA CAA TTA AAA CTT ACA CAA CAA TAC         720
Asp Val Ala Glu Phe Tyr Arg Arg Gln Leu Lys Leu Thr Gln Gln Tyr
225                 230                 235                 240

ACT GAC CAT TGT GTT AAT TGG TAT AAT GTT GGA TTA AAT GGT TTA AGA         768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA         816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT         864
Met Thr Leu Thr Val Leu Asp Leu Ile Val Leu Phe Pro Phe Tyr Asp
                275                 280                 285

ATT CGG TTA TAC TCA AAA GGG GTT AAA ACA GAA CTA ACA AGA GAC ATT         912
Ile Arg Leu Tyr Ser Lys Gly Val Lys Thr Glu Leu Thr Arg Asp Ile
        290                 295                 300

TTT ACG GAT CCA ATT TTT TCA CTT AAT ACT CTT CAG GAG TAT GGA CCA         960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT        1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT        1056
Tyr Leu Gln Gly Ile Glu Phe His Thr Arg Leu Gln Pro Gly Tyr Phe
                340                 345                 350

GGG AAA GAT TCT TTC AAT TAT TGG TCT GGT AAT TAT GTA GAA ACT AGA        1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT        1152
Pro Ser Ile Gly Ser Ser Lys Thr Ile Thr Ser Pro Phe Tyr Gly Asp
        370                 375                 380

AAA TCT ACT GAA CCT GTA CAA AAG CTA AGC TTT GAT GGA CAA AAA GTT        1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG        1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA        1296
Val Tyr Leu Gly Val Thr Lys Val Asp Phe Ser Gln Tyr Asp Asp Gln
                420                 425                 430

AAA AAT GAA ACT AGT ACA CAA ACA TAT GAT TCA AAA AGA AAC AAT GGC        1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA        1392
His Val Ser Ala Gln Asp Ser Ile Asp Gln Leu Pro Pro Glu Thr Thr
        450                 455                 460
```

```
GAT GAA CCA CTT GAA AAA GCA TAT AGT CAT CAG CTT AAT TAC GCG GAA       1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG       1488
Cys Phe Leu Met Gln Asp Arg Arg Gly Thr Ile Pro Phe Phe Thr Trp
                    485                 490                 495

ACA CAT AGA AGT GTA GAC TTT TTT AAT ACA ATT GAT GCT GAA AAG ATT       1536
Thr His Arg Ser Val Asp Phe Phe Asn Thr Ile Asp Ala Glu Lys Ile
                500                 505                 510

ACT CAA CTT CCA GTA GTG AAA GCA TAT GCC TTG TCT TCA GGT GCT TCC       1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA       1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA       1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT       1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC       1776
Asn Leu Arg Leu Phe Val Gln Asn Ser Asn Asn Asp Phe Leu Val Ile
                580                 585                 590

TAC ATT AAT AAA ACT ATG AAT AAA GAT GAT GAT TTA ACA TAT CAA ACA       1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG       1872
Phe Asp Leu Ala Thr Thr Asn Ser Asn Met Gly Phe Ser Gly Asp Lys
610                 615                 620

AAT GAA CTT ATA ATA GGA GCA GAA TCT TTC GTT TCT AAT GAA AAA ATC       1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                   1959
Tyr Ile Asp Lys Ile Glu Phe Ile Pro Val Gln Leu
                645                 650
```

(2) INFORMATION FOR SEQ ID NO:8:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:8:

```
Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
                20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
        50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95
```

-continued

```
Asn Thr Ile Trp Pro Ser Asp Ala Asp Pro Trp Lys Ala Phe Met Ala
            100                 105                 110
Gln Val Glu Val Leu Ile Asp Lys Lys Ile Glu Glu Tyr Ala Lys Ser
        115                 120                 125
Lys Ala Leu Ala Glu Leu Gln Gly Leu Gln Asn Asn Phe Glu Asp Tyr
    130                 135                 140
Val Asn Ala Leu Asn Ser Trp Lys Lys Thr Pro Leu Ser Leu Arg Ser
145                 150                 155                 160
Lys Arg Ser Gln Asp Arg Ile Arg Glu Leu Phe Ser Gln Ala Glu Ser
                165                 170                 175
His Phe Arg Asn Ser Met Pro Ser Phe Ala Val Ser Lys Phe Glu Val
            180                 185                 190
Leu Phe Leu Pro Thr Tyr Ala Gln Ala Ala Asn Thr His Leu Leu Leu
        195                 200                 205
Leu Lys Asp Ala Gln Val Phe Gly Glu Glu Trp Gly Tyr Ser Ser Glu
    210                 215                 220
Asp Val Ala Glu Phe Tyr Arg Arg Gln Leu Lys Leu Thr Gln Gln Tyr
225                 230                 235                 240
Thr Asp His Cys Val Asn Trp Tyr Asn Val Gly Leu Asn Gly Leu Arg
                245                 250                 255
Gly Ser Thr Tyr Asp Ala Trp Val Lys Phe Asn Arg Phe Arg Arg Glu
            260                 265                 270
Met Thr Leu Thr Val Leu Asp Leu Ile Val Leu Phe Pro Phe Tyr Asp
        275                 280                 285
Ile Arg Leu Tyr Ser Lys Gly Val Lys Thr Glu Leu Thr Arg Asp Ile
    290                 295                 300
Phe Thr Asp Pro Ile Phe Ser Leu Asn Thr Leu Gln Glu Tyr Gly Pro
305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Gln Pro Gly Tyr Phe
            340                 345                 350
Gly Lys Asp Ser Phe Asn Tyr Trp Ser Gly Asn Tyr Val Glu Thr Arg
        355                 360                 365
Pro Ser Ile Gly Ser Ser Lys Thr Ile Thr Ser Pro Phe Tyr Gly Asp
    370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
            420                 425                 430
Lys Asn Glu Thr Ser Thr Gln Thr Tyr Asp Ser Lys Arg Asn Asn Gly
        435                 440                 445
His Val Ser Ala Gln Asp Ser Ile Asp Gln Leu Pro Pro Glu Thr Thr
    450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Phe Asn Thr Ile Asp Ala Glu Lys Ile
            500                 505                 510
Thr Gln Leu Pro Val Val Lys Ala Tyr Ala Leu Ser Ser Gly Ala Ser
```

```
                515                 520                      525
Ile Ile Glu Gly Pro Gly Phe Thr Gly Gly Asn Leu Leu Phe Leu Lys
        530                 535             540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
        580                 585                 590

Tyr Ile Asn Lys Thr Met Asn Lys Asp Asp Leu Thr Tyr Gln Thr
        595                 600                 605

Phe Asp Leu Ala Thr Thr Asn Ser Asn Met Gly Phe Ser Gly Asp Lys
        610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:9:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
         (A) NAME/KEY: CDS
         (B) LOCATION: 1..1956

(xi) SEQUENCE DESCRIPTION: SEQ ID NO:9:

ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA     240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT     288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA     336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT     480
Val Asn Ala Leu Asn Ser Trp Lys Lys Thr Pro Leu Ser Leu Arg Ser
```

```
                145                 150                 155                 160
AAA AGA AGC CAA GAT CGA ATA AGG GAA CTT TTT TCT CAA GCA GAA AGT        528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG        576
His Phe Arg Asn Ser Met Pro Ser Phe Ala Val Ser Lys Phe Glu Val
                180                 185                 190

CTG TTT CTA CCA ACA TAT GCA CAA GCT GCA AAT ACA CAT TTA TTG CTA        624
Leu Phe Leu Pro Thr Tyr Ala Gln Ala Ala Asn Thr His Leu Leu Leu
                195                 200                 205

TTA AAA GAT GCT CAA GTT TTT GGA GAA GAA TGG GGA TAT TCT TCA GAA        672
Leu Lys Asp Ala Gln Val Phe Gly Glu Glu Trp Gly Tyr Ser Ser Glu
        210                 215                 220

GAT GTT GCT GAA TTC TAT AAT AGA CAA TTA AAA CTT ACA CAA CAA TAC        720
Asp Val Ala Glu Phe Tyr Asn Arg Gln Leu Lys Leu Thr Gln Gln Tyr
225                 230                 235                 240

TCT GAC CAT TGT GTT AAT TGG TAT AAT GTT GGA TTA AAT GGT TTA AGA        768
Ser Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA        816
Gly Ser Thr Tyr Asp Ala Trp Val Lys Phe Asn Arg Phe Arg Arg Glu
                260                 265                 270

ATG ACT TTA ACT GTA TTA GAT CTA ATT GTA CTT TTC CCA TTT TAT GAT        864
Met Thr Leu Thr Val Leu Asp Leu Ile Val Leu Phe Pro Phe Tyr Asp
                275                 280                 285

ATT CGG TTA TAC TCA AAA GGG GTT AAA ACA GAA CTA ACA AGA GAC ATT        912
Ile Arg Leu Tyr Ser Lys Gly Val Lys Thr Glu Leu Thr Arg Asp Ile
        290                 295                 300

TTT ACG GAT CCA ATT TTT TCA CTT AAT ACT CTT CAG GAG TAT GGA CCA        960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT       1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT       1056
Tyr Leu Gln Gly Ile Glu Phe His Thr Arg Leu Gln Pro Gly Tyr Phe
                340                 345                 350

GGG AAA GAT TCT TTC AAT TAT TGG TCT GGT AAT TAT GTA GAA ACT AGA       1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT       1152
Pro Ser Ile Gly Ser Ser Lys Thr Ile Thr Ser Pro Phe Tyr Gly Asp
        370                 375                 380

AAA TCT ACT GAA CCT GTA CAA AAG CTA AGC TTT GAT GGA CAA AAA GTT       1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG       1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA       1296
Val Tyr Leu Gly Val Thr Lys Val Asp Phe Ser Gln Tyr Asp Asp Gln
                420                 425                 430

AAA AAT GAA ACT AGT ACA CAA ACA TAT GAT TCA AAA AGA AAC AAT GGC       1344
Lys Asn Glu Thr Ser Thr Gln Thr Tyr Asp Ser Lys Arg Asn Asn Gly
                435                 440                 445

CAT GTA AGT GCA CAG GAT TCT ATT GAC CAA TTA CCG CCA GAA ACA ACA       1392
His Val Ser Ala Gln Asp Ser Ile Asp Gln Leu Pro Pro Glu Thr Thr
        450                 455                 460

GAT GAA CCA CTT GAA AAA GCA TAT AGT CAT CAG CTT AAT TAC GCG GAA       1440
```

```
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG       1488
Cys Phe Leu Met Gln Asp Arg Arg Gly Thr Ile Pro Phe Phe Thr Trp
                    485                 490                 495

ACA CAT AGA AGT GTA GAC TTT TTT AAT ACA ATT GAT GCT GAA AAG ATT       1536
Thr His Arg Ser Val Asp Phe Phe Asn Thr Ile Asp Ala Glu Lys Ile
                500                 505                 510

ACT CAA CTT CCA GTA GTG AAA GCA TAT GCC TTG TCT TCA GGT GCT TCC       1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA       1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA       1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT       1728
Ala Leu Leu Gln Arg Tyr Arg Val Arg Ile Arg Tyr Ala Ser Thr Thr
                    565                 570                 575

AAC TTA CGA CTT TTT GTG CAA AAT TCA AAC AAT GAT TTT CTT GTC ATC       1776
Asn Leu Arg Leu Phe Val Gln Asn Ser Asn Asn Asp Phe Leu Val Ile
                580                 585                 590

TAC ATT AAT AAA ACT ATG AAT AAA GAT GAT GAT TTA ACA TAT CAA ACA       1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG       1872
Phe Asp Leu Ala Thr Thr Asn Ser Asn Met Gly Phe Ser Gly Asp Lys
        610                 615                 620

AAT GAA CTT ATA ATA GGA GCA GAA TCT TTC GTT TCT AAT GAA AAA ATC       1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                   1959
Tyr Ile Asp Lys Ile Glu Phe Ile Pro Val Gln Leu
                645                 650

(2) INFORMATION FOR SEQ ID NO:10:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:10:

Met Asn Pro Asn Asn Arg Ser Glu His Asp Thr Ile Lys Val Thr Pro
  1               5                  10                  15

Asn Ser Glu Leu Gln Thr Asn His Asn Gln Tyr Pro Leu Ala Asp Asn
                 20                  25                  30

Pro Asn Ser Thr Leu Glu Glu Leu Asn Tyr Lys Glu Phe Leu Arg Met
             35                  40                  45

Thr Glu Asp Ser Ser Thr Glu Val Leu Asp Asn Ser Thr Val Lys Asp
         50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                     85                  90                  95

Asn Thr Ile Trp Pro Ser Asp Ala Asp Pro Trp Lys Ala Phe Met Ala
                100                 105                 110
```

```
Gln Val Glu Val Leu Ile Asp Lys Lys Ile Glu Tyr Ala Lys Ser
    115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
    210                 215                 220

Asp Val Ala Glu Phe Tyr Asn Arg Gln Leu Lys Leu Thr Gln Gln Tyr
225                 230                 235                 240

Ser Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
    290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525
```

```
Ile Ile Glu Gly Pro Gly Phe Thr Gly Gly Asn Leu Leu Phe Leu Lys
        530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                    565                 570                 575

Asn Leu Arg Leu Phe Val Gln Asn Ser Asn Asn Asp Phe Leu Val Ile
                580                 585                 590

Tyr Ile Asn Lys Thr Met Asn Lys Asp Asp Asp Leu Thr Tyr Gln Thr
        595                 600                 605

Phe Asp Leu Ala Thr Thr Asn Ser Asn Met Gly Phe Ser Gly Asp Lys
                610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:11:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:11:

ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
1               5                   10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
            20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
        35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
    50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160
```

-continued

```
AAA AGA AGC CAA GAT CGA ATA AGG GAA CTT TTT TCT CAA GCA GAA AGT        528
Lys Arg Ser Gln Asp Arg Ile Arg Glu Leu Phe Ser Gln Ala Glu Ser
            165                 170                 175

CAT TTT CGT AAT TCC ATG CCG TCA TTT GCA GTT TCC AAA TTC GAA GTG        576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA        624
Leu Phe Leu Pro Thr Tyr Ala Gln Ala Ala Asn Thr His Leu Leu Leu
            195                 200                 205

TTA AAA GAT GCT CAA GTT TTT GGA GAA GAA TGG GGA TAT TCT TCA GAA        672
Leu Lys Asp Ala Gln Val Phe Gly Glu Glu Trp Gly Tyr Ser Ser Glu
210                 215                 220

GAT GTT GCT GAA TTC TAT ACC AGA CAA TTA AAA CTT ACA CAA CAA TAC        720
Asp Val Ala Glu Phe Tyr Thr Arg Gln Leu Lys Leu Thr Gln Gln Tyr
225                 230                 235                 240

ACT GAC CAT TGT GTT AAT TGG TAT AAT GTT GGA TTA AAT GGT TTA AGA        768
Thr Asp His Cys Val Asn Trp Tyr Asn Val Gly Leu Asn Gly Leu Arg
            245                 250                 255

GGT TCA ACT TAT GAT GCA TGG GTC AAA TTT AAC CGT TTT CGC AGA GAA        816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT        864
Met Thr Leu Thr Val Leu Asp Leu Ile Val Leu Phe Pro Phe Tyr Asp
            275                 280                 285

ATT CGG TTA TAC TCA AAA GGG GTT AAA ACA GAA CTA ACA AGA GAC ATT        912
Ile Arg Leu Tyr Ser Lys Gly Val Lys Thr Glu Leu Thr Arg Asp Ile
            290                 295                 300

TTT ACG GAT CCA ATT TTT TCA CTT AAT ACT CTT CAG GAG TAT GGA CCA        960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT       1008
Thr Phe Leu Ser Ile Glu Asn Ser Ile Arg Lys Pro His Leu Phe Asp
            325                 330                 335

TAT TTA CAG GGG ATT GAA TTT CAT ACG CGT CTT CAA CCT GGT TAC TTT       1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA       1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT       1152
Pro Ser Ile Gly Ser Ser Lys Thr Ile Thr Ser Pro Phe Tyr Gly Asp
370                 375                 380

AAA TCT ACT GAA CCT GTA CAA AAG CTA AGC TTT GAT GGA CAA AAA GTT       1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG       1248
Tyr Arg Thr Ile Ala Asn Thr Asp Val Ala Ala Trp Pro Asn Gly Lys
            405                 410                 415

GTA TAT TTA GGT GTT ACG AAA GTT GAT TTT AGT CAA TAT GAT GAT CAA       1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC       1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA       1392
His Val Ser Ala Gln Asp Ser Ile Asp Gln Leu Pro Pro Glu Thr Thr
            450                 455                 460

GAT GAA CCA CTT GAA AAA GCA TAT AGT CAT CAG CTT AAT TAC GCG GAA       1440
Asp Glu Pro Leu Glu Lys Ala Tyr Ser His Gln Leu Asn Tyr Ala Glu
465                 470                 475                 480
```

```
TGT TTC TTA ATG CAG GAC CGT CGT GGA ACA ATT CCA TTT TTT ACT TGG    1488
Cys Phe Leu Met Gln Asp Arg Arg Gly Thr Ile Pro Phe Phe Thr Trp
            485                 490                 495

ACA CAT AGA AGT GTA GAC TTT TTT AAT ACA ATT GAT GCT GAA AAG ATT    1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC    1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA    1632
Ile Ile Glu Gly Pro Gly Phe Thr Gly Gly Asn Leu Leu Phe Leu Lys
            530                 535                 540

GAA TCT AGT AAT TCA ATT GCT AAA TTT AAA GTT ACA TTA AAT TCA GCA    1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT    1728
Ala Leu Leu Gln Arg Tyr Arg Val Arg Ile Arg Tyr Ala Ser Thr Thr
            565                 570                 575

AAC TTA CGA CTT TTT GTG CAA AAT TCA AAC AAT GAT TTT CTT GTC ATC    1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
            610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
            645                 650
```

(2) INFORMATION FOR SEQ ID NO:12:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:12:

```
Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
            50                  55                  60

Ala Val Gly Thr Gly Ile Ser Val Val Gly Gln Ile Leu Gly Val Val
65              70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
```

```
            115                 120                 125
Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
                180                 185                 190

Leu Phe Leu Pro Thr Tyr Ala Gln Ala Asn Thr His Leu Leu Leu
        195                 200                 205

Leu Lys Asp Ala Gln Val Phe Gly Glu Glu Trp Gly Tyr Ser Ser Glu
210                 215                 220

Asp Val Ala Glu Phe Tyr Thr Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
        370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
530                 535                 540
```

```
Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
            565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Leu Thr Tyr Gln Thr
        595                 600                 605

Phe Asp Leu Ala Thr Thr Asn Ser Asn Met Gly Phe Ser Gly Asp Lys
    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
            645                 650

(2) INFORMATION FOR SEQ ID NO:13:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:13:

ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
 50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT       528
Lys Arg Ser Gln Asp Arg Ile Arg Glu Leu Phe Ser Gln Ala Glu Ser
```

```
                    165                 170                 175
CAT TTT CGT AAT TCC ATG CCG TCA TTT GCA GTT TCC AAA TTC GAA GTG      576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA      624
Leu Phe Leu Pro Thr Tyr Ala Gln Ala Ala Asn Thr His Leu Leu Leu
            195                 200                 205

TTA AAA GAT GCT CAA GTT TTT GGA GAA GAA TGG GGA TAT TCT TCA GAA      672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC      720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA      768
Thr Asp His Cys Val Asn Trp Tyr Asn Val Gly Leu Asn Gly Leu Arg
            245                 250                 255

GGT TCA ACT TAT GAT GCA TGG GTC AAA TTT AAC CGT TTT CGC AGA GAA      816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT      864
Met Thr Leu Thr Val Leu Asp Leu Ile Val Leu Phe Pro Phe Tyr Asp
            275                 280                 285

ATT AAT TTA TAC TCA AAA GGG GTT AAA ACA GAA CTA ACA AGA GAC ATT      912
Ile Asn Leu Tyr Ser Lys Gly Val Lys Thr Glu Leu Thr Arg Asp Ile
            290                 295                 300

TTT ACG GAT CCA ATT TTT TCA CTT AAT ACT CTT CAG GAG TAT GGA CCA      960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
            325                 330                 335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
    370                 375                 380

AAA TCT ACT GAA CCT GTA CAA AAG CTA AGC TTT GAT GGA CAA AAA GTT     1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG     1248
Tyr Arg Thr Ile Ala Asn Thr Asp Val Ala Ala Trp Pro Asn Gly Lys
            405                 410                 415

GTA TAT TTA GGT GTT ACG AAA GTT GAT TTT AGT CAA TAT GAT GAT CAA     1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC     1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA     1392
His Val Ser Ala Gln Asp Ser Ile Asp Gln Leu Pro Pro Glu Thr Thr
            450                 455                 460

GAT GAA CCA CTT GAA AAA GCA TAT AGT CAT CAG CTT AAT TAC GCG GAA     1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG     1488
```

```
                  Cys Phe Leu Met Gln Asp Arg Arg Gly Thr Ile Pro Phe Phe Thr Trp
                                  485                 490                 495

ACA CAT AGA AGT GTA GAC TTT TTT AAT ACA ATT GAT GCT GAA AAG ATT                1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC                1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA                1632
Ile Ile Glu Gly Pro Gly Phe Thr Gly Gly Asn Leu Leu Phe Leu Lys
    530                 535                 540

GAA TCT AGT AAT TCA ATT GCT AAA TTT AAA GTT ACA TTA AAT TCA GCA                1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT                1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC                1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA                1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG                1872
Phe Asp Leu Ala Thr Thr Asn Ser Asn Met Gly Phe Ser Gly Asp Lys
    610                 615                 620

AAT GAA CTT ATA ATA GGA GCA GAA TCT TTC GTT TCT AAT GAA AAA ATC                1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                            1959
Tyr Ile Asp Lys Ile Glu Phe Ile Pro Val Gln Leu
                645                 650

(2) INFORMATION FOR SEQ ID NO:14:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:14:

Met Asn Pro Asn Asn Arg Ser Glu His Asp Thr Ile Lys Val Thr Pro
  1               5                  10                  15

Asn Ser Glu Leu Gln Thr Asn His Asn Gln Tyr Pro Leu Ala Asp Asn
                 20                  25                  30

Pro Asn Ser Thr Leu Glu Glu Leu Asn Tyr Lys Glu Phe Leu Arg Met
             35                  40                  45

Thr Glu Asp Ser Ser Thr Glu Val Leu Asp Asn Ser Thr Val Lys Asp
         50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
                100                 105                 110

Gln Val Glu Val Leu Ile Asp Lys Lys Ile Glu Glu Tyr Ala Lys Ser
            115                 120                 125
```

-continued

Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
                180                 185                 190

Leu Phe Leu Pro Thr Tyr Ala Gln Ala Ala Asn Thr His Leu Leu Leu
            195                 200                 205

Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Asn Leu Tyr Ser Lys Gly Val Lys Thr Glu Leu Thr Arg Asp Ile
    290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala

```
                                      545                 550                 555                 560
                            Ala Leu Leu Gln Arg Tyr Arg Val Arg Ile Arg Tyr Ala Ser Thr Thr
                                                565                 570                 575

Asn Leu Arg Leu Phe Val Gln Asn Ser Asn Asn Asp Phe Leu Val Ile
                                            580                 585                 590

Tyr Ile Asn Lys Thr Met Asn Lys Asp Asp Asp Leu Thr Tyr Gln Thr
                                        595                 600                 605

Phe Asp Leu Ala Thr Thr Asn Ser Asn Met Gly Phe Ser Gly Asp Lys
                                    610                 615                 620

Asn Glu Leu Ile Ile Gly Ala Glu Ser Phe Val Ser Asn Glu Lys Ile
                            625                 630                 635                 640

Tyr Ile Asp Lys Ile Glu Phe Ile Pro Val Gln Leu
                                            645                 650

(2) INFORMATION FOR SEQ ID NO:15:

(i) SEQUENCE CHARACTERISTICS:
            (A) LENGTH: 1959 base pairs
            (B) TYPE: nucleic acid
            (C) STRANDEDNESS: single
            (D) TOPOLOGY: linear (ix) FEATURE:
            (A) NAME/KEY: CDS
            (B) LOCATION: 1..1956

(xi) SEQUENCE DESCRIPTION: SEQ ID NO:15:

ATG AAT CCA AAC AAT CGA AGT GAA CAT GAT ACG ATA AAG GTT ACA CCT              48
    Met Asn Pro Asn Asn Arg Ser Glu His Asp Thr Ile Lys Val Thr Pro
      1               5                  10                  15

AAC AGT GAA TTG CAA ACT AAC CAT AAT CAA TAT CCT TTA GCT GAC AAT              96
    Asn Ser Glu Leu Gln Thr Asn His Asn Gln Tyr Pro Leu Ala Asp Asn
                     20                  25                  30

CCA AAT TCA ACA CTA GAA GAA TTA AAT TAT AAA GAA TTT TTA AGA ATG             144
    Pro Asn Ser Thr Leu Glu Glu Leu Asn Tyr Lys Glu Phe Leu Arg Met
                 35                  40                  45

ACT GAA GAC AGT TCT ACG GAA GTG CTA GAC AAC TCT ACA GTA AAA GAT             192
    Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA             240
    Ala Val Gly Thr Gly Ile Ser Val Val Gly Gln Ile Leu Gly Val Val
     65                  70                  75                  80

GGA GTT CCA TTT GCT GGG GCA CTC ACT TCA TTT TAT CAA TCA TTT CTT             288
    Gly Val Pro Phe Ala Gly Ala Leu Thr Ser Phe Tyr Gln Ser Phe Leu
                     85                  90                  95

AAC ACT ATA TGG CCA AGT GAT GCT GAC CCA TGG AAG GCT TTT ATG GCA             336
    Asn Thr Ile Trp Pro Ser Asp Ala Asp Pro Trp Lys Ala Phe Met Ala
                100                 105                 110

CAA GTT GAA GTA CTG ATA GAT AAG AAA ATA GAG GAG TAT GCT AAA AGT             384
    Gln Val Glu Val Leu Ile Asp Lys Lys Ile Glu Glu Tyr Ala Lys Ser
            115                 120                 125

AAA GCT CTT GCA GAG TTA CAG GGT CTT CAA AAT AAT TTC GAA GAT TAT             432
    Lys Ala Leu Ala Glu Leu Gln Gly Leu Gln Asn Asn Phe Glu Asp Tyr
        130                 135                 140

GTT AAT GCG TTA AAT TCC TGG AAG AAA ACA CCT TTA AGT TTG CGA AGT             480
    Val Asn Ala Leu Asn Ser Trp Lys Lys Thr Pro Leu Ser Leu Arg Ser
    145                 150                 155                 160

AAA AGA AGC CAA GAT CGA ATA AGG GAA CTT TTT TCT CAA GCA GAA AGT             528
    Lys Arg Ser Gln Asp Arg Ile Arg Glu Leu Phe Ser Gln Ala Glu Ser
                    165                 170                 175
```

```
CAT TTT CGT AAT TCC ATG CCG TCA TTT GCA GTT TCC AAA TTC GAA GTG      576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA      624
Leu Phe Leu Pro Thr Tyr Ala Gln Ala Ala Asn Thr His Leu Leu Leu
            195                 200                 205

TTA AAA GAT GCT CAA GTT TTT GGA GAA GAA TGG GGA TAT TCT TCA GAA      672
Leu Lys Asp Ala Gln Val Phe Gly Glu Glu Trp Gly Tyr Ser Ser Glu
210                 215                 220

GAT GTT GCT GAA TTT TAT CAT AGA CAA TTA AAA CTT ACA CAA CAA TAC      720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA      768
Thr Asp His Cys Val Asn Trp Tyr Asn Val Gly Leu Asn Gly Leu Arg
            245                 250                 255

GGT TCA ACT TAT GAT GCA TGG GTC AAA TTT AAC CGT TTT CGC AGA GAA      816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT      864
Met Thr Leu Thr Val Leu Asp Leu Ile Val Leu Phe Pro Phe Tyr Asp
            275                 280                 285

ATT CGG TTA TAC TCA AAA GGG GTT AAA ACA GAA CTA ACA AGA GAC ATT      912
Ile Arg Leu Tyr Ser Lys Gly Val Lys Thr Glu Leu Thr Arg Asp Ile
            290                 295                 300

TTT ACG GAT CCA ATT TTT TTA CTT ACG CTT CAG AAG TAC GGA CCA          960
Phe Thr Asp Pro Ile Phe Leu Leu Thr Thr Leu Gln Lys Tyr Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
            325                 330                 335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
370                 375                 380

AAA TCT ACT GAA CCT GTA CAA AAG CTA AGC TTT GAT GGA CAA AAA GTT     1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG     1248
Tyr Arg Thr Ile Ala Asn Thr Asp Val Ala Ala Trp Pro Asn Gly Lys
            405                 410                 415

GTA TAT TTA GGT GTT ACG AAA GTT GAT TTT AGT CAA TAT GAT GAT CAA     1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC     1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA     1392
His Val Ser Ala Gln Asp Ser Ile Asp Gln Leu Pro Pro Glu Thr Thr
            450                 455                 460

GAT GAA CCA CTT GAA AAA GCA TAT AGT CAT CAG CTT AAT TAC GCG GAA     1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG     1488
Cys Phe Leu Met Gln Asp Arg Arg Gly Thr Ile Pro Phe Phe Thr Trp
            485                 490                 495
```

```
ACA CAT AGA AGT GTA GAC TTT TTT AAT ACA ATT GAT GCT GAA AAG ATT      1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC      1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA      1632
Ile Ile Glu Gly Pro Gly Phe Thr Gly Gly Asn Leu Leu Phe Leu Lys
            530                 535                 540

GAA TCT AGT AAT TCA ATT GCT AAA TTT AAA GTT ACA TTA AAT TCA GCA      1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT      1728
Ala Leu Leu Gln Arg Tyr Arg Val Arg Ile Arg Tyr Ala Ser Thr Thr
            565                 570                 575

AAC TTA CGA CTT TTT GTG CAA AAT TCA AAC AAT GAT TTT CTT GTC ATC      1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA      1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG      1872
Phe Asp Leu Ala Thr Thr Asn Ser Asn Met Gly Phe Ser Gly Asp Lys
            610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
Tyr Ile Asp Lys Ile Glu Phe Ile Pro Val Gln Leu
            645                 650
```

(2) INFORMATION FOR SEQ ID NO:16:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:16:

```
Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
    130                 135                 140
```

```
Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
            165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Asn Thr His Leu Leu Leu
        195                 200                 205

Leu Lys Asp Ala Gln Val Phe Gly Glu Glu Trp Gly Tyr Ser Ser Glu
        210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
290                 295                 300

Phe Thr Asp Pro Ile Phe Leu Leu Thr Thr Leu Gln Lys Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
            355                 360                 365

Pro Ser Ile Gly Ser Ser Lys Thr Ile Thr Ser Pro Phe Tyr Gly Asp
        370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
        450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
        530                 535                 540

Glu Ser Ser Asn Ser Ile Ala Lys Phe Lys Val Thr Leu Asn Ser Ala
545                 550                 555                 560
```

-continued

```
Ala Leu Leu Gln Arg Tyr Arg Val Arg Ile Arg Tyr Ala Ser Thr Thr
            565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
            595                 600                 605

Phe Asp Leu Ala Thr Thr Asn Ser Asn Met Gly Phe Ser Gly Asp Lys
    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
            645                 650
```

(2) INFORMATION FOR SEQ ID NO:17:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:17:

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
  1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA     240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT     288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA     336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT     480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT     528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG     576
His Phe Arg Asn Ser Met Pro Ser Phe Ala Val Ser Lys Phe Glu Val
```

-continued

| | 180 | | | | 185 | | | | 190 | | | | |
|---|---|---|---|---|---|---|---|---|---|---|---|---|---|
| CTG | TTT | CTA | CCA | ACA | TAT | GCA | CAA | GCT | GCA | AAT | ACA | CAT | TTA | TTG | CTA | 624 |
| Leu | Phe | Leu | Pro | Thr | Tyr | Ala | Gln | Ala | Ala | Asn | Thr | His | Leu | Leu | Leu | |
| | | 195 | | | | 200 | | | | 205 | | | | | | |

```
CTG TTT CTA CCA ACA TAT GCA CAA GCT GCA AAT ACA CAT TTA TTG CTA      624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA      672
Leu Lys Asp Ala Gln Val Phe Gly Glu Glu Trp Gly Tyr Ser Ser Glu
210             215                 220

GAT GTT GCT GAA TTT TAT CAT AGA CAA TTA AAA CTT ACA CAA CAA TAC      720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA      768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA      816
Gly Ser Thr Tyr Asp Ala Trp Val Lys Phe Asn Arg Phe Arg Arg Glu
        260                 265                 270

ATG ACT TTA ACT GTA TTA GAT CTA ATT GTA CTT TTC CCA TTT TAT GAT      864
Met Thr Leu Thr Val Leu Asp Leu Ile Val Leu Phe Pro Phe Tyr Asp
        275                 280                 285

ATT CGG TTA TAC TCA AAA GGG GTT AAA ACA GAA CTA ACA AGA GAC ATT      912
Ile Arg Leu Tyr Ser Lys Gly Val Lys Thr Glu Leu Thr Arg Asp Ile
        290                 295                 300

TTT ACG GAT CCA ATT TTT ACC CTT AAT ACA CTA CAG AAG TGC GGA CCA      960
Phe Thr Asp Pro Ile Phe Thr Leu Asn Thr Leu Gln Lys Cys Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
    370                 375                 380

AAA TCT ACT GAA CCT GTA CAA AAG CTA AGC TTT GAT GGA CAA AAA GTT     1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG     1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA     1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC     1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA     1392
His Val Ser Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCG GAA     1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG     1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT     1536
```

```
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC    1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA    1632
Ile Ile Glu Gly Pro Gly Phe Thr Gly Gly Asn Leu Leu Phe Leu Lys
            530                 535                 540

GAA TCT AGT AAT TCA ATT GCT AAA TTT AAA GTT ACA TTA AAT TCA GCA    1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT    1728
Ala Leu Leu Gln Arg Tyr Arg Val Arg Ile Arg Tyr Ala Ser Thr Thr
            565                 570                 575

AAC TTA CGA CTT TTT GTG CAA AAT TCA AAC AAT GAT TTT CTT GTC ATC    1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
            610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
            645                 650
```

(2) INFORMATION FOR SEQ ID NO:18:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:18:

```
Met Asn Pro Asn Asn Arg Ser Glu His Asp Thr Ile Lys Val Thr Pro
  1               5                  10                  15

Asn Ser Glu Leu Gln Thr Asn His Asn Gln Tyr Pro Leu Ala Asp Asn
                 20                  25                  30

Pro Asn Ser Thr Leu Glu Glu Leu Asn Tyr Lys Glu Phe Leu Arg Met
                 35                  40                  45

Thr Glu Asp Ser Ser Thr Glu Val Leu Asp Asn Ser Thr Val Lys Asp
            50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
                100                 105                 110

Gln Val Glu Val Leu Ile Asp Lys Lys Ile Glu Glu Tyr Ala Lys Ser
                115                 120                 125

Lys Ala Leu Ala Glu Leu Gln Gly Leu Gln Asn Asn Phe Glu Asp Tyr
            130                 135                 140

Val Asn Ala Leu Asn Ser Trp Lys Lys Thr Pro Leu Ser Leu Arg Ser
```

-continued

```
               145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
                180                 185                 190

Leu Phe Leu Pro Thr Tyr Ala Gln Ala Asn Thr His Leu Leu Leu
                195                 200                 205

Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
                260                 265                 270

Met Thr Leu Thr Val Leu Asp Leu Ile Val Leu Phe Pro Phe Tyr Asp
            275                 280                 285

Ile Arg Leu Tyr Ser Lys Gly Val Lys Thr Glu Leu Thr Arg Asp Ile
    290                 295                 300

Phe Thr Asp Pro Ile Phe Thr Leu Asn Thr Leu Gln Lys Cys Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
                340                 345                 350

Gly Lys Asp Ser Phe Asn Tyr Trp Ser Gly Asn Tyr Val Glu Thr Arg
                355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
                435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Asn Thr Ile Asp Ala Glu Lys Ile
                500                 505                 510

Thr Gln Leu Pro Val Val Lys Ala Tyr Ala Leu Ser Ser Gly Ala Ser
            515                 520                 525

Ile Ile Glu Gly Pro Gly Phe Thr Gly Gly Asn Leu Leu Phe Leu Lys
                530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575
```

```
Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
        595                 600                 605

Phe Asp Leu Ala Thr Thr Asn Ser Asn Met Gly Phe Ser Gly Asp Lys
        610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:19:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:19:
```

| | |
|---|---|
| ATG AAT CCA AAC AAT CGA AGT GAA CAT GAT ACG ATA AAG GTT ACA CCT<br>Met Asn Pro Asn Asn Arg Ser Glu His Asp Thr Ile Lys Val Thr Pro<br>1               5                   10                  15 | 48 |
| AAC AGT GAA TTG CAA ACT AAC CAT AAT CAA TAT CCT TTA GCT GAC AAT<br>Asn Ser Glu Leu Gln Thr Asn His Asn Gln Tyr Pro Leu Ala Asp Asn<br>            20                  25                  30 | 96 |
| CCA AAT TCA ACA CTA GAA GAA TTA AAT TAT AAA GAA TTT TTA AGA ATG<br>Pro Asn Ser Thr Leu Glu Glu Leu Asn Tyr Lys Glu Phe Leu Arg Met<br>        35                  40                  45 | 144 |
| ACT GAA GAC AGT TCT ACG GAA GTG CTA GAC AAC TCT ACA GTA AAA GAT<br>Thr Glu Asp Ser Ser Thr Glu Val Leu Asp Asn Ser Thr Val Lys Asp<br>    50                  55                  60 | 192 |
| GCA GTT GGG ACA GGA ATT TCT GTT GTA GGG CAG ATT TTA GGT GTT GTA<br>Ala Val Gly Thr Gly Ile Ser Val Val Gly Gln Ile Leu Gly Val Val<br>65                  70                  75                  80 | 240 |
| GGA GTT CCA TTT GCT GGG GCA CTC ACT TCA TTT TAT CAA TCA TTT CTT<br>Gly Val Pro Phe Ala Gly Ala Leu Thr Ser Phe Tyr Gln Ser Phe Leu<br>            85                  90                  95 | 288 |
| AAC ACT ATA TGG CCA AGT GAT GCT GAC CCA TGG AAG GCT TTT ATG GCA<br>Asn Thr Ile Trp Pro Ser Asp Ala Asp Pro Trp Lys Ala Phe Met Ala<br>        100                 105                 110 | 336 |
| CAA GTT GAA GTA CTG ATA GAT AAG AAA ATA GAG GAG TAT GCT AAA AGT<br>Gln Val Glu Val Leu Ile Asp Lys Lys Ile Glu Glu Tyr Ala Lys Ser<br>    115                 120                 125 | 384 |
| AAA GCT CTT GCA GAG TTA CAG GGT CTT CAA AAT AAT TTC GAA GAT TAT<br>Lys Ala Leu Ala Glu Leu Gln Gly Leu Gln Asn Asn Phe Glu Asp Tyr<br>130                 135                 140 | 432 |
| GTT AAT GCG TTA AAT TCC TGG AAG AAA ACA CCT TTA AGT TTG CGA AGT<br>Val Asn Ala Leu Asn Ser Trp Lys Lys Thr Pro Leu Ser Leu Arg Ser<br>145                 150                 155                 160 | 480 |
| AAA AGA AGC CAA GAT CGA ATA AGG GAA CTT TTT TCT CAA GCA GAA AGT<br>Lys Arg Ser Gln Asp Arg Ile Arg Glu Leu Phe Ser Gln Ala Glu Ser<br>            165                 170                 175 | 528 |
| CAT TTT CGT AAT TCC ATG CCG TCA TTT GCA GTT TCC AAA TTC GAA GTG<br>His Phe Arg Asn Ser Met Pro Ser Phe Ala Val Ser Lys Phe Glu Val<br>        180                 185                 190 | 576 |

```
CTG TTT CTA CCA ACA TAT GCA CAA GCT GCA AAT ACA CAT TTA TTG CTA        624
Leu Phe Leu Pro Thr Tyr Ala Gln Ala Ala Asn Thr His Leu Leu Leu
    195                 200                 205

TTA AAA GAT GCT CAA GTT TTT GGA GAA GAA TGG GGA TAT TCT TCA GAA        672
Leu Lys Asp Ala Gln Val Phe Gly Glu Glu Trp Gly Tyr Ser Ser Glu
210                 215                 220

GAT GTT GCT GAA TTT TAT CAT AGA CAA TTA AAA CTT ACA CAA CAA TAC        720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA        768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA        816
Gly Ser Thr Tyr Asp Ala Trp Val Lys Phe Asn Arg Phe Arg Arg Glu
        260                 265                 270

ATG ACT TTA ACT GTA TTA GAT CTA ATT GTA CTT TTC CCA TTT TAT GAT        864
Met Thr Leu Thr Val Leu Asp Leu Ile Val Leu Phe Pro Phe Tyr Asp
            275                 280                 285

ATT CGG TTA TAC TCA AAA GGG GTT AAA ACA GAA CTA ACA AGA GAC ATT        912
Ile Arg Leu Tyr Ser Lys Gly Val Lys Thr Glu Leu Thr Arg Asp Ile
290                 295                 300

TTT ACG GAT CCA ATT TTT GCC GTT AAT ACT CTG TGG GAA TAC GGA CCA        960
Phe Thr Asp Pro Ile Phe Ala Val Asn Thr Leu Trp Glu Tyr Gly Pro
305                 310                 315                 320

ACT TTT TTG AGT ATA GAA AAC TCT ATT CGA AAA CCT CAT TTA TTT GAT       1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT       1056
Tyr Leu Gln Gly Ile Glu Phe His Thr Arg Leu Gln Pro Gly Tyr Phe
                340                 345                 350

GGG AAA GAT TCT TTC AAT TAT TGG TCT GGT AAT TAT GTA GAA ACT AGA       1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT       1152
Pro Ser Ile Gly Ser Ser Lys Thr Ile Thr Ser Pro Phe Tyr Gly Asp
        370                 375                 380

AAA TCT ACT GAA CCT GTA CAA AAG CTA AGC TTT GAT GGA CAA AAA GTT       1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG       1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA       1296
Val Tyr Leu Gly Val Thr Lys Val Asp Phe Ser Gln Tyr Asp Asp Gln
                420                 425                 430

AAA AAT GAA ACT AGT ACA CAA ACA TAT GAT TCA AAA AGA AAC AAT GGC       1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA       1392
His Val Ser Ala Gln Asp Ser Ile Asp Gln Leu Pro Pro Glu Thr Thr
        450                 455                 460

GAT GAA CCA CTT GAA AAA GCA TAT AGT CAT CAG CTT AAT TAC GCG GAA       1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG       1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT       1536
Thr His Arg Ser Val Asp Phe Phe Asn Thr Ile Asp Ala Glu Lys Ile
                500                 505                 510
```

```
ACT CAA CTT CCA GTA GTG AAA GCA TAT GCC TTG TCT TCA GGT GCT TCC    1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA    1632
Ile Ile Glu Gly Pro Gly Phe Thr Gly Gly Asn Leu Leu Phe Leu Lys
    530                 535                 540

GAA TCT AGT AAT TCA ATT GCT AAA TTT AAA GTT ACA TTA AAT TCA GCA    1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT    1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC    1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
    610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650
```

(2) INFORMATION FOR SEQ ID NO:20:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:20:

```
Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160
```

```
Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Asn Thr His Leu Leu Leu
        195                 200                 205

Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
            245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
    290                 295                 300

Phe Thr Asp Pro Ile Phe Ala Val Asn Thr Leu Trp Glu Tyr Gly Pro
305                 310                 315                 320

Thr Phe Leu Ser Ile Glu Asn Ser Ile Arg Lys Pro His Leu Phe Asp
            325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
            405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
            485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
            565                 570                 575

Asn Leu Arg Leu Phe Val Gln Asn Ser Asn Asn Asp Phe Leu Val Ile
```

```
                580                 585                 590
Tyr Ile Asn Lys Thr Met Asn Lys Asp Asp Leu Thr Tyr Gln Thr
                595                 600                 605

Phe Asp Leu Ala Thr Thr Asn Ser Asn Met Gly Phe Ser Gly Asp Lys
        610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:21:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:21:

ATG AAT CCA AAC AAT CGA AGT GAA CAT GAT ACG ATA AAG GTT ACA CCT         48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT         96
Asn Ser Glu Leu Gln Thr Asn His Asn Gln Tyr Pro Leu Ala Asp Asn
            20                  25                  30

CCA AAT TCA ACA CTA GAA GAA TTA AAT TAT AAA GAA TTT TTA AGA ATG        144
Pro Asn Ser Thr Leu Glu Glu Leu Asn Tyr Lys Glu Phe Leu Arg Met
        35                  40                  45

ACT GAA GAC AGT TCT ACG GAA GTG CTA GAC AAC TCT ACA GTA AAA GAT        192
Thr Glu Asp Ser Ser Thr Glu Val Leu Asp Asn Ser Thr Val Lys Asp
    50                  55                  60

GCA GTT GGG ACA GGA ATT TCT GTT GTA GGG CAG ATT TTA GGT GTT GTA        240
Ala Val Gly Thr Gly Ile Ser Val Val Gly Gln Ile Leu Gly Val Val
65                  70                  75                  80

GGA GTT CCA TTT GCT GGG GCA CTC ACT TCA TTT TAT CAA TCA TTT CTT        288
Gly Val Pro Phe Ala Gly Ala Leu Thr Ser Phe Tyr Gln Ser Phe Leu
                85                  90                  95

AAC ACT ATA TGG CCA AGT GAT GCT GAC CCA TGG AAG GCT TTT ATG GCA        336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT        384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT        432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT        480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT        528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG        576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA        624
Leu Phe Leu Pro Thr Tyr Ala Gln Ala Ala Asn Thr His Leu Leu Leu
```

```
                195                     200                     205
TTA AAA GAT GCT CAA GTT TTT GGA GAA GAA TGG GGA TAT TCT TCA GAA    672
Leu Lys Asp Ala Gln Val Phe Gly Glu Glu Trp Gly Tyr Ser Ser Glu
        210                     215                     220

GAT GTT GCT GAA TTC TAT CGT AGA CAA TTA AAA CTT ACA CAA CAA TAC    720
Asp Val Ala Glu Phe Tyr Arg Arg Gln Leu Lys Leu Thr Gln Gln Tyr
225                     230                     235                     240

ACT GAC CAT TGT GTT AAT TGG TAT AAT GTT GGA TTA AAT GGT TTA AGA    768
Thr Asp His Cys Val Asn Trp Tyr Asn Val Gly Leu Asn Gly Leu Arg
                245                     250                     255

GGT TCA ACT TAT GAT GCA TGG GTC AAA TTT AAC CGT TTT CGC AGA GAA    816
Gly Ser Thr Tyr Asp Ala Trp Val Lys Phe Asn Arg Phe Arg Arg Glu
            260                     265                     270

ATG ACT TTA ACT GTA TTA GAT CTA ATT GTA CTT TTC CCA TTT TAT GAT    864
Met Thr Leu Thr Val Leu Asp Leu Ile Val Leu Phe Pro Phe Tyr Asp
        275                     280                     285

ATT CGG TTA TAC TCA AAA GGG GTT AAA ACA GAA CTA ACA AGA GAC ATT    912
Ile Arg Leu Tyr Ser Lys Gly Val Lys Thr Glu Leu Thr Arg Asp Ile
    290                     295                     300

TTT ACG GAT CCA ATT TTT TTA CTT ACT ACG CTT CAG AAG TAC GGA CCA    960
Phe Thr Asp Pro Ile Phe Leu Leu Thr Thr Leu Gln Lys Tyr Gly Pro
305                     310                     315                     320

ACT TTT TTG AGT ATA GAA AAC TCT ATT CGA AAA CCT CAT TTA TTT GAT   1008
Thr Phe Leu Ser Ile Glu Asn Ser Ile Arg Lys Pro His Leu Phe Asp
                325                     330                     335

TAT TTA CAG GGG ATT GAA TTT CAT ACG CGT CTT CAA CCT GGT TAC TTT   1056
Tyr Leu Gln Gly Ile Glu Phe His Thr Arg Leu Gln Pro Gly Tyr Phe
            340                     345                     350

GGG AAA GAT TCT TTC AAT TAT TGG TCT GGT AAT TAT GTA GAA ACT AGA   1104
Gly Lys Asp Ser Phe Asn Tyr Trp Ser Gly Asn Tyr Val Glu Thr Arg
        355                     360                     365

CCT AGT ATA GGA TCT AGT AAG ACA ATT ACT TCC CCA TTT TAT GGA GAT   1152
Pro Ser Ile Gly Ser Ser Lys Thr Ile Thr Ser Pro Phe Tyr Gly Asp
    370                     375                     380

AAA TCT ACT GAA CCT GTA CAA AAG CTA AGC TTT GAT GGA CAA AAA GTT   1200
Lys Ser Thr Glu Pro Val Gln Lys Leu Ser Phe Asp Gly Gln Lys Val
385                     390                     395                     400

TAT CGA ACT ATA GCT AAT ACA GAC GTA GCG GCT TGG CCG AAT GGT AAG   1248
Tyr Arg Thr Ile Ala Asn Thr Asp Val Ala Ala Trp Pro Asn Gly Lys
                405                     410                     415

GTA TAT TTA GGT GTT ACG AAA GTT GAT TTT AGT CAA TAT GAT GAT CAA   1296
Val Tyr Leu Gly Val Thr Lys Val Asp Phe Ser Gln Tyr Asp Asp Gln
            420                     425                     430

AAA AAT GAA ACT AGT ACA CAA ACA TAT GAT TCA AAA AGA AAC AAT GGC   1344
Lys Asn Glu Thr Ser Thr Gln Thr Tyr Asp Ser Lys Arg Asn Asn Gly
        435                     440                     445

CAT GTA AGT GCA CAG GAT TCT ATT GAC CAA TTA CCG CCA GAA ACA ACA   1392
His Val Ser Ala Gln Asp Ser Ile Asp Gln Leu Pro Pro Glu Thr Thr
    450                     455                     460

GAT GAA CCA CTT GAA AAA GCA TAT AGT CAT CAG CTT AAT TAC GCG GAA   1440
Asp Glu Pro Leu Glu Lys Ala Tyr Ser His Gln Leu Asn Tyr Ala Glu
465                     470                     475                     480

TGT TTC TTA ATG CAG GAC CGT CGT GGA ACA ATT CCA TTT TTT ACT TGG   1488
Cys Phe Leu Met Gln Asp Arg Arg Gly Thr Ile Pro Phe Phe Thr Trp
                485                     490                     495

ACA CAT AGA AGT GTA GAC TTT TTT AAT ACA ATT GAT GCT GAA AAG ATT   1536
Thr His Arg Ser Val Asp Phe Phe Asn Thr Ile Asp Ala Glu Lys Ile
            500                     505                     510

ACT CAA CTT CCA GTA GTG AAA GCA TAT GCC TTG TCT TCA GGT GCT TCC   1584
```

```
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA        1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA        1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT        1728
Ala Leu Leu Gln Arg Tyr Arg Val Arg Ile Arg Tyr Ala Ser Thr Thr
            565                 570                 575

AAC TTA CGA CTT TTT GTG CAA AAT TCA AAC AAT GAT TTT CTT GTC ATC        1776
Asn Leu Arg Leu Phe Val Gln Asn Ser Asn Asn Asp Phe Leu Val Ile
                580                 585                 590

TAC ATT AAT AAA ACT ATG AAT AAA GAT GAT GAT TTA ACA TAT CAA ACA        1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG        1872
Phe Asp Leu Ala Thr Thr Asn Ser Asn Met Gly Phe Ser Gly Asp Lys
610                 615                 620

AAT GAA CTT ATA ATA GGA GCA GAA TCT TTC GTT TCT AAT GAA AAA ATC        1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                    1959
Tyr Ile Asp Lys Ile Glu Phe Ile Pro Val Gln Leu
            645                 650

(2) INFORMATION FOR SEQ ID NO:22:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:22:

Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175
```

-continued

```
His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
    210                 215                 220

Asp Val Ala Glu Phe Tyr Arg Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
    290                 295                 300

Phe Thr Asp Pro Ile Phe Leu Leu Thr Thr Leu Gln Lys Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590
```

```
Tyr Ile Asn Lys Thr Met Asn Lys Asp Asp Leu Thr Tyr Gln Thr
            595             600             605

Phe Asp Leu Ala Thr Thr Asn Ser Asn Met Gly Phe Ser Gly Asp Lys
        610             615             620

Asn Glu Leu Ile Ile Gly Ala Glu Ser Phe Val Ser Asn Glu Lys Ile
625             630             635             640

Tyr Ile Asp Lys Ile Glu Phe Ile Pro Val Gln Leu
            645             650
```

(2) INFORMATION FOR SEQ ID NO:23:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:23:

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
            20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
        35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
    50                  55                  60

GCA GTT GGG ACA GGA ATT TCT GTT GTA GGG CAG ATT TTA GGT GTT GTA     240
Ala Val Gly Thr Gly Ile Ser Val Val Gly Gln Ile Leu Gly Val Val
65                  70                  75                  80

GGA GTT CCA TTT GCT GGG GCA CTC ACT TCA TTT TAT CAA TCA TTT CTT     288
Gly Val Pro Phe Ala Gly Ala Leu Thr Ser Phe Tyr Gln Ser Phe Leu
                85                  90                  95

AAC ACT ATA TGG CCA AGT GAT GCT GAC CCA TGG AAG GCT TTT ATG GCA     336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT     480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT     528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG     576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA     624
Leu Phe Leu Pro Thr Tyr Ala Gln Ala Ala Asn Thr His Leu Leu Leu
        195                 200                 205
```

```
TTA AAA GAT GCT CAA GTT TTT GGA GAA GAA TGG GGA TAT TCT TCA GAA        672
Leu Lys Asp Ala Gln Val Phe Gly Glu Glu Trp Gly Tyr Ser Ser Glu
    210             215                 220

GAT GTT GCT GAA TTT TAT CAT AGA CAA TTA AAA CTT ACA CAA CAA TAC        720
Asp Val Ala Glu Phe Tyr His Arg Gln Leu Lys Leu Thr Gln Gln Tyr
225             230                 235                 240

ACT GAC CAT TGT GTT AAT TGG TAT AAT GTT GGA TTA AAT GGT TTA AGA        768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA        816
Gly Ser Thr Tyr Asp Ala Trp Val Lys Phe Asn Arg Phe Arg Arg Glu
        260                 265                 270

ATG ACT TTA ACT GTA TTA GAT CTA ATT GTA CTT TTC CCA TTT TAT GAT        864
Met Thr Leu Thr Val Leu Asp Leu Ile Val Leu Phe Pro Phe Tyr Asp
            275                 280                 285

ATT CGG TTA TAC TCA AAA GGG GTT AAA ACA GAA CTA ACA AGA GAC ATT        912
Ile Arg Leu Tyr Ser Lys Gly Val Lys Thr Glu Leu Thr Arg Asp Ile
                290                 295                 300

TTT ACG GAT CCA ATT TTT ACG CCA ACC ACC CTA CAG GAT TAC GGA CCA        960
Phe Thr Asp Pro Ile Phe Thr Pro Thr Thr Leu Gln Asp Tyr Gly Pro
305             310                 315                 320

ACT TTT TTG AGT ATA GAA AAC TCT ATT CGA AAA CCT CAT TTA TTT GAT       1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT       1056
Tyr Leu Gln Gly Ile Glu Phe His Thr Arg Leu Gln Pro Gly Tyr Phe
        340                 345                 350

GGG AAA GAT TCT TTC AAT TAT TGG TCT GGT AAT TAT GTA GAA ACT AGA       1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT       1152
Pro Ser Ile Gly Ser Ser Lys Thr Ile Thr Ser Pro Phe Tyr Gly Asp
                370                 375                 380

AAA TCT ACT GAA CCT GTA CAA AAG CTA AGC TTT GAT GGA CAA AAA GTT       1200
Lys Ser Thr Glu Pro Val Gln Lys Leu Ser Phe Asp Gly Gln Lys Val
385             390                 395                 400

TAT CGA ACT ATA GCT AAT ACA GAC GTA GCG GCT TGG CCG AAT GGT AAG       1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA       1296
Val Tyr Leu Gly Val Thr Lys Val Asp Phe Ser Gln Tyr Asp Asp Gln
        420                 425                 430

AAA AAT GAA ACT AGT ACA CAA ACA TAT GAT TCA AAA AGA AAC AAT GGC       1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA       1392
His Val Ser Ala Gln Asp Ser Ile Asp Gln Leu Pro Pro Glu Thr Thr
                450                 455                 460

GAT GAA CCA CTT GAA AAA GCA TAT AGT CAT CAG CTT AAT TAC GCG GAA       1440
Asp Glu Pro Leu Glu Lys Ala Tyr Ser His Gln Leu Asn Tyr Ala Glu
465             470                 475                 480

TGT TTC TTA ATG CAG GAC CGT CGT GGA ACA ATT CCA TTT TTT ACT TGG       1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT       1536
Thr His Arg Ser Val Asp Phe Phe Asn Thr Ile Asp Ala Glu Lys Ile
        500                 505                 510

ACT CAA CTT CCA GTA GTG AAA GCA TAT GCC TTG TCT TCA GGT GCT TCC       1584
Thr Gln Leu Pro Val Val Lys Ala Tyr Ala Leu Ser Ser Gly Ala Ser
            515                 520                 525
```

```
ATT ATT GAA GGT CCA GGA TTC ACA GGA GGA AAT TTA CTA TTC CTA AAA      1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA      1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT      1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC      1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA      1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG      1872
Phe Asp Leu Ala Thr Thr Asn Ser Asn Met Gly Phe Ser Gly Asp Lys
610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
Tyr Ile Asp Lys Ile Glu Phe Ile Pro Val Gln Leu
                645                 650
```

(2) INFORMATION FOR SEQ ID NO:24:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:24:

```
Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
```

-continued

```
            180                 185                 190
Leu Phe Leu Pro Thr Tyr Ala Gln Ala Ala Asn Thr His Leu Leu Leu
            195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
                260                 265                 270

Met Thr Leu Thr Val Leu Asp Leu Ile Val Leu Phe Pro Phe Tyr Asp
            275                 280                 285

Ile Arg Leu Tyr Ser Lys Gly Val Lys Thr Glu Leu Thr Arg Asp Ile
        290                 295                 300

Phe Thr Asp Pro Ile Phe Thr Pro Thr Thr Leu Gln Asp Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
                340                 345                 350

Gly Lys Asp Ser Phe Asn Tyr Trp Ser Gly Asn Tyr Val Glu Thr Arg
            355                 360                 365

Pro Ser Ile Gly Ser Ser Lys Thr Ile Thr Ser Pro Phe Tyr Gly Asp
        370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
        595                 600                 605
```

```
Phe Asp Leu Ala Thr Thr Asn Ser Asn Met Gly Phe Ser Gly Asp Lys
        610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:25:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:25:

ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
                20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
            35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
 65                 70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT       528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG       576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA       624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA       672
Leu Lys Asp Ala Gln Val Phe Gly Glu Glu Trp Gly Tyr Ser Ser Glu
```

```
            210                 215                 220
GAT GTT GCT GAA TTT TAT CAT AGA CAA TTA AAA CTT ACA CAA CAA TAC    720
Asp Val Ala Glu Phe Tyr His Arg Gln Leu Lys Leu Thr Gln Gln Tyr
225             230                 235                 240

ACT GAC CAT TGT GTT AAT TGG TAT AAT GTT GGA TTA AAT GGT TTA AGA    768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA    816
Gly Ser Thr Tyr Asp Ala Trp Val Lys Phe Asn Arg Phe Arg Arg Glu
                260                 265                 270

ATG ACT TTA ACT GTA TTA GAT CTA ATT GTA CTT TTC CCA TTT TAT GAT    864
Met Thr Leu Thr Val Leu Asp Leu Ile Val Leu Phe Pro Phe Tyr Asp
                275                 280                 285

ATT CGG TTA TAC TCA AAA GGG GTT AAA ACA GAA CTA ACA AGA GAC ATT    912
Ile Arg Leu Tyr Ser Lys Gly Val Lys Thr Glu Leu Thr Arg Asp Ile
        290                 295                 300

TTT ACG GAT CCA ATT TTT GCC CTG AAT ACC TTA GAC GAG TAC GGA CCA    960
Phe Thr Asp Pro Ile Phe Ala Leu Asn Thr Leu Asp Glu Tyr Gly Pro
305                 310                 315                 320

ACT TTT TTG AGT ATA GAA AAC TCT ATT CGA AAA CCT CAT TTA TTT GAT   1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT   1056
Tyr Leu Gln Gly Ile Glu Phe His Thr Arg Leu Gln Pro Gly Tyr Phe
                340                 345                 350

GGG AAA GAT TCT TTC AAT TAT TGG TCT GGT AAT TAT GTA GAA ACT AGA   1104
Gly Lys Asp Ser Phe Asn Tyr Trp Ser Gly Asn Tyr Val Glu Thr Arg
                355                 360                 365

CCT AGT ATA GGA TCT AGT AAG ACA ATT ACT TCC CCA TTT TAT GGA GAT   1152
Pro Ser Ile Gly Ser Ser Lys Thr Ile Thr Ser Pro Phe Tyr Gly Asp
370                 375                 380

AAA TCT ACT GAA CCT GTA CAA AAG CTA AGC TTT GAT GGA CAA AAA GTT   1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG   1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA   1296
Val Tyr Leu Gly Val Thr Lys Val Asp Phe Ser Gln Tyr Asp Asp Gln
                420                 425                 430

AAA AAT GAA ACT AGT ACA CAA ACA TAT GAT TCA AAA AGA AAC AAT GGC   1344
Lys Asn Glu Thr Ser Thr Gln Thr Tyr Asp Ser Lys Arg Asn Asn Gly
                435                 440                 445

CAT GTA AGT GCA CAG GAT TCT ATT GAC CAA TTA CCG CCA GAA ACA ACA   1392
His Val Ser Ala Gln Asp Ser Ile Asp Gln Leu Pro Pro Glu Thr Thr
450                 455                 460

GAT GAA CCA CTT GAA AAA GCA TAT AGT CAT CAG CTT AAT TAC GCG GAA   1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG   1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT   1536
Thr His Arg Ser Val Asp Phe Phe Asn Thr Ile Asp Ala Glu Lys Ile
                500                 505                 510

ACT CAA CTT CCA GTA GTG AAA GCA TAT GCC TTG TCT TCA GGT GCT TCC   1584
Thr Gln Leu Pro Val Val Lys Ala Tyr Ala Leu Ser Ser Gly Ala Ser
                515                 520                 525

ATT ATT GAA GGT CCA GGA TTC ACA GGA GGA AAT TTA CTA TTC CTA AAA   1632
```

```
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA       1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT       1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC       1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA       1824
Tyr Ile Asn Lys Thr Met Asn Lys Asp Asp Asp Leu Thr Tyr Gln Thr
                595                 600                 605

TTT GAT CTC GCA ACT ACT AAT TCT AAT ATG GGG TTC TCG GGT GAT AAG       1872
Phe Asp Leu Ala Thr Thr Asn Ser Asn Met Gly Phe Ser Gly Asp Lys
610                 615                 620

AAT GAA CTT ATA ATA GGA GCA GAA TCT TTC GTT TCT AAT GAA AAA ATC       1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                   1959
Tyr Ile Asp Lys Ile Glu Phe Ile Pro Val Gln Leu
                645                 650
```

(2) INFORMATION FOR SEQ ID NO:26:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:26:

```
Met Asn Pro Asn Asn Arg Ser Glu His Asp Thr Ile Lys Val Thr Pro
1                   5                   10                  15

Asn Ser Glu Leu Gln Thr Asn His Asn Gln Tyr Pro Leu Ala Asp Asn
                20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
    115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190
```

```
Leu Phe Leu Pro Thr Tyr Ala Gln Ala Ala Asn Thr His Leu Leu Leu
            195                 200                 205

Leu Lys Asp Ala Gln Val Phe Gly Glu Glu Trp Gly Tyr Ser Ser Glu
        210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
            245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
            275                 280                 285

Ile Arg Leu Tyr Ser Lys Gly Val Lys Thr Glu Leu Thr Arg Asp Ile
        290                 295                 300

Phe Thr Asp Pro Ile Phe Ala Leu Asn Thr Leu Asp Glu Tyr Gly Pro
305                 310                 315                 320

Thr Phe Leu Ser Ile Glu Asn Ser Ile Arg Lys Pro His Leu Phe Asp
            325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
        370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
            405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
        450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
            485                 490                 495

Thr His Arg Ser Val Asp Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
        530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
            565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Leu Thr Tyr Gln Thr
        595                 600                 605

Phe Asp Leu Ala Thr Thr Asn Ser Asn Met Gly Phe Ser Gly Asp Lys
```

```
            610                 615                 620
Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650
```

(2) INFORMATION FOR SEQ ID NO:27:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:27:

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
                20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
            35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
        50                  55                  60

GCA GTT GGG ACA GGA ATT TCT GTT GTA GGG CAG ATT TTA GGT GTT GTA     240
Ala Val Gly Thr Gly Ile Ser Val Val Gly Gln Ile Leu Gly Val Val
65                  70                  75                  80

GGA GTT CCA TTT GCT GGG GCA CTC ACT TCA TTT TAT CAA TCA TTT CTT     288
Gly Val Pro Phe Ala Gly Ala Leu Thr Ser Phe Tyr Gln Ser Phe Leu
                85                  90                  95

AAC ACT ATA TGG CCA AGT GAT GCT GAC CCA TGG AAG GCT TTT ATG GCA     336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT     480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT     528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG     576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA     624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA     672
Leu Lys Asp Ala Gln Val Phe Gly Glu Glu Trp Gly Tyr Ser Ser Glu
    210                 215                 220
```

-continued

```
GAT GTT GCT GAA TTT TAT CAT AGA CAA TTA AAA CTT ACA CAA CAA TAC       720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA       768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA       816
Gly Ser Thr Tyr Asp Ala Trp Val Lys Phe Asn Arg Phe Arg Arg Glu
                260                 265                 270

ATG ACT TTA ACT GTA TTA GAT CTA ATT GTA CTT TTC CCA TTT TAC GAT       864
Met Thr Leu Thr Val Leu Asp Leu Ile Val Leu Phe Pro Phe Tyr Asp
            275                 280                 285

ACT AGG CGA TTC AGA AAG GGG GTT AAA ACA GAA CTA ACA AGA GAC ATT       912
Thr Arg Arg Phe Arg Lys Gly Val Lys Thr Glu Leu Thr Arg Asp Ile
        290                 295                 300

TTT ACG GAT CCA ATT TTT TCA CTT AAT ACT CTT CAG GAG TAT GGA CCA       960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT      1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT      1056
Tyr Leu Gln Gly Ile Glu Phe His Thr Arg Leu Gln Pro Gly Tyr Phe
                340                 345                 350

GGG AAA GAT TCT TTC AAT TAT TGG TCT GGT AAT TAT GTA GAA ACT AGA      1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT      1152
Pro Ser Ile Gly Ser Ser Lys Thr Ile Thr Ser Pro Phe Tyr Gly Asp
        370                 375                 380

AAA TCT ACT GAA CCT GTA CAA AAG CTA AGC TTT GAT GGA CAA AAA GTT      1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG      1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA      1296
Val Tyr Leu Gly Val Thr Lys Val Asp Phe Ser Gln Tyr Asp Asp Gln
                420                 425                 430

AAA AAT GAA ACT AGT ACA CAA ACA TAT GAT TCA AAA AGA AAC AAT GGC      1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA      1392
His Val Ser Ala Gln Asp Ser Ile Asp Gln Leu Pro Pro Glu Thr Thr
        450                 455                 460

GAT GAA CCA CTT GAA AAA GCA TAT AGT CAT CAG CTT AAT TAC GCG GAA      1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG      1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT      1536
Thr His Arg Ser Val Asp Phe Phe Asn Thr Ile Asp Ala Glu Lys Ile
                500                 505                 510

ACT CAA CTT CCA GTA GTG AAA GCA TAT GCC TTG TCT TCA GGT GCT TCC      1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA      1632
Ile Ile Glu Gly Pro Gly Phe Thr Gly Gly Asn Leu Leu Phe Leu Lys
        530                 535                 540
```

-continued

```
GAA TCT AGT AAT TCA ATT GCT AAA TTT AAA GTT ACA TTA AAT TCA GCA      1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT      1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC      1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA      1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG      1872
Phe Asp Leu Ala Thr Thr Asn Ser Asn Met Gly Phe Ser Gly Asp Lys
    610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
Tyr Ile Asp Lys Ile Glu Phe Ile Pro Val Gln Leu
                645                 650
```

(2) INFORMATION FOR SEQ ID NO:28:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:28:

```
Met Asn Pro Asn Asn Arg Ser Glu His Asp Thr Ile Lys Val Thr Pro
1               5                  10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205
```

-continued

```
Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
                260                 265                 270

Met Thr Leu Thr Val Leu Asp Leu Ile Val Leu Phe Pro Phe Tyr Asp
        275                 280                 285

Thr Arg Arg Phe Arg Lys Gly Val Lys Thr Glu Leu Thr Arg Asp Ile
    290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
                340                 345                 350

Gly Lys Asp Ser Phe Asn Tyr Trp Ser Gly Asn Tyr Val Glu Thr Arg
            355                 360                 365

Pro Ser Ile Gly Ser Ser Lys Thr Ile Thr Ser Pro Phe Tyr Gly Asp
        370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
        595                 600                 605

Phe Asp Leu Ala Thr Thr Asn Ser Asn Met Gly Phe Ser Gly Asp Lys
610                 615                 620
```

```
Asn Glu Leu Ile Ile Gly Ala Glu Ser Phe Val Ser Asn Lys Ile
625                 630                 635                 640

Tyr Ile Asp Lys Ile Glu Phe Ile Pro Val Gln Leu
                645                 650
```

(2) INFORMATION FOR SEQ ID NO:29:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:29:

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
  1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA     240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT     288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA     336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT     480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT     528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG     576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA     624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA     672
Leu Lys Asp Ala Gln Val Phe Gly Glu Glu Trp Gly Tyr Ser Ser Glu
    210                 215                 220

GAT GTT GCT GAA TTC TAT CGT AGA CAA TTA AAA CTT ACA CAA CAA TAC     720
Asp Val Ala Glu Phe Tyr Arg Arg Gln Leu Lys Leu Thr Gln Gln Tyr
```

```
            225                 230                 235                 240
ACT GAC CAT TGT GTT AAT TGG TAT AAT GTT GGA TTA AAT GGT TTA AGA            768
Thr Asp His Cys Val Asn Trp Tyr Asn Val Gly Leu Asn Gly Leu Arg
            245                 250                 255

GGT TCA ACT TAT GAT GCA TGG GTC AAA TTT AAC CGT TTT CGC AGA GAA            816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT            864
Met Thr Leu Thr Val Leu Asp Leu Ile Val Leu Phe Pro Phe Tyr Asp
            275                 280                 285

ATT CGG TTA TAC TCA AAA GGG GTT AAA ACA GAA CTA ACA AGA GAC ATT            912
Ile Arg Leu Tyr Ser Lys Gly Val Lys Thr Glu Leu Thr Arg Asp Ile
            290                 295                 300

TTT ACG GAT CCA ATT TTT TTA CTT AAT ACT CTT CAG GAG TAT GGA CCA            960
Phe Thr Asp Pro Ile Phe Leu Leu Asn Thr Leu Gln Glu Tyr Gly Pro
305                 310                 315                 320

ACT TTT TTG AGT ATA GAA AAC TCT ATT CGA AAA CCT CAT TTA TTT GAT           1008
Thr Phe Leu Ser Ile Glu Asn Ser Ile Arg Lys Pro His Leu Phe Asp
            325                 330                 335

TAT TTA CAG GGG ATT GAA TTT CAT ACG CGT CTT CAA CCT GGT TAC TTT           1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA           1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT           1152
Pro Ser Ile Gly Ser Ser Lys Thr Ile Thr Ser Pro Phe Tyr Gly Asp
            370                 375                 380

AAA TCT ACT GAA CCT GTA CAA AAG CTA AGC TTT GAT GGA CAA AAA GTT           1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG           1248
Tyr Arg Thr Ile Ala Asn Thr Asp Val Ala Ala Trp Pro Asn Gly Lys
            405                 410                 415

GTA TAT TTA GGT GTT ACG AAA GTT GAT TTT AGT CAA TAT GAT GAT CAA           1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC           1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA           1392
His Val Ser Ala Gln Asp Ser Ile Asp Gln Leu Pro Pro Glu Thr Thr
            450                 455                 460

GAT GAA CCA CTT GAA AAA GCA TAT AGT CAT CAG CTT AAT TAC GCG GAA           1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG           1488
Cys Phe Leu Met Gln Asp Arg Arg Gly Thr Ile Pro Phe Phe Thr Trp
            485                 490                 495

ACA CAT AGA AGT GTA GAC TTT TTT AAT ACA ATT GAT GCT GAA AAG ATT           1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC           1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA           1632
Ile Ile Glu Gly Pro Gly Phe Thr Gly Gly Asn Leu Leu Phe Leu Lys
            530                 535                 540

GAA TCT AGT AAT TCA ATT GCT AAA TTT AAA GTT ACA TTA AAT TCA GCA           1680
```

```
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT      1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC      1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA      1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG      1872
Phe Asp Leu Ala Thr Thr Asn Ser Asn Met Gly Phe Ser Gly Asp Lys
610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
Tyr Ile Asp Lys Ile Glu Phe Ile Pro Val Gln Leu
                645                 650
```

(2) INFORMATION FOR SEQ ID NO:30:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:30:

```
Met Asn Pro Asn Asn Arg Ser Glu His Asp Thr Ile Lys Val Thr Pro
1                   5                   10                  15

Asn Ser Glu Leu Gln Thr Asn His Asn Gln Tyr Pro Leu Ala Asp Asn
                20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
        50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
```

-continued

```
            210                 215                 220
Asp Val Ala Glu Phe Tyr Arg Arg Gln Leu Lys Leu Thr Gln Gln Tyr
225                 230                 235                 240

Thr Asp His Cys Val Asn Trp Tyr Asn Val Gly Leu Asn Gly Leu Arg
                    245                 250                 255

Gly Ser Thr Tyr Asp Ala Trp Val Lys Phe Asn Arg Phe Arg Arg Glu
                260                 265                 270

Met Thr Leu Thr Val Leu Asp Leu Ile Val Leu Phe Pro Phe Tyr Asp
            275                 280                 285

Ile Arg Leu Tyr Ser Lys Gly Val Lys Thr Glu Leu Thr Arg Asp Ile
        290                 295                 300

Phe Thr Asp Pro Ile Phe Leu Leu Asn Thr Leu Gln Glu Tyr Gly Pro
305                 310                 315                 320

Thr Phe Leu Ser Ile Glu Asn Ser Ile Arg Lys Pro His Leu Phe Asp
                    325                 330                 335

Tyr Leu Gln Gly Ile Glu Phe His Thr Arg Leu Gln Pro Gly Tyr Phe
                340                 345                 350

Gly Lys Asp Ser Phe Asn Tyr Trp Ser Gly Asn Tyr Val Glu Thr Arg
            355                 360                 365

Pro Ser Ile Gly Ser Ser Lys Thr Ile Thr Ser Pro Phe Tyr Gly Asp
        370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                    405                 410                 415

Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
        450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                    485                 490                 495

Thr His Arg Ser Val Asp Phe Phe Asn Thr Ile Asp Ala Glu Lys Ile
                500                 505                 510

Thr Gln Leu Pro Val Val Lys Ala Tyr Ala Leu Ser Ser Gly Ala Ser
            515                 520                 525

Ile Ile Glu Gly Pro Gly Phe Thr Gly Gly Asn Leu Leu Phe Leu Lys
        530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                    565                 570                 575

Asn Leu Arg Leu Phe Val Gln Asn Ser Asn Asn Asp Phe Leu Val Ile
                580                 585                 590

Tyr Ile Asn Lys Thr Met Asn Lys Asp Asp Asp Leu Thr Tyr Gln Thr
            595                 600                 605

Phe Asp Leu Ala Thr Thr Asn Ser Asn Met Gly Phe Ser Gly Asp Lys
        610                 615                 620

Asn Glu Leu Ile Ile Gly Ala Glu Ser Phe Val Ser Asn Glu Lys Ile
625                 630                 635                 640
```

```
Tyr Ile Asp Lys Ile Glu Phe Ile Pro Val Gln Leu
                645                 650
```

(2) INFORMATION FOR SEQ ID NO:31:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:31:

```
ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
                20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
 50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT       528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG       576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA       624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA       672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC       720
Asp Val Ala Glu Phe Tyr His Arg Gln Leu Lys Leu Thr Gln Gln Tyr
225                 230                 235                 240
```

-continued

```
ACT GAC CAT TGT GTT AAT TGG TAT AAT GTT GGA TTA AAT GGT TTA AGA        768
Thr Asp His Cys Val Asn Trp Tyr Asn Val Gly Leu Asn Gly Leu Arg
            245                 250                 255

GGT TCA ACT TAT GAT GCA TGG GTC AAA TTT AAC CGT TTT CGC AGA GAA        816
Gly Ser Thr Tyr Asp Ala Trp Val Lys Phe Asn Arg Phe Arg Arg Glu
        260                 265                 270

ATG ACT TTA ACT GTA TTA GAT CTA ATT GTA CTT TTC CCA TTT TAT GAT        864
Met Thr Leu Thr Val Leu Asp Leu Ile Val Leu Phe Pro Phe Tyr Asp
            275                 280                 285

ATT CGG TTA TAC TCA AAA GGG GTT AAA ACA GAA CTA ACA AGA GAC ATT        912
Ile Arg Leu Tyr Ser Lys Gly Val Lys Thr Glu Leu Thr Arg Asp Ile
        290                 295                 300

TTT ACG GAT CCA ATT TTT ATC CTC AAT ACG CTA CAG GAG TAC GGA CCA        960
Phe Thr Asp Pro Ile Phe Ile Leu Asn Thr Leu Gln Glu Tyr Gly Pro
305                 310                 315                 320

ACT TTT TTG AGT ATA GAA AAC TCT ATT CGA AAA CCT CAT TTA TTT GAT       1008
Thr Phe Leu Ser Ile Glu Asn Ser Ile Arg Lys Pro His Leu Phe Asp
            325                 330                 335

TAT TTA CAG GGG ATT GAA TTT CAT ACG CGT CTT CAA CCT GGT TAC TTT       1056
Tyr Leu Gln Gly Ile Glu Phe His Thr Arg Leu Gln Pro Gly Tyr Phe
        340                 345                 350

GGG AAA GAT TCT TTC AAT TAT TGG TCT GGT AAT TAT GTA GAA ACT AGA       1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT       1152
Pro Ser Ile Gly Ser Ser Lys Thr Ile Thr Ser Pro Phe Tyr Gly Asp
        370                 375                 380

AAA TCT ACT GAA CCT GTA CAA AAG CTA AGC TTT GAT GGA CAA AAA GTT       1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG       1248
Tyr Arg Thr Ile Ala Asn Thr Asp Val Ala Ala Trp Pro Asn Gly Lys
            405                 410                 415

GTA TAT TTA GGT GTT ACG AAA GTT GAT TTT AGT CAA TAT GAT GAT CAA       1296
Val Tyr Leu Gly Val Thr Lys Val Asp Phe Ser Gln Tyr Asp Asp Gln
        420                 425                 430

AAA AAT GAA ACT AGT ACA CAA ACA TAT GAT TCA AAA AGA AAC AAT GGC       1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA       1392
His Val Ser Ala Gln Asp Ser Ile Asp Gln Leu Pro Pro Glu Thr Thr
450                 455                 460

GAT GAA CCA CTT GAA AAA GCA TAT AGT CAT CAG CTT AAT TAC GCG GAA       1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG       1488
Cys Phe Leu Met Gln Asp Arg Arg Gly Thr Ile Pro Phe Phe Thr Trp
            485                 490                 495

ACA CAT AGA AGT GTA GAC TTT TTT AAT ACA ATT GAT GCT GAA AAG ATT       1536
Thr His Arg Ser Val Asp Phe Phe Asn Thr Ile Asp Ala Glu Lys Ile
        500                 505                 510

ACT CAA CTT CCA GTA GTG AAA GCA TAT GCC TTG TCT TCA GGT GCT TCC       1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA       1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA       1680
Glu Ser Ser Asn Ser Ile Ala Lys Phe Lys Val Thr Leu Asn Ser Ala
545                 550                 555                 560
```

```
GCC TTG TTA CAA CGA TAT CGT GTA AGA ATA CGC TAT GCT TCT ACC ACT      1728
Ala Leu Leu Gln Arg Tyr Arg Val Arg Ile Arg Tyr Ala Ser Thr Thr
            565                 570                 575

AAC TTA CGA CTT TTT GTG CAA AAT TCA AAC AAT GAT TTT CTT GTC ATC      1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA      1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG      1872
Phe Asp Leu Ala Thr Thr Asn Ser Asn Met Gly Phe Ser Gly Asp Lys
            610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
Tyr Ile Asp Lys Ile Glu Phe Ile Pro Val Gln Leu
                645                 650
```

(2) INFORMATION FOR SEQ ID NO:32:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:32:

```
Met Asn Pro Asn Asn Arg Ser Glu His Asp Thr Ile Lys Val Thr Pro
1                   5                  10                  15

Asn Ser Glu Leu Gln Thr Asn His Asn Gln Tyr Pro Leu Ala Asp Asn
                20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
        50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
    210                 215                 220
```

-continued

```
Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
            245                 250                 255

Gly Ser Thr Tyr Asp Ala Trp Val Lys Phe Asn Arg Phe Arg Arg Glu
                260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
        290                 295                 300

Phe Thr Asp Pro Ile Phe Ile Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
                340                 345                 350

Gly Lys Asp Ser Phe Asn Tyr Trp Ser Gly Asn Tyr Val Glu Thr Arg
            355                 360                 365

Pro Ser Ile Gly Ser Ser Lys Thr Ile Thr Ser Pro Phe Tyr Gly Asp
370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
        450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
        530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
        595                 600                 605

Phe Asp Leu Ala Thr Thr Asn Ser Asn Met Gly Phe Ser Gly Asp Lys
        610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
```

(2) INFORMATION FOR SEQ ID NO:33:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:33:

```
ATG AAT CCA AAC AAT CGA AGT GAA CAT GAT ACG ATA AAG GTT ACA CCT       48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT       96
Asn Ser Glu Leu Gln Thr Asn His Asn Gln Tyr Pro Leu Ala Asp Asn
                 20                  25                  30

CCA AAT TCA ACA CTA GAA GAA TTA AAT TAT AAA GAA TTT TTA AGA ATG      144
Pro Asn Ser Thr Leu Glu Glu Leu Asn Tyr Lys Glu Phe Leu Arg Met
             35                  40                  45

ACT GAA GAC AGT TCT ACG GAA GTG CTA GAC AAC TCT ACA GTA AAA GAT      192
Thr Glu Asp Ser Ser Thr Glu Val Leu Asp Asn Ser Thr Val Lys Asp
 50                  55                  60

GCA GTT GGG ACA GGA ATT TCT GTT GTA GGG CAG ATT TTA GGT GTT GTA      240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT      288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA      336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT      384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT      432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT      480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT      528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG      576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA      624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA      672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC      720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA      768
Thr Asp His Cys Val Asn Trp Tyr Asn Val Gly Leu Asn Gly Leu Arg
```

```
                  245                 250                 255
GGT TCA ACT TAT GAT GCA TGG GTC AAA TTT AAC CGT TTT CGC AGA GAA        816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT        864
Met Thr Leu Thr Val Leu Asp Leu Ile Val Leu Phe Pro Phe Tyr Asp
            275                 280                 285

ATT CGG TTA TAC TCA AAA GGG GTT AAA ACA GAA CTA ACA AGA GAC ATT        912
Ile Arg Leu Tyr Ser Lys Gly Val Lys Thr Glu Leu Thr Arg Asp Ile
            290                 295                 300

TTT ACG GAT CCA ATT TTT ATC CTA CAT ACG CTG CAG GAG TAC GGA CCA        960
Phe Thr Asp Pro Ile Phe Ile Leu His Thr Leu Gln Glu Tyr Gly Pro
305                 310                 315                 320

ACT TTT TTG AGT ATA GAA AAC TCT ATT CGA AAA CCT CAT TTA TTT GAT        1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT        1056
Tyr Leu Gln Gly Ile Glu Phe His Thr Arg Leu Gln Pro Gly Tyr Phe
                340                 345                 350

GGG AAA GAT TCT TTC AAT TAT TGG TCT GGT AAT TAT GTA GAA ACT AGA        1104
Gly Lys Asp Ser Phe Asn Tyr Trp Ser Gly Asn Tyr Val Glu Thr Arg
                355                 360                 365

CCT AGT ATA GGA TCT AGT AAG ACA ATT ACT TCC CCA TTT TAT GGA GAT        1152
Pro Ser Ile Gly Ser Ser Lys Thr Ile Thr Ser Pro Phe Tyr Gly Asp
        370                 375                 380

AAA TCT ACT GAA CCT GTA CAA AAG CTA AGC TTT GAT GGA CAA AAA GTT        1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG        1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA        1296
Val Tyr Leu Gly Val Thr Lys Val Asp Phe Ser Gln Tyr Asp Asp Gln
                420                 425                 430

AAA AAT GAA ACT AGT ACA CAA ACA TAT GAT TCA AAA AGA AAC AAT GGC        1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA        1392
His Val Ser Ala Gln Asp Ser Ile Asp Gln Leu Pro Pro Glu Thr Thr
        450                 455                 460

GAT GAA CCA CTT GAA AAA GCA TAT AGT CAT CAG CTT AAT TAC GCG GAA        1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG        1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT        1536
Thr His Arg Ser Val Asp Phe Phe Asn Thr Ile Asp Ala Glu Lys Ile
                500                 505                 510

ACT CAA CTT CCA GTA GTG AAA GCA TAT GCC TTG TCT TCA GGT GCT TCC        1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA        1632
Ile Ile Glu Gly Pro Gly Phe Thr Gly Gly Asn Leu Leu Phe Leu Lys
            530                 535                 540

GAA TCT AGT AAT TCA ATT GCT AAA TTT AAA GTT ACA TTA AAT TCA GCA        1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT        1728
```

```
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC    1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
        610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650

(2) INFORMATION FOR SEQ ID NO:34:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:34:

Met Asn Pro Asn Asn Arg Ser Glu His Asp Thr Ile Lys Val Thr Pro
  1               5                  10                  15

Asn Ser Glu Leu Gln Thr Asn His Asn Gln Tyr Pro Leu Ala Asp Asn
                 20                  25                  30

Pro Asn Ser Thr Leu Glu Glu Leu Asn Tyr Lys Glu Phe Leu Arg Met
             35                  40                  45

Thr Glu Asp Ser Ser Thr Glu Val Leu Asp Asn Ser Thr Val Lys Asp
 50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
                100                 105                 110

Gln Val Glu Val Leu Ile Asp Lys Lys Ile Glu Glu Tyr Ala Lys Ser
            115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
                180                 185                 190

Leu Phe Leu Pro Thr Tyr Ala Gln Ala Ala Asn Thr His Leu Leu Leu
            195                 200                 205

Leu Lys Asp Ala Gln Val Phe Gly Glu Glu Trp Gly Tyr Ser Ser Glu
            210                 215                 220

Asp Val Ala Glu Phe Tyr His Arg Gln Leu Lys Leu Thr Gln Gln Tyr
225                 230                 235                 240
```

-continued

```
Thr Asp His Cys Val Asn Trp Tyr Asn Val Gly Leu Asn Gly Leu Arg
            245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
            275                 280                 285

Ile Arg Leu Tyr Ser Lys Gly Val Lys Thr Glu Leu Thr Arg Asp Ile
            290                 295                 300

Phe Thr Asp Pro Ile Phe Ile Leu His Thr Leu Gln Glu Tyr Gly Pro
305                 310                 315                 320

Thr Phe Leu Ser Ile Glu Asn Ser Ile Arg Lys Pro His Leu Phe Asp
            325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
            355                 360                 365

Pro Ser Ile Gly Ser Ser Lys Thr Ile Thr Ser Pro Phe Tyr Gly Asp
            370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
            405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
            450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
            485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
            515                 520                 525

Ile Ile Glu Gly Pro Gly Phe Thr Gly Gly Asn Leu Leu Phe Leu Lys
            530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
            565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
            595                 600                 605

Phe Asp Leu Ala Thr Thr Asn Ser Asn Met Gly Phe Ser Gly Asp Lys
            610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
            645                 650
```

(2) INFORMATION FOR SEQ ID NO:35:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:35:

```
ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
 50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT       528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG       576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA       624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA       672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC       720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA       768
Thr Asp His Cys Val Asn Trp Tyr Asn Val Gly Leu Asn Gly Leu Arg
                245                 250                 255
```

-continued

```
GGT TCA ACT TAT GAT GCA TGG GTC AAA TTT AAC CGT TTT CGC AGA GAA         816
Gly Ser Thr Tyr Asp Ala Trp Val Lys Phe Asn Arg Phe Arg Arg Glu
        260                 265                 270

ATG ACT TTA ACT GTA TTA GAT CTA ATT GTA CTT TTC CCA TTT TAT GAT         864
Met Thr Leu Thr Val Leu Asp Leu Ile Val Leu Phe Pro Phe Tyr Asp
            275                 280                 285

ATT CGG TTA TAC TCA AAA GGG GTT AAA ACA GAA CTA ACA AGA GAC ATT         912
Ile Arg Leu Tyr Ser Lys Gly Val Lys Thr Glu Leu Thr Arg Asp Ile
        290                 295                 300

TTT ACG GAT CCA ATT TTT TCC CTC GTT AAC CTA ATG GTG TAC GGA CCA         960
Phe Thr Asp Pro Ile Phe Ser Leu Val Asn Leu Met Val Tyr Gly Pro
305                 310                 315                 320

ACT TTT TTG AGT ATA GAA AAC TCT ATT CGA AAA CCT CAT TTA TTT GAT        1008
Thr Phe Leu Ser Ile Glu Asn Ser Ile Arg Lys Pro His Leu Phe Asp
            325                 330                 335

TAT TTA CAG GGG ATT GAA TTT CAT ACG CGT CTT CAA CCT GGT TAC TTT        1056
Tyr Leu Gln Gly Ile Glu Phe His Thr Arg Leu Gln Pro Gly Tyr Phe
        340                 345                 350

GGG AAA GAT TCT TTC AAT TAT TGG TCT GGT AAT TAT GTA GAA ACT AGA        1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT        1152
Pro Ser Ile Gly Ser Ser Lys Thr Ile Thr Ser Pro Phe Tyr Gly Asp
370                 375                 380

AAA TCT ACT GAA CCT GTA CAA AAG CTA AGC TTT GAT GGA CAA AAA GTT        1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG        1248
Tyr Arg Thr Ile Ala Asn Thr Asp Val Ala Ala Trp Pro Asn Gly Lys
            405                 410                 415

GTA TAT TTA GGT GTT ACG AAA GTT GAT TTT AGT CAA TAT GAT GAT CAA        1296
Val Tyr Leu Gly Val Thr Lys Val Asp Phe Ser Gln Tyr Asp Asp Gln
        420                 425                 430

AAA AAT GAA ACT AGT ACA CAA ACA TAT GAT TCA AAA AGA AAC AAT GGC        1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA        1392
His Val Ser Ala Gln Asp Ser Ile Asp Gln Leu Pro Pro Glu Thr Thr
        450                 455                 460

GAT GAA CCA CTT GAA AAA GCA TAT AGT CAT CAG CTT AAT TAC GCG GAA        1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG        1488
Cys Phe Leu Met Gln Asp Arg Arg Gly Thr Ile Pro Phe Phe Thr Trp
            485                 490                 495

ACA CAT AGA AGT GTA GAC TTT TTT AAT ACA ATT GAT GCT GAA AAG ATT        1536
Thr His Arg Ser Val Asp Phe Phe Asn Thr Ile Asp Ala Glu Lys Ile
        500                 505                 510

ACT CAA CTT CCA GTA GTG AAA GCA TAT GCC TTG TCT TCA GGT GCT TCC        1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA        1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA        1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT        1728
Ala Leu Leu Gln Arg Tyr Arg Val Arg Ile Arg Tyr Ala Ser Thr Thr
            565                 570                 575
```

```
AAC TTA CGA CTT TTT GTG CAA AAT TCA AAC AAT GAT TTT CTT GTC ATC    1776
Asn Leu Arg Leu Phe Val Gln Asn Ser Asn Asn Asp Phe Leu Val Ile
        580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
        610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650
```

(2) INFORMATION FOR SEQ ID NO:36:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:36:

```
Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65              70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
```

-continued

```
                245                 250                 255
Gly Ser Thr Tyr Asp Ala Trp Val Lys Phe Asn Arg Phe Arg Glu
                260                 265                 270

Met Thr Leu Thr Val Leu Asp Leu Ile Val Leu Phe Pro Phe Tyr Asp
                275                 280                 285

Ile Arg Leu Tyr Ser Lys Gly Val Lys Thr Glu Leu Thr Arg Asp Ile
    290                 295                 300

Phe Thr Asp Pro Ile Phe Ser Leu Val Asn Leu Met Val Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
                340                 345                 350

Gly Lys Asp Ser Phe Asn Tyr Trp Ser Gly Asn Tyr Val Glu Thr Arg
                355                 360                 365

Pro Ser Ile Gly Ser Ser Lys Thr Ile Thr Ser Pro Phe Tyr Gly Asp
                370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
                435                 440                 445

His Val Ser Ala Gln Asp Ser Ile Asp Gln Leu Pro Pro Glu Thr Thr
                450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
                500                 505                 510

Thr Gln Leu Pro Val Val Lys Ala Tyr Ala Leu Ser Ser Gly Ala Ser
                515                 520                 525

Ile Ile Glu Gly Pro Gly Phe Thr Gly Gly Asn Leu Leu Phe Leu Lys
530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
                580                 585                 590

Tyr Ile Asn Lys Thr Met Asn Lys Asp Asp Asp Leu Thr Tyr Gln Thr
                595                 600                 605

Phe Asp Leu Ala Thr Thr Asn Ser Asn Met Gly Phe Ser Gly Asp Lys
                610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650
```

(2) INFORMATION FOR SEQ ID NO:37:

```
    (i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:37:

ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
1               5                  10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
            20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
        35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
    50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT       528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG       576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA       624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA       672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC       720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA       768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA       816
Gly Ser Thr Tyr Asp Ala Trp Val Lys Phe Asn Arg Phe Arg Arg Glu
```

-continued

```
                           260                     265                     270
ATG ACT TTA ACT GTA TTA GAT CTA ATT GTA CTT TTC CCA TTT TAT GAT         864
Met Thr Leu Thr Val Leu Asp Leu Ile Val Leu Phe Pro Phe Tyr Asp
        275                     280                     285

ATT CGG TTA TAC TCA AAA GGG GTT AAA ACA GAA CTA ACA AGA GAC ATT         912
Ile Arg Leu Tyr Ser Lys Gly Val Lys Thr Glu Leu Thr Arg Asp Ile
290                     295                     300

TTT ACG GAT CCA ATT TTT TCT CTT AGG ACA CCA CTT GCG TAC GGA CCA         960
Phe Thr Asp Pro Ile Phe Ser Leu Arg Thr Pro Leu Ala Tyr Gly Pro
305                     310                     315                     320

ACT TTT TTG AGT ATA GAA AAC TCT ATT CGA AAA CCT CAT TTA TTT GAT        1008
Thr Phe Leu Ser Ile Glu Asn Ser Ile Arg Lys Pro His Leu Phe Asp
                325                     330                     335

TAT TTA CAG GGG ATT GAA TTT CAT ACG CGT CTT CAA CCT GGT TAC TTT        1056
Tyr Leu Gln Gly Ile Glu Phe His Thr Arg Leu Gln Pro Gly Tyr Phe
                340                     345                     350

GGG AAA GAT TCT TTC AAT TAT TGG TCT GGT AAT TAT GTA GAA ACT AGA        1104
Gly Lys Asp Ser Phe Asn Tyr Trp Ser Gly Asn Tyr Val Glu Thr Arg
                355                     360                     365

CCT AGT ATA GGA TCT AGT AAG ACA ATT ACT TCC CCA TTT TAT GGA GAT        1152
Pro Ser Ile Gly Ser Ser Lys Thr Ile Thr Ser Pro Phe Tyr Gly Asp
        370                     375                     380

AAA TCT ACT GAA CCT GTA CAA AAG CTA AGC TTT GAT GGA CAA AAA GTT        1200
Lys Ser Thr Glu Pro Val Gln Lys Leu Ser Phe Asp Gly Gln Lys Val
385                     390                     395                     400

TAT CGA ACT ATA GCT AAT ACA GAC GTA GCG GCT TGG CCG AAT GGT AAG        1248
Tyr Arg Thr Ile Ala Asn Thr Asp Val Ala Ala Trp Pro Asn Gly Lys
                405                     410                     415

GTA TAT TTA GGT GTT ACG AAA GTT GAT TTT AGT CAA TAT GAT GAT CAA        1296
Val Tyr Leu Gly Val Thr Lys Val Asp Phe Ser Gln Tyr Asp Asp Gln
                420                     425                     430

AAA AAT GAA ACT AGT ACA CAA ACA TAT GAT TCA AAA AGA AAC AAT GGC        1344
Lys Asn Glu Thr Ser Thr Gln Thr Tyr Asp Ser Lys Arg Asn Asn Gly
                435                     440                     445

CAT GTA AGT GCA CAG GAT TCT ATT GAC CAA TTA CCG CCA GAA ACA ACA        1392
His Val Ser Ala Gln Asp Ser Ile Asp Gln Leu Pro Pro Glu Thr Thr
        450                     455                     460

GAT GAA CCA CTT GAA AAA GCA TAT AGT CAT CAG CTT AAT TAC GCG GAA        1440
Asp Glu Pro Leu Glu Lys Ala Tyr Ser His Gln Leu Asn Tyr Ala Glu
465                     470                     475                     480

TGT TTC TTA ATG CAG GAC CGT CGT GGA ACA ATT CCA TTT TTT ACT TGG        1488
Cys Phe Leu Met Gln Asp Arg Arg Gly Thr Ile Pro Phe Phe Thr Trp
                485                     490                     495

ACA CAT AGA AGT GTA GAC TTT TTT AAT ACA ATT GAT GCT GAA AAG ATT        1536
Thr His Arg Ser Val Asp Phe Phe Asn Thr Ile Asp Ala Glu Lys Ile
                500                     505                     510

ACT CAA CTT CCA GTA GTG AAA GCA TAT GCC TTG TCA TCA GGT GCT TCC        1584
Thr Gln Leu Pro Val Val Lys Ala Tyr Ala Leu Ser Ser Gly Ala Ser
        515                     520                     525

ATT ATT GAA GGT CCA GGA TTC ACA GGA GGA AAT TTA CTA TTC CTA AAA        1632
Ile Ile Glu Gly Pro Gly Phe Thr Gly Gly Asn Leu Leu Phe Leu Lys
        530                     535                     540

GAA TCT AGT AAT TCA ATT GCT AAA TTT AAA GTT ACA TTA AAT TCA GCA        1680
Glu Ser Ser Asn Ser Ile Ala Lys Phe Lys Val Thr Leu Asn Ser Ala
545                     550                     555                     560

GCC TTG TTA CAA CGA TAT CGT GTA AGA ATA CGC TAT GCT TCT ACC ACT        1728
Ala Leu Leu Gln Arg Tyr Arg Val Arg Ile Arg Tyr Ala Ser Thr Thr
                565                     570                     575

AAC TTA CGA CTT TTT GTG CAA AAT TCA AAC AAT GAT TTT CTT GTC ATC        1776
```

```
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
    610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650
```

(2) INFORMATION FOR SEQ ID NO:38:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:38:

```
Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255
```

```
Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
            275                 280                 285

Ile Arg Leu Tyr Ser Lys Gly Val Lys Thr Glu Leu Thr Arg Asp Ile
            290                 295                 300

Phe Thr Asp Pro Ile Phe Ser Leu Arg Thr Pro Leu Ala Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
            355                 360                 365

Pro Ser Ile Gly Ser Ser Lys Thr Ile Thr Ser Pro Phe Tyr Gly Asp
370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
        450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
            515                 520                 525

Ile Ile Glu Gly Pro Gly Phe Thr Gly Gly Asn Leu Leu Phe Leu Lys
            530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
            595                 600                 605

Phe Asp Leu Ala Thr Thr Asn Ser Asn Met Gly Phe Ser Gly Asp Lys
610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650
```

(2) INFORMATION FOR SEQ ID NO:39:

(i) SEQUENCE CHARACTERISTICS:

(A) LENGTH: 1959 base pairs
         (B) TYPE: nucleic acid
         (C) STRANDEDNESS: single
         (D) TOPOLOGY: linear (ix) FEATURE:
         (A) NAME/KEY: CDS
         (B) LOCATION: 1..1956

(xi) SEQUENCE DESCRIPTION: SEQ ID NO:39:

```
ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT       528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG       576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA       624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA       672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC       720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA       768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA       816
Gly Ser Thr Tyr Asp Ala Trp Val Lys Phe Asn Arg Phe Arg Arg Glu
            260                 265                 270
```

```
ATG ACT TTA ACT GTA TTA GAT CTA ATT GTA CTT TTC CCA TTT TTC AAT      864
Met Thr Leu Thr Val Leu Asp Leu Ile Val Leu Phe Pro Phe Phe Asn
        275                 280                 285

ATT TTG CTT TAC AGT AAA GGG GTT AAA ACA GAA CTA ACA AGA GAC ATT      912
Ile Leu Leu Tyr Ser Lys Gly Val Lys Thr Glu Leu Thr Arg Asp Ile
        290                 295                 300

TTT ACG GAT CCA ATT TTT TCA CTT AAT ACT CTT CAG GAG TAT GGA CCA      960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
            325                 330                 335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
        340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
370                 375                 380

AAA TCT ACT GAA CCT GTA CAA AAG CTA AGC TTT GAT GGA CAA AAA GTT     1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG     1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA     1296
Val Tyr Leu Gly Val Thr Lys Val Asp Phe Ser Gln Tyr Asp Asp Gln
        420                 425                 430

AAA AAT GAA ACT AGT ACA CAA ACA TAT GAT TCA AAA AGA AAC AAT GGC     1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA     1392
His Val Ser Ala Gln Asp Ser Ile Asp Gln Leu Pro Pro Glu Thr Thr
        450                 455                 460

GAT GAA CCA CTT GAA AAA GCA TAT AGT CAT CAG CTT AAT TAC GCG GAA     1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG     1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT     1536
Thr His Arg Ser Val Asp Phe Phe Asn Thr Ile Asp Ala Glu Lys Ile
        500                 505                 510

ACT CAA CTT CCA GTA GTG AAA GCA TAT GCC TTG TCT TCA GGT GCT TCC     1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA     1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA     1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT     1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC     1776
Asn Leu Arg Leu Phe Val Gln Asn Ser Asn Asn Asp Phe Leu Val Ile
        580                 585                 590
```

```
TAC ATT AAT AAA ACT ATG AAT AAA GAT GAT GAT TTA ACA TAT CAA ACA        1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG        1872
Phe Asp Leu Ala Thr Thr Asn Ser Asn Met Gly Phe Ser Gly Asp Lys
        610                 615                 620

AAT GAA CTT ATA ATA GGA GCA GAA TCT TTC GTT TCT AAT GAA AAA ATC        1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                    1959
Tyr Ile Asp Lys Ile Glu Phe Ile Pro Val Gln Leu
                645                 650
```

(2) INFORMATION FOR SEQ ID NO:40:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:40:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270
```

```
Met Thr Leu Thr Val Leu Asp Leu Ile Val Leu Phe Pro Phe Phe Asn
        275                 280                 285
Ile Leu Leu Tyr Ser Lys Gly Val Lys Thr Glu Leu Thr Arg Asp Ile
        290                 295                 300
Phe Thr Asp Pro Ile Phe Ser Leu Asn Thr Leu Gln Glu Tyr Gly Pro
305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Gln Pro Gly Tyr Phe
                340                 345                 350
Gly Lys Asp Ser Phe Asn Tyr Trp Ser Gly Asn Tyr Val Glu Thr Arg
                355                 360                 365
Pro Ser Ile Gly Ser Ser Lys Thr Ile Thr Ser Pro Phe Tyr Gly Asp
        370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
                420                 425                 430
Lys Asn Glu Thr Ser Thr Gln Thr Tyr Asp Ser Lys Arg Asn Asn Gly
                435                 440                 445
His Val Ser Ala Gln Asp Ser Ile Asp Gln Leu Pro Pro Glu Thr Thr
                450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Asn Thr Ile Asp Ala Glu Lys Ile
                500                 505                 510
Thr Gln Leu Pro Val Val Lys Ala Tyr Ala Leu Ser Ser Gly Ala Ser
                515                 520                 525
Ile Ile Glu Gly Pro Gly Phe Thr Gly Gly Asn Leu Leu Phe Leu Lys
                530                 535                 540
Glu Ser Ser Asn Ser Ile Ala Lys Phe Lys Val Thr Leu Asn Ser Ala
545                 550                 555                 560
Ala Leu Leu Gln Arg Tyr Arg Val Arg Ile Arg Tyr Ala Ser Thr Thr
                565                 570                 575
Asn Leu Arg Leu Phe Val Gln Asn Ser Asn Asn Asp Phe Leu Val Ile
                580                 585                 590
Tyr Ile Asn Lys Thr Met Asn Lys Asp Asp Asp Leu Thr Tyr Gln Thr
                595                 600                 605
Phe Asp Leu Ala Thr Thr Asn Ser Asn Met Gly Phe Ser Gly Asp Lys
                610                 615                 620
Asn Glu Leu Ile Ile Gly Ala Glu Ser Phe Val Ser Asn Glu Lys Ile
625                 630                 635                 640
Tyr Ile Asp Lys Ile Glu Phe Ile Pro Val Gln Leu
                645                 650
```

(2) INFORMATION FOR SEQ ID NO:41:

(i) SEQUENCE CHARACTERISTICS:
        (A) LENGTH: 1959 base pairs
        (B) TYPE: nucleic acid

```
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:41:

ATG AAT CCA AAC AAT CGA AGT GAA CAT GAT ACG ATA AAG GTT ACA CCT         48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT         96
Asn Ser Glu Leu Gln Thr Asn His Asn Gln Tyr Pro Leu Ala Asp Asn
                 20                  25                  30

CCA AAT TCA ACA CTA GAA GAA TTA AAT TAT AAA GAA TTT TTA AGA ATG        144
Pro Asn Ser Thr Leu Glu Glu Leu Asn Tyr Lys Glu Phe Leu Arg Met
             35                  40                  45

ACT GAA GAC AGT TCT ACG GAA GTG CTA GAC AAC TCT ACA GTA AAA GAT        192
Thr Glu Asp Ser Ser Thr Glu Val Leu Asp Asn Ser Thr Val Lys Asp
         50                  55                  60

GCA GTT GGG ACA GGA ATT TCT GTT GTA GGG CAG ATT TTA GGT GTT GTA        240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT        288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA        336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT        384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT        432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT        480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT        528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG        576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA        624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA        672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC        720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA        768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA        816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT        864
Met Thr Leu Thr Val Leu Asp Leu Ile Val Leu Phe Pro Phe Tyr Asp
```

-continued

|  | 275 |  |  |  | 280 |  |  |  | 285 |  |  |  |  |  |
|---|---|---|---|---|---|---|---|---|---|---|---|---|---|---|
| ATT | GTG | TTA | TAC | TCA | AAA | GGG | GTT | AAA | ACA | GAA | CTA | ACA | AGA | GAC | ATT | 912 |
| Ile | Val | Leu | Tyr | Ser | Lys | Gly | Val | Lys | Thr | Glu | Leu | Thr | Arg | Asp | Ile | |
|  |  | 290 |  |  |  | 295 |  |  |  | 300 |  |  |  |  |  |

```
ATT GTG TTA TAC TCA AAA GGG GTT AAA ACA GAA CTA ACA AGA GAC ATT      912
Ile Val Leu Tyr Ser Lys Gly Val Lys Thr Glu Leu Thr Arg Asp Ile
        290             295             300

TTT ACG GAT CCA ATT TTT TCA CTT AAT ACT CTT CAG GAG TAT GGA CCA      960
Phe Thr Asp Pro Ile Phe Ser Leu Asn Thr Leu Gln Glu Tyr Gly Pro
305             310             315             320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
                325             330             335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
            340             345             350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
        355             360             365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
    370             375             380

AAA TCT ACT GAA CCT GTA CAA AAG CTA AGC TTT GAT GGA CAA AAA GTT     1200
Lys Ser Thr Glu Pro Val Gln Lys Leu Ser Phe Asp Gly Gln Lys Val
385             390             395             400

TAT CGA ACT ATA GCT AAT ACA GAC GTA GCG GCT TGG CCG AAT GGT AAG     1248
Tyr Arg Thr Ile Ala Asn Thr Asp Val Ala Ala Trp Pro Asn Gly Lys
                405             410             415

GTA TAT TTA GGT GTT ACG AAA GTT GAT TTT AGT CAA TAT GAT GAT CAA     1296
Val Tyr Leu Gly Val Thr Lys Val Asp Phe Ser Gln Tyr Asp Asp Gln
            420             425             430

AAA AAT GAA ACT AGT ACA CAA ACA TAT GAT TCA AAA AGA AAC AAT GGC     1344
Lys Asn Glu Thr Ser Thr Gln Thr Tyr Asp Ser Lys Arg Asn Asn Gly
        435             440             445

CAT GTA AGT GCA CAG GAT TCT ATT GAC CAA TTA CCG CCA GAA ACA ACA     1392
His Val Ser Ala Gln Asp Ser Ile Asp Gln Leu Pro Pro Glu Thr Thr
    450             455             460

GAT GAA CCA CTT GAA AAA GCA TAT AGT CAT CAG CTT AAT TAC GCG GAA     1440
Asp Glu Pro Leu Glu Lys Ala Tyr Ser His Gln Leu Asn Tyr Ala Glu
465             470             475             480

TGT TTC TTA ATG CAG GAC CGT CGT GGA ACA ATT CCA TTT TTT ACT TGG     1488
Cys Phe Leu Met Gln Asp Arg Arg Gly Thr Ile Pro Phe Phe Thr Trp
                485             490             495

ACA CAT AGA AGT GTA GAC TTT TTT AAT ACA ATT GAT GCT GAA AAG ATT     1536
Thr His Arg Ser Val Asp Phe Phe Asn Thr Ile Asp Ala Glu Lys Ile
            500             505             510

ACT CAA CTT CCA GTA GTG AAA GCA TAT GCC TTG TCA TCA GGT GCT TCC     1584
Thr Gln Leu Pro Val Val Lys Ala Tyr Ala Leu Ser Ser Gly Ala Ser
        515             520             525

ATT ATT GAA GGT CCA GGA TTC ACA GGA GGA AAT TTA CTA TTC CTA AAA     1632
Ile Ile Glu Gly Pro Gly Phe Thr Gly Gly Asn Leu Leu Phe Leu Lys
    530             535             540

GAA TCT AGT AAT TCA ATT GCT AAA TTT AAA GTT ACA TTA AAT TCA GCA     1680
Glu Ser Ser Asn Ser Ile Ala Lys Phe Lys Val Thr Leu Asn Ser Ala
545             550             555             560

GCC TTG TTA CAA CGA TAT CGT GTA AGA ATA CGC TAT GCT TCT ACC ACT     1728
Ala Leu Leu Gln Arg Tyr Arg Val Arg Ile Arg Tyr Ala Ser Thr Thr
                565             570             575

AAC TTA CGA CTT TTT GTG CAA AAT TCA AAC AAT GAT TTT CTT GTC ATC     1776
Asn Leu Arg Leu Phe Val Gln Asn Ser Asn Asn Asp Phe Leu Val Ile
            580             585             590

TAC ATT AAT AAA ACT ATG AAT AAA GAT GAT GAT TTA ACA TAT CAA ACA     1824
```

-continued

```
Tyr Ile Asn Lys Thr Met Asn Lys Asp Asp Leu Thr Tyr Gln Thr
            595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650
```

(2) INFORMATION FOR SEQ ID NO:42:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:42:

```
Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
```

```
                275                 280                 285
Ile Val Leu Tyr Ser Lys Gly Val Lys Thr Glu Leu Thr Arg Asp Ile
290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
                340                 345                 350

Gly Lys Asp Ser Phe Asn Tyr Trp Ser Gly Asn Tyr Val Glu Thr Arg
                355                 360                 365

Pro Ser Ile Gly Ser Ser Lys Thr Ile Thr Ser Pro Phe Tyr Gly Asp
370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
435                 440                 445

His Val Ser Ala Gln Asp Ser Ile Asp Gln Leu Pro Pro Glu Thr Thr
450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
                500                 505                 510

Thr Gln Leu Pro Val Val Lys Ala Tyr Ala Leu Ser Ser Gly Ala Ser
                515                 520                 525

Ile Ile Glu Gly Pro Gly Phe Thr Gly Gly Asn Leu Leu Phe Leu Lys
530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
                580                 585                 590

Tyr Ile Asn Lys Thr Met Asn Lys Asp Asp Leu Thr Tyr Gln Thr
                595                 600                 605

Phe Asp Leu Ala Thr Thr Asn Ser Asn Met Gly Phe Ser Gly Asp Lys
610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:43:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear
```

(ix) FEATURE:
        (A) NAME/KEY: CDS
        (B) LOCATION: 1..1956

(xi) SEQUENCE DESCRIPTION: SEQ ID NO:43:

| | | | | | | | | | | | | | | | | |
|---|---|---|---|---|---|---|---|---|---|---|---|---|---|---|---|---|
|ATG|AAT|CCA|AAC|AAT|CGA|AGT|GAA|CAT|GAT|ACG|ATA|AAG|GTT|ACA|CCT|48|
|Met|Asn|Pro|Asn|Asn|Arg|Ser|Glu|His|Asp|Thr|Ile|Lys|Val|Thr|Pro| |
|1| | | |5| | | | |10| | | | |15| | |

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
  1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
 50                  55                  60

GCA GTT GGG ACA GGA ATT TCT GTT GTA GGG CAG ATT TTA GGT GTT GTA     240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT     288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA     336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT     384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT     432
Lys Ala Leu Ala Glu Leu Gln Gly Leu Gln Asn Asn Phe Glu Asp Tyr
130                 135                 140

GTT AAT GCG TTA AAT TCC TGG AAG AAA ACA CCT TTA AGT TTG CGA AGT     480
Val Asn Ala Leu Asn Ser Trp Lys Lys Thr Pro Leu Ser Leu Arg Ser
145                 150                 155                 160

AAA AGA AGC CAA GGT CGA ATA AGG GAA CTT TTT TCT CAA GCA GAA AGT     528
Lys Arg Ser Gln Gly Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG     576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA     624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA     672
Leu Lys Asp Ala Gln Val Phe Gly Glu Glu Trp Gly Tyr Ser Ser Glu
210                 215                 220

GAT GTT GCT GAA TTT TAT CAT AGA CAA TTA AAA CTT ACA CAA CAA TAC     720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA     768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA     816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT     864
Met Thr Leu Thr Val Leu Asp Leu Ile Val Leu Phe Pro Phe Tyr Asp
        275                 280                 285
```

```
ATT CGG TTA TAC TCA AAA GGG GTT AAA ACA GAA CTA ACA AGA GAC ATT      912
Ile Arg Leu Tyr Ser Lys Gly Val Lys Thr Glu Leu Thr Arg Asp Ile
    290                 295                 300

TTT ACG GAT CCA ATT TTT TCA CTT AAT ACT CTT CAG GAG TAT GGA CCA      960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
370                 375                 380

AAA TCT ACT GAA CCT GTA CAA AAG CTA AGC TTT GAT GGA CAA AAA GTT     1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG     1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA     1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC     1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA     1392
His Val Ser Ala Gln Asp Ser Ile Asp Gln Leu Pro Pro Glu Thr Thr
450                 455                 460

GAT GAA CCA CTT GAA AAA GCA TAT AGT CAT CAG CTT AAT TAC GCG GAA     1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG     1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT     1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC     1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA     1632
Ile Ile Glu Gly Pro Gly Phe Thr Gly Gly Asn Leu Leu Phe Leu Lys
530                 535                 540

GAA TCT AGT AAT TCA ATT GCT AAA TTT AAA GTT ACA TTA AAT TCA GCA     1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT     1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC     1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA     1824
Tyr Ile Asn Lys Thr Met Asn Lys Asp Asp Asp Leu Thr Tyr Gln Thr
        595                 600                 605
```

```
TTT GAT CTC GCA ACT ACT AAT TCT AAT ATG GGG TTC TCG GGT GAT AAG     1872
Phe Asp Leu Ala Thr Thr Asn Ser Asn Met Gly Phe Ser Gly Asp Lys
            610                 615                 620

AAT GAA CTT ATA ATA GGA GCA GAA TCT TTC GTT TCT AAT GAA AAA ATC     1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                 1959
Tyr Ile Asp Lys Ile Glu Phe Ile Pro Val Gln Leu
                645                 650
```

(2) INFORMATION FOR SEQ ID NO:44:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:44:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
             20                  25                  30

Pro Asn Ser Thr Leu Glu Glu Leu Asn Tyr Lys Glu Phe Leu Arg Met
         35                  40                  45

Thr Glu Asp Ser Ser Thr Glu Val Leu Asp Asn Ser Thr Val Lys Asp
50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Gly Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285
```

```
Ile Arg Leu Tyr Ser Lys Gly Val Lys Thr Glu Leu Thr Arg Asp Ile
    290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
        595                 600                 605

Phe Asp Leu Ala Thr Thr Asn Ser Asn Met Gly Phe Ser Gly Asp Lys
    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:45:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
```

(A) NAME/KEY: CDS
        (B) LOCATION: 1..1956

(xi) SEQUENCE DESCRIPTION: SEQ ID NO:45:

```
ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
  1               5                  10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AAT       480
Val Asn Ala Leu Asn Ser Trp Lys Lys Thr Pro Leu Ser Leu Arg Asn
145                 150                 155                 160

CCA CAC AGC CAA GGT CGA ATA AGG GAA CTT TTT TCT CAA GCA GAA AGT       528
Pro His Ser Gln Gly Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG       576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA       624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA       672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC       720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA       768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA       816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT       864
Met Thr Leu Thr Val Leu Asp Leu Ile Val Leu Phe Pro Phe Tyr Asp
        275                 280                 285

ATT CGG TTA TAC TCA AAA GGG GTT AAA ACA GAA CTA ACA AGA GAC ATT       912
Ile Arg Leu Tyr Ser Lys Gly Val Lys Thr Glu Leu Thr Arg Asp Ile
```

```
             290                     295                     300
TTT ACG GAT CCA ATT TTT TCA CTT AAT ACT CTT CAG GAG TAT GGA CCA      960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
370                 375                 380

AAA TCT ACT GAA CCT GTA CAA AAG CTA AGC TTT GAT GGA CAA AAA GTT     1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG     1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA     1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC     1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA     1392
His Val Ser Ala Gln Asp Ser Ile Asp Gln Leu Pro Pro Glu Thr Thr
450                 455                 460

GAT GAA CCA CTT GAA AAA GCA TAT AGT CAT CAG CTT AAT TAC GCG GAA     1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG     1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT     1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC     1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA     1632
Ile Ile Glu Gly Pro Gly Phe Thr Gly Gly Asn Leu Leu Phe Leu Lys
530                 535                 540

GAA TCT AGT AAT TCA ATT GCT AAA TTT AAA GTT ACA TTA AAT TCA GCA     1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT     1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC     1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA     1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG     1872
```

```
Phe Asp Leu Ala Thr Thr Asn Ser Asn Met Gly Phe Ser Gly Asp Lys
        610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                   1959
Tyr Ile Asp Lys Ile Glu Phe Ile Pro Val Gln Leu
                645                 650
```

(2) INFORMATION FOR SEQ ID NO:46:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:46:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Asn
145                 150                 155                 160

Pro His Ser Gln Gly Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
290                 295                 300
```

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
            325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
            355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
                435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
    515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
            595                 600                 605

Phe Asp Leu Ala Thr Thr Asn Ser Asn Met Gly Phe Ser Gly Asp Lys
    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:47:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:47:

```
ATG AAT CCA AAC AAT CGA AGT GAA CAT GAT ACG ATA AAG GTT ACA CCT         48
Met Asn Pro Asn Asn Arg Ser Glu His Asp Thr Ile Lys Val Thr Pro
  1               5                  10                  15

AAC AGT GAA TTG CAA ACT AAC CAT AAT CAA TAT CCT TTA GCT GAC AAT         96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG        144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT        192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA        240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT        288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA        336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT        384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT        432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT        480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT        528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG        576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA        624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA        672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC        720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA        768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA        816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT        864
Met Thr Leu Thr Val Leu Asp Leu Ile Val Leu Phe Pro Phe Tyr Asp
        275                 280                 285

GTT CGG TTA TAC CCA AAA GGG GTT AAA ACA GAA CTA ACA AGA GAC ATT        912
Val Arg Leu Tyr Pro Lys Gly Val Lys Thr Glu Leu Thr Arg Asp Ile
    290                 295                 300
```

```
TTT ACG GAT CCA ATT TTT TCA CTT AAT ACT CTT CAG GAG TAT GGA CCA      960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
        340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
370                 375                 380

AAA TCT ACT GAA CCT GTA CAA AAG CTA AGC TTT GAT GGA CAA AAA GTT     1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG     1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA     1296
Val Tyr Leu Gly Val Thr Lys Val Asp Phe Ser Gln Tyr Asp Asp Gln
        420                 425                 430

AAA AAT GAA ACT AGT ACA CAA ACA TAT GAT TCA AAA AGA AAC AAT GGC     1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA     1392
His Val Ser Ala Gln Asp Ser Ile Asp Gln Leu Pro Pro Glu Thr Thr
450                 455                 460

GAT GAA CCA CTT GAA AAA GCA TAT AGT CAT CAG CTT AAT TAC GCG GAA     1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG     1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT     1536
Thr His Arg Ser Val Asp Phe Phe Asn Thr Ile Asp Ala Glu Lys Ile
        500                 505                 510

ACT CAA CTT CCA GTA GTG AAA GCA TAT GCC TTG TCT TCA GGT GCT TCC     1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA     1632
Ile Ile Glu Gly Pro Gly Phe Thr Gly Gly Asn Leu Leu Phe Leu Lys
530                 535                 540

GAA TCT AGT AAT TCA ATT GCT AAA TTT AAA GTT ACA TTA AAT TCA GCA     1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT     1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC     1776
Asn Leu Arg Leu Phe Val Gln Asn Ser Asn Asn Asp Phe Leu Val Ile
        580                 585                 590

TAC ATT AAT AAA ACT ATG AAT AAA GAT GAT GAT TTA ACA TAT CAA ACA     1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG     1872
Phe Asp Leu Ala Thr Thr Asn Ser Asn Met Gly Phe Ser Gly Asp Lys
610                 615                 620
```

```
AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
Tyr Ile Asp Lys Ile Glu Phe Ile Pro Val Gln Leu
                645                 650
```

(2) INFORMATION FOR SEQ ID NO:48:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:48:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
             20                  25                  30

Pro Asn Ser Thr Leu Glu Glu Leu Asn Tyr Lys Glu Phe Leu Arg Met
         35                  40                  45

Thr Glu Asp Ser Ser Thr Glu Val Leu Asp Asn Ser Thr Val Lys Asp
 50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
             85                  90                  95

Asn Thr Ile Trp Pro Ser Asp Ala Asp Pro Trp Lys Ala Phe Met Ala
             100                 105                 110

Gln Val Glu Val Leu Ile Asp Lys Lys Ile Glu Glu Tyr Ala Lys Ser
             115                 120                 125

Lys Ala Leu Ala Glu Leu Gln Gly Leu Gln Asn Asn Phe Glu Asp Tyr
 130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
             180                 185                 190

Leu Phe Leu Pro Thr Tyr Ala Gln Ala Ala Asn Thr His Leu Leu Leu
             195                 200                 205

Leu Lys Asp Ala Gln Val Phe Gly Glu Glu Trp Gly Tyr Ser Ser Glu
 210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
             260                 265                 270

Met Thr Leu Thr Val Leu Asp Leu Ile Val Leu Phe Pro Phe Tyr Asp
             275                 280                 285

Val Arg Leu Tyr Pro Lys Gly Val Lys Thr Glu Leu Thr Arg Asp Ile
 290                 295                 300

Phe Thr Asp Pro Ile Phe Ser Leu Asn Thr Leu Gln Glu Tyr Gly Pro
```

```
                305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Gln Pro Gly Tyr Phe
                340                 345                 350
Gly Lys Asp Ser Phe Asn Tyr Trp Ser Gly Asn Tyr Val Glu Thr Arg
                355                 360                 365
Pro Ser Ile Gly Ser Ser Lys Thr Ile Thr Ser Pro Phe Tyr Gly Asp
        370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
                420                 425                 430
Lys Asn Glu Thr Ser Thr Gln Thr Tyr Asp Ser Lys Arg Asn Asn Gly
                435                 440                 445
His Val Ser Ala Gln Asp Ser Ile Asp Gln Leu Pro Pro Glu Thr Thr
        450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Phe Asn Thr Ile Asp Ala Glu Lys Ile
                500                 505                 510
Thr Gln Leu Pro Val Val Lys Ala Tyr Ala Leu Ser Ser Gly Ala Ser
                515                 520                 525
Ile Ile Glu Gly Pro Gly Phe Thr Gly Gly Asn Leu Leu Phe Leu Lys
        530                 535                 540
Glu Ser Ser Asn Ser Ile Ala Lys Phe Lys Val Thr Leu Asn Ser Ala
545                 550                 555                 560
Ala Leu Leu Gln Arg Tyr Arg Val Arg Ile Arg Tyr Ala Ser Thr Thr
                565                 570                 575
Asn Leu Arg Leu Phe Val Gln Asn Ser Asn Asn Asp Phe Leu Val Ile
                580                 585                 590
Tyr Ile Asn Lys Thr Met Asn Lys Asp Asp Asp Leu Thr Tyr Gln Thr
                595                 600                 605
Phe Asp Leu Ala Thr Thr Asn Ser Asn Met Gly Phe Ser Gly Asp Lys
        610                 615                 620
Asn Glu Leu Ile Ile Gly Ala Glu Ser Phe Val Ser Asn Glu Lys Ile
625                 630                 635                 640
Tyr Ile Asp Lys Ile Glu Phe Ile Pro Val Gln Leu
                645                 650
```

(2) INFORMATION FOR SEQ ID NO:49:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:49:

-continued

```
ATG AAT CCA AAC AAT CGA AGT GAA CAT GAT ACG ATA AAG GTT ACA CCT          48
Met Asn Pro Asn Asn Arg Ser Glu His Asp Thr Ile Lys Val Thr Pro
  1               5                  10                  15

AAC AGT GAA TTG CAA ACT AAC CAT AAT CAA TAT CCT TTA GCT GAC AAT          96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG         144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT         192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA         240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT         288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA         336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT         384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT         432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AAT         480
Val Asn Ala Leu Asn Ser Trp Lys Lys Thr Pro Leu Ser Leu Arg Asn
145                 150                 155                 160

CCA CAC AGC CAA GGT CGA ATA AGG GAA CTT TTT TCT CAA GCA GAA AGT         528
Pro His Ser Gln Gly Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG         576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA         624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA         672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC         720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA         768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA         816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT         864
Met Thr Leu Thr Val Leu Asp Leu Ile Val Leu Phe Pro Phe Tyr Asp
        275                 280                 285

GTT CGG TTA TAC CCA AAA GGG GTT AAA ACA GAA CTA ACA AGA GAC ATT         912
Val Arg Leu Tyr Pro Lys Gly Val Lys Thr Glu Leu Thr Arg Asp Ile
    290                 295                 300

TTT ACG GAT CCA ATT TTT TCA CTT AAT ACT CTT CAG GAG TAT GGA CCA         960
Phe Thr Asp Pro Ile Phe Ser Leu Asn Thr Leu Gln Glu Tyr Gly Pro
```

```
                                                              -continued
305                     310                     315                     320
ACT TTT TTG AGT ATA GAA AAC TCT ATT CGA AAA CCT CAT TTA TTT GAT          1008
Thr Phe Leu Ser Ile Glu Asn Ser Ile Arg Lys Pro His Leu Phe Asp
                        325                     330                 335

TAT TTA CAG GGG ATT GAA TTT CAT ACG CGT CTT CAA CCT GGT TAC TTT          1056
Tyr Leu Gln Gly Ile Glu Phe His Thr Arg Leu Gln Pro Gly Tyr Phe
                340                     345                 350

GGG AAA GAT TCT TTC AAT TAT TGG TCT GGT AAT TAT GTA GAA ACT AGA          1104
Gly Lys Asp Ser Phe Asn Tyr Trp Ser Gly Asn Tyr Val Glu Thr Arg
            355                     360                 365

CCT AGT ATA GGA TCT AGT AAG ACA ATT ACT TCC CCA TTT TAT GGA GAT          1152
Pro Ser Ile Gly Ser Ser Lys Thr Ile Thr Ser Pro Phe Tyr Gly Asp
        370                     375                 380

AAA TCT ACT GAA CCT GTA CAA AAG CTA AGC TTT GAT GGA CAA AAA GTT          1200
Lys Ser Thr Glu Pro Val Gln Lys Leu Ser Phe Asp Gly Gln Lys Val
385                     390                     395                 400

TAT CGA ACT ATA GCT AAT ACA GAC GTA GCG GCT TGG CCG AAT GGT AAG          1248
Tyr Arg Thr Ile Ala Asn Thr Asp Val Ala Ala Trp Pro Asn Gly Lys
                    405                     410                 415

GTA TAT TTA GGT GTT ACG AAA GTT GAT TTT AGT CAA TAT GAT GAT CAA          1296
Val Tyr Leu Gly Val Thr Lys Val Asp Phe Ser Gln Tyr Asp Asp Gln
                420                     425                 430

AAA AAT GAA ACT AGT ACA CAA ACA TAT GAT TCA AAA AGA AAC AAT GGC          1344
Lys Asn Glu Thr Ser Thr Gln Thr Tyr Asp Ser Lys Arg Asn Asn Gly
            435                     440                 445

CAT GTA AGT GCA CAG GAT TCT ATT GAC CAA TTA CCG CCA GAA ACA ACA          1392
His Val Ser Ala Gln Asp Ser Ile Asp Gln Leu Pro Pro Glu Thr Thr
        450                     455                 460

GAT GAA CCA CTT GAA AAA GCA TAT AGT CAT CAG CTT AAT TAC GCG GAA          1440
Asp Glu Pro Leu Glu Lys Ala Tyr Ser His Gln Leu Asn Tyr Ala Glu
465                     470                     475                 480

TGT TTC TTA ATG CAG GAC CGT CGT GGA ACA ATT CCA TTT TTT ACT TGG          1488
Cys Phe Leu Met Gln Asp Arg Arg Gly Thr Ile Pro Phe Phe Thr Trp
                    485                     490                 495

ACA CAT AGA AGT GTA GAC TTT TTT AAT ACA ATT GAT GCT GAA AAG ATT          1536
Thr His Arg Ser Val Asp Phe Phe Asn Thr Ile Asp Ala Glu Lys Ile
                500                     505                 510

ACT CAA CTT CCA GTA GTG AAA GCA TAT GCC TTG TCT TCA GGT GCT TCC          1584
Thr Gln Leu Pro Val Val Lys Ala Tyr Ala Leu Ser Ser Gly Ala Ser
            515                     520                 525

ATT ATT GAA GGT CCA GGA TTC ACA GGA GGA AAT TTA CTA TTC CTA AAA          1632
Ile Ile Glu Gly Pro Gly Phe Thr Gly Gly Asn Leu Leu Phe Leu Lys
        530                     535                 540

GAA TCT AGT AAT TCA ATT GCT AAA TTT AAA GTT ACA TTA AAT TCA GCA          1680
Glu Ser Ser Asn Ser Ile Ala Lys Phe Lys Val Thr Leu Asn Ser Ala
545                     550                     555                 560

GCC TTG TTA CAA CGA TAT CGT GTA AGA ATA CGC TAT GCT TCT ACC ACT          1728
Ala Leu Leu Gln Arg Tyr Arg Val Arg Ile Arg Tyr Ala Ser Thr Thr
                    565                     570                 575

AAC TTA CGA CTT TTT GTG CAA AAT TCA AAC AAT GAT TTT CTT GTC ATC          1776
Asn Leu Arg Leu Phe Val Gln Asn Ser Asn Asn Asp Phe Leu Val Ile
                580                     585                 590

TAC ATT AAT AAA ACT ATG AAT AAA GAT GAT GAT TTA ACA TAT CAA ACA          1824
Tyr Ile Asn Lys Thr Met Asn Lys Asp Asp Asp Leu Thr Tyr Gln Thr
            595                     600                 605

TTT GAT CTC GCA ACT ACT AAT TCT AAT ATG GGG TTC TCG GGT GAT AAG          1872
Phe Asp Leu Ala Thr Thr Asn Ser Asn Met Gly Phe Ser Gly Asp Lys
        610                     615                 620

AAT GAA CTT ATA ATA GGA GCA GAA TCT TTC GTT TCT AAT GAA AAA ATC          1920
```

```
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650
```

(2) INFORMATION FOR SEQ ID NO:50:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:50:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
                20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
        50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
                100                 105                 110

Gln Val Glu Val Leu Ile Asp Lys Lys Ile Glu Glu Tyr Ala Lys Ser
            115                 120                 125

Lys Ala Leu Ala Glu Leu Gln Gly Leu Gln Asn Asn Phe Glu Asp Tyr
        130                 135                 140

Val Asn Ala Leu Asn Ser Trp Lys Lys Thr Pro Leu Ser Leu Arg Asn
145                 150                 155                 160

Pro His Ser Gln Gly Arg Ile Arg Glu Leu Phe Ser Gln Ala Glu Ser
                165                 170                 175

His Phe Arg Asn Ser Met Pro Ser Phe Ala Val Ser Lys Phe Glu Val
                180                 185                 190

Leu Phe Leu Pro Thr Tyr Ala Gln Ala Ala Asn Thr His Leu Leu Leu
            195                 200                 205

Leu Lys Asp Ala Gln Val Phe Gly Glu Glu Trp Gly Tyr Ser Ser Glu
        210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
                260                 265                 270

Met Thr Leu Thr Val Leu Asp Leu Ile Val Leu Phe Pro Phe Tyr Asp
            275                 280                 285

Val Arg Leu Tyr Pro Lys Gly Val Lys Thr Glu Leu Thr Arg Asp Ile
        290                 295                 300

Phe Thr Asp Pro Ile Phe Ser Leu Asn Thr Leu Gln Glu Tyr Gly Pro
305                 310                 315                 320
```

```
Thr Phe Leu Ser Ile Glu Asn Ser Ile Arg Lys Pro His Leu Phe Asp
            325                 330                 335

Tyr Leu Gln Gly Ile Glu Phe His Thr Arg Leu Gln Pro Gly Tyr Phe
        340                 345                 350

Gly Lys Asp Ser Phe Asn Tyr Trp Ser Gly Asn Tyr Val Glu Thr Arg
    355                 360                 365

Pro Ser Ile Gly Ser Ser Lys Thr Ile Thr Ser Pro Phe Tyr Gly Asp
370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
        595                 600                 605

Phe Asp Leu Ala Thr Thr Asn Ser Asn Met Gly Phe Ser Gly Asp Lys
    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:51:

(i) SEQUENCE CHARACTERISTICS:
        (A) LENGTH: 1956 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1953

(xi) SEQUENCE DESCRIPTION: SEQ ID NO:51:

ATG AAT CCA AAC AAT CGA AGT GAA CAT GAT ACG ATA AAG GTT ACA CCT         48
```

-continued

| | | | |
|---|---|---|---|
| Met Asn Pro Asn Asn Arg Ser Glu His Asp Thr Ile Lys Val Thr Pro<br>1               5                   10                  15 | | | |
| AAC AGT GAA TTG CAA ACT AAC CAT AAT CAA TAT CCT TTA GCT GAC AAT<br>Asn Ser Glu Leu Gln Thr Asn His Asn Gln Tyr Pro Leu Ala Asp Asn<br>            20                  25                  30 | | | 96 |
| CCA AAT TCA ACA CTA GAA GAA TTA AAT TAT AAA GAA TTT TTA AGA ATG<br>Pro Asn Ser Thr Leu Glu Glu Leu Asn Tyr Lys Glu Phe Leu Arg Met<br>        35                  40                  45 | | | 144 |
| ACT GAA GAC AGT TCT ACG GAA GTG CTA GAC AAC TCT ACA GTA AAA GAT<br>Thr Glu Asp Ser Ser Thr Glu Val Leu Asp Asn Ser Thr Val Lys Asp<br>    50                  55                  60 | | | 192 |
| GCA GTT GGG ACA GGA ATT TCT GTT GTA GGG CAG ATT TTA GGT GTT GTA<br>Ala Val Gly Thr Gly Ile Ser Val Val Gly Gln Ile Leu Gly Val Val<br>65                  70                  75                  80 | | | 240 |
| GGA GTT CCA TTT GCT GGG GCA CTC ACT TCA TTT TAT CAA TCA TTT CTT<br>Gly Val Pro Phe Ala Gly Ala Leu Thr Ser Phe Tyr Gln Ser Phe Leu<br>                85                  90                  95 | | | 288 |
| AAC ACT ATA TGG CCA AGT GAA GAC CCA TGG AAG GCT TTT ATG GCA CAA<br>Asn Thr Ile Trp Pro Ser Glu Asp Pro Trp Lys Ala Phe Met Ala Gln<br>            100                 105                 110 | | | 336 |
| GTT GAA GTA CTG ATA GAT AAG AAA ATA GAG GAG TAT GCT AAA AGT AAA<br>Val Glu Val Leu Ile Asp Lys Lys Ile Glu Glu Tyr Ala Lys Ser Lys<br>        115                 120                 125 | | | 384 |
| GCT CTT GCA GAG TTA CAG GGT CTT CAA AAT AAT TTC GAA GAT TAT GTT<br>Ala Leu Ala Glu Leu Gln Gly Leu Gln Asn Asn Phe Glu Asp Tyr Val<br>    130                 135                 140 | | | 432 |
| AAT GCG TTA AAT TCC TGG AAG AAA ACA CCT TTA AGT TTG CGA AGT AAA<br>Asn Ala Leu Asn Ser Trp Lys Lys Thr Pro Leu Ser Leu Arg Ser Lys<br>145                 150                 155                 160 | | | 480 |
| AGA AGC CAA GAT CGA ATA AGG GAA CTT TTT TCT CAA GCA GAA AGT CAT<br>Arg Ser Gln Asp Arg Ile Arg Glu Leu Phe Ser Gln Ala Glu Ser His<br>                165                 170                 175 | | | 528 |
| TTT CGT AAT TCC ATG CCG TCA TTT GCA GTT TCC AAA TTC GAA GTG CTG<br>Phe Arg Asn Ser Met Pro Ser Phe Ala Val Ser Lys Phe Glu Val Leu<br>            180                 185                 190 | | | 576 |
| TTT CTA CCA ACA TAT GCA CAA GCT GCA AAT ACA CAT TTA TTG CTA TTA<br>Phe Leu Pro Thr Tyr Ala Gln Ala Ala Asn Thr His Leu Leu Leu Leu<br>        195                 200                 205 | | | 624 |
| AAA GAT GCT CAA GTT TTT GGA GAA GAA TGG GGA TAT TCT TCA GAA GAT<br>Lys Asp Ala Gln Val Phe Gly Glu Glu Trp Gly Tyr Ser Ser Glu Asp<br>    210                 215                 220 | | | 672 |
| GTT GCT GAA TTT TAT CAT AGA CAA TTA AAA CTT ACA CAA CAA TAC ACT<br>Val Ala Glu Phe Tyr His Arg Gln Leu Lys Leu Thr Gln Gln Tyr Thr<br>225                 230                 235                 240 | | | 720 |
| GAC CAT TGT GTT AAT TGG TAT AAT GTT GGA TTA AAT GGT TTA AGA GGT<br>Asp His Cys Val Asn Trp Tyr Asn Val Gly Leu Asn Gly Leu Arg Gly<br>                245                 250                 255 | | | 768 |
| TCA ACT TAT GAT GCA TGG GTC AAA TTT AAC CGT TTT CGC AGA GAA ATG<br>Ser Thr Tyr Asp Ala Trp Val Lys Phe Asn Arg Phe Arg Arg Glu Met<br>            260                 265                 270 | | | 816 |
| ACT TTA ACT GTA TTA GAT CTA ATT GTA CTT TTC CCA TTT TAT GAT ATT<br>Thr Leu Thr Val Leu Asp Leu Ile Val Leu Phe Pro Phe Tyr Asp Ile<br>        275                 280                 285 | | | 864 |
| CGG TTA TAC TCA AAA GGG GTT AAA ACA GAA CTA ACA AGA GAC ATT TTT<br>Arg Leu Tyr Ser Lys Gly Val Lys Thr Glu Leu Thr Arg Asp Ile Phe<br>    290                 295                 300 | | | 912 |
| ACG GAT CCA ATT TTT TCA CTT AAT ACT CTT CAG GAG TAT GGA CCA ACT<br>Thr Asp Pro Ile Phe Ser Leu Asn Thr Leu Gln Glu Tyr Gly Pro Thr<br>305                 310                 315                 320 | | | 960 |

```
TTT TTG AGT ATA GAA AAC TCT ATT CGA AAA CCT CAT TTA TTT GAT TAT      1008
Phe Leu Ser Ile Glu Asn Ser Ile Arg Lys Pro His Leu Phe Asp Tyr
            325                 330                 335

TTA CAG GGG ATT GAA TTT CAT ACG CGT CTT CAA CCT GGT TAC TTT GGG      1056
Leu Gln Gly Ile Glu Phe His Thr Arg Leu Gln Pro Gly Tyr Phe Gly
            340                 345                 350

AAA GAT TCT TTC AAT TAT TGG TCT GGT AAT TAT GTA GAA ACT AGA CCT      1104
Lys Asp Ser Phe Asn Tyr Trp Ser Gly Asn Tyr Val Glu Thr Arg Pro
            355                 360                 365

AGT ATA GGA TCT AGT AAG ACA ATT ACT TCC CCA TTT TAT GGA GAT AAA      1152
Ser Ile Gly Ser Ser Lys Thr Ile Thr Ser Pro Phe Tyr Gly Asp Lys
            370                 375                 380

TCT ACT GAA CCT GTA CAA AAG CTA AGC TTT GAT GGA CAA AAA GTT TAT      1200
Ser Thr Glu Pro Val Gln Lys Leu Ser Phe Asp Gly Gln Lys Val Tyr
385                 390                 395                 400

CGA ACT ATA GCT AAT ACA GAC GTA GCG GCT TGG CCG AAT GGT AAG GTA      1248
Arg Thr Ile Ala Asn Thr Asp Val Ala Ala Trp Pro Asn Gly Lys Val
            405                 410                 415

TAT TTA GGT GTT ACG AAA GTT GAT TTT AGT CAA TAT GAT GAT CAA AAA      1296
Tyr Leu Gly Val Thr Lys Val Asp Phe Ser Gln Tyr Asp Asp Gln Lys
            420                 425                 430

AAT GAA ACT AGT ACA CAA ACA TAT GAT TCA AAA AGA AAC AAT GGC CAT      1344
Asn Glu Thr Ser Thr Gln Thr Tyr Asp Ser Lys Arg Asn Asn Gly His
            435                 440                 445

GTA AGT GCA CAG GAT TCT ATT GAC CAA TTA CCG CCA GAA ACA ACA GAT      1392
Val Ser Ala Gln Asp Ser Ile Asp Gln Leu Pro Pro Glu Thr Thr Asp
            450                 455                 460

GAA CCA CTT GAA AAA GCA TAT AGT CAT CAG CTT AAT TAC GCG GAA TGT      1440
Glu Pro Leu Glu Lys Ala Tyr Ser His Gln Leu Asn Tyr Ala Glu Cys
465                 470                 475                 480

TTC TTA ATG CAG GAC CGT CGT GGA ACA ATT CCA TTT TTT ACT TGG ACA      1488
Phe Leu Met Gln Asp Arg Arg Gly Thr Ile Pro Phe Phe Thr Trp Thr
            485                 490                 495

CAT AGA AGT GTA GAC TTT TTT AAT ACA ATT GAT GCT GAA AAG ATT ACT      1536
His Arg Ser Val Asp Phe Phe Asn Thr Ile Asp Ala Glu Lys Ile Thr
            500                 505                 510

CAA CTT CCA GTA GTG AAA GCA TAT GCC TTG TCT TCA GGT GCT TCC ATT      1584
Gln Leu Pro Val Val Lys Ala Tyr Ala Leu Ser Ser Gly Ala Ser Ile
            515                 520                 525

ATT GAA GGT CCA GGA TTC ACA GGA GGA AAT TTA CTA TTC CTA AAA GAA      1632
Ile Glu Gly Pro Gly Phe Thr Gly Gly Asn Leu Leu Phe Leu Lys Glu
530                 535                 540

TCT AGT AAT TCA ATT GCT AAA TTT AAA GTT ACA TTA AAT TCA GCA GCC      1680
Ser Ser Asn Ser Ile Ala Lys Phe Lys Val Thr Leu Asn Ser Ala Ala
545                 550                 555                 560

TTG TTA CAA CGA TAT CGT GTA AGA ATA CGC TAT GCT TCT ACC ACT AAC      1728
Leu Leu Gln Arg Tyr Arg Val Arg Ile Arg Tyr Ala Ser Thr Thr Asn
            565                 570                 575

TTA CGA CTT TTT GTG CAA AAT TCA AAC AAT GAT TTT CTT GTC ATC TAC      1776
Leu Arg Leu Phe Val Gln Asn Ser Asn Asn Asp Phe Leu Val Ile Tyr
            580                 585                 590

ATT AAT AAA ACT ATG AAT AAA GAT GAT GAT TTA ACA TAT CAA ACA TTT      1824
Ile Asn Lys Thr Met Asn Lys Asp Asp Asp Leu Thr Tyr Gln Thr Phe
            595                 600                 605

GAT CTC GCA ACT ACT AAT TCT AAT ATG GGG TTC TCG GGT GAT AAG AAT      1872
Asp Leu Ala Thr Thr Asn Ser Asn Met Gly Phe Ser Gly Asp Lys Asn
            610                 615                 620

GAA CTT ATA ATA GGA GCA GAA TCT TTC GTT TCT AAT GAA AAA ATC TAT      1920
Glu Leu Ile Ile Gly Ala Glu Ser Phe Val Ser Asn Glu Lys Ile Tyr
625                 630                 635                 640
```

```
ATA GAT AAG ATA GAA TTT ATC CCA GTA CAA TTG TAA                    1956
Ile Asp Lys Ile Glu Phe Ile Pro Val Gln Leu
            645                 650
```

(2) INFORMATION FOR SEQ ID NO:52:

(i) SEQUENCE CHARACTERISTICS:
        (A) LENGTH: 651 amino acids
        (B) TYPE: amino acid
        (D) TOPOLOGY: linear (ii) MOLECULE TYPE: protein (xi) SEQUENCE DESCRIPTION: SEQ ID NO:52:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                85                  90                  95

Asn Thr Ile Trp Pro Ser Glu Asp Pro Trp Lys Ala Phe Met Ala Gln
            100                 105                 110

Val Glu Val Leu Ile Asp Lys Lys Ile Glu Glu Tyr Ala Lys Ser Lys
        115                 120                 125

Ala Leu Ala Glu Leu Gln Gly Leu Gln Asn Asn Phe Glu Asp Tyr Val
    130                 135                 140

Asn Ala Leu Asn Ser Trp Lys Lys Thr Pro Leu Ser Leu Arg Ser Lys
145                 150                 155                 160

Arg Ser Gln Asp Arg Ile Arg Glu Leu Phe Ser Gln Ala Glu Ser His
                165                 170                 175

Phe Arg Asn Ser Met Pro Ser Phe Ala Val Ser Lys Phe Glu Val Leu
            180                 185                 190

Phe Leu Pro Thr Tyr Ala Gln Ala Ala Asn Thr His Leu Leu Leu Leu
        195                 200                 205

Lys Asp Ala Gln Val Phe Gly Glu Glu Trp Gly Tyr Ser Ser Glu Asp
    210                 215                 220

Val Ala Glu Phe Tyr His Arg Gln Leu Lys Leu Thr Gln Gln Tyr Thr
225                 230                 235                 240

Asp His Cys Val Asn Trp Tyr Asn Val Gly Leu Asn Gly Leu Arg Gly
                245                 250                 255

Ser Thr Tyr Asp Ala Trp Val Lys Phe Asn Arg Phe Arg Arg Glu Met
            260                 265                 270

Thr Leu Thr Val Leu Asp Leu Ile Val Leu Phe Pro Phe Tyr Asp Ile
        275                 280                 285

Arg Leu Tyr Ser Lys Gly Val Lys Thr Glu Leu Thr Arg Asp Ile Phe
    290                 295                 300

Thr Asp Pro Ile Phe Ser Leu Asn Thr Leu Gln Glu Tyr Gly Pro Thr
305                 310                 315                 320

Phe Leu Ser Ile Glu Asn Ser Ile Arg Lys Pro His Leu Phe Asp Tyr
                325                 330                 335
```

-continued

```
Leu Gln Gly Ile Glu Phe His Thr Arg Leu Gln Pro Gly Tyr Phe Gly
            340                 345                 350

Lys Asp Ser Phe Asn Tyr Trp Ser Gly Asn Tyr Val Glu Thr Arg Pro
        355                 360                 365

Ser Ile Gly Ser Ser Lys Thr Ile Thr Ser Pro Phe Tyr Gly Asp Lys
    370                 375                 380

Ser Thr Glu Pro Val Gln Lys Leu Ser Phe Asp Gly Gln Lys Val Tyr
385                 390                 395                 400

Arg Thr Ile Ala Asn Thr Asp Val Ala Ala Trp Pro Asn Gly Lys Val
                405                 410                 415

Tyr Leu Gly Val Thr Lys Val Asp Phe Ser Gln Tyr Asp Gln Lys
                420                 425                 430

Asn Glu Thr Ser Thr Gln Thr Tyr Asp Ser Lys Arg Asn Asn Gly His
            435                 440                 445

Val Ser Ala Gln Asp Ser Ile Asp Gln Leu Pro Pro Glu Thr Thr Asp
    450                 455                 460

Glu Pro Leu Glu Lys Ala Tyr Ser His Gln Leu Asn Tyr Ala Glu Cys
465                 470                 475                 480

Phe Leu Met Gln Asp Arg Arg Gly Thr Ile Pro Phe Phe Thr Trp Thr
                485                 490                 495

His Arg Ser Val Asp Phe Phe Asn Thr Ile Asp Ala Glu Lys Ile Thr
            500                 505                 510

Gln Leu Pro Val Val Lys Ala Tyr Ala Leu Ser Ser Gly Ala Ser Ile
        515                 520                 525

Ile Glu Gly Pro Gly Phe Thr Gly Gly Asn Leu Leu Phe Leu Lys Glu
    530                 535                 540

Ser Ser Asn Ser Ile Ala Lys Phe Lys Val Thr Leu Asn Ser Ala Ala
545                 550                 555                 560

Leu Leu Gln Arg Tyr Arg Val Arg Ile Arg Tyr Ala Ser Thr Thr Asn
                565                 570                 575

Leu Arg Leu Phe Val Gln Asn Ser Asn Asn Asp Phe Leu Val Ile Tyr
            580                 585                 590

Ile Asn Lys Thr Met Asn Lys Asp Asp Asp Leu Thr Tyr Gln Thr Phe
        595                 600                 605

Asp Leu Ala Thr Thr Asn Ser Asn Met Gly Phe Ser Gly Asp Lys Asn
    610                 615                 620

Glu Leu Ile Ile Gly Ala Glu Ser Phe Val Ser Asn Glu Lys Ile Tyr
625                 630                 635                 640

Ile Asp Lys Ile Glu Phe Ile Pro Val Gln Leu
                645                 650
```

(2) INFORMATION FOR SEQ ID NO:53:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:53:

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
 1               5                  10                  15
```

```
AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT       528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC GGA TTC GAA GTG       576
His Phe Arg Asn Ser Met Pro Ser Phe Ala Val Ser Gly Phe Glu Val
            180                 185                 190

CTG TTT CTA CCA ACA TAT GCA CAA GCT GCA AAT ACA CAT TTA TTG CTA       624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA       672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC       720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA       768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA       816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT       864
Met Thr Leu Thr Val Leu Asp Leu Ile Val Leu Phe Pro Phe Tyr Asp
        275                 280                 285

ATT CGG TTA TAC TCA AAA GGG GTT AAA ACA GAA CTA ACA AGA GAC ATT       912
Ile Arg Leu Tyr Ser Lys Gly Val Lys Thr Glu Leu Thr Arg Asp Ile
    290                 295                 300

TTT ACG GAT CCA ATT TTT TCA CTT AAT ACT CTT CAG GAG TAT GGA CCA       960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT      1008
Thr Phe Leu Ser Ile Glu Asn Ser Ile Arg Lys Pro His Leu Phe Asp
```

```
                 325                 330                 335
TAT TTA CAG GGG ATT GAA TTT CAT ACG CGT CTT CAA CCT GGT TAC TTT      1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA      1104
Gly Lys Asp Ser Phe Asn Tyr Trp Ser Gly Asn Tyr Val Glu Thr Arg
            355                 360                 365

CCT AGT ATA GGA TCT AGT AAG ACA ATT ACT TCC CCA TTT TAT GGA GAT      1152
Pro Ser Ile Gly Ser Ser Lys Thr Ile Thr Ser Pro Phe Tyr Gly Asp
        370                 375                 380

AAA TCT ACT GAA CCT GTA CAA AAG CTA AGC TTT GAT GGA CAA AAA GTT      1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG      1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA      1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC      1344
Lys Asn Glu Thr Ser Thr Gln Thr Tyr Asp Ser Lys Arg Asn Asn Gly
            435                 440                 445

CAT GTA AGT GCA CAG GAT TCT ATT GAC CAA TTA CCG CCA GAA ACA ACA      1392
His Val Ser Ala Gln Asp Ser Ile Asp Gln Leu Pro Pro Glu Thr Thr
        450                 455                 460

GAT GAA CCA CTT GAA AAA GCA TAT AGT CAT CAG CTT AAT TAC GCG GAA      1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG      1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT      1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC      1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA      1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA      1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT      1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC      1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA      1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG      1872
Phe Asp Leu Ala Thr Thr Asn Ser Asn Met Gly Phe Ser Gly Asp Lys
        610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
```

-continued

```
Tyr Ile Asp Lys Ile Glu Phe Ile Pro Val Gln Leu
                645                 650
```

(2) INFORMATION FOR SEQ ID NO:54:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:54:

```
Met Asn Pro Asn Asn Arg Ser Glu His Asp Thr Ile Lys Val Thr Pro
  1               5                  10                  15

Asn Ser Glu Leu Gln Thr Asn His Asn Gln Tyr Pro Leu Ala Asp Asn
             20                  25                  30

Pro Asn Ser Thr Leu Glu Glu Leu Asn Tyr Lys Glu Phe Leu Arg Met
         35                  40                  45

Thr Glu Asp Ser Ser Thr Glu Val Leu Asp Asn Ser Thr Val Lys Asp
     50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Gly Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
```

```
                    340              345               350
Gly Lys Asp Ser Phe Asn Tyr Trp Ser Gly Asn Tyr Val Glu Thr Arg
                355              360              365

Pro Ser Ile Gly Ser Ser Lys Thr Ile Thr Ser Pro Phe Tyr Gly Asp
    370              375              380

Lys Ser Thr Glu Pro Val Gln Lys Leu Ser Phe Asp Gly Gln Lys Val
385              390              395              400

Tyr Arg Thr Ile Ala Asn Thr Asp Val Ala Ala Trp Pro Asn Gly Lys
                405              410              415

Val Tyr Leu Gly Val Thr Lys Val Asp Phe Ser Gln Tyr Asp Asp Gln
            420              425              430

Lys Asn Glu Thr Ser Thr Gln Thr Tyr Asp Ser Lys Arg Asn Asn Gly
        435              440              445

His Val Ser Ala Gln Asp Ser Ile Asp Gln Leu Pro Pro Glu Thr Thr
    450              455              460

Asp Glu Pro Leu Glu Lys Ala Tyr Ser His Gln Leu Asn Tyr Ala Glu
465              470              475              480

Cys Phe Leu Met Gln Asp Arg Arg Gly Thr Ile Pro Phe Phe Thr Trp
                485              490              495

Thr His Arg Ser Val Asp Phe Phe Asn Thr Ile Asp Ala Glu Lys Ile
            500              505              510

Thr Gln Leu Pro Val Val Lys Ala Tyr Ala Leu Ser Ser Gly Ala Ser
        515              520              525

Ile Ile Glu Gly Pro Gly Phe Thr Gly Gly Asn Leu Leu Phe Leu Lys
    530              535              540

Glu Ser Ser Asn Ser Ile Ala Lys Phe Lys Val Thr Leu Asn Ser Ala
545              550              555              560

Ala Leu Leu Gln Arg Tyr Arg Val Arg Ile Arg Tyr Ala Ser Thr Thr
                565              570              575

Asn Leu Arg Leu Phe Val Gln Asn Ser Asn Asn Asp Phe Leu Val Ile
            580              585              590

Tyr Ile Asn Lys Thr Met Asn Lys Asp Asp Asp Leu Thr Tyr Gln Thr
        595              600              605

Phe Asp Leu Ala Thr Thr Asn Ser Asn Met Gly Phe Ser Gly Asp Lys
    610              615              620

Asn Glu Leu Ile Ile Gly Ala Glu Ser Phe Val Ser Asn Glu Lys Ile
625              630              635              640

Tyr Ile Asp Lys Ile Glu Phe Ile Pro Val Gln Leu
                645              650

(2) INFORMATION FOR SEQ ID NO:55:

(i) SEQUENCE CHARACTERISTICS:
        (A) LENGTH: 1956 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1953

(xi) SEQUENCE DESCRIPTION: SEQ ID NO:55:

ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT      96
```

-continued

```
                Asn Ser Glu Leu Gln Thr Asn His Asn Gln Tyr Pro Leu Ala Asp Asn
                            20                  25                  30
CCA AAT TCA ACA CTA GAA GAA TTA AAT TAT AAA GAA TTT TTA AGA ATG             144
Pro Asn Ser Thr Leu Glu Glu Leu Asn Tyr Lys Glu Phe Leu Arg Met
             35                  40                  45
ACT GAA GAC AGT TCT ACG GAA GTG CTA GAC AAC TCT ACA GTA AAA GAT             192
Thr Glu Asp Ser Ser Thr Glu Val Leu Asp Asn Ser Thr Val Lys Asp
 50                  55                  60
GCA GTT GGG ACA GGA ATT TCT GTT GTA GGG CAG ATT TTA GGT GTT GTA             240
Ala Val Gly Thr Gly Ile Ser Val Val Gly Gln Ile Leu Gly Val Val
 65                  70                  75                  80
GGA GTT CCA TTT GCT GGG GCA CTC ACT TCA TTT TAT CAA TCA TTT CTT             288
Gly Val Pro Phe Ala Gly Ala Leu Thr Ser Phe Tyr Gln Ser Phe Leu
                 85                  90                  95
AAC ACT ATA TGG CCA AGT GAA GAC CCA TGG AAG GCT TTT ATG GCA CAA             336
Asn Thr Ile Trp Pro Ser Glu Asp Pro Trp Lys Ala Phe Met Ala Gln
                100                 105                 110
GTT GAA GTA CTG ATA GAT AAG AAA ATA GAG GAG TAT GCT AAA AGT AAA             384
Val Glu Val Leu Ile Asp Lys Lys Ile Glu Glu Tyr Ala Lys Ser Lys
            115                 120                 125
GCT CTT GCA GAG TTA CAG GGT CTT CAA AAT AAT TTC GAA GAT TAT GTT             432
Ala Leu Ala Glu Leu Gln Gly Leu Gln Asn Asn Phe Glu Asp Tyr Val
130                 135                 140
AAT GCG TTA AAT TCC TGG AAG AAA ACA CCT TTA AGT TTG CGA AAT CCA             480
Asn Ala Leu Asn Ser Trp Lys Lys Thr Pro Leu Ser Leu Arg Asn Pro
145                 150                 155                 160
CAC AGC CAA GGT CGA ATA AGG GAA CTT TTT TCT CAA GCA GAA AGT CAT             528
His Ser Gln Gly Arg Ile Arg Glu Leu Phe Ser Gln Ala Glu Ser His
                165                 170                 175
TTT CGT AAT TCC ATG CCG TCA TTT GCA GTT TCC AAA TTC GAA GTG CTG             576
Phe Arg Asn Ser Met Pro Ser Phe Ala Val Ser Lys Phe Glu Val Leu
            180                 185                 190
TTT CTA CCA ACA TAT GCA CAA GCT GCA AAT ACA CAT TTA TTG CTA TTA             624
Phe Leu Pro Thr Tyr Ala Gln Ala Ala Asn Thr His Leu Leu Leu Leu
            195                 200                 205
AAA GAT GCT CAA GTT TTT GGA GAA GAA TGG GGA TAT TCT TCA GAA GAT             672
Lys Asp Ala Gln Val Phe Gly Glu Glu Trp Gly Tyr Ser Ser Glu Asp
210                 215                 220
GTT GCT GAA TTT TAT CAT AGA CAA TTA AAA CTT ACA CAA CAA TAC ACT             720
Val Ala Glu Phe Tyr His Arg Gln Leu Lys Leu Thr Gln Gln Tyr Thr
225                 230                 235                 240
GAC CAT TGT GTT AAT TGG TAT AAT GTT GGA TTA AAT GGT TTA AGA GGT             768
Asp His Cys Val Asn Trp Tyr Asn Val Gly Leu Asn Gly Leu Arg Gly
                245                 250                 255
TCA ACT TAT GAT GCA TGG GTC AAA TTT AAC CGT TTT CGC AGA GAA ATG             816
Ser Thr Tyr Asp Ala Trp Val Lys Phe Asn Arg Phe Arg Arg Glu Met
            260                 265                 270
ACT TTA ACT GTA TTA GAT CTA ATT GTA CTT TTC CCA TTT TAT GAT ATT             864
Thr Leu Thr Val Leu Asp Leu Ile Val Leu Phe Pro Phe Tyr Asp Ile
            275                 280                 285
CGG TTA TAC TCA AAA GGG GTT AAA ACA GAA CTA ACA AGA GAC ATT TTT             912
Arg Leu Tyr Ser Lys Gly Val Lys Thr Glu Leu Thr Arg Asp Ile Phe
        290                 295                 300
ACG GAT CCA ATT TTT TCA CTT AAT ACT CTT CAG GAG TAT GGA CCA ACT             960
Thr Asp Pro Ile Phe Ser Leu Asn Thr Leu Gln Glu Tyr Gly Pro Thr
305                 310                 315                 320
TTT TTG AGT ATA GAA AAC TCT ATT CGA AAA CCT CAT TTA TTT GAT TAT            1008
Phe Leu Ser Ile Glu Asn Ser Ile Arg Lys Pro His Leu Phe Asp Tyr
            325                 330                 335
```

```
TTA CAG GGG ATT GAA TTT CAT ACG CGT CTT CAA CCT GGT TAC TTT GGG          1056
Leu Gln Gly Ile Glu Phe His Thr Arg Leu Gln Pro Gly Tyr Phe Gly
        340                 345                 350

AAA GAT TCT TTC AAT TAT TGG TCT GGT AAT TAT GTA GAA ACT AGA CCT          1104
Lys Asp Ser Phe Asn Tyr Trp Ser Gly Asn Tyr Val Glu Thr Arg Pro
            355                 360                 365

AGT ATA GGA TCT AGT AAG ACA ATT ACT TCC CCA TTT TAT GGA GAT AAA          1152
Ser Ile Gly Ser Ser Lys Thr Ile Thr Ser Pro Phe Tyr Gly Asp Lys
    370                 375                 380

TCT ACT GAA CCT GTA CAA AAG CTA AGC TTT GAT GGA CAA AAA GTT TAT          1200
Ser Thr Glu Pro Val Gln Lys Leu Ser Phe Asp Gly Gln Lys Val Tyr
385                 390                 395                 400

CGA ACT ATA GCT AAT ACA GAC GTA GCG GCT TGG CCG AAT GGT AAG GTA          1248
Arg Thr Ile Ala Asn Thr Asp Val Ala Ala Trp Pro Asn Gly Lys Val
                405                 410                 415

TAT TTA GGT GTT ACG AAA GTT GAT TTT AGT CAA TAT GAT GAT CAA AAA          1296
Tyr Leu Gly Val Thr Lys Val Asp Phe Ser Gln Tyr Asp Asp Gln Lys
        420                 425                 430

AAT GAA ACT AGT ACA CAA ACA TAT GAT TCA AAA AGA AAC AAT GGC CAT          1344
Asn Glu Thr Ser Thr Gln Thr Tyr Asp Ser Lys Arg Asn Asn Gly His
            435                 440                 445

GTA AGT GCA CAG GAT TCT ATT GAC CAA TTA CCG CCA GAA ACA ACA GAT          1392
Val Ser Ala Gln Asp Ser Ile Asp Gln Leu Pro Pro Glu Thr Thr Asp
    450                 455                 460

GAA CCA CTT GAA AAA GCA TAT AGT CAT CAG CTT AAT TAC GCG GAA TGT          1440
Glu Pro Leu Glu Lys Ala Tyr Ser His Gln Leu Asn Tyr Ala Glu Cys
465                 470                 475                 480

TTC TTA ATG CAG GAC CGT CGT GGA ACA ATT CCA TTT TTT ACT TGG ACA          1488
Phe Leu Met Gln Asp Arg Arg Gly Thr Ile Pro Phe Phe Thr Trp Thr
                485                 490                 495

CAT AGA AGT GTA GAC TTT TTT AAT ACA ATT GAT GCT GAA AAG ATT ACT          1536
His Arg Ser Val Asp Phe Phe Asn Thr Ile Asp Ala Glu Lys Ile Thr
        500                 505                 510

CAA CTT CCA GTA GTG AAA GCA TAT GCC TTG TCT TCA GGT GCT TCC ATT          1584
Gln Leu Pro Val Val Lys Ala Tyr Ala Leu Ser Ser Gly Ala Ser Ile
            515                 520                 525

ATT GAA GGT CCA GGA TTC ACA GGA GGA AAT TTA CTA TTC CTA AAA GAA          1632
Ile Glu Gly Pro Gly Phe Thr Gly Gly Asn Leu Leu Phe Leu Lys Glu
    530                 535                 540

TCT AGT AAT TCA ATT GCT AAA TTT AAA GTT ACA TTA AAT TCA GCA GCC          1680
Ser Ser Asn Ser Ile Ala Lys Phe Lys Val Thr Leu Asn Ser Ala Ala
545                 550                 555                 560

TTG TTA CAA CGA TAT CGT GTA AGA ATA CGC TAT GCT TCT ACC ACT AAC          1728
Leu Leu Gln Arg Tyr Arg Val Arg Ile Arg Tyr Ala Ser Thr Thr Asn
                565                 570                 575

TTA CGA CTT TTT GTG CAA AAT TCA AAC AAT GAT TTT CTT GTC ATC TAC          1776
Leu Arg Leu Phe Val Gln Asn Ser Asn Asn Asp Phe Leu Val Ile Tyr
        580                 585                 590

ATT AAT AAA ACT ATG AAT AAA GAT GAT GAT TTA ACA TAT CAA ACA TTT          1824
Ile Asn Lys Thr Met Asn Lys Asp Asp Asp Leu Thr Tyr Gln Thr Phe
            595                 600                 605

GAT CTC GCA ACT ACT AAT TCT AAT ATG GGG TTC TCG GGT GAT AAG AAT          1872
Asp Leu Ala Thr Thr Asn Ser Asn Met Gly Phe Ser Gly Asp Lys Asn
    610                 615                 620

GAA CTT ATA ATA GGA GCA GAA TCT TTC GTT TCT AAT GAA AAA ATC TAT          1920
Glu Leu Ile Ile Gly Ala Glu Ser Phe Val Ser Asn Glu Lys Ile Tyr
625                 630                 635                 640

ATA GAT AAG ATA GAA TTT ATC CCA GTA CAA TTG TAA                          1956
Ile Asp Lys Ile Glu Phe Ile Pro Val Gln Leu
                645                 650
```

(2) INFORMATION FOR SEQ ID NO:56:

(i) SEQUENCE CHARACTERISTICS:
        (A) LENGTH: 651 amino acids
        (B) TYPE: amino acid
        (D) TOPOLOGY: linear (ii) MOLECULE TYPE: protein (xi) SEQUENCE DESCRIPTION: SEQ ID NO:56:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
 50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                85                  90                  95

Asn Thr Ile Trp Pro Ser Glu Asp Pro Trp Lys Ala Phe Met Ala Gln
            100                 105                 110

Val Glu Val Leu Ile Asp Lys Lys Ile Glu Glu Tyr Ala Lys Ser Lys
        115                 120                 125

Ala Leu Ala Glu Leu Gln Gly Leu Gln Asn Asn Phe Glu Asp Tyr Val
130                 135                 140

Asn Ala Leu Asn Ser Trp Lys Lys Thr Pro Leu Ser Leu Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Val Ser Lys Phe Glu Val Leu
            180                 185                 190

Phe Leu Pro Thr Tyr Ala Gln Ala Ala Asn Thr His Leu Leu Leu Leu
        195                 200                 205

Lys Asp Ala Gln Val Phe Gly Glu Glu Trp Gly Tyr Ser Ser Glu Asp
210                 215                 220

Val Ala Glu Phe Tyr His Arg Gln Leu Lys Leu Thr Gln Gln Tyr Thr
225                 230                 235                 240

Asp His Cys Val Asn Trp Tyr Asn Val Gly Leu Asn Gly Leu Arg Gly
                245                 250                 255

Ser Thr Tyr Asp Ala Trp Val Lys Phe Asn Arg Phe Arg Arg Glu Met
            260                 265                 270

Thr Leu Thr Val Leu Asp Leu Ile Val Leu Phe Pro Phe Tyr Asp Ile
        275                 280                 285

Arg Leu Tyr Ser Lys Gly Val Lys Thr Glu Leu Thr Arg Asp Ile Phe
        290                 295                 300

Thr Asp Pro Ile Phe Ser Leu Asn Thr Leu Gln Glu Tyr Gly Pro Thr
305                 310                 315                 320

Phe Leu Ser Ile Glu Asn Ser Ile Arg Lys Pro His Leu Phe Asp Tyr
                325                 330                 335

Leu Gln Gly Ile Glu Phe His Thr Arg Leu Gln Pro Gly Tyr Phe Gly
            340                 345                 350
```

```
Lys Asp Ser Phe Asn Tyr Trp Ser Gly Asn Tyr Val Glu Thr Arg Pro
        355                 360                 365

Ser Ile Gly Ser Ser Lys Thr Ile Thr Ser Pro Phe Tyr Gly Asp Lys
    370                 375                 380

Ser Thr Glu Pro Val Gln Lys Leu Ser Phe Asp Gly Gln Lys Val Tyr
385                 390                 395                 400

Arg Thr Ile Ala Asn Thr Asp Val Ala Ala Trp Pro Asn Gly Lys Val
                405                 410                 415

Tyr Leu Gly Val Thr Lys Val Asp Phe Ser Gln Tyr Asp Asp Gln Lys
            420                 425                 430

Asn Glu Thr Ser Thr Gln Thr Tyr Asp Ser Lys Arg Asn Asn Gly His
        435                 440                 445

Val Ser Ala Gln Asp Ser Ile Asp Gln Leu Pro Pro Glu Thr Thr Asp
    450                 455                 460

Glu Pro Leu Glu Lys Ala Tyr Ser His Gln Leu Asn Tyr Ala Glu Cys
465                 470                 475                 480

Phe Leu Met Gln Asp Arg Arg Gly Thr Ile Pro Phe Phe Thr Trp Thr
                485                 490                 495

His Arg Ser Val Asp Phe Phe Asn Thr Ile Asp Ala Glu Lys Ile Thr
            500                 505                 510

Gln Leu Pro Val Val Lys Ala Tyr Ala Leu Ser Ser Gly Ala Ser Ile
        515                 520                 525

Ile Glu Gly Pro Gly Phe Thr Gly Gly Asn Leu Leu Phe Leu Lys Glu
    530                 535                 540

Ser Ser Asn Ser Ile Ala Lys Phe Lys Val Thr Leu Asn Ser Ala Ala
545                 550                 555                 560

Leu Leu Gln Arg Tyr Arg Val Arg Ile Arg Tyr Ala Ser Thr Thr Asn
                565                 570                 575

Leu Arg Leu Phe Val Gln Asn Ser Asn Asn Asp Phe Leu Val Ile Tyr
            580                 585                 590

Ile Asn Lys Thr Met Asn Lys Asp Asp Asp Leu Thr Tyr Gln Thr Phe
        595                 600                 605

Asp Leu Ala Thr Thr Asn Ser Asn Met Gly Phe Ser Gly Asp Lys Asn
    610                 615                 620

Glu Leu Ile Ile Gly Ala Glu Ser Phe Val Ser Asn Glu Lys Ile Tyr
625                 630                 635                 640

Ile Asp Lys Ile Glu Phe Ile Pro Val Gln Leu
                645                 650
```

(2) INFORMATION FOR SEQ ID NO:57:

(i) SEQUENCE CHARACTERISTICS:
        (A) LENGTH: 1956 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1953

(xi) SEQUENCE DESCRIPTION: SEQ ID NO:57:

```
ATG AAT CCA AAC AAT CGA AGT GAA CAT GAT ACG ATA AAG GTT ACA CCT       48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT       96
Asn Ser Glu Leu Gln Thr Asn His Asn Gln Tyr Pro Leu Ala Asp Asn
            20                  25                  30
```

```
CCA AAT TCA ACA CTA GAA GAA TTA AAT TAT AAA GAA TTT TTA AGA ATG      144
Pro Asn Ser Thr Leu Glu Glu Leu Asn Tyr Lys Glu Phe Leu Arg Met
         35                  40                  45

ACT GAA GAC AGT TCT ACG GAA GTG CTA GAC AAC TCT ACA GTA AAA GAT      192
Thr Glu Asp Ser Ser Thr Glu Val Leu Asp Asn Ser Thr Val Lys Asp
 50                  55                  60

GCA GTT GGG ACA GGA ATT TCT GTT GTA GGG CAG ATT TTA GGT GTT GTA      240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT      288
Gly Val Pro Phe Ala Gly Ala Leu Thr Ser Phe Tyr Gln Ser Phe Leu
                 85                  90                  95

AAC ACT ATA TGG CCA AGT GAA GAC CCA TGG AAG GCT TTT ATG GCA CAA      336
Asn Thr Ile Trp Pro Ser Glu Asp Pro Trp Lys Ala Phe Met Ala Gln
             100                 105                 110

GTT GAA GTA CTG ATA GAT AAG AAA ATA GAG GAG TAT GCT AAA AGT AAA      384
Val Glu Val Leu Ile Asp Lys Lys Ile Glu Glu Tyr Ala Lys Ser Lys
             115                 120                 125

GCT CTT GCA GAG TTA CAG GGT CTT CAA AAT AAT TTC GAA GAT TAT GTT      432
Ala Leu Ala Glu Leu Gln Gly Leu Gln Asn Asn Phe Glu Asp Tyr Val
130                 135                 140

AAT GCG TTA AAT TCC TGG AAG AAA TTT CAC CAT TCT CGT CGT TCT AAA      480
Asn Ala Leu Asn Ser Trp Lys Lys Phe His His Ser Arg Arg Ser Lys
145                 150                 155                 160

AGA AGC CAA GAT CGA ATA AGG GAA CTT TTT TCT CAA GCA GAA AGT CAT      528
Arg Ser Gln Asp Arg Ile Arg Glu Leu Phe Ser Gln Ala Glu Ser His
                165                 170                 175

TTT CGT AAT TCC ATG CCG TCA TTT GCA GTT TCC AAA TTC GAA GTG CTG      576
Phe Arg Asn Ser Met Pro Ser Phe Ala Val Ser Lys Phe Glu Val Leu
                180                 185                 190

TTT CTA CCA ACA TAT GCA CAA GCT GCA AAT ACA CAT TTA TTG CTA TTA      624
Phe Leu Pro Thr Tyr Ala Gln Ala Ala Asn Thr His Leu Leu Leu Leu
            195                 200                 205

AAA GAT GCT CAA GTT TTT GGA GAA GAA TGG GGA TAT TCT TCA GAA GAT      672
Lys Asp Ala Gln Val Phe Gly Glu Glu Trp Gly Tyr Ser Ser Glu Asp
            210                 215                 220

GTT GCT GAA TTT TAT CAT AGA CAA TTA AAA CTT ACA CAA CAA TAC ACT      720
Val Ala Glu Phe Tyr His Arg Gln Leu Lys Leu Thr Gln Gln Tyr Thr
225                 230                 235                 240

GAC CAT TGT GTT AAT TGG TAT AAT GTT GGA TTA AAT GGT TTA AGA GGT      768
Asp His Cys Val Asn Trp Tyr Asn Val Gly Leu Asn Gly Leu Arg Gly
                245                 250                 255

TCA ACT TAT GAT GCA TGG GTC AAA TTT AAC CGT TTT CGC AGA GAA ATG      816
Ser Thr Tyr Asp Ala Trp Val Lys Phe Asn Arg Phe Arg Arg Glu Met
                260                 265                 270

ACT TTA ACT GTA TTA GAT CTA ATT GTA CTT TTC CCA TTT TAT GAT ATT      864
Thr Leu Thr Val Leu Asp Leu Ile Val Leu Phe Pro Phe Tyr Asp Ile
            275                 280                 285

CGG TTA TAC TCA AAA GGG GTT AAA ACA GAA CTA ACA AGA GAC ATT TTT      912
Arg Leu Tyr Ser Lys Gly Val Lys Thr Glu Leu Thr Arg Asp Ile Phe
            290                 295                 300

ACG GAT CCA ATT TTT TCA CTT AAT ACT CTT CAG GAG TAT GGA CCA ACT      960
Thr Asp Pro Ile Phe Ser Leu Asn Thr Leu Gln Glu Tyr Gly Pro Thr
305                 310                 315                 320

TTT TTG AGT ATA GAA AAC TCT ATT CGA AAA CCT CAT TTA TTT GAT TAT     1008
Phe Leu Ser Ile Glu Asn Ser Ile Arg Lys Pro His Leu Phe Asp Tyr
                325                 330                 335

TTA CAG GGG ATT GAA TTT CAT ACG CGT CTT CAA CCT GGT TAC TTT GGG     1056
Leu Gln Gly Ile Glu Phe His Thr Arg Leu Gln Pro Gly Tyr Phe Gly
```

```
                    340             345             350
AAA GAT TCT TTC AAT TAT TGG TCT GGT AAT TAT GTA GAA ACT AGA CCT    1104
Lys Asp Ser Phe Asn Tyr Trp Ser Gly Asn Tyr Val Glu Thr Arg Pro
        355             360             365

AGT ATA GGA TCT AGT AAG ACA ATT ACT TCC CCA TTT TAT GGA GAT AAA    1152
Ser Ile Gly Ser Ser Lys Thr Ile Thr Ser Pro Phe Tyr Gly Asp Lys
    370             375             380

TCT ACT GAA CCT GTA CAA AAG CTA AGC TTT GAT GGA CAA AAA GTT TAT    1200
Ser Thr Glu Pro Val Gln Lys Leu Ser Phe Asp Gly Gln Lys Val Tyr
385             390             395             400

CGA ACT ATA GCT AAT ACA GAC GTA GCG GCT TGG CCG AAT GGT AAG GTA    1248
Arg Thr Ile Ala Asn Thr Asp Val Ala Ala Trp Pro Asn Gly Lys Val
            405             410             415

TAT TTA GGT GTT ACG AAA GTT GAT TTT AGT CAA TAT GAT GAT CAA AAA    1296
Tyr Leu Gly Val Thr Lys Val Asp Phe Ser Gln Tyr Asp Asp Gln Lys
        420             425             430

AAT GAA ACT AGT ACA CAA ACA TAT GAT TCA AAA AGA AAC AAT GGC CAT    1344
Asn Glu Thr Ser Thr Gln Thr Tyr Asp Ser Lys Arg Asn Asn Gly His
    435             440             445

GTA AGT GCA CAG GAT TCT ATT GAC CAA TTA CCG CCA GAA ACA ACA GAT    1392
Val Ser Ala Gln Asp Ser Ile Asp Gln Leu Pro Pro Glu Thr Thr Asp
450             455             460

GAA CCA CTT GAA AAA GCA TAT AGT CAT CAG CTT AAT TAC GCG GAA TGT    1440
Glu Pro Leu Glu Lys Ala Tyr Ser His Gln Leu Asn Tyr Ala Glu Cys
465             470             475             480

TTC TTA ATG CAG GAC CGT CGT GGA ACA ATT CCA TTT TTT ACT TGG ACA    1488
Phe Leu Met Gln Asp Arg Arg Gly Thr Ile Pro Phe Phe Thr Trp Thr
            485             490             495

CAT AGA AGT GTA GAC TTT TTT AAT ACA ATT GAT GCT GAA AAG ATT ACT    1536
His Arg Ser Val Asp Phe Phe Asn Thr Ile Asp Ala Glu Lys Ile Thr
        500             505             510

CAA CTT CCA GTA GTG AAA GCA TAT GCC TTG TCT TCA GGT GCT TCC ATT    1584
Gln Leu Pro Val Val Lys Ala Tyr Ala Leu Ser Ser Gly Ala Ser Ile
    515             520             525

ATT GAA GGT CCA GGA TTC ACA GGA GGA AAT TTA CTA TTC CTA AAA GAA    1632
Ile Glu Gly Pro Gly Phe Thr Gly Gly Asn Leu Leu Phe Leu Lys Glu
530             535             540

TCT AGT AAT TCA ATT GCT AAA TTT AAA GTT ACA TTA AAT TCA GCA GCC    1680
Ser Ser Asn Ser Ile Ala Lys Phe Lys Val Thr Leu Asn Ser Ala Ala
545             550             555             560

TTG TTA CAA CGA TAT CGT GTA AGA ATA CGC TAT GCT TCT ACC ACT AAC    1728
Leu Leu Gln Arg Tyr Arg Val Arg Ile Arg Tyr Ala Ser Thr Thr Asn
            565             570             575

TTA CGA CTT TTT GTG CAA AAT TCA AAC AAT GAT TTT CTT GTC ATC TAC    1776
Leu Arg Leu Phe Val Gln Asn Ser Asn Asn Asp Phe Leu Val Ile Tyr
        580             585             590

ATT AAT AAA ACT ATG AAT AAA GAT GAT GAT TTA ACA TAT CAA ACA TTT    1824
Ile Asn Lys Thr Met Asn Lys Asp Asp Asp Leu Thr Tyr Gln Thr Phe
    595             600             605

GAT CTC GCA ACT ACT AAT TCT AAT ATG GGG TTC TCG GGT GAT AAG AAT    1872
Asp Leu Ala Thr Thr Asn Ser Asn Met Gly Phe Ser Gly Asp Lys Asn
610             615             620

GAA CTT ATA ATA GGA GCA GAA TCT TTC GTT TCT AAT GAA AAA ATC TAT    1920
Glu Leu Ile Ile Gly Ala Glu Ser Phe Val Ser Asn Glu Lys Ile Tyr
625             630             635             640

ATA GAT AAG ATA GAA TTT ATC CCA GTA CAA TTG TAA                    1956
Ile Asp Lys Ile Glu Phe Ile Pro Val Gln Leu
            645             650
```

-continued (2) INFORMATION FOR SEQ ID NO:58:

(i) SEQUENCE CHARACTERISTICS:
        (A) LENGTH: 651 amino acids
        (B) TYPE: amino acid
        (D) TOPOLOGY: linear (ii) MOLECULE TYPE: protein (xi) SEQUENCE DESCRIPTION: SEQ ID NO:58:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
             20                  25                  30

Pro Asn Ser Thr Leu Glu Glu Leu Asn Tyr Lys Glu Phe Leu Arg Met
         35                  40                  45

Thr Glu Asp Ser Ser Thr Glu Val Leu Asp Asn Ser Thr Val Lys Asp
 50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Glu Asp Pro Trp Lys Ala Phe Met Ala Gln
            100                 105                 110

Val Glu Val Leu Ile Asp Lys Lys Ile Glu Glu Tyr Ala Lys Ser Lys
        115                 120                 125

Ala Leu Ala Glu Leu Gln Gly Leu Gln Asn Asn Phe Glu Asp Tyr Val
130                 135                 140

Asn Ala Leu Asn Ser Trp Lys Lys Phe His His Ser Arg Arg Ser Lys
145                 150                 155                 160

Arg Ser Gln Asp Arg Ile Arg Glu Leu Phe Ser Gln Ala Glu Ser His
                165                 170                 175

Phe Arg Asn Ser Met Pro Ser Phe Ala Val Ser Lys Phe Glu Val Leu
            180                 185                 190

Phe Leu Pro Thr Tyr Ala Gln Ala Ala Asn Thr His Leu Leu Leu Leu
        195                 200                 205

Lys Asp Ala Gln Val Phe Gly Glu Glu Trp Gly Tyr Ser Ser Glu Asp
210                 215                 220

Val Ala Glu Phe Tyr His Arg Gln Leu Lys Leu Thr Gln Gln Tyr Thr
225                 230                 235                 240

Asp His Cys Val Asn Trp Tyr Asn Val Gly Leu Asn Gly Leu Arg Gly
                245                 250                 255

Ser Thr Tyr Asp Ala Trp Val Lys Phe Asn Arg Phe Arg Arg Glu Met
            260                 265                 270

Thr Leu Thr Val Leu Asp Leu Ile Val Leu Phe Pro Phe Tyr Asp Ile
        275                 280                 285

Arg Leu Tyr Ser Lys Gly Val Lys Thr Glu Leu Thr Arg Asp Ile Phe
290                 295                 300

Thr Asp Pro Ile Phe Ser Leu Asn Thr Leu Gln Glu Tyr Gly Pro Thr
305                 310                 315                 320

Phe Leu Ser Ile Glu Asn Ser Ile Arg Lys Pro His Leu Phe Asp Tyr
                325                 330                 335

Leu Gln Gly Ile Glu Phe His Thr Arg Leu Gln Pro Gly Tyr Phe Gly
            340                 345                 350

Lys Asp Ser Phe Asn Tyr Trp Ser Gly Asn Tyr Val Glu Thr Arg Pro
        355                 360                 365
```

-continued

```
Ser Ile Gly Ser Ser Lys Thr Ile Thr Ser Pro Phe Tyr Gly Asp Lys
    370                 375                 380

Ser Thr Glu Pro Val Gln Lys Leu Ser Phe Asp Gly Gln Lys Val Tyr
385                 390                 395                 400

Arg Thr Ile Ala Asn Thr Asp Val Ala Ala Trp Pro Asn Gly Lys Val
                405                 410                 415

Tyr Leu Gly Val Thr Lys Val Asp Phe Ser Gln Tyr Asp Asp Gln Lys
                420                 425                 430

Asn Glu Thr Ser Thr Gln Thr Tyr Asp Ser Lys Arg Asn Asn Gly His
            435                 440                 445

Val Ser Ala Gln Asp Ser Ile Asp Gln Leu Pro Pro Glu Thr Thr Asp
450                 455                 460

Glu Pro Leu Glu Lys Ala Tyr Ser His Gln Leu Asn Tyr Ala Glu Cys
465                 470                 475                 480

Phe Leu Met Gln Asp Arg Arg Gly Thr Ile Pro Phe Phe Thr Trp Thr
                485                 490                 495

His Arg Ser Val Asp Phe Phe Asn Thr Ile Asp Ala Glu Lys Ile Thr
                500                 505                 510

Gln Leu Pro Val Val Lys Ala Tyr Ala Leu Ser Ser Gly Ala Ser Ile
            515                 520                 525

Ile Glu Gly Pro Gly Phe Thr Gly Gly Asn Leu Leu Phe Leu Lys Glu
530                 535                 540

Ser Ser Asn Ser Ile Ala Lys Phe Lys Val Thr Leu Asn Ser Ala Ala
545                 550                 555                 560

Leu Leu Gln Arg Tyr Arg Val Arg Ile Arg Tyr Ala Ser Thr Thr Asn
                565                 570                 575

Leu Arg Leu Phe Val Gln Asn Ser Asn Asn Asp Phe Leu Val Ile Tyr
                580                 585                 590

Ile Asn Lys Thr Met Asn Lys Asp Asp Leu Thr Tyr Gln Thr Phe
            595                 600                 605

Asp Leu Ala Thr Thr Asn Ser Asn Met Gly Phe Ser Gly Asp Lys Asn
    610                 615                 620

Glu Leu Ile Ile Gly Ala Glu Ser Phe Val Ser Asn Glu Lys Ile Tyr
625                 630                 635                 640

Ile Asp Lys Ile Glu Phe Ile Pro Val Gln Leu
                645                 650
```

(2) INFORMATION FOR SEQ ID NO:59:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:59:

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
  1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG     144
```

```
                Pro Asn Ser Thr Leu Glu Glu Leu Asn Tyr Lys Glu Phe Leu Arg Met
                                35                  40                  45

ACT GAA GAC AGT TCT ACG GAA GTG CTA GAC AAC TCT ACA GTA AAA GAT                 192
Thr Glu Asp Ser Ser Thr Glu Val Leu Asp Asn Ser Thr Val Lys Asp
 50                  55                  60

GCA GTT GGG ACA GGA ATT TCT GTT GTA GGG CAG ATT TTA GGT GTT GTA                 240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT                 288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA                 336
Asn Thr Ile Trp Pro Ser Asp Ala Asp Pro Trp Lys Ala Phe Met Ala
                100                 105                 110

CAA GTT GAA GTA CTG ATA GAT AAG AAA ATA GAG GAG TAT GCT AAA AGT                 384
Gln Val Glu Val Leu Ile Asp Lys Lys Ile Glu Glu Tyr Ala Lys Ser
                115                 120                 125

AAA GCT CTT GCA GAG TTA CAG GGT CTT CAA AAT AAT TTC GAA GAT TAT                 432
Lys Ala Leu Ala Glu Leu Gln Gly Leu Gln Asn Asn Phe Glu Asp Tyr
130                 135                 140

GTT AAT GCG TTA AAT TCC TGG AAG AAA ACA CCT TTA AGT TTG CGA AGT                 480
Val Asn Ala Leu Asn Ser Trp Lys Lys Thr Pro Leu Ser Leu Arg Ser
145                 150                 155                 160

AAA AGA AGC CAA GGT CGA ATA AGG GAA CTT TTT TCT CAA GCA GAA AGT                 528
Lys Arg Ser Gln Gly Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG                 576
His Phe Arg Asn Ser Met Pro Ser Phe Ala Val Ser Lys Phe Glu Val
                180                 185                 190

CTG TTT CTA CCA ACA TAT GCA CAA GCT GCA AAT ACA CAT TTA TTG CTA                 624
Leu Phe Leu Pro Thr Tyr Ala Gln Ala Ala Asn Thr His Leu Leu Leu
                195                 200                 205

TTA AAA GAT GCT CAA GTT TTT GGA GAA GAA TGG GGA TAT TCT TCA GAA                 672
Leu Lys Asp Ala Gln Val Phe Gly Glu Glu Trp Gly Tyr Ser Ser Glu
210                 215                 220

GAT GTT GCT GAA TTT TAT CAT AGA CAA TTA AAA CTT ACA CAA CAA TAC                 720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA                 768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA                 816
Gly Ser Thr Tyr Asp Ala Trp Val Lys Phe Asn Arg Phe Arg Arg Glu
                260                 265                 270

ATG ACT TTA ACT GTA TTA GAT CTA ATT GTA CTT TTC CCA TTT TAT GAT                 864
Met Thr Leu Thr Val Leu Asp Leu Ile Val Leu Phe Pro Phe Tyr Asp
                275                 280                 285

ATT CGG TTA TAC TCA AAA GGG GTT AAA ACA GAA CTA ACA AGA GAC ATT                 912
Ile Arg Leu Tyr Ser Lys Gly Val Lys Thr Glu Leu Thr Arg Asp Ile
290                 295                 300

TTT ACG GAT CCA ATT TTT ACC CTT AAT ACA CTA CAG AAG TAC GGA CCA                 960
Phe Thr Asp Pro Ile Phe Thr Leu Asn Thr Leu Gln Lys Tyr Gly Pro
305                 310                 315                 320

ACT TTT TTG AGT ATA GAA AAC TCT ATT CGA AAA CCT CAT TTA TTT GAT                1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT                1056
Tyr Leu Gln Gly Ile Glu Phe His Thr Arg Leu Gln Pro Gly Tyr Phe
                340                 345                 350
```

```
GGG AAA GAT TCT TTC AAT TAT TGG TCT GGT AAT TAT GTA GAA ACT AGA      1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT      1152
Pro Ser Ile Gly Ser Ser Lys Thr Ile Thr Ser Pro Phe Tyr Gly Asp
    370                 375                 380

AAA TCT ACT GAA CCT GTA CAA AAG CTA AGC TTT GAT GGA CAA AAA GTT      1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG      1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA      1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC      1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA      1392
His Val Ser Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCG GAA      1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG      1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT      1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCA TCA GGT GCT TCC      1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA      1632
Ile Ile Glu Gly Pro Gly Phe Thr Gly Gly Asn Leu Leu Phe Leu Lys
    530                 535                 540

GAA TCT AGT AAT TCA ATT GCT AAA TTT AAA GTT ACA TTA AAT TCA GCA      1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT      1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC      1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA      1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG      1872
Phe Asp Leu Ala Thr Thr Asn Ser Asn Met Gly Phe Ser Gly Asp Lys
    610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
Tyr Ile Asp Lys Ile Glu Phe Ile Pro Val Gln Leu
                645                 650

(2) INFORMATION FOR SEQ ID NO:60:
```

(i) SEQUENCE CHARACTERISTICS:
    (A) LENGTH: 652 amino acids
    (B) TYPE: amino acid
    (D) TOPOLOGY: linear (ii) MOLECULE TYPE: protein (xi) SEQUENCE DESCRIPTION: SEQ ID NO:60:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
             20                  25                  30

Pro Asn Ser Thr Leu Glu Glu Leu Asn Tyr Lys Glu Phe Leu Arg Met
         35                  40                  45

Thr Glu Asp Ser Ser Thr Glu Val Leu Asp Asn Ser Thr Val Lys Asp
     50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Gly Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
    290                 295                 300

Phe Thr Asp Pro Ile Phe Thr Leu Asn Thr Leu Gln Lys Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
```

```
                 370                 375                 380
Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
                435                 440                 445

His Val Ser Ala Gln Asp Ser Ile Asp Gln Leu Pro Pro Glu Thr Thr
                450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
                500                 505                 510

Thr Gln Leu Pro Val Val Lys Ala Tyr Ala Leu Ser Ser Gly Ala Ser
                515                 520                 525

Ile Ile Glu Gly Pro Gly Phe Thr Gly Gly Asn Leu Leu Phe Leu Lys
                530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
                580                 585                 590

Tyr Ile Asn Lys Thr Met Asn Lys Asp Asp Asp Leu Thr Tyr Gln Thr
                595                 600                 605

Phe Asp Leu Ala Thr Thr Asn Ser Asn Met Gly Phe Ser Gly Asp Lys
                610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:61:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:61:

ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
  1               5                  10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
             20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
         35                  40                  45
```

| | |
|---|---|
| ACT GAA GAC AGT TCT ACG GAA GTG CTA GAC AAC TCT ACA GTA AAA GAT<br>Thr Glu Asp Ser Ser Thr Glu Val Leu Asp Asn Ser Thr Val Lys Asp<br>     50                        55                       60 | 192 |
| GCA GTT GGG ACA GGA ATT TCT GTT GTA GGG CAG ATT TTA GGT GTT GTA<br>Ala Val Gly Thr Gly Ile Ser Val Val Gly Gln Ile Leu Gly Val Val<br>65                      70                      75                      80 | 240 |
| GGA GTT CCA TTT GCT GGG GCA CTC ACT TCA TTT TAT CAA TCA TTT CTT<br>Gly Val Pro Phe Ala Gly Ala Leu Thr Ser Phe Tyr Gln Ser Phe Leu<br>                       85                      90                      95 | 288 |
| AAC ACT ATA TGG CCA AGT GAT GCT GAC CCA TGG AAG GCT TTT ATG GCA<br>Asn Thr Ile Trp Pro Ser Asp Ala Asp Pro Trp Lys Ala Phe Met Ala<br>             100                     105                   110 | 336 |
| CAA GTT GAA GTA CTG ATA GAT AAG AAA ATA GAG GAG TAT GCT AAA AGT<br>Gln Val Glu Val Leu Ile Asp Lys Lys Ile Glu Glu Tyr Ala Lys Ser<br>             115                     120                   125 | 384 |
| AAA GCT CTT GCA GAG TTA CAG GGT CTT CAA AAT AAT TTC GAA GAT TAT<br>Lys Ala Leu Ala Glu Leu Gln Gly Leu Gln Asn Asn Phe Glu Asp Tyr<br>130                     135                     140 | 432 |
| GTT AAT GCG TTA AAT TCC TGG AAG AAA ACA CCT TTA AGT TTG CGA AGT<br>Val Asn Ala Leu Asn Ser Trp Lys Lys Thr Pro Leu Ser Leu Arg Ser<br>145                     150                     155                   160 | 480 |
| AAA AGA AGC CAA GGT CGA ATA AGG GAA CTT TTT TCT CAA GCA GAA AGT<br>Lys Arg Ser Gln Gly Arg Ile Arg Glu Leu Phe Ser Gln Ala Glu Ser<br>                 165                     170                   175 | 528 |
| CAT TTT CGT AAT TCC ATG CCG TCA TTT GCA GTT TCC AAA TTC GAA GTG<br>His Phe Arg Asn Ser Met Pro Ser Phe Ala Val Ser Lys Phe Glu Val<br>                     180                     185                   190 | 576 |
| CTG TTT CTA CCA ACA TAT GCA CAA GCT GCA AAT ACA CAT TTA TTG CTA<br>Leu Phe Leu Pro Thr Tyr Ala Gln Ala Ala Asn Thr His Leu Leu Leu<br>         195                     200                     205 | 624 |
| TTA AAA GAT GCT CAA GTT TTT GGA GAA GAA TGG GGA TAT TCT TCA GAA<br>Leu Lys Asp Ala Gln Val Phe Gly Glu Glu Trp Gly Tyr Ser Ser Glu<br>210                     215                     220 | 672 |
| GAT GTT GCT GAA TTT TAT CAT AGA CAA TTA AAA CTT ACA CAA CAA TAC<br>Asp Val Ala Glu Phe Tyr His Arg Gln Leu Lys Leu Thr Gln Gln Tyr<br>225                     230                     235                   240 | 720 |
| ACT GAC CAT TGT GTT AAT TGG TAT AAT GTT GGA TTA AAT GGT TTA AGA<br>Thr Asp His Cys Val Asn Trp Tyr Asn Val Gly Leu Asn Gly Leu Arg<br>                 245                     250                   255 | 768 |
| GGT TCA ACT TAT GAT GCA TGG GTC AAA TTT AAC CGT TTT CGC AGA GAA<br>Gly Ser Thr Tyr Asp Ala Trp Val Lys Phe Asn Arg Phe Arg Arg Glu<br>             260                     265                   270 | 816 |
| ATG ACT TTA ACT GTA TTA GAT CTA ATT GTA CTT TTC CCA TTT TAT GAT<br>Met Thr Leu Thr Val Leu Asp Leu Ile Val Leu Phe Pro Phe Tyr Asp<br>             275                     280                   285 | 864 |
| GTT CGG TTA TAC CCA AAA GGG GTT AAA ACA GAA CTA ACA AGA GAC ATT<br>Val Arg Leu Tyr Pro Lys Gly Val Lys Thr Glu Leu Thr Arg Asp Ile<br>290                     295                     300 | 912 |
| TCT ACG GAT CCA ATT TTT GCC GTT AAT ACT CTG TGG GAA TAC GGA CCA<br>Ser Thr Asp Pro Ile Phe Ala Val Asn Thr Leu Trp Glu Tyr Gly Pro<br>305                     310                     315                   320 | 960 |
| ACT TTT TTG AGT ATA GAA AAC TCT ATT CGA AAA CCT CAT TTA TTT GAT<br>Thr Phe Leu Ser Ile Glu Asn Ser Ile Arg Lys Pro His Leu Phe Asp<br>                     325                     330                   335 | 1008 |
| TAT TTA CAG GGG ATT GAA TTT CAT ACG CGT CTT CGA CCT GGT TAC TTT<br>Tyr Leu Gln Gly Ile Glu Phe His Thr Arg Leu Arg Pro Gly Tyr Phe<br>             340                     345                   350 | 1056 |
| GGG AAA GAT TCT TTC AAT TAT TGG TCT GGT AAT TAT GCA GAA ACT AGA<br>Gly Lys Asp Ser Phe Asn Tyr Trp Ser Gly Asn Tyr Ala Glu Thr Arg | 1104 |

```
            355                 360                 365
CCT AGT ATA GGA TCT AGT AAG ACA ATT ACT TCC CCA TTT TAT GGA GAT    1152
Pro Ser Ile Gly Ser Ser Lys Thr Ile Thr Ser Pro Phe Tyr Gly Asp
    370                 375                 380

AAA TCT ACT GAA CCT GTA CAA AAG CTA AGC TTT GAT GGA CAA AAA GTT    1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG    1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA    1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC    1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA    1392
His Val Ser Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCG GAA    1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG    1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT    1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC    1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA    1632
Ile Ile Glu Gly Pro Gly Phe Thr Gly Gly Asn Leu Leu Phe Leu Lys
    530                 535                 540

GAA TCT AGT AAT TCA ATT GCT AAA TTT AAA GTT ACA TTA AAT TCA GCA    1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT    1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC    1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
    610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650
```

(2) INFORMATION FOR SEQ ID NO:62:

(i) SEQUENCE CHARACTERISTICS:
        (A) LENGTH: 652 amino acids (B) TYPE: amino acid
        (D) TOPOLOGY: linear (ii) MOLECULE TYPE: protein (xi) SEQUENCE DESCRIPTION: SEQ ID NO:62:

Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
             20                  25                  30

Pro Asn Ser Thr Leu Glu Glu Leu Asn Tyr Lys Glu Phe Leu Arg Met
         35                  40                  45

Thr Glu Asp Ser Ser Thr Glu Val Leu Asp Asn Ser Thr Val Lys Asp
 50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Gly Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Val Arg Leu Tyr Pro Lys Gly Val Lys Thr Glu Leu Thr Arg Asp Ile
290                 295                 300

Ser Thr Asp Pro Ile Phe Ala Val Asn Thr Leu Trp Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Arg Pro Gly Tyr Phe
            340                 345                 350

Gly Lys Asp Ser Phe Asn Tyr Trp Ser Gly Asn Tyr Ala Glu Thr Arg
        355                 360                 365

Pro Ser Ile Gly Ser Ser Lys Thr Ile Thr Ser Pro Phe Tyr Gly Asp
370                 375                 380

```
Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
            405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
            450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
            485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
            515                 520                 525

Ile Ile Glu Gly Pro Gly Phe Thr Gly Gly Asn Leu Leu Phe Leu Lys
530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
            565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
            595                 600                 605

Phe Asp Leu Ala Thr Thr Asn Ser Asn Met Gly Phe Ser Gly Asp Lys
            610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
            645                 650

(2) INFORMATION FOR SEQ ID NO:63:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:63:

ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
1               5                   10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
            20                  25                  30

CCA AAT TCA ACA CTA GAA GAA TTA AAT TAT AAA GAA TTT TTA AGA ATG        144
Pro Asn Ser Thr Leu Glu Glu Leu Asn Tyr Lys Glu Phe Leu Arg Met
        35                  40                  45

ACT GAA GAC AGT TCT ACG GAA GTG CTA GAC AAC TCT ACA GTA AAA GAT        192
```

-continued

```
Thr Glu Asp Ser Ser Thr Glu Val Leu Asp Asn Ser Thr Val Lys Asp
     50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT       528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG       576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA       624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA       672
Leu Lys Asp Ala Gln Val Phe Gly Glu Glu Trp Gly Tyr Ser Ser Glu
210                 215                 220

GAT GTT GCT GAA TTT TAT CAT AGA CAA TTA AAA CTT ACA CAA CAA TAC       720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA       768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA       816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT       864
Met Thr Leu Thr Val Leu Asp Leu Ile Val Leu Phe Pro Phe Tyr Asp
        275                 280                 285

GTT CGG TTA TAC CCA AAA GGG GTT AAA ACA GAA CTA ACA AGA GAC ATT       912
Val Arg Leu Tyr Pro Lys Gly Val Lys Thr Glu Leu Thr Arg Asp Ile
290                 295                 300

TTT ACG GAT CCA ATT TTT TCA CTT AAT ACT CTT CAG GAG TAT GGA CCA       960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT      1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CGA CCT GGT TAC TTT      1056
Tyr Leu Gln Gly Ile Glu Phe His Thr Arg Leu Arg Pro Gly Tyr Phe
            340                 345                 350

GGG AAA GAT TCT TTC AAT TAT TGG TCT GGT AAT TAT GTA GAA ACT AGA      1104
Gly Lys Asp Ser Phe Asn Tyr Trp Ser Gly Asn Tyr Val Glu Thr Arg
        355                 360                 365
```

```
CCT AGT ATA GGA TCT AGT AAG ACA ATT ACT TCC CCA TTT TAT GGA GAT      1152
Pro Ser Ile Gly Ser Ser Lys Thr Ile Thr Ser Pro Phe Tyr Gly Asp
    370                 375                 380

AAA TCT ACT GAA CCT GTA CAA AAG CTA AGC TTT GAT GGA CAA AAA GTT      1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG      1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA      1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC      1344
Lys Asn Glu Thr Ser Thr Gln Thr Tyr Asp Ser Lys Arg Asn Asn Gly
                435                 440                 445

CAT GTA AGT GCA CAG GAT TCT ATT GAC CAA TTA CCG CCA GAA ACA ACA      1392
His Val Ser Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCG GAA      1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG      1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT      1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC      1584
Thr Gln Leu Pro Val Val Lys Ala Tyr Ala Leu Ser Ser Gly Ala Ser
                515                 520                 525

ATT ATT GAA GGT CCA GGA TTC ACA GGA GGA AAT TTA CTA TTC CTA AAA      1632
Ile Ile Glu Gly Pro Gly Phe Thr Gly Gly Asn Leu Leu Phe Leu Lys
    530                 535                 540

GAA TCT AGT AAT TCA ATT GCT AAA TTT AAA GTT ACA TTA AAT TCA GCA      1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT      1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC      1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA      1824
Tyr Ile Asn Lys Thr Met Asn Lys Asp Asp Asp Leu Thr Tyr Gln Thr
                595                 600                 605

TTT GAT CTC GCA ACT ACT AAT TCT AAT ATG GGG TTC TCG GGT GAT AAG      1872
Phe Asp Leu Ala Thr Thr Asn Ser Asn Met Gly Phe Ser Gly Asp Lys
    610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
Tyr Ile Asp Lys Ile Glu Phe Ile Pro Val Gln Leu
                645                 650

(2) INFORMATION FOR SEQ ID NO:64:

(i) SEQUENCE CHARACTERISTICS:
        (A) LENGTH: 652 amino acids
        (B) TYPE: amino acid
        (D) TOPOLOGY: linear
```

(ii) MOLECULE TYPE: protein (xi) SEQUENCE DESCRIPTION: SEQ ID NO:64:

| Met | Asn | Pro | Asn | Asn | Arg | Ser | Glu | His | Asp | Thr | Ile | Lys | Val | Thr | Pro |
|---|---|---|---|---|---|---|---|---|---|---|---|---|---|---|---|
| 1 | | | | 5 | | | | | 10 | | | | | 15 | |

Asn Ser Glu Leu Gln Thr Asn His Asn Gln Tyr Pro Leu Ala Asp Asn
          20                    25                    30

Pro Asn Ser Thr Leu Glu Glu Leu Asn Tyr Lys Glu Phe Leu Arg Met
          35                    40                    45

Thr Glu Asp Ser Ser Thr Glu Val Leu Asp Asn Ser Thr Val Lys Asp
    50                    55                    60

Ala Val Gly Thr Gly Ile Ser Val Val Gly Gln Ile Leu Gly Val Val
65                    70                    75                  80

Gly Val Pro Phe Ala Gly Ala Leu Thr Ser Phe Tyr Gln Ser Phe Leu
                  85                    90                    95

Asn Thr Ile Trp Pro Ser Asp Ala Asp Pro Trp Lys Ala Phe Met Ala
                100                 105                110

Gln Val Glu Val Leu Ile Asp Lys Lys Ile Glu Tyr Ala Lys Ser
        115                  120                125

Lys Ala Leu Ala Glu Leu Gln Gly Leu Gln Asn Asn Phe Glu Asp Tyr
     130                  135                140

Val Asn Ala Leu Asn Ser Trp Lys Lys Thr Pro Leu Ser Leu Arg Ser
145                  150                  155              160

Lys Arg Ser Gln Asp Arg Ile Arg Glu Leu Phe Ser Gln Ala Glu Ser
                165                 170                175

His Phe Arg Asn Ser Met Pro Ser Phe Ala Val Ser Lys Phe Glu Val
            180                  185                190

Leu Phe Leu Pro Thr Tyr Ala Gln Ala Ala Asn Thr His Leu Leu Leu
        195                  200                205

Leu Lys Asp Ala Gln Val Phe Gly Glu Glu Trp Gly Tyr Ser Ser Glu
    210                  215                220

Asp Val Ala Glu Phe Tyr His Arg Gln Leu Lys Leu Thr Gln Gln Tyr
225                  230                  235              240

Thr Asp His Cys Val Asn Trp Tyr Asn Val Gly Leu Asn Gly Leu Arg
            245                  250                255

Gly Ser Thr Tyr Asp Ala Trp Val Lys Phe Asn Arg Phe Arg Arg Glu
        260                  265                270

Met Thr Leu Thr Val Leu Asp Leu Ile Val Leu Phe Pro Phe Tyr Asp
     275                  280                285

Val Arg Leu Tyr Pro Lys Gly Val Lys Thr Glu Leu Thr Arg Asp Ile
    290                  295                300

Phe Thr Asp Pro Ile Phe Ser Leu Asn Thr Leu Gln Glu Tyr Gly Pro
305                  310                  315              320

Thr Phe Leu Ser Ile Glu Asn Ser Ile Arg Lys Pro His Leu Phe Asp
            325                  330                335

Tyr Leu Gln Gly Ile Glu Phe His Thr Arg Leu Arg Pro Gly Tyr Phe
        340                  345                350

Gly Lys Asp Ser Phe Asn Tyr Trp Ser Gly Asn Tyr Val Glu Thr Arg
     355                  360                365

Pro Ser Ile Gly Ser Ser Lys Thr Ile Thr Ser Pro Phe Tyr Gly Asp
    370                  375                380

Lys Ser Thr Glu Pro Val Gln Lys Leu Ser Phe Asp Gly Gln Lys Val
385                  390                  395              400

```
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
            420                 425                 430
Lys Asn Glu Thr Ser Thr Gln Thr Tyr Asp Ser Lys Arg Asn Asn Gly
            435                 440                 445
His Val Ser Ala Gln Asp Ser Ile Asp Gln Leu Pro Pro Glu Thr Thr
            450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Phe Asn Thr Ile Asp Ala Glu Lys Ile
            500                 505                 510
Thr Gln Leu Pro Val Val Lys Ala Tyr Ala Leu Ser Ser Gly Ala Ser
            515                 520                 525
Ile Ile Glu Gly Pro Gly Phe Thr Gly Gly Asn Leu Leu Phe Leu Lys
            530                 535                 540
Glu Ser Ser Asn Ser Ile Ala Lys Phe Lys Val Thr Leu Asn Ser Ala
545                 550                 555                 560
Ala Leu Leu Gln Arg Tyr Arg Val Arg Ile Arg Tyr Ala Ser Thr Thr
                565                 570                 575
Asn Leu Arg Leu Phe Val Gln Asn Ser Asn Asn Asp Phe Leu Val Ile
            580                 585                 590
Tyr Ile Asn Lys Thr Met Asn Lys Asp Asp Asp Leu Thr Tyr Gln Thr
            595                 600                 605
Phe Asp Leu Ala Thr Thr Asn Ser Asn Met Gly Phe Ser Gly Asp Lys
            610                 615                 620
Asn Glu Leu Ile Ile Gly Ala Glu Ser Phe Val Ser Asn Glu Lys Ile
625                 630                 635                 640
Tyr Ile Asp Lys Ile Glu Phe Ile Pro Val Gln Leu
                645                 650
```

(2) INFORMATION FOR SEQ ID NO:65:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:65:

```
ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
                20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
            35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
         50                  55                  60
```

```
GCA GTT GGG ACA GGA ATT TCT GTT GTA GGG CAG ATT TTA GGT GTT GTA      240
Ala Val Gly Thr Gly Ile Ser Val Val Gly Gln Ile Leu Gly Val Val
 65              70                  75                  80

GGA GTT CCA TTT GCT GGG GCA CTC ACT TCA TTT TAT CAA TCA TTT CTT      288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA      336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT      384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT      432
Lys Ala Leu Ala Glu Leu Gln Gly Leu Gln Asn Asn Phe Glu Asp Tyr
130                 135                 140

GTT AAT GCG TTA AAT TCC TGG AAG AAA ACA CCT TTA AGT TTG CGA AGT      480
Val Asn Ala Leu Asn Ser Trp Lys Lys Thr Pro Leu Ser Leu Arg Ser
145                 150                 155                 160

AAA AGA AGC CAA GGT CGA ATA AGG GAA CTT TTT TCT CAA GCA GAA AGT      528
Lys Arg Ser Gln Gly Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG      576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA      624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA      672
Leu Lys Asp Ala Gln Val Phe Gly Glu Glu Trp Gly Tyr Ser Ser Glu
210                 215                 220

GAT GTT GCT GAA TTT TAT CAT AGA CAA TTA AAA CTT ACA CAA CAA TAC      720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA      768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA      816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT      864
Met Thr Leu Thr Val Leu Asp Leu Ile Val Leu Phe Pro Phe Tyr Asp
        275                 280                 285

ATT CGG TTA TAC TCA AAA GGG GTT AAA ACA GAA CTA ACA AGA GAC ATT      912
Ile Arg Leu Tyr Ser Lys Gly Val Lys Thr Glu Leu Thr Arg Asp Ile
        290                 295                 300

TTT ACG GAT CCA ATT TTT TTA CTT AAT ACT CTT CAG GAG TAT GGA CCA      960
Phe Thr Asp Pro Ile Phe Leu Leu Asn Thr Leu Gln Glu Tyr Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT     1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
```

```
            370                 375                 380
AAA TCT ACT GAA CCT GTA CAA AAG CTA AGC TTT GAT GGA CAA AAA GTT      1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG      1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA      1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC      1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA      1392
His Val Ser Ala Gln Asp Ser Ile Asp Gln Leu Pro Pro Glu Thr Thr
        450                 455                 460

GAT GAA CCA CTT GAA AAA GCA TAT AGT CAT CAG CTT AAT TAC GCG GAA      1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG      1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT      1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC      1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA      1632
Ile Ile Glu Gly Pro Gly Phe Thr Gly Gly Asn Leu Leu Phe Leu Lys
530                 535                 540

GAA TCT AGT AAT TCA ATT GCT AAA TTT AAA GTT ACA TTA AAT TCA GCA      1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT      1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC      1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA      1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG      1872
Phe Asp Leu Ala Thr Thr Asn Ser Asn Met Gly Phe Ser Gly Asp Lys
        610                 615                 620

AAT GAA CTT ATA ATA GGA GCA GAA TCT TTC GTT TCT AAT GAA AAA ATC      1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                  1959
Tyr Ile Asp Lys Ile Glu Phe Ile Pro Val Gln Leu
                645                 650
```

(2) INFORMATION FOR SEQ ID NO:66:

(i) SEQUENCE CHARACTERISTICS:
        (A) LENGTH: 652 amino acids
        (B) TYPE: amino acid
        (D) TOPOLOGY: linear (ii) MOLECULE TYPE: protein -continued (xi) SEQUENCE DESCRIPTION: SEQ ID NO:66:

```
Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
             20                  25                  30

Pro Asn Ser Thr Leu Glu Glu Leu Asn Tyr Lys Glu Phe Leu Arg Met
         35                  40                  45

Thr Glu Asp Ser Ser Thr Glu Val Leu Asp Asn Ser Thr Val Lys Asp
     50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                 85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
    130                 135                 140

Val Asn Ala Leu Asn Ser Trp Lys Lys Thr Pro Leu Ser Leu Arg Ser
145                 150                 155                 160

Lys Arg Ser Gln Gly Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
        195                 200                 205

Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
    290                 295                 300

Phe Thr Asp Pro Ile Phe Leu Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
```

-continued

```
                        405                 410                 415
Val Tyr Leu Gly Val Thr Lys Val Asp Phe Ser Gln Tyr Asp Asp Gln
                420                 425                 430

Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
        450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
        595                 600                 605

Phe Asp Leu Ala Thr Thr Asn Ser Asn Met Gly Phe Ser Gly Asp Lys
    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:67:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:67:

ATG AAT CCA AAC AAT CGA AGT GAA CAT GAT ACG ATA AAG GTT ACA CCT      48
Met Asn Pro Asn Asn Arg Ser Glu His Asp Thr Ile Lys Val Thr Pro
 1               5                  10                  15

AAC AGT GAA TTG CAA ACT AAC CAT AAT CAA TAT CCT TTA GCT GAC AAT      96
Asn Ser Glu Leu Gln Thr Asn His Asn Gln Tyr Pro Leu Ala Asp Asn
                20                  25                  30

CCA AAT TCA ACA CTA GAA GAA TTA AAT TAT AAA GAA TTT TTA AGA ATG     144
Pro Asn Ser Thr Leu Glu Glu Leu Asn Tyr Lys Glu Phe Leu Arg Met
            35                  40                  45

ACT GAA GAC AGT TCT ACG GAA GTG CTA GAC AAC TCT ACA GTA AAA GAT     192
Thr Glu Asp Ser Ser Thr Glu Val Leu Asp Asn Ser Thr Val Lys Asp
         50                  55                  60

GCA GTT GGG ACA GGA ATT TCT GTT GTA GGG CAG ATT TTA GGT GTT GTA     240
```

-continued

```
Ala Val Gly Thr Gly Ile Ser Val Val Gly Gln Ile Leu Gly Val Val
 65                  70                  75                  80

GGA GTT CCA TTT GCT GGG GCA CTC ACT TCA TTT TAT CAA TCA TTT CTT      288
Gly Val Pro Phe Ala Gly Ala Leu Thr Ser Phe Tyr Gln Ser Phe Leu
                 85                  90                  95

AAC ACT ATA TGG CCA AGT GAT GCT GAC CCA TGG AAG GCT TTT ATG GCA      336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT      384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT      432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT      480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT      528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG      576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA      624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA      672
Leu Lys Asp Ala Gln Val Phe Gly Glu Glu Trp Gly Tyr Ser Ser Glu
    210                 215                 220

GAT GTT GCT GAA TTT TAT CAT AGA CAA TTA AAA CTT ACA CAA CAA TAC      720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA      768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA      816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT      864
Met Thr Leu Thr Val Leu Asp Leu Ile Val Leu Phe Pro Phe Tyr Asp
        275                 280                 285

ATT CGG TTA TAC TCA AAA GGG GTT AAA ACA GAA CTA ACA AGA GAC ATT      912
Ile Arg Leu Tyr Ser Lys Gly Val Lys Thr Glu Leu Thr Arg Asp Ile
    290                 295                 300

TTT ACG GAT CCA ATT TTT TCA CTT AAT ACT CTT CAG GAG TAT GGA CCA      960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT     1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CGA CCT GGT TAC TTT     1056
Tyr Leu Gln Gly Ile Glu Phe His Thr Arg Leu Arg Pro Gly Tyr Phe
            340                 345                 350

GGG AAA GAT TCT TTC AAT TAT TGG TCT GGT AAT TAT GTA GAA ACT AGA     1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT     1152
Pro Ser Ile Gly Ser Ser Lys Thr Ile Thr Ser Pro Phe Tyr Gly Asp
    370                 375                 380
```

```
AAA TCT ACT GAA CCT GTA CAA AAG CTA AGC TTT GAT GGA CAA AAA GTT    1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG    1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA    1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC    1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA    1392
His Val Ser Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCG GAA    1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG    1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT    1536
Thr His Arg Ser Val Asp Phe Phe Asn Thr Ile Asp Ala Glu Lys Ile
                500                 505                 510

ACT CAA CTT CCA GTA GTG AAA GCA TAT GCC TTG TCT TCA GGT GCT TCC    1584
Thr Gln Leu Pro Val Val Lys Ala Tyr Ala Leu Ser Ser Gly Ala Ser
            515                 520                 525

ATT ATT GAA GGT CCA GGA TTC ACA GGA GGA AAT TTA CTA TTC CTA AAA    1632
Ile Ile Glu Gly Pro Gly Phe Thr Gly Gly Asn Leu Leu Phe Leu Lys
        530                 535                 540

GAA TCT AGT AAT TCA ATT GCT AAA TTT AAA GTT ACA TTA AAT TCA GCA    1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT    1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC    1776
Asn Leu Arg Leu Phe Val Gln Asn Ser Asn Asn Asp Phe Leu Val Ile
                580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
            595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
        610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650
```

(2) INFORMATION FOR SEQ ID NO:68:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:68:

```
Met Asn Pro Asn Asn Arg Ser Glu His Asp Thr Ile Lys Val Thr Pro
 1               5                  10                  15
Asn Ser Glu Leu Gln Thr Asn His Asn Gln Tyr Pro Leu Ala Asp Asn
            20                  25                  30
Pro Asn Ser Thr Leu Glu Glu Leu Asn Tyr Lys Glu Phe Leu Arg Met
        35                  40                  45
Thr Glu Asp Ser Ser Thr Glu Val Leu Asp Asn Ser Thr Val Lys Asp
    50                  55                  60
Ala Val Gly Thr Gly Ile Ser Val Val Gly Gln Ile Leu Gly Val Val
65                  70                  75                  80
Gly Val Pro Phe Ala Gly Ala Leu Thr Ser Phe Tyr Gln Ser Phe Leu
                85                  90                  95
Asn Thr Ile Trp Pro Ser Asp Ala Asp Pro Trp Lys Ala Phe Met Ala
            100                 105                 110
Gln Val Glu Val Leu Ile Asp Lys Lys Ile Glu Glu Tyr Ala Lys Ser
        115                 120                 125
Lys Ala Leu Ala Glu Leu Gln Gly Leu Gln Asn Asn Phe Glu Asp Tyr
    130                 135                 140
Val Asn Ala Leu Asn Ser Trp Lys Lys Thr Pro Leu Ser Leu Arg Ser
145                 150                 155                 160
Lys Arg Ser Gln Asp Arg Ile Arg Glu Leu Phe Ser Gln Ala Glu Ser
                165                 170                 175
His Phe Arg Asn Ser Met Pro Ser Phe Ala Val Ser Lys Phe Glu Val
            180                 185                 190
Leu Phe Leu Pro Thr Tyr Ala Gln Ala Ala Asn Thr His Leu Leu Leu
        195                 200                 205
Leu Lys Asp Ala Gln Val Phe Gly Glu Glu Trp Gly Tyr Ser Ser Glu
    210                 215                 220
Asp Val Ala Glu Phe Tyr His Arg Gln Leu Lys Leu Thr Gln Gln Tyr
225                 230                 235                 240
Thr Asp His Cys Val Asn Trp Tyr Asn Val Gly Leu Asn Gly Leu Arg
                245                 250                 255
Gly Ser Thr Tyr Asp Ala Trp Val Lys Phe Asn Arg Phe Arg Arg Glu
            260                 265                 270
Met Thr Leu Thr Val Leu Asp Leu Ile Val Leu Phe Pro Phe Tyr Asp
        275                 280                 285
Ile Arg Leu Tyr Ser Lys Gly Val Lys Thr Glu Leu Thr Arg Asp Ile
    290                 295                 300
Phe Thr Asp Pro Ile Phe Ser Leu Asn Thr Leu Gln Glu Tyr Gly Pro
305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Arg Pro Gly Tyr Phe
            340                 345                 350
Gly Lys Asp Ser Phe Asn Tyr Trp Ser Gly Asn Tyr Val Glu Thr Arg
        355                 360                 365
Pro Ser Ile Gly Ser Ser Lys Thr Ile Thr Ser Pro Phe Tyr Gly Asp
    370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
```

```
Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
            435                 440                 445

His Val Ser Ala Gln Asp Ser Ile Asp Gln Leu Pro Pro Glu Thr Thr
            450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
            515                 520                 525

Ile Ile Glu Gly Pro Gly Phe Thr Gly Gly Asn Leu Leu Phe Leu Lys
            530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
                580                 585                 590

Tyr Ile Asn Lys Thr Met Asn Lys Asp Asp Leu Thr Tyr Gln Thr
                595                 600                 605

Phe Asp Leu Ala Thr Thr Asn Ser Asn Met Gly Phe Ser Gly Asp Lys
            610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:69:

(i) SEQUENCE CHARACTERISTICS:
        (A) LENGTH: 1482 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1479

(xi) SEQUENCE DESCRIPTION: SEQ ID NO:69:

AGT AAA AGA AGC CAA GAT CGA ATA AGG GAA CTT TTT TCT CAA GCA GAA        48
Ser Lys Arg Ser Gln Asp Arg Ile Arg Glu Leu Phe Ser Gln Ala Glu
  1               5                  10                  15

AGT CAT TTT CGT AAT TCC ATG CCG TCA TTT GCA GTT TCC AAA TTC GAA        96
Ser His Phe Arg Asn Ser Met Pro Ser Phe Ala Val Ser Lys Phe Glu
              20                  25                  30

GTG CTG TTT CTA CCA ACA TAT GCA CAA GCT GCA AAT ACA CAT TTA TTG       144
Val Leu Phe Leu Pro Thr Tyr Ala Gln Ala Ala Asn Thr His Leu Leu
          35                  40                  45

CTA TTA AAA GAT GCT CAA GTT TTT GGA GAA GAA TGG GGA TAT TCT TCA       192
Leu Leu Lys Asp Ala Gln Val Phe Gly Glu Glu Trp Gly Tyr Ser Ser
     50                  55                  60

GAA GAT GTT GCT GAA TTT TAT CAT AGA CAA TTA AAA CTT ACA CAA CAA       240
Glu Asp Val Ala Glu Phe Tyr His Arg Gln Leu Lys Leu Thr Gln Gln
 65                  70                  75                  80
```

```
TAC ACT GAC CAT TGT GTT AAT TGG TAT AAT GTT GGA TTA AAT GGT TTA        288
Tyr Thr Asp His Cys Val Asn Trp Tyr Asn Val Gly Leu Asn Gly Leu
                85                  90                  95

AGA GGT TCA ACT TAT GAT GCA TGG GTC AAA TTT AAC CGT TTT CGC AGA        336
Arg Gly Ser Thr Tyr Asp Ala Trp Val Lys Phe Asn Arg Phe Arg Arg
            100                 105                 110

GAA ATG ACT TTA ACT GTA TTA GAT CTA ATT GTA CTT TTC CCA TTT TAT        384
Glu Met Thr Leu Thr Val Leu Asp Leu Ile Val Leu Phe Pro Phe Tyr
        115                 120                 125

GAT ATT CGG TTA TAC TCA AAA GGG GTT AAA ACA GAA CTA ACA AGA GAC        432
Asp Ile Arg Leu Tyr Ser Lys Gly Val Lys Thr Glu Leu Thr Arg Asp
    130                 135                 140

ATT TTT ACG GAT CCA ATT TTT TCA CTT AAT ACT CTT CAG GAG TAT GGA        480
Ile Phe Thr Asp Pro Ile Phe Ser Leu Asn Thr Leu Gln Glu Tyr Gly
145                 150                 155                 160

CCA ACT TTT TTG AGT ATA GAA AAC TCT ATT CGA AAA CCT CAT TTA TTT        528
Pro Thr Phe Leu Ser Ile Glu Asn Ser Ile Arg Lys Pro His Leu Phe
                165                 170                 175

GAT TAT TTA CAG GGG ATT GAA TTT CAT ACG CGT CTT CAA CCT GGT TAC        576
Asp Tyr Leu Gln Gly Ile Glu Phe His Thr Arg Leu Gln Pro Gly Tyr
            180                 185                 190

TTT GGG AAA GAT TCT TTC AAT TAT TGG TCT GGT AAT TAT GTA GAA ACT        624
Phe Gly Lys Asp Ser Phe Asn Tyr Trp Ser Gly Asn Tyr Val Glu Thr
        195                 200                 205

AGA CCT AGT ATA GGA TCT AGT AAG ACA ATT ACT TCC CCA TTT TAT GGA        672
Arg Pro Ser Ile Gly Ser Ser Lys Thr Ile Thr Ser Pro Phe Tyr Gly
    210                 215                 220

GAT AAA TCT ACT GAA CCT GTA CAA AAG CTA AGC TTT GAT GGA CAA AAA        720
Asp Lys Ser Thr Glu Pro Val Gln Lys Leu Ser Phe Asp Gly Gln Lys
225                 230                 235                 240

GTT TAT CGA ACT ATA GCT AAT ACA GAC GTA GCG GCT TGG CCG AAT GGT        768
Val Tyr Arg Thr Ile Ala Asn Thr Asp Val Ala Ala Trp Pro Asn Gly
                245                 250                 255

AAG GTA TAT TTA GGT GTT ACG AAA GTT GAT TTT AGT CAA TAT GAT GAT        816
Lys Val Tyr Leu Gly Val Thr Lys Val Asp Phe Ser Gln Tyr Asp Asp
            260                 265                 270

CAA AAA AAT GAA ACT AGT ACA CAA ACA TAT GAT TCA AAA AGA AAC AAT        864
Gln Lys Asn Glu Thr Ser Thr Gln Thr Tyr Asp Ser Lys Arg Asn Asn
        275                 280                 285

GGC CAT GTA AGT GCA CAG GAT TCT ATT GAC CAA TTA CCG CCA GAA ACA        912
Gly His Val Ser Ala Gln Asp Ser Ile Asp Gln Leu Pro Pro Glu Thr
    290                 295                 300

ACA GAT GAA CCA CTT GAA AAA GCA TAT AGT CAT CAG CTT AAT TAC GCG        960
Thr Asp Glu Pro Leu Glu Lys Ala Tyr Ser His Gln Leu Asn Tyr Ala
305                 310                 315                 320

GAA TGT TTC TTA ATG CAG GAC CGT CGT GGA ACA ATT CCA TTT TTT ACT       1008
Glu Cys Phe Leu Met Gln Asp Arg Arg Gly Thr Ile Pro Phe Phe Thr
                325                 330                 335

TGG ACA CAT AGA AGT GTA GAC TTT TTT AAT ACA ATT GAT GCT GAA AAG       1056
Trp Thr His Arg Ser Val Asp Phe Phe Asn Thr Ile Asp Ala Glu Lys
            340                 345                 350

ATT ACT CAA CTT CCA GTA GTG AAA GCA TAT GCC TTG TCT TCA GGT GCT       1104
Ile Thr Gln Leu Pro Val Val Lys Ala Tyr Ala Leu Ser Ser Gly Ala
        355                 360                 365

TCC ATT ATT GAA GGT CCA GGA TTC ACA GGA GGA AAT TTA CTA TTC CTA       1152
Ser Ile Ile Glu Gly Pro Gly Phe Thr Gly Gly Asn Leu Leu Phe Leu
    370                 375                 380

AAA GAA TCT AGT AAT TCA ATT GCT AAA TTT AAA GTT ACA TTA AAT TCA       1200
Lys Glu Ser Ser Asn Ser Ile Ala Lys Phe Lys Val Thr Leu Asn Ser
```

```
                385                 390                 395                 400
GCA GCC TTG TTA CAA CGA TAT CGT GTA AGA ATA CGC TAT GCT TCT ACC           1248
Ala Ala Leu Leu Gln Arg Tyr Arg Val Arg Ile Arg Tyr Ala Ser Thr
                    405                 410                 415

ACT AAC TTA CGA CTT TTT GTG CAA AAT TCA AAC AAT GAT TTT CTT GTC           1296
Thr Asn Leu Arg Leu Phe Val Gln Asn Ser Asn Asn Asp Phe Leu Val
                420                 425                 430

ATC TAC ATT AAT AAA ACT ATG AAT AAA GAT GAT GAT TTA ACA TAT CAA           1344
Ile Tyr Ile Asn Lys Thr Met Asn Lys Asp Asp Asp Leu Thr Tyr Gln
                    435                 440                 445

ACA TTT GAT CTC GCA ACT ACT AAT TCT AAT ATG GGG TTC TCG GGT GAT           1392
Thr Phe Asp Leu Ala Thr Thr Asn Ser Asn Met Gly Phe Ser Gly Asp
                450                 455                 460

AAG AAT GAA CTT ATA ATA GGA GCA GAA TCT TTC GTT TCT AAT GAA AAA           1440
Lys Asn Glu Leu Ile Ile Gly Ala Glu Ser Phe Val Ser Asn Glu Lys
465                 470                 475                 480

ATC TAT ATA GAT AAG ATA GAA TTT ATC CCA GTA CAA TTG TAA                   1482
Ile Tyr Ile Asp Lys Ile Glu Phe Ile Pro Val Gln Leu
                    485                 490

(2) INFORMATION FOR SEQ ID NO:70:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO:70:

Ser Lys Arg Ser Gln Asp Arg Ile Arg Glu Leu Phe Ser Gln Ala Glu
1               5                  10                  15

Ser His Phe Arg Asn Ser Met Pro Ser Phe Ala Val Ser Lys Phe Glu
            20                  25                  30

Val Leu Phe Leu Pro Thr Tyr Ala Gln Ala Ala Asn Thr His Leu Leu
        35                  40                  45

Leu Leu Lys Asp Ala Gln Val Phe Gly Glu Glu Trp Gly Tyr Ser Ser
    50                  55                  60

Glu Asp Val Ala Glu Phe Tyr His Arg Gln Leu Lys Leu Thr Gln Gln
65                  70                  75                  80

Tyr Thr Asp His Cys Val Asn Trp Tyr Asn Val Gly Leu Asn Gly Leu
                85                  90                  95

Arg Gly Ser Thr Tyr Asp Ala Trp Val Lys Phe Asn Arg Phe Arg Arg
            100                 105                 110

Glu Met Thr Leu Thr Val Leu Asp Leu Ile Val Leu Phe Pro Phe Tyr
        115                 120                 125

Asp Ile Arg Leu Tyr Ser Lys Gly Val Lys Thr Glu Leu Thr Arg Asp
130                 135                 140

Ile Phe Thr Asp Pro Ile Phe Ser Leu Asn Thr Leu Gln Glu Tyr Gly
145                 150                 155                 160

Pro Thr Phe Leu Ser Ile Glu Asn Ser Ile Arg Lys Pro His Leu Phe
                165                 170                 175

Asp Tyr Leu Gln Gly Ile Glu Phe His Thr Arg Leu Gln Pro Gly Tyr
            180                 185                 190

Phe Gly Lys Asp Ser Phe Asn Tyr Trp Ser Gly Asn Tyr Val Glu Thr
        195                 200                 205

Arg Pro Ser Ile Gly Ser Ser Lys Thr Ile Thr Ser Pro Phe Tyr Gly
    210                 215                 220
```

```
Asp Lys Ser Thr Glu Pro Val Gln Lys Leu Ser Phe Asp Gly Gln Lys
225                 230                 235                 240

Val Tyr Arg Thr Ile Ala Asn Thr Asp Val Ala Ala Trp Pro Asn Gly
            245                 250                 255

Lys Val Tyr Leu Gly Val Thr Lys Val Asp Phe Ser Gln Tyr Asp Asp
                260                 265                 270

Gln Lys Asn Glu Thr Ser Thr Gln Thr Tyr Asp Ser Lys Arg Asn Asn
            275                 280                 285

Gly His Val Ser Ala Gln Asp Ser Ile Asp Gln Leu Pro Pro Glu Thr
        290                 295                 300

Thr Asp Glu Pro Leu Glu Lys Ala Tyr Ser His Gln Leu Asn Tyr Ala
305                 310                 315                 320

Glu Cys Phe Leu Met Gln Asp Arg Arg Gly Thr Ile Pro Phe Phe Thr
                325                 330                 335

Trp Thr His Arg Ser Val Asp Phe Phe Asn Thr Ile Asp Ala Glu Lys
            340                 345                 350

Ile Thr Gln Leu Pro Val Val Lys Ala Tyr Ala Leu Ser Ser Gly Ala
                355                 360                 365

Ser Ile Ile Glu Gly Pro Gly Phe Thr Gly Gly Asn Leu Leu Phe Leu
370                 375                 380

Lys Glu Ser Ser Asn Ser Ile Ala Lys Phe Lys Val Thr Leu Asn Ser
385                 390                 395                 400

Ala Ala Leu Leu Gln Arg Tyr Arg Val Arg Ile Arg Tyr Ala Ser Thr
                405                 410                 415

Thr Asn Leu Arg Leu Phe Val Gln Asn Ser Asn Asn Asp Phe Leu Val
            420                 425                 430

Ile Tyr Ile Asn Lys Thr Met Asn Lys Asp Asp Asp Leu Thr Tyr Gln
                435                 440                 445

Thr Phe Asp Leu Ala Thr Thr Asn Ser Asn Met Gly Phe Ser Gly Asp
                450                 455                 460

Lys Asn Glu Leu Ile Ile Gly Ala Glu Ser Phe Val Ser Asn Glu Lys
465                 470                 475                 480

Ile Tyr Ile Asp Lys Ile Glu Phe Ile Pro Val Gln Leu
                485                 490
```

(2) INFORMATION FOR SEQ ID NO:71:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:71:

AGACAACTCT ACAGTAAAAG ATG                                            23

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:72:

GGTAATTGGT CAATAGAATC                                                  20

(2) INFORMATION FOR SEQ ID NO:73:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 21..23
        (D) OTHER INFORMATION: /note= "N = A, T, G, C (25% each)"

(xi) SEQUENCE DESCRIPTION: SEQ ID NO:73:

CAGAAGATGT TGCTGAATTC NNNCATAGAC AATTAAAAC                                    39

(2) INFORMATION FOR SEQ ID NO:74:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 19..21
        (D) OTHER INFORMATION: /note= "N = A, T, G, C (25% each)"

(xi) SEQUENCE DESCRIPTION: SEQ ID NO:74:

GATGTTGCTG AATTCTATNN NAGACAATTA AAAC                                         34

(2) INFORMATION FOR SEQ ID NO:75:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 17
        (D) OTHER INFORMATION: /note= "N = A, T, C or G"

(ix) FEATURE:
        (A) NAME/KEY: modified_base
        (B) LOCATION: 18
        (D) OTHER INFORMATION: /note= "N = T, G, C or A"

(ix) FEATURE:
        (A) NAME/KEY: modified_base
        (B) LOCATION: 19
        (D) OTHER INFORMATION: /note= "N = A, T, G, C"

(xi) SEQUENCE DESCRIPTION: SEQ ID NO:75:

CCCATTTTAT GATATTNNNT TATACTCAAA AGG                                          33

(2) INFORMATION FOR SEQ ID NO:76:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 24
        (D) OTHER INFORMATION: /note= "N = T, G, C or A"

(ix) FEATURE:
        (A) NAME/KEY: modified_base

```
            (B) LOCATION: one-of(25, 27, 28, 30, 34, 36, 39, 43)
            (D) OTHER INFORMATION: /note= "N = A, T, G or C"

(ix) FEATURE:
            (A) NAME/KEY: modified_base
            (B) LOCATION: one-of(31, 33, 35, 37, 42, 44)
            (D) OTHER INFORMATION: /note= "N = A, G, C or T"

(ix) FEATURE:
            (A) NAME/KEY: modified_base
            (B) LOCATION: 40
            (D) OTHER INFORMATION: /note= "N = A, T, C or G"

(ix) FEATURE:
            (A) NAME/KEY: modified_base
            (B) LOCATION: one-of(26, 29, 32, 38, 41)
            (D) OTHER INFORMATION: /note= "N = A, T, G or C"

(xi) SEQUENCE DESCRIPTION: SEQ ID NO:76:

AGCTATGCTG GTCTCGGAAG AAANNNNNNN NNNNNNNNNN NNNNAAAAGA AGCCAAGATC      60

GAAT                                                                  64

(2) INFORMATION FOR SEQ ID NO:77:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:77:

GGTCACCTAG GTCTCTCTTC CAGGAATTTA ACGCATTAAC                            40

(2) INFORMATION FOR SEQ ID NO:78:

(i) SEQUENCE CHARACTERISTICS:
            (A) LENGTH: 65 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: one-of(22, 27, 29, 30, 37, 42)
            (D) OTHER INFORMATION: /note= "N = A, G, C or T"

(ix) FEATURE:
            (A) NAME/KEY: modified_base
            (B) LOCATION: one-of(23, 26, 28, 31, 38, 40, 43, 44)
            (D) OTHER INFORMATION: /note= "N = T, G, C or A"

(ix) FEATURE:
            (A) NAME/KEY: modified_base
            (B) LOCATION: one-of(24, 39)
            (D) OTHER INFORMATION: /note= "N = A, T, G or C"

(ix) FEATURE:
            (A) NAME/KEY: modified_base
            (B) LOCATION: one-of(25, 32, 33, 41, 46, 47, 48)
            (D) OTHER INFORMATION: /note= "N = A, T, C or G"

(ix) FEATURE:
            (A) NAME/KEY: modified_base
            (B) LOCATION: 34
            (D) OTHER INFORMATION: /note= "N = A, T, G or C"

(ix) FEATURE:
            (A) NAME/KEY: modified_base
            (B) LOCATION: 45
            (D) OTHER INFORMATION: /note= "N = A, T, G or C"

(ix) FEATURE:
            (A) NAME/KEY: modified_base
            (B) LOCATION: 35..36
```

(D) OTHER INFORMATION: /note= "N = A, G, C or T"

(xi) SEQUENCE DESCRIPTION: SEQ ID NO:78:

AGCTATGCTG GTCTCCCATT TNNNNNNNNN NNNNNNNNNN NNNNNNNNGT TAAAACAGAA      60

CTAAC                                                                 65

(2) INFORMATION FOR SEQ ID NO:79:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (xi) SEQUENCE DESCRIPTION: SEQ ID NO:79:

ATCCAGTGGG GTCTCAAATG GGAAAAGTAC AATTAG                                36

(2) INFORMATION FOR SEQ ID NO:80:

(i) SEQUENCE CHARACTERISTICS:
           (A) LENGTH: 63 base pairs
           (B) TYPE: nucleic acid
           (C) STRANDEDNESS: single
           (D) TOPOLOGY: linear (ix) FEATURE:
           (A) NAME/KEY: modified_base
           (B) LOCATION: one-of(23, 27, 31, 36, 44)
           (D) OTHER INFORMATION: /note= "N = A, G, C or T"

(ix) FEATURE:
           (A) NAME/KEY: modified_base
           (B) LOCATION: one-of(24, 25, 26, 33, 35, 38)
           (D) OTHER INFORMATION: /note= "N = A, T, G or C"

(ix) FEATURE:
           (A) NAME/KEY: modified_base
           (B) LOCATION: one-of(28, 34, 37)
           (D) OTHER INFORMATION: /note= "N = A, T, G or C"

(ix) FEATURE:
           (A) NAME/KEY: modified_base
           (B) LOCATION: one-of(29, 30, 32, 39, 42, 45)
           (D) OTHER INFORMATION: /note= "N = T, G, C or A"

(ix) FEATURE:
           (A) NAME/KEY: modified_base
           (B) LOCATION: one-of(40, 43)
           (D) OTHER INFORMATION: /note= "N = A, T, C or G"

(ix) FEATURE:
           (A) NAME/KEY: modified_base
           (B) LOCATION: 41
           (D) OTHER INFORMATION: /note= "N = A, C, T or G"

(ix) FEATURE:
           (A) NAME/KEY: modified_base
           (B) LOCATION: 46
           (D) OTHER INFORMATION: /note= "N = A, T, G or C"

(xi) SEQUENCE DESCRIPTION: SEQ ID NO:80:

CATTTTTACG GATCCAATTT TTNNNNNNNN NNNNNNNNNN NNNNNNGGAC CAACTTTTTT      60

GAG                                                                   63

(2) INFORMATION FOR SEQ ID NO:81:

(i) SEQUENCE CHARACTERISTICS:
           (A) LENGTH: 62 base pairs
           (B) TYPE: nucleic acid
           (C) STRANDEDNESS: single
           (D) TOPOLOGY: linear

```
    (ix) FEATURE:
          (A) NAME/KEY: modified_base
          (B) LOCATION: one-of(28, 31, 32, 33, 42)
          (D) OTHER INFORMATION: /note= "N = A, G, C or T"

(ix) FEATURE:
          (A) NAME/KEY: modified_base
          (B) LOCATION: one-of(29, 38, 39, 41)
          (D) OTHER INFORMATION: /note= "N = T, G, C or A"

(ix) FEATURE:
          (A) NAME/KEY: modified_base
          (B) LOCATION: 30
          (D) OTHER INFORMATION: /note= "N = A, T, G or C"

(ix) FEATURE:
          (A) NAME/KEY: modified_base
          (B) LOCATION: one-of(34, 35, 40)
          (D) OTHER INFORMATION: /note= "N = A, T, C or G"

(ix) FEATURE:
          (A) NAME/KEY: modified_base
          (B) LOCATION: 36
          (D) OTHER INFORMATION: /note= "N = A, T, G or C"

(ix) FEATURE:
          (A) NAME/KEY: modified_base
          (B) LOCATION: 37
          (D) OTHER INFORMATION: /note= "N = A, T, G, or C"

(xi) SEQUENCE DESCRIPTION: SEQ ID NO:81:

GAATTTCATA CGCGTCTTCA ACCTGGTNNN NNNNNNNNNN NNTCTTTCAA TTATTGGTCT      60

GG                                                                    62

(2) INFORMATION FOR SEQ ID NO:82:

(i) SEQUENCE CHARACTERISTICS:
          (A) LENGTH: 73 base pairs
          (B) TYPE: nucleic acid
          (C) STRANDEDNESS: single
          (D) TOPOLOGY: linear (ix) FEATURE:
          (A) NAME/KEY: modified_base
          (B) LOCATION: one-of(41, 49, 52)
          (D) OTHER INFORMATION: /note= "N = A, G, C or T"

(ix) FEATURE:
          (A) NAME/KEY: modified_base
          (B) LOCATION: 42..43
          (D) OTHER INFORMATION: /note= "N = A, T, C or G"

(ix) FEATURE:
          (A) NAME/KEY: modified_base
          (B) LOCATION: 44..45
          (D) OTHER INFORMATION: /note= "N = A, T, G or C"

(ix) FEATURE:
          (A) NAME/KEY: modified_base
          (B) LOCATION: 46
          (D) OTHER INFORMATION: /note= "N = A, T, G or C"

(ix) FEATURE:
          (A) NAME/KEY: modified_base
          (B) LOCATION: one-of(47, 48, 53, 54)
          (D) OTHER INFORMATION: /note= "N = T, G, C or A"

(ix) FEATURE:
          (A) NAME/KEY: modified_base
          (B) LOCATION: one-of(50, 51, 55)
          (D) OTHER INFORMATION: /note= "N = A, T, C or G"

(xi) SEQUENCE DESCRIPTION: SEQ ID NO:82:

AAAAGTTTAT CGAACTATAG CTAATACAGA CGTAGCGGCT NNNNNNNNNN NNNNNGTATA      60
```

```
TTTAGGTGTT ACG                                                              73

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:83:

GGAGTTCCAT TTGCTGGGGC                                                       20

(2) INFORMATION FOR SEQ ID NO:84:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:84:

ATCTCCATAA AATGGGG                                                          17

(2) INFORMATION FOR SEQ ID NO:85:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:85:

GCGAAGTAAA AGAAGCCAAG GTCGAATAAG GG                                         32

(2) INFORMATION FOR SEQ ID NO:86:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:86:

CCTTTAAGTT TGCGAAATCC ACACAGCCAA GGTCGAATAA GGG                             43

(2) INFORMATION FOR SEQ ID NO:87:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:87:

CCCATTTTAT GATGTTCGGT TATACCCAAA AGGGG                                      35

(2) INFORMATION FOR SEQ ID NO:88:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:88:
```

```
GGCCAAGTGA AGACCCATGG AAGGC                                                         25
```

(2) INFORMATION FOR SEQ ID NO:89:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:89:

```
GCAGTTTCCG GATTCGAAGT GC                                                            22
```

(2) INFORMATION FOR SEQ ID NO:90:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:90:

```
CCGCTACGTC TGTATTA                                                                  17
```

(2) INFORMATION FOR SEQ ID NO:91:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:91:

```
ATAATGGAAG CACCTGA                                                                  17
```

(2) INFORMATION FOR SEQ ID NO:92:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(22, 26, 29)
        (D) OTHER INFORMATION: /note= "N = T, G, C or A"

(ix) FEATURE:
        (A) NAME/KEY: modified_base
        (B) LOCATION: one-of(23, 33, 36)
        (D) OTHER INFORMATION: /note= "N = A, G, C or T"

(ix) FEATURE:
        (A) NAME/KEY: modified_base
        (B) LOCATION: one-of(24, 27, 28, 32, 35, 37, 38)
        (D) OTHER INFORMATION: /note= "N = A, T, C or G"

(ix) FEATURE:
        (A) NAME/KEY: modified_base
        (B) LOCATION: one-of(25, 30, 31, 34)
        (D) OTHER INFORMATION: /note= "N = A, T, G or C"

(ix) FEATURE:
        (A) NAME/KEY: modified_base
        (B) LOCATION: 39
        (D) OTHER INFORMATION: /note= "N = A, T, G or C"

(xi) SEQUENCE DESCRIPTION: SEQ ID NO:92:

```
AGCTATGCTG GTCTCTTCTT ANNNNNNNNN NNNNNNNNNA CAATTCCATT TTTTACTTGG                    60
```

(2) INFORMATION FOR SEQ ID NO:93:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:93:

ATCCAGTTGG GTCTCTAAGA AACAAACCGC GTAATTAAGC                              40

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:94:

CCTCAAGGGT TATAACATCC                                                    20

(2) INFORMATION FOR SEQ ID NO:95:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(19, 22, 23, 31)
        (D) OTHER INFORMATION: /note= "N = A, T, C or G"

(ix) FEATURE:
        (A) NAME/KEY: modified_base
        (B) LOCATION: one-of(20, 26, 27, 29, 30, 35)
        (D) OTHER INFORMATION: /note= "N = T, G, C or A"

(ix) FEATURE:
        (A) NAME/KEY: modified_base
        (B) LOCATION: one-of(21, 32, 34)
        (D) OTHER INFORMATION: /note= "N = A, G, C or T"

(ix) FEATURE:
        (A) NAME/KEY: modified_base
        (B) LOCATION: one-of(24, 33)
        (D) OTHER INFORMATION: /note= "N = A, T, G or C"

(ix) FEATURE:
        (A) NAME/KEY: modified_base
        (B) LOCATION: 25
        (D) OTHER INFORMATION: /note= "N = A, G, T or C"

(ix) FEATURE:
        (A) NAME/KEY: modified_base
        (B) LOCATION: 28
        (D) OTHER INFORMATION: /note= "N = A, T, G or C"

(ix) FEATURE:
        (A) NAME/KEY: modified_base
        (B) LOCATION: 36
        (D) OTHER INFORMATION: /note= "N = A, G, C or T"

(xi) SEQUENCE DESCRIPTION: SEQ ID NO:95:

GTACAAAAGC TAAGCTTTNN NNNNNNNNNN NNNNNNCGAA CTATAGCTAA TACAG             55

(2) INFORMATION FOR SEQ ID NO:96:

(i) SEQUENCE CHARACTERISTICS:
        (A) LENGTH: 7 amino acids (B) TYPE: amino acid
        (C) STRANDEDNESS:
        (D) TOPOLOGY: linear (xi) SEQUENCE DESCRIPTION: SEQ ID NO:96:

Ser Lys Arg Ser Gln Asp Arg
    1               5

(2) INFORMATION FOR SEQ ID NO:97:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1956

(xi) SEQUENCE DESCRIPTION: SEQ ID NO:97:

```
ATG AAT CCA AAC AAT CGA AGT GAA CAT GAT ACG ATA AAG GTT ACA CCT        48
Met Asn Pro Asn Asn Arg Ser Glu His Asp Thr Ile Lys Val Thr Pro
1               5                   10                  15

AAC AGT GAA TTG CAA ACT AAC CAT AAT CAA TAT CCT TTA GCT GAC AAT        96
Asn Ser Glu Leu Gln Thr Asn His Asn Gln Tyr Pro Leu Ala Asp Asn
            20                  25                  30

CCA AAT TCA ACA CTA GAA GAA TTA AAT TAT AAA GAA TTT TTA AGA ATG       144
Pro Asn Ser Thr Leu Glu Glu Leu Asn Tyr Lys Glu Phe Leu Arg Met
        35                  40                  45

ACT GAA GAC AGT TCT ACG GAA GTG CTA GAC AAC TCT ACA GTA AAA GAT       192
Thr Glu Asp Ser Ser Thr Glu Val Leu Asp Asn Ser Thr Val Lys Asp
    50                  55                  60

GCA GTT GGG ACA GGA ATT TCT GTT GTA GGG CAG ATT TTA GGT GTT GTA       240
Ala Val Gly Thr Gly Ile Ser Val Val Gly Gln Ile Leu Gly Val Val
65                  70                  75                  80

GGA GTT CCA TTT GCT GGG GCA CTC ACT TCA TTT TAT CAA TCA TTT CTT       288
Gly Val Pro Phe Ala Gly Ala Leu Thr Ser Phe Tyr Gln Ser Phe Leu
                85                  90                  95

AAC ACT ATA TGG CCA AGT GAT GCT GAC CCA TGG AAG GCT TTT ATG GCA       336
Asn Thr Ile Trp Pro Ser Asp Ala Asp Pro Trp Lys Ala Phe Met Ala
            100                 105                 110

CAA GTT GAA GTA CTG ATA GAT AAG AAA ATA GAG GAG TAT GCT AAA AGT       384
Gln Val Glu Val Leu Ile Asp Lys Lys Ile Glu Glu Tyr Ala Lys Ser
        115                 120                 125

AAA GCT CTT GCA GAG TTA CAG GGT CTT CAA AAT AAT TTC GAA GAT TAT       432
Lys Ala Leu Ala Glu Leu Gln Gly Leu Gln Asn Asn Phe Glu Asp Tyr
    130                 135                 140

GTT AAT GCG TTA AAT TCC TGG AAG AAA ACA CCT TTA AGT TTG CGA AGT       480
Val Asn Ala Leu Asn Ser Trp Lys Lys Thr Pro Leu Ser Leu Arg Ser
145                 150                 155                 160

AAA AGA AGC CAA GAT CGA ATA AGG GAA CTT TTT TCT CAA GCA GAA AGT       528
Lys Arg Ser Gln Asp Arg Ile Arg Glu Leu Phe Ser Gln Ala Glu Ser
                165                 170                 175

CAT TTT CGT AAT TCC ATG CCG TCA TTT GCA GTT TCC AAA TTC GAA GTG       576
His Phe Arg Asn Ser Met Pro Ser Phe Ala Val Ser Lys Phe Glu Val
            180                 185                 190

CTG TTT CTA CCA ACA TAT GCA CAA GCT GCA AAT ACA CAT TTA TTG CTA       624
Leu Phe Leu Pro Thr Tyr Ala Gln Ala Ala Asn Thr His Leu Leu Leu
        195                 200                 205

TTA AAA GAT GCT CAA GTT TTT GGA GAA GAA TGG GGA TAT TCT TCA GAA       672
Leu Lys Asp Ala Gln Val Phe Gly Glu Glu Trp Gly Tyr Ser Ser Glu
    210                 215                 220
```

```
GAT GTT GCT GAA TTT TAT CAT AGA CAA TTA AAA CTT ACA CAA CAA TAC       720
Asp Val Ala Glu Phe Tyr His Arg Gln Leu Lys Leu Thr Gln Gln Tyr
225                 230                 235                 240

ACT GAC CAT TGT GTT AAT TGG TAT AAT GTT GGA TTA AAT GGT TTA AGA       768
Thr Asp His Cys Val Asn Trp Tyr Asn Val Gly Leu Asn Gly Leu Arg
                245                 250                 255

GGT TCA ACT TAT GAT GCA TGG GTC AAA TTT AAC CGT TTT CGC AGA GAA       816
Gly Ser Thr Tyr Asp Ala Trp Val Lys Phe Asn Arg Phe Arg Arg Glu
            260                 265                 270

ATG ACT TTA ACT GTA TTA GAT CTA ATT GTA CTT TTC CCA TTT TAT GAT       864
Met Thr Leu Thr Val Leu Asp Leu Ile Val Leu Phe Pro Phe Tyr Asp
        275                 280                 285

ATT CGG TTA TAC TCA AAA GGG GTT AAA ACA GAA CTA ACA AGA GAC ATT       912
Ile Arg Leu Tyr Ser Lys Gly Val Lys Thr Glu Leu Thr Arg Asp Ile
    290                 295                 300

TTT ACG GAT CCA ATT TTT TCA CTT AAT ACT CTT CAG GAG TAT GGA CCA       960
Phe Thr Asp Pro Ile Phe Ser Leu Asn Thr Leu Gln Glu Tyr Gly Pro
305                 310                 315                 320

ACT TTT TTG AGT ATA GAA AAC TCT ATT CGA AAA CCT CAT TTA TTT GAT      1008
Thr Phe Leu Ser Ile Glu Asn Ser Ile Arg Lys Pro His Leu Phe Asp
                325                 330                 335

TAT TTA CAG GGG ATT GAA TTT CAT ACG CGT CTT CAA CCT GGT TAC TTT      1056
Tyr Leu Gln Gly Ile Glu Phe His Thr Arg Leu Gln Pro Gly Tyr Phe
            340                 345                 350

GGG AAA GAT TCT TTC AAT TAT TGG TCT GGT AAT TAT GTA GAA ACT AGA      1104
Gly Lys Asp Ser Phe Asn Tyr Trp Ser Gly Asn Tyr Val Glu Thr Arg
        355                 360                 365

CCT AGT ATA GGA TCT AGT AAG ACA ATT ACT TCC CCA TTT TAT GGA GAT      1152
Pro Ser Ile Gly Ser Ser Lys Thr Ile Thr Ser Pro Phe Tyr Gly Asp
    370                 375                 380

AAA TCT ACT GAA CCT GTA CAA AAG CTA AGC TTT GAT GGA CAA AAA GTT      1200
Lys Ser Thr Glu Pro Val Gln Lys Leu Ser Phe Asp Gly Gln Lys Val
385                 390                 395                 400

TAT CGA ACT ATA GCT AAT ACA GAC GTA GCG GCT TGG CCG AAT GGT AAG      1248
Tyr Arg Thr Ile Ala Asn Thr Asp Val Ala Ala Trp Pro Asn Gly Lys
                405                 410                 415

GTA TAT TTA GGT GTT ACG AAA GTT GAT TTT AGT CAA TAT GAT GAT CAA      1296
Val Tyr Leu Gly Val Thr Lys Val Asp Phe Ser Gln Tyr Asp Asp Gln
            420                 425                 430

AAA AAT GAA ACT AGT ACA CAA ACA TAT GAT TCA AAA AGA AAC AAT GGC      1344
Lys Asn Glu Thr Ser Thr Gln Thr Tyr Asp Ser Lys Arg Asn Asn Gly
        435                 440                 445

CAT GTA AGT GCA CAG GAT TCT ATT GAC CAA TTA CCG CCA GAA ACA ACA      1392
His Val Ser Ala Gln Asp Ser Ile Asp Gln Leu Pro Pro Glu Thr Thr
    450                 455                 460

GAT GAA CCA CTT GAA AAA GCA TAT AGT CAT CAG CTT AAT TAC GCG GAA      1440
Asp Glu Pro Leu Glu Lys Ala Tyr Ser His Gln Leu Asn Tyr Ala Glu
465                 470                 475                 480

TGT TTC TTA ATG CAG GAC CGT CGT GGA ACA ATT CCA TTT TTT ACT TGG      1488
Cys Phe Leu Met Gln Asp Arg Arg Gly Thr Ile Pro Phe Phe Thr Trp
                485                 490                 495

ACA CAT AGA AGT GTA GAC TTT TTT AAT ACA ATT GAT GCT GAA AAG ATT      1536
Thr His Arg Ser Val Asp Phe Phe Asn Thr Ile Asp Ala Glu Lys Ile
            500                 505                 510

ACT CAA CTT CCA GTA GTG AAA GCA TAT GCC TTG TCT TCA GGT GCT TCC      1584
Thr Gln Leu Pro Val Val Lys Ala Tyr Ala Leu Ser Ser Gly Ala Ser
        515                 520                 525

ATT ATT GAA GGT CCA GGA TTC ACA GGA GGA AAT TTA CTA TTC CTA AAA      1632
Ile Ile Glu Gly Pro Gly Phe Thr Gly Gly Asn Leu Leu Phe Leu Lys
```

```
         530               535                540
GAA TCT AGT AAT TCA ATT GCT AAA TTT AAA GTT ACA TTA AAT TCA GCA    1680
Glu Ser Ser Asn Ser Ile Ala Lys Phe Lys Val Thr Leu Asn Ser Ala
545                 550                 555                 560

GCC TTG TTA CAA CGA TAT CGT GTA AGA ATA CGC TAT GCT TCT ACC ACT    1728
Ala Leu Leu Gln Arg Tyr Arg Val Arg Ile Arg Tyr Ala Ser Thr Thr
                565                 570                 575

AAC TTA CGA CTT TTT GTG CAA AAT TCA AAC AAT GAT TTT CTT GTC ATC    1776
Asn Leu Arg Leu Phe Val Gln Asn Ser Asn Asn Asp Phe Leu Val Ile
            580                 585                 590

TAC ATT AAT AAA ACT ATG AAT AAA GAT GAT GAT TTA ACA TAT CAA ACA    1824
Tyr Ile Asn Lys Thr Met Asn Lys Asp Asp Asp Leu Thr Tyr Gln Thr
        595                 600                 605

TTT GAT CTC GCA ACT ACT AAT TCT AAT ATG GGG TTC TCG GGT GAT AAG    1872
Phe Asp Leu Ala Thr Thr Asn Ser Asn Met Gly Phe Ser Gly Asp Lys
610                 615                 620

AAT GAA CTT ATA ATA GGA GCA GAA TCT TTC GTT TCT AAT GAA AAA ATC    1920
Asn Glu Leu Ile Ile Gly Ala Glu Ser Phe Val Ser Asn Glu Lys Ile
625                 630                 635                 640

TAT ATA GAT AAG ATA GAA TTT ATC CCA GTA CAA TTG TAA                1959
Tyr Ile Asp Lys Ile Glu Phe Ile Pro Val Gln Leu
                645                 650

(2) INFORMATION FOR SEQ ID NO:98:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:98:

Met Asn Pro Asn Asn Arg Ser Glu His Asp Thr Ile Lys Val Thr Pro
 1               5                  10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
 50                  55                  60

Ala Val Gly Thr Gly Ile Ser Val Val Gly Gln Ile Leu Gly Val Val
 65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
            180                 185                 190

Leu Phe Leu Pro Thr Tyr Ala Gln Ala Ala Asn Thr His Leu Leu Leu
```

-continued

```
                195                 200                 205
Leu Lys Asp Ala Gln Val Phe Gly Glu Glu Trp Gly Tyr Ser Ser Glu
    210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
        275                 280                 285

Ile Arg Leu Tyr Ser Lys Gly Val Lys Thr Glu Leu Thr Arg Asp Ile
    290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Phe
            340                 345                 350

Gly Lys Asp Ser Phe Asn Tyr Trp Ser Gly Asn Tyr Val Glu Thr Arg
        355                 360                 365

Pro Ser Ile Gly Ser Ser Lys Thr Ile Thr Ser Pro Phe Tyr Gly Asp
    370                 375                 380

Lys Ser Thr Glu Pro Val Gln Lys Leu Ser Phe Asp Gly Gln Lys Val
385                 390                 395                 400

Tyr Arg Thr Ile Ala Asn Thr Asp Val Ala Ala Trp Pro Asn Gly Lys
                405                 410                 415

Val Tyr Leu Gly Val Thr Lys Val Asp Phe Ser Gln Tyr Asp Asp Gln
            420                 425                 430

Lys Asn Glu Thr Ser Thr Gln Thr Tyr Asp Ser Lys Arg Asn Asn Gly
        435                 440                 445

His Val Ser Ala Gln Asp Ser Ile Asp Gln Leu Pro Pro Glu Thr Thr
    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                485                 490                 495

Thr His Arg Ser Val Asp Phe Phe Asn Thr Ile Asp Ala Glu Lys Ile
            500                 505                 510

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
        595                 600                 605

Phe Asp Leu Ala Thr Thr Asn Ser Asn Met Gly Phe Ser Gly Asp Lys
610                 615                 620
```

```
Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650
```

(2) INFORMATION FOR SEQ ID NO:99:

(i) SEQUENCE CHARACTERISTICS:
        (A) LENGTH: 2000 base pairs
        (B) TYPE: nucleic acid
        (C) STRANDEDNESS: single
        (D) TOPOLOGY: linear (xi) SEQUENCE DESCRIPTION: SEQ ID NO:99:

```
CCATCCATGG CAAACCCTAA CAATCGTTCC GAACACGACA CCATCAAGGT TACTCCAAAC      60

TCTGAGTTGC AAACTAATCA CAACCAGTAC CCATTGGCTG ACAATCCTAA CAGTACTCTT     120

GAGGAACTTA ACTACAAGGA GTTTCTCCGG ATGACCGAAG ATAGCTCCAC TGAGGTTCTC     180

GATAACTCTA CAGTGAAGGA CGCTGTTGGA ACTGGCATTA GCGTTGTGGG ACAGATTCTT     240

GGAGTGGTTG GTGTTCCATT CGCTGGAGCT TTGACCAGCT TCTACCAGTC CTTTCTCAAC     300

ACCATCTGGC CTTCAGATGC TGATCCCTGG AAGGCTTTCA TGGCCCAAGT GGAAGTCTTG     360

ATCGATAAGA AGATCGAAGA GTATGCCAAG TCTAAAGCCT TGGCTGAGTT GCAAGGTTTG     420

CAGAACAACT TCGAGGATTA CGTCAACGCA CTCAACAGCT GGAAGAAAAC TCCCTTGAGT     480

CTCAGGTCTA AGCGTTCCCA GGACCGTATT CGTGAACTTT TCAGCCAAGC CGAATCCCAC     540

TTCAGAAACT CCATGCCTAG CTTTGCCGTT TCTAAGTTCG AGGTGCTCTT CTTGCCAACA     600

TACGCACAAG CTGCCAACAC TCATCTCTTG CTTCTCAAAG ACGCTCAGGT GTTTGGTGAG     660

GAATGGGGTT ACTCCAGTGA AGATGTTGCC GAGTTCTACC GTAGGCAGCT CAAGTTGACT     720

CAACAGTACA CAGACCACTG CGTCAACTGG TACAACGTTG GGCTCAATGG TCTTAGAGGA     780

TCTACCTACG ACGCATGGGT GAAGTTCAAC AGGTTTCGTA GAGAGATGAC CTTGACTGTG     840

CTCGATCTTA TCGTTCTCTT TCCATTCTAC GACATTCGTC TTTACTCCAA AGGCGTTAAG     900

ACAGAGCTGA CCAGAGACAT CTTCACCGAT CCCATCTTCC TACTTACGAC CCTGCAGAAA     960

TACGGTCCAA CTTTTCTCTC CATTGAGAAC AGCATCAGGA AGCCTCACCT CTTCGACTAT    1020

CTGCAAGGCA TTGAGTTTCA CACCAGGTTG CAACCTGGTT ACTTCGGTAA GGATTCCTTC    1080

AACTACTGGA GCGGAAACTA CGTTGAAACC AGACCATCCA TCGGATCTAG CAAGACCATC    1140

ACTTCTCCAT TCTACGGTGA CAAGAGCACT GAGCCAGTGC AGAAGTTGAG CTTCGATGGG    1200

CAGAAGGTGT ATAGAACCAT CGCCAATACC GATGTTGCAG CTTGGCCTAA TGGCAAGGTC    1260

TACCTTGGAG TTACTAAAGT GGACTTCTCC CAATACGACG ATCAGAAGAA CGAGACATCT    1320

ACTCAAACCT ACGATAGTAA GAGGAACAAT GGCCATGTTT CCGCACAAGA CTCCATTGAC    1380

CAACTTCCAC CTGAAACCAC TGATGAACCA TTGGAGAAGG CTTACAGTCA CCAACTTAAC    1440

TACGCCGAAT GCTTTCTCAT GCAAGACAGG CGTGGCACCA TTCCGTTCTT TACATGGACT    1500

CACAGGTCTG TCGACTTCTT TAACACTATC GACGCTGAGA AGATTACCCA ACTTCCCGTG    1560

GTCAAGGCTT ATGCCTTGTC CAGCGGAGCT TCCATCATTG AAGGTCCAGG CTTCACCGGT    1620

GGCAACTTGC TCTTCCTTAA GGAGTCCAGC AACTCCATCG CCAAGTTCAA AGTGACACTT    1680

AACTCAGCAG CCTTGCTCCA ACGTTACAGG GTTCGTATCA GATACGCAAG CACTACCAAT    1740

CTTCGCCTCT TTGTCCAGAA CAGCAACAAT GATTTCCTTG TCATCTACAT CAACAAGACT    1800

ATGAACAAAG ACGATGACCT CACCTACCAA ACATTCGATC TTGCCACTAC CAATAGTAAC    1860
```

```
ATGGGATTCT CTGGTGACAA GAACGAGCTG ATCATAGGTG CTGAGAGCTT TGTCTCTAAT      1920

GAGAAGATTT ACATAGACAA GATCGAGTTC ATTCCAGTTC AACTCTAATA GATCCCCCGG      1980

GCTGCAGGAA TTCGATATCA                                                  2000
```

(2) INFORMATION FOR SEQ ID NO:100:

(i) SEQUENCE CHARACTERISTICS:
        (A) LENGTH: 653 amino acids
        (B) TYPE: amino acid
        (C) STRANDEDNESS:
        (D) TOPOLOGY: linear (xi) SEQUENCE DESCRIPTION: SEQ ID NO:100:

```
Met Ala Asn Pro Asn Asn Arg Ser Glu His Asp Thr Ile Lys Val Thr
1               5                   10                  15

Pro Asn Ser Glu Leu Gln Thr Asn His Asn Gln Tyr Pro Leu Ala Asp
            20                  25                  30

Asn Pro Asn Ser Thr Leu Glu Glu Leu Asn Tyr Lys Glu Phe Leu Arg
        35                  40                  45

Met Thr Glu Asp Ser Ser Thr Glu Val Leu Asp Asn Ser Thr Val Lys
    50                  55                  60

Asp Ala Val Gly Thr Gly Ile Ser Val Val Gly Gln Ile Leu Gly Val
65                  70                  75                  80

Val Gly Val Pro Phe Ala Gly Ala Leu Thr Ser Phe Tyr Gln Ser Phe
                85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125

Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255

Arg Gly Ser Thr Tyr Asp Ala Trp Val Lys Phe Asn Arg Phe Arg Arg
            260                 265                 270

Glu Met Thr Leu Thr Val Leu Asp Leu Ile Val Leu Phe Pro Phe Tyr
        275                 280                 285

Asp Ile Arg Leu Tyr Ser Lys Gly Val Lys Thr Glu Leu Thr Arg Asp
    290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
```

```
            325                 330                 335
Asp Tyr Leu Gln Gly Ile Glu Phe His Thr Arg Leu Gln Pro Gly Tyr
            340                 345                 350
Phe Gly Lys Asp Ser Phe Asn Tyr Trp Ser Gly Asn Tyr Val Glu Thr
            355                 360                 365
Arg Pro Ser Ile Gly Ser Ser Lys Thr Ile Thr Ser Pro Phe Tyr Gly
            370                 375                 380
Asp Lys Ser Thr Glu Pro Val Gln Lys Leu Ser Phe Asp Gly Gln Lys
385                 390                 395                 400
Val Tyr Arg Thr Ile Ala Asn Thr Asp Val Ala Ala Trp Pro Asn Gly
                    405                 410                 415
Lys Val Tyr Leu Gly Val Thr Lys Val Asp Phe Ser Gln Tyr Asp Asp
                    420                 425                 430
Gln Lys Asn Glu Thr Ser Thr Gln Thr Tyr Asp Ser Lys Arg Asn Asn
                    435                 440                 445
Gly His Val Ser Ala Gln Asp Ser Ile Asp Gln Leu Pro Pro Glu Thr
                    450                 455                 460
Thr Asp Glu Pro Leu Glu Lys Ala Tyr Ser His Gln Leu Asn Tyr Ala
465                 470                 475                 480
Glu Cys Phe Leu Met Gln Asp Arg Arg Gly Thr Ile Pro Phe Phe Thr
                    485                 490                 495
Trp Thr His Arg Ser Val Asp Phe Phe Asn Thr Ile Asp Ala Glu Lys
                    500                 505                 510
Ile Thr Gln Leu Pro Val Val Lys Ala Tyr Ala Leu Ser Ser Gly Ala
                    515                 520                 525
Ser Ile Ile Glu Gly Pro Gly Phe Thr Gly Gly Asn Leu Leu Phe Leu
                    530                 535                 540
Lys Glu Ser Ser Asn Ser Ile Ala Lys Phe Lys Val Thr Leu Asn Ser
545                 550                 555                 560
Ala Ala Leu Leu Gln Arg Tyr Arg Val Arg Ile Arg Tyr Ala Ser Thr
                    565                 570                 575
Thr Asn Leu Arg Leu Phe Val Gln Asn Ser Asn Asn Asp Phe Leu Val
                    580                 585                 590
Ile Tyr Ile Asn Lys Thr Met Asn Lys Asp Asp Asp Leu Thr Tyr Gln
                    595                 600                 605
Thr Phe Asp Leu Ala Thr Thr Asn Ser Asn Met Gly Phe Ser Gly Asp
                    610                 615                 620
Lys Asn Glu Leu Ile Ile Gly Ala Glu Ser Phe Val Ser Asn Glu Lys
625                 630                 635                 640
Ile Tyr Ile Asp Lys Ile Glu Phe Ile Pro Val Gln Leu
                    645                 650

(2) INFORMATION FOR SEQ ID NO:101:

(i) SEQUENCE CHARACTERISTICS:
        (A) LENGTH: 2050 base pairs
        (B) TYPE: nucleic acid
        (C) STRANDEDNESS: single
        (D) TOPOLOGY: linear (xi) SEQUENCE DESCRIPTION: SEQ ID NO:101:

TGGAGCTCCA CCGCGGTGGC GGCCGCTCTA GAACTAGTGG ATCTAGGCCT CCATATGAAC      60

CCTAACAATC GTTCCGAACA CGACACCATC AAGGTTACTC AAACTCTGA GTTGCAAACT      120

AATCACAACC AGTACCCATT GGCTGACAAT CCTAACAGTA CTCTTGAGGA ACTTAACTAC     180
```

```
AAGGAGTTTC TCCGGATGAC CGAAGATAGC TCCACTGAGG TTCTCGATAA CTCTACAGTG    240

AAGGACGCTG TTGGAACTGG CATTAGCGTT GTGGGACAGA TTCTTGGAGT GGTTGGTGTT    300

CCATTCGCTG GAGCTTTGAC CAGCTTCTAC CAGTCCTTTC TCAACACCAT CTGGCCTTCA    360

GATGCTGATC CCTGGAAGGC TTTCATGGCC CAAGTGGAAG TCTTGATCGA TAAGAAGATC    420

GAAGAGTATG CCAAGTCTAA AGCCTTGGCT GAGTTGCAAG GTTTGCAGAA CAACTTCGAG    480

GATTACGTCA ACGCACTCAA CAGCTGGAAG AAAACTCCCT TGAGTCTCAG GTCTAAGCGT    540

TCCCAGGACC GTATTCGTGA ACTTTTCAGC CAAGCCGAAT CCCACTTCAG AAACTCCATG    600

CCTAGCTTTG CCGTTTCTAA GTTCGAGGTG CTCTTCTTGC AACATACGC ACAAGCTGCC    660

AACACTCATC TCTTGCTTCT CAAAGACGCT CAGGTGTTTG GTGAGGAATG GGGTTACTCC    720

AGTGAAGATG TTGCCGAGTT CTACCATAGG CAGCTCAAGT TGACTCAACA GTACACAGAC    780

CACTGCGTCA ACTGGTACAA CGTTGGGCTC AATGGTCTTA GAGGATCTAC CTACGACGCA    840

TGGGTGAAGT TCAACAGGTT TCGTAGAGAG ATGACCTTGA CTGTGCTCGA TCTTATCGTT    900

CTCTTTCCAT TCTACGACAT TCGTCTTTAC TCCAAAGGCG TTAAGACAGA GCTGACCAGA    960

GACATCTTCA CCGATCCCAT CTTCTCACTT AACACCCTGC AGGAATACGG TCCAACTTTT   1020

CTCTCCATTG AGAACAGCAT CAGGAAGCCT CACCTCTTCG ACTATCTGCA AGGCATTGAG   1080

TTTCACACCA GGTTGCAACC TGGTTACTTC GGTAAGGATT CCTTCAACTA CTGGAGCGGA   1140

AACTACGTTG AAACCAGACC ATCCATCGGA TCTAGCAAGA CCATCACTTC TCCATTCTAC   1200

GGTGACAAGA GCACTGAGCC AGTGCAGAAG TTGAGCTTCG ATGGGCAGAA GGTGTATAGA   1260

ACCATCGCCA ATACCGATGT TGCAGCTTGG CCTAATGGCA AGGTCTACCT TGGAGTTACT   1320

AAAGTGGACT TCTCCCAATA CGACGATCAG AAGAACGAGA CATCTACTCA AACCTACGAT   1380

AGTAAGAGGA ACAATGGCCA TGTTTCCGCA CAAGACTCCA TTGACCAACT TCCACCTGAA   1440

ACCACTGATG AACCATTGGA GAAGGCTTAC AGTCACCAAC TTAACTACGC CGAATGCTTT   1500

CTCATGCAAG ACAGGCGTGG CACCATTCCG TTCTTTACAT GGACTCACAG GTCTGTCGAC   1560

TTCTTTAACA CTATCGACGC TGAGAAGATT ACCCAACTTC CCGTGGTCAA GGCTTATGCC   1620

TTGTCCAGCG GAGCTTCCAT CATTGAAGGT CCAGGCTTCA CCGGTGGCAA CTTGCTCTTC   1680

CTTAAGGAGT CCAGCAACTC CATCGCCAAG TTCAAAGTGA CACTTAACTC AGCAGCCTTG   1740

CTCCAACGTT ACAGGGTTCG TATCAGATAC GCAAGCACTA CCAATCTTCG CCTCTTTGTC   1800

CAGAACAGCA ACAATGATTT CCTTGTCATC TACATCAACA AGACTATGAA CAAAGACGAT   1860

GACCTCACCT ACAACACATT CGATCTTGCC ACTACCAATA GTAACATGGG ATTCTCTGGT   1920

GACAAGAACG AGCTGATCAT AGGTGCTGAG AGCTTTGTCT CTAATGAGAA GATTTACATA   1980

GACAAGATCG AGTTCATTCC AGTTCAACTC TAATAGATCC CCCGGGCTGC AGGAATTCGA   2040

TATCAAGCTT                                                          2050
```

(2) INFORMATION FOR SEQ ID NO:102:

(i) SEQUENCE CHARACTERISTICS:
        (A) LENGTH: 2280 base pairs
        (B) TYPE: nucleic acid
        (C) STRANDEDNESS: single
        (D) TOPOLOGY: linear (xi) SEQUENCE DESCRIPTION: SEQ ID NO:102:

```
TTAAAATTAA TTTTGTATAC TTTTCATTGT AATAATATGA TTTAAAAAC GAAAAGTGC      60

ATATACAACT TATCAGGAGG GGGGGGATGC ACAAAGAAGA AAGAATAAG AAGTGAATGT    120
```

```
TTATAATGTT CAATAGTTTT ATGGGAAGGC ATTTTATCAG GTAGAAAGTT ATGTATTATG    180

ATAAGAATGG GAGGAAGAAA AATGAATCCA AACAATCGAA GTGAACATGA TACGATAAAG    240

GTTACACCTA ACAGTGAATT GCAAACTAAC CATAATCAAT ATCCTTTAGC TGACAATCCA    300

AATTCAACAC TAGAAGAATT AAATTATAAA GAATTTTTAA GAATGACTGA AGACAGTTCT    360

ACGGAAGTGC TAGACAACTC TACAGTAAAA GATGCAGTTG GGACAGGAAT TTCTGTTGTA    420

GGGCAGATTT TAGGTGTTGT AGGAGTTCCA TTTGCTGGGG CACTCACTTC ATTTTATCAA    480

TCATTTCTTA ACACTATATG GCCAAGTGAT GCTGACCCAT GGAAGGCTTT TATGGCACAA    540

GTTGAAGTAC TGATAGATAA GAAAATAGAG GAGTATGCTA AAAGTAAAGC TCTTGCAGAG    600

TTACAGGGTC TTCAAAATAA TTTCGAAGAT TATGTTAATG CGTTAAATTC CTGGAAGAAA    660

ACACCTTTAA GTTTGCGAAG TAAAAGAAGC CAAGATCGAA TAAGGGAACT TTTTTCTCAA    720

GCAGAAAGTC ATTTTCGTAA TTCCATGCCG TCATTTGCAG TTTCCAAATT CGAAGTGCTG    780

TTTCTACCAA CATATGCACA AGCTGCAAAT ACACATTTAT TGCTATTAAA AGATGCTCAA    840

GTTTTTGGAG AAGAATGGGG ATATTCTTCA GAAGATGTTG CTGAATTTTA TCATAGACAA    900

TTAAAACTTA CACAACAATA CACTGACCAT TGTGTTAATT GGTATAATGT TGGATTAAAT    960

GGTTTAAGAG GTTCAACTTA TGATGCATGG GTCAAATTTA ACCGTTTTCG CAGAGAAATG   1020

ACTTTAACTG TATTAGATCT AATTGTACTT TTCCCATTTT ATGATATTCG GTTATACTCA   1080

AAAGGGGTTA AAACAGAACT AACAAGAGAC ATTTTTACGG ATCCAATTTT TTCACTTAAT   1140

ACTCTTCAGG AGTATGGACC AACTTTTTTG AGTATAGAAA ACTCTATTCG AAAACCTCAT   1200

TTATTTGATT ATTTACAGGG GATTGAATTT CATACGCGTC TTCAACCTGG TTACTTTGGG   1260

AAAGATTCTT TCAATTATTG GTCTGGTAAT TATGTAGAAA CTAGACCTAG TATAGGATCT   1320

AGTAAGACAA TTACTTCCCC ATTTTATGGA GATAAATCTA CTGAACCTGT ACAAAAGCTA   1380

AGCTTTGATG GACAAAAAGT TTATCGAACT ATAGCTAATA CAGACGTAGC GGCTTGGCCG   1440

AATGGTAAGG TATATTTAGG TGTTACGAAA GTTGATTTTA GTCAATATGA TGATCAAAAA   1500

AATGAAACTA GTACACAAAC ATATGATTCA AAAAGAAACA ATGGCCATGT AAGTGCACAG   1560

GATTCTATTG ACCAATTACC GCCAGAAACA ACAGATGAAC CACTTGAAAA AGCATATAGT   1620

CATCAGCTTA ATTACGCGGA ATGTTTCTTA ATGCAGGACC GTCGTGGAAC AATTCCATTT   1680

TTTACTTGGA CACATAGAAG TGTAGACTTT TTTAATACAA TTGATGCTGA AAAGATTACT   1740

CAACTTCCAG TAGTGAAAGC ATATGCCTTG TCTTCAGGTG CTTCCATTAT TGAAGGTCCA   1800

GGATTCACAG GAGGAAATTT ACTATTCCTA AAAGAATCTA GTAATTCAAT TGCTAAATTT   1860

AAAGTTACAT TAAATTCAGC AGCCTTGTTA CAACGTATAT CGTGTAAGAAT ACGCTATGCT   1920

TCTACCACTA ACTTACGACT TTTTGTGCAA AATTCAAACA ATGATTTTCT TGTCATCTAC   1980

ATTAATAAAA CTATGAATAA AGATGATGAT TTAACATATC AAACATTTGA TCTCGCAACT   2040

ACTAATTCTA ATATGGGGTT CTCGGGTGAT AAGAATGAAC TTATAATAGG AGCAGAATCT   2100

TTCGTTTCTA ATGAAAAAAT CTATATAGAT AAGATAGAAT TTATCCCAGT ACAATTGTAA   2160

GGAGATTTTA AAATGTTGGG TGATGGTCAA AATGAAAGAA TAGGAAGGTG AATTTTGATG   2220

GTTAGGAAAG ATTCTTTTAA CAAAAGCAAC ATGGAAAAGT ATACAGTACA AATATTAACC   2280
```

(2) INFORMATION FOR SEQ ID NO:103:

(i) SEQUENCE CHARACTERISTICS:
        (A) LENGTH: 32 base pairs
        (B) TYPE: nucleic acid
        (C) STRANDEDNESS: single (D) TOPOLOGY: linear (xi) SEQUENCE DESCRIPTION: SEQ ID NO:103:

TAGGCCTCCA TCCATGGCAA ACCCTAACAA TC                                      32

(2) INFORMATION FOR SEQ ID NO:104:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:104:

TCCCATCTTC CTACTTACGA CCCTGCAGAA ATACGGTCCA AC                           42

(2) INFORMATION FOR SEQ ID NO:105:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:105:

GACCTCACCT ACCAAACATT CGATCTTG                                           28

(2) INFORMATION FOR SEQ ID NO:106:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:106:

CGAGTTCTAC CGTAGGCAGC TCAAG                                              25

(2) INFORMATION FOR SEQ ID NO:107:

(i) SEQUENCE CHARACTERISTICS:
        (A) LENGTH: 1959 base pairs
        (B) TYPE: nucleic acid
        (C) STRANDEDNESS: single
        (D) TOPOLOGY: linear (xi) SEQUENCE DESCRIPTION: SEQ ID NO:107:

ATGAATCCAA ACAATCGAAG TGAACATGAT ACGATAAAGG TTACACCTAA CAGTGAATTG         60

CAAACTAACC ATAATCAATA TCCTTTAGCT GACAATCCAA ATTCAACACT AGAAGAATTA        120

AATTATAAAG AATTTTTAAG AATGACTGAA GACAGTTCTA CGGAAGTGCT AGACAACTCT        180

ACAGTAAAAG ATGCAGTTGG GACAGGAATT TCTGTTGTAG GGCAGATTTT AGGTGTTGTA        240

GGAGTTCCAT TTGCTGGGGC ACTCACTTCA TTTTATCAAT CATTTCTTAA CACTATATGG        300

CCAAGTGATG CTGACCCATG GAAGGCTTTT ATGGCACAAG TTGAAGTACT GATAGATAAG        360

AAAATAGAGG AGTATGCTAA AAGTAAAGCT CTTGCAGAGT TACAGGGTCT TCAAAATAAT        420

TTCGAAGATT ATGTTAATGC GTTAAATTCC TGGAAGAAAA CACCTTTAAG TTTGCGAAGT        480

AAAAGAAGCC AAGGTCGAAT AAGGGAACTT TTTTCTCAAG CAGAAAGTCA TTTTCGTAAT        540

TCCATGCCGT CATTTGCAGT TTCCAAATTC GAAGTGCTGT TTCTACCAAC ATATGCACAA        600

GCTGCAAATA CACATTTATT GCTATTAAAA GATGCTCAAG TTTTTGGAGA AGAATGGGGA        660

TATTCTTCAG AAGATGTTGC TGAATTCTAT CGTAGACAAT AAAACTTAC ACAACAATAC        720

```
ACTGACCATT GTGTTAATTG GTATAATGTT GGATTAAATG GTTAAGAGG TTCAACTTAT      780

GATGCATGGG TCAAATTTAA CCGTTTTCGC AGAGAAATGA CTTTAACTGT ATTAGATCTA      840

ATTGTACTTT TCCCATTTTA TGATATTCGG TTATACTCAA AAGGGGTTAA AACAGAACTA      900

ACAAGAGACA TTTTTACGGA TCCAATTTTT TTACTTACTA CGCTTCAGAA GTACGGACCA      960

ACTTTTTTGA GTATAGAAAA CTCTATTCGA AAACCTCATT TATTTGATTA TTTACAGGGG     1020

ATTGAATTTC ATACGCGTCT TCAACCTGGT TACTTTGGGA AAGATTCTTT CAATTATTGG     1080

TCTGGTAATT ATGTAGAAAC TAGACCTAGT ATAGGATCTA GTAAGACAAT TACTTCCCCA     1140

TTTTATGGAG ATAAATCTAC TGAACCTGTA CAAAAGCTAA GCTTTGATGG ACAAAAAGTT     1200

TATCGAACTA TAGCTAATAC AGACGTAGCG GCTTGGCCGA ATGGTAAGGT ATATTTAGGT     1260

GTTACGAAAG TTGATTTTAG TCAATATGAT GATCAAAAAA ATGAAACTAG TACACAAACA     1320

TATGATTCAA AAAGAAACAA TGGCCATGTA AGTGCACAGG ATTCTATTGA CCAATTACCG     1380

CCAGAAACAA CAGATGAACC ACTTGAAAAA GCATATAGTC ATCAGCTTAA TTACGCGGAA     1440

TGTTTCTTAA TGCAGGACCG TCGTGGAACA ATTCCATTTT TTACTTGGAC ACATAGAAGT     1500

GTAGACTTTT TTAATACAAT TGATGCTGAA AAGATTACTC AACTTCCAGT AGTGAAAGCA     1560

TATGCCTTGT CTTCAGGTGC TTCCATTATT GAAGGTCCAG GATTCACAGG AGGAAATTTA     1620

CTATTCCTAA AAGAATCTAG TAATTCAATT GCTAAATTTA AAGTTACATT AAATTCAGCA     1680

GCCTTGTTAC AACGATATCG TGTAAGAATA CGCTATGCTT CTACCACTAA CTTACGACTT     1740

TTTGTGCAAA ATTCAAACAA TGATTTTCTT GTCATCTACA TTAATAAAAC TATGAATAAA     1800

GATGATGATT TAACATATCA AACATTTGAT CTCGCAACTA CTAATTCTAA TATGGGGTTC     1860

TCGGGTGATA AGAATGAACT TATAATAGGA GCAGAATCTT TCGTTTCTAA TGAAAAAATC     1920

TATATAGATA AGATAGAATT TATCCCAGTA CAATTGTAA                            1959

(2) INFORMATION FOR SEQ ID NO:108:

(i) SEQUENCE CHARACTERISTICS:
        (A) LENGTH: 652 amino acids
        (B) TYPE: amino acid
        (C) STRANDEDNESS:
        (D) TOPOLOGY: linear (xi) SEQUENCE DESCRIPTION: SEQ ID NO:108:

Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asn Thr Ile Trp Pro Ser Asp Ala Asp Pro Trp Lys Ala Phe Met Ala
            100                 105                 110

Gln Val Glu Val Leu Ile Asp Lys Lys Ile Glu Glu Tyr Ala Lys Ser
        115                 120                 125

Lys Ala Leu Ala Glu Leu Gln Gly Leu Gln Asn Asn Phe Glu Asp Tyr
```

-continued

```
            130                 135                 140
Val Asn Ala Leu Asn Ser Trp Lys Lys Thr Pro Leu Ser Leu Arg Ser
145                 150                 155                 160
Lys Arg Ser Gln Gly Arg Ile Arg Glu Leu Phe Ser Gln Ala Glu Ser
                165                 170                 175
His Phe Arg Asn Ser Met Pro Ser Phe Ala Val Ser Lys Phe Glu Val
                180                 185                 190
Leu Phe Leu Pro Thr Tyr Ala Gln Ala Asn Thr His Leu Leu Leu
            195                 200                 205
Leu Lys Asp Ala Gln Val Phe Gly Glu Glu Trp Gly Tyr Ser Ser Glu
    210                 215                 220
Asp Val Ala Glu Phe Tyr Arg Arg Gln Leu Lys Leu Thr Gln Gln Tyr
225                 230                 235                 240
Thr Asp His Cys Val Asn Trp Tyr Asn Val Gly Leu Asn Gly Leu Arg
                245                 250                 255
Gly Ser Thr Tyr Asp Ala Trp Val Lys Phe Asn Arg Phe Arg Arg Glu
                260                 265                 270
Met Thr Leu Thr Val Leu Asp Leu Ile Val Leu Phe Pro Phe Tyr Asp
            275                 280                 285
Ile Arg Leu Tyr Ser Lys Gly Val Lys Thr Glu Leu Thr Arg Asp Ile
    290                 295                 300
Phe Thr Asp Pro Ile Phe Leu Leu Thr Thr Leu Gln Lys Tyr Gly Pro
305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Gln Pro Gly Tyr Phe
            340                 345                 350
Gly Lys Asp Ser Phe Asn Tyr Trp Ser Gly Asn Tyr Val Glu Thr Arg
    355                 360                 365
Pro Ser Ile Gly Ser Ser Lys Thr Ile Thr Ser Pro Phe Tyr Gly Asp
370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
            420                 425                 430
Lys Asn Glu Thr Ser Thr Gln Thr Tyr Asp Ser Lys Arg Asn Asn Gly
            435                 440                 445
His Val Ser Ala Gln Asp Ser Ile Asp Gln Leu Pro Pro Glu Thr Thr
    450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Asn Thr Ile Asp Ala Glu Lys Ile
                500                 505                 510
Thr Gln Leu Pro Val Val Lys Ala Tyr Ala Leu Ser Ser Gly Ala Ser
            515                 520                 525
Ile Ile Glu Gly Pro Gly Phe Thr Gly Gly Asn Leu Leu Phe Leu Lys
    530                 535                 540
Glu Ser Ser Asn Ser Ile Ala Lys Phe Lys Val Thr Leu Asn Ser Ala
545                 550                 555                 560
```

```
Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Asp Leu Thr Tyr Gln Thr
            595                 600                 605

Phe Asp Leu Ala Thr Thr Asn Ser Asn Met Gly Phe Ser Gly Asp Lys
            610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:109:

(i) SEQUENCE CHARACTERISTICS:
        (A) LENGTH: 649 amino acids
        (B) TYPE: amino acid
        (C) STRANDEDNESS:
        (D) TOPOLOGY: linear (xi) SEQUENCE DESCRIPTION: SEQ ID NO:109:

Met Asn Pro Asn Asn Arg Ser Glu His Asp Thr Ile Lys Ala Thr Glu
1               5                   10                  15

Asn Asn Glu Val Ser Asn Asn His Ala Gln Tyr Pro Leu Ala Asp Thr
            20                  25                  30

Pro Thr Leu Glu Glu Leu Asn Tyr Lys Glu Phe Leu Arg Arg Thr Thr
            35                  40                  45

Asp Asn Asn Val Glu Ala Leu Asp Ser Ser Thr Thr Lys Asp Ala Ile
    50                  55                  60

Gln Lys Gly Ile Ser Ile Ile Gly Asp Leu Leu Gly Val Val Gly Phe
65                  70                  75                  80

Pro Tyr Gly Gly Ala Leu Val Ser Phe Tyr Thr Asn Leu Leu Asn Thr
                85                  90                  95

Ile Trp Pro Gly Glu Asp Pro Leu Lys Ala Phe Met Gln Gln Val Glu
            100                 105                 110

Ala Leu Ile Asp Gln Lys Ile Ala Asp Tyr Ala Lys Asp Lys Ala Thr
            115                 120                 125

Ala Glu Leu Gln Gly Leu Lys Asn Val Phe Lys Asp Tyr Val Ser Ala
        130                 135                 140

Leu Asp Ser Trp Asp Lys Thr Pro Leu Thr Leu Arg Asp Gly Arg Ser
145                 150                 155                 160

Gln Gly Arg Ile Arg Glu Leu Phe Ser Gln Ala Glu Ser His Phe Arg
                165                 170                 175

Arg Ser Met Pro Ser Phe Ala Val Ser Gly Tyr Glu Val Leu Phe Leu
            180                 185                 190

Pro Thr Tyr Ala Gln Ala Ala Asn Thr His Leu Leu Leu Leu Lys Asp
            195                 200                 205

Ala Gln Ile Tyr Gly Thr Asp Trp Gly Tyr Ser Thr Asp Asp Leu Asn
        210                 215                 220

Glu Phe His Thr Lys Gln Lys Asp Leu Thr Ile Glu Tyr Thr Asn His
225                 230                 235                 240

Cys Ala Lys Trp Tyr Lys Ala Gly Leu Asp Lys Leu Arg Gly Ser Thr
                245                 250                 255

Tyr Glu Glu Trp Val Lys Phe Asn Arg Tyr Arg Arg Glu Met Thr Leu
```

```
                260                 265                 270
Thr Val Leu Asp Leu Ile Thr Leu Phe Pro Leu Tyr Asp Val Arg Thr
            275                 280                 285

Tyr Thr Lys Gly Val Lys Thr Glu Leu Thr Arg Asp Val Leu Thr Asp
290                 295                 300

Pro Ile Val Ala Val Asn Asn Met Asn Gly Tyr Gly Thr Thr Phe Ser
305                 310                 315                 320

Asn Ile Glu Asn Tyr Ile Arg Lys Pro His Leu Phe Asp Tyr Leu His
            325                 330                 335

Ala Ile Gln Phe His Ser Arg Leu Gln Pro Gly Tyr Phe Gly Thr Asp
            340                 345                 350

Ser Phe Asn Tyr Trp Ser Gly Asn Tyr Val Ser Thr Arg Ser Ser Ile
            355                 360                 365

Gly Ser Asp Glu Ile Ile Arg Ser Pro Phe Tyr Gly Asn Lys Ser Thr
370                 375                 380

Leu Asp Val Gln Asn Leu Glu Phe Asn Gly Glu Lys Val Phe Arg Ala
385                 390                 395                 400

Val Ala Asn Gly Asn Leu Ala Val Trp Pro Val Gly Thr Gly Gly Thr
                405                 410                 415

Lys Ile His Ser Gly Val Thr Lys Val Gln Phe Ser Gln Tyr Asn Asp
            420                 425                 430

Arg Lys Asp Glu Val Arg Thr Gln Thr Tyr Asp Ser Lys Arg Asn Val
            435                 440                 445

Gly Gly Ile Val Phe Asp Ser Ile Asp Gln Leu Pro Pro Ile Thr Thr
            450                 455                 460

Asp Glu Ser Leu Glu Lys Ala Tyr Ser His Gln Leu Asn Tyr Val Arg
465                 470                 475                 480

Cys Phe Leu Leu Gln Gly Gly Arg Gly Ile Ile Pro Val Phe Thr Trp
                485                 490                 495

Thr His Lys Ser Val Asp Phe Tyr Asn Thr Leu Asp Ser Glu Lys Ile
            500                 505                 510

Thr Gln Ile Pro Phe Val Lys Ala Phe Ile Leu Val Asn Ser Thr Ser
            515                 520                 525

Val Val Ala Gly Pro Gly Phe Thr Gly Gly Asp Ile Ile Lys Cys Thr
            530                 535                 540

Asn Gly Ser Gly Leu Thr Leu Tyr Val Thr Pro Ala Pro Asp Leu Thr
545                 550                 555                 560

Tyr Ser Lys Thr Tyr Lys Ile Arg Ile Arg Tyr Ala Ser Thr Ser Gln
                565                 570                 575

Val Arg Phe Gly Ile Asp Leu Gly Ser Tyr Thr His Ser Ile Ser Tyr
            580                 585                 590

Phe Asp Lys Thr Met Asp Lys Gly Asn Thr Leu Thr Tyr Asn Ser Phe
            595                 600                 605

Asn Leu Ser Ser Val Ser Arg Pro Ile Glu Ile Ser Gly Gly Asn Lys
610                 615                 620

Ile Gly Val Ser Val Gly Gly Ile Gly Ser Gly Asp Glu Val Tyr Ile
625                 630                 635                 640

Asp Lys Ile Glu Phe Ile Pro Met Asp
                645
```

(2) INFORMATION FOR SEQ ID NO:110:

(i) SEQUENCE CHARACTERISTICS:
        (A) LENGTH: 652 amino acids (B) TYPE: amino acid
(C) STRANDEDNESS:
(D) TOPOLOGY: linear (xi) SEQUENCE DESCRIPTION: SEQ ID NO:110:

```
Met Asn Pro Asn Asn Arg Ser Glu His Asp Thr Ile Lys Val Thr Pro
1               5                   10                  15

Asn Ser Glu Leu Pro Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
            35                  40                  45

Thr Glu Asp Ser Ser Thr Glu Val Leu Asp Asn Ser Thr Val Lys Asp
            50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

Asp Thr Ile Trp Pro Ser Asp Ala Asp Pro Trp Lys Ala Phe Met Ala
                100                 105                 110

Gln Val Glu Val Leu Ile Asp Lys Lys Ile Glu Glu Tyr Ala Lys Ser
            115                 120                 125

Lys Ala Leu Ala Glu Leu Gln Gly Leu Gln Asn Asn Phe Glu Asp Tyr
            130                 135                 140

Val Asn Ala Leu Asn Ser Trp Lys Lys Thr Pro Leu Ser Leu Arg Ser
145                 150                 155                 160

Lys Arg Ser Gln Asp Arg Ile Arg Glu Leu Phe Ser Gln Ala Glu Ser
                165                 170                 175

His Phe Arg Asn Ser Met Pro Ser Phe Ala Val Ser Lys Phe Glu Val
                180                 185                 190

Leu Phe Leu Pro Thr Tyr Ala Gln Ala Ala Asn Thr His Leu Leu Leu
            195                 200                 205

Leu Lys Asp Ala Gln Val Phe Gly Glu Glu Trp Gly Tyr Ser Ser Glu
210                 215                 220

Asp Val Ala Glu Phe Tyr His Arg Gln Leu Lys Leu Thr Gln Gln Tyr
225                 230                 235                 240

Thr Asp His Cys Val Asn Trp Tyr Asn Val Gly Leu Asn Gly Leu Arg
                245                 250                 255

Gly Ser Thr Tyr Asp Ala Trp Val Lys Phe Asn Arg Phe Arg Arg Glu
            260                 265                 270

Met Thr Leu Thr Val Leu Asp Leu Ile Val Leu Phe Pro Phe Tyr Asp
            275                 280                 285

Val Arg Leu Tyr Ser Lys Gly Val Lys Thr Glu Leu Thr Arg Asp Ile
290                 295                 300

Phe Thr Asp Pro Ile Phe Ser Leu Asn Thr Leu Gln Glu Tyr Gly Pro
305                 310                 315                 320

Thr Phe Leu Ser Ile Glu Asn Ser Ile Arg Lys Pro His Leu Phe Asp
                325                 330                 335

Tyr Leu Gln Gly Ile Glu Phe His Thr Arg Leu Gln Pro Gly Tyr Ser
            340                 345                 350

Gly Lys Asp Ser Phe Asn Tyr Trp Ser Gly Asn Tyr Val Glu Thr Arg
            355                 360                 365

Pro Ser Ile Gly Ser Ser Lys Thr Ile Thr Ser Pro Phe Tyr Gly Asp
            370                 375                 380

Lys Ser Thr Glu Pro Val Gln Lys Leu Ser Phe Asp Gly Gln Lys Val
```

-continued

```
                385                 390                 395                 400

Tyr Arg Thr Ile Ala Asn Thr Asp Val Ala Ala Trp Pro Asn Gly Lys
                    405                 410                 415

Ile Tyr Phe Gly Val Thr Lys Val Asp Phe Ser Gln Tyr Asp Asp Gln
                    420                 425                 430

Lys Asn Glu Thr Ser Thr Gln Thr Tyr Asp Ser Lys Arg Asn Asn Gly
                    435                 440                 445

His Val Gly Ala Gln Asp Ser Ile Asp Gln Leu Pro Pro Glu Thr Thr
                    450                 455                 460

Asp Glu Pro Leu Glu Lys Ala Tyr Ser His Gln Leu Asn Tyr Ala Glu
465                 470                 475                 480

Cys Phe Leu Met Gln Asp Arg Arg Gly Thr Ile Pro Phe Phe Thr Trp
                    485                 490                 495

Thr His Arg Ser Val Asp Phe Asn Thr Ile Asp Ala Glu Lys Ile
                    500                 505                 510

Thr Gln Leu Pro Val Val Lys Ala Tyr Ala Leu Ser Ser Gly Ala Ser
                    515                 520                 525

Ile Ile Glu Gly Pro Gly Phe Thr Gly Gly Asn Leu Leu Phe Leu Lys
                    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                    565                 570                 575

Asn Leu Arg Leu Phe Val Gln Asn Ser Asn Asn Asp Phe Ile Val Ile
                    580                 585                 590

Tyr Ile Asn Lys Thr Met Asn Ile Asp Asp Asp Leu Thr Tyr Gln Thr
                    595                 600                 605

Phe Asp Leu Ala Thr Thr Asn Ser Asn Met Gly Phe Ser Gly Asp Thr
                    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                    645                 650

(2) INFORMATION FOR SEQ ID NO:111:

(i) SEQUENCE CHARACTERISTICS:
        (A) LENGTH: 652 amino acids
        (B) TYPE: amino acid
        (C) STRANDEDNESS:
        (D) TOPOLOGY: linear (xi) SEQUENCE DESCRIPTION: SEQ ID NO:111:

Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
                    20                  25                  30

Pro Asn Ser Thr Leu Glu Glu Leu Asn Tyr Lys Glu Phe Leu Arg Met
                    35                  40                  45

Thr Glu Asp Ser Ser Thr Glu Val Leu Asp Asn Ser Thr Val Lys Asp
                    50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                    85                  90                  95
```

-continued

```
Asn Thr Ile Trp Pro Ser Asp Ala Asp Pro Trp Lys Ala Phe Met Ala
            100                 105                 110
Gln Val Glu Val Leu Ile Asp Lys Lys Ile Glu Glu Tyr Ala Lys Ser
        115                 120                 125
Lys Ala Leu Ala Glu Leu Gln Gly Leu Gln Asn Asn Phe Glu Asp Tyr
    130                 135                 140
Val Asn Ala Leu Asn Ser Trp Lys Lys Thr Pro Leu Ser Leu Arg Ser
145                 150                 155                 160
Lys Arg Ser Gln Asp Arg Ile Arg Glu Leu Phe Ser Gln Ala Glu Ser
                165                 170                 175
His Phe Arg Asn Ser Met Pro Ser Phe Ala Val Ser Lys Phe Glu Val
            180                 185                 190
Leu Phe Leu Pro Thr Tyr Ala Gln Ala Ala Asn Thr His Leu Leu Leu
        195                 200                 205
Leu Lys Asp Ala Gln Val Phe Gly Glu Glu Trp Gly Tyr Ser Ser Glu
    210                 215                 220
Asp Val Ala Glu Phe Tyr His Arg Gln Leu Lys Leu Thr Gln Gln Tyr
225                 230                 235                 240
Thr Asp His Cys Val Asn Trp Tyr Asn Val Gly Leu Asn Gly Leu Arg
                245                 250                 255
Gly Ser Thr Tyr Asp Ala Trp Val Lys Phe Asn Arg Phe Arg Arg Glu
            260                 265                 270
Met Thr Leu Thr Val Leu Asp Leu Ile Val Leu Phe Pro Phe Tyr Asp
        275                 280                 285
Ile Arg Leu Tyr Ser Lys Gly Val Lys Thr Glu Leu Thr Arg Asp Ile
    290                 295                 300
Phe Thr Asp Pro Ile Phe Ser Leu Asn Thr Leu Gln Glu Tyr Gly Pro
305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Gln Pro Gly Tyr Phe
            340                 345                 350
Gly Lys Asp Ser Phe Asn Tyr Trp Ser Gly Asn Tyr Val Glu Thr Arg
        355                 360                 365
Pro Ser Ile Gly Ser Ser Lys Thr Ile Thr Ser Pro Phe Tyr Gly Asp
    370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
            420                 425                 430
Lys Asn Glu Thr Ser Thr Gln Thr Tyr Asp Ser Lys Arg Asn Asn Gly
        435                 440                 445
His Val Ser Ala Gln Asp Ser Ile Asp Gln Leu Pro Pro Glu Thr Thr
    450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Phe Asn Thr Ile Asp Ala Glu Lys Ile
            500                 505                 510
Thr Gln Leu Pro Val Val Lys Ala Tyr Ala Leu Ser Ser Gly Ala Ser
```

-continued

```
                515                 520                 525
Ile Ile Glu Gly Pro Gly Phe Thr Gly Gly Asn Leu Leu Phe Leu Lys
        530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
                580                 585                 590

Tyr Ile Asn Lys Thr Met Asn Lys Asp Asp Asp Leu Thr Tyr Gln Thr
                595                 600                 605

Phe Asp Leu Ala Thr Thr Asn Ser Asn Met Gly Phe Ser Gly Asp Lys
                610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

(2) INFORMATION FOR SEQ ID NO:112:

(i) SEQUENCE CHARACTERISTICS:
        (A) LENGTH: 659 amino acids
        (B) TYPE: amino acid
        (C) STRANDEDNESS:
        (D) TOPOLOGY: linear (xi) SEQUENCE DESCRIPTION: SEQ ID NO:112:

Met Ile Arg Met Gly Gly Arg Lys Met Asn Pro Asn Asn Arg Ser Glu
1               5                   10                  15

Tyr Asp Thr Ile Lys Val Thr Pro Asn Ser Glu Leu Pro Thr Asn His
                20                  25                  30

Asn Gln Tyr Pro Leu Ala Asp Asn Pro Asn Ser Thr Leu Glu Glu Leu
                35                  40                  45

Asn Tyr Lys Glu Phe Leu Arg Met Thr Ala Asp Asn Ser Thr Glu Val
            50                  55                  60

Leu Asp Ser Ser Thr Val Lys Asp Ala Val Gly Thr Gly Ile Ser Val
65                  70                  75                  80

Val Gly Gln Ile Leu Gly Val Val Gly Val Pro Phe Ala Gly Ala Leu
                85                  90                  95

Thr Ser Phe Tyr Gln Ser Phe Leu Asn Ala Ile Trp Pro Ser Asp Ala
                100                 105                 110

Asp Pro Trp Lys Ala Phe Met Ala Gln Val Glu Val Leu Ile Asp Lys
                115                 120                 125

Lys Ile Glu Glu Tyr Ala Lys Ser Lys Ala Leu Ala Glu Leu Gln Gly
            130                 135                 140

Leu Gln Asn Asn Phe Glu Asp Tyr Val Asn Ala Leu Asp Ser Trp Lys
145                 150                 155                 160

Lys Ala Pro Val Asn Leu Arg Ser Arg Arg Ser Gln Asp Arg Ile Arg
                165                 170                 175

Glu Leu Phe Ser Gln Ala Glu Ser His Phe Arg Asn Ser Met Pro Ser
                180                 185                 190

Phe Ala Val Ser Lys Phe Glu Val Leu Phe Leu Pro Thr Tyr Ala Gln
                195                 200                 205

Ala Ala Asn Thr His Leu Leu Leu Leu Lys Asp Ala Gln Val Phe Gly
            210                 215                 220
```

-continued

```
Glu Glu Trp Gly Tyr Ser Ser Glu Asp Ile Ala Glu Phe Tyr Gln Arg
225                 230                 235                 240

Gln Leu Lys Leu Thr Gln Gln Tyr Thr Asp His Cys Val Asn Trp Tyr
            245                 250                 255

Asn Val Gly Leu Asn Ser Leu Arg Gly Ser Thr Tyr Asp Ala Trp Val
                260                 265                 270

Lys Phe Asn Arg Phe Arg Arg Glu Met Thr Leu Thr Val Leu Asp Leu
            275                 280                 285

Ile Val Leu Phe Pro Phe Tyr Asp Val Arg Leu Tyr Ser Lys Gly Val
        290                 295                 300

Lys Thr Glu Leu Thr Arg Asp Ile Phe Thr Asp Pro Ile Phe Thr Leu
305                 310                 315                 320

Asn Ala Leu Gln Glu Tyr Gly Pro Thr Phe Ser Ser Ile Glu Asn Ser
                325                 330                 335

Ile Arg Lys Pro His Leu Phe Asp Tyr Leu Arg Gly Ile Glu Phe His
            340                 345                 350

Thr Arg Leu Arg Pro Gly Tyr Ser Gly Lys Asp Ser Phe Asn Tyr Trp
        355                 360                 365

Ser Gly Asn Tyr Val Glu Thr Arg Pro Ser Ile Gly Ser Asn Asp Thr
    370                 375                 380

Ile Thr Ser Pro Phe Tyr Gly Asp Lys Ser Ile Glu Pro Ile Gln Lys
385                 390                 395                 400

Leu Ser Phe Asp Gly Gln Lys Val Tyr Arg Thr Ile Ala Asn Thr Asp
                405                 410                 415

Ile Ala Ala Phe Pro Asp Gly Lys Ile Tyr Phe Gly Val Thr Lys Val
            420                 425                 430

Asp Phe Ser Gln Tyr Asp Asp Gln Lys Asn Glu Thr Ser Thr Gln Thr
        435                 440                 445

Tyr Asp Ser Lys Arg Tyr Asn Gly Tyr Leu Gly Ala Gln Asp Ser Ile
    450                 455                 460

Asp Gln Leu Pro Pro Glu Thr Thr Asp Glu Pro Leu Glu Lys Ala Tyr
465                 470                 475                 480

Ser His Gln Leu Asn Tyr Ala Glu Cys Phe Leu Met Gln Asp Arg Arg
                485                 490                 495

Gly Thr Ile Pro Phe Phe Thr Trp Thr His Arg Ser Val Asp Phe Phe
            500                 505                 510

Asn Thr Ile Asp Ala Glu Lys Ile Thr Gln Leu Pro Val Val Lys Ala
        515                 520                 525

Tyr Ala Leu Ser Ser Gly Ala Ser Ile Ile Glu Gly Pro Gly Phe Thr
    530                 535                 540

Gly Gly Asn Leu Leu Phe Leu Lys Glu Ser Ser Asn Ser Ile Ala Lys
545                 550                 555                 560

Phe Lys Val Thr Leu Asn Ser Ala Ala Leu Leu Gln Arg Tyr Arg Val
                565                 570                 575

Arg Ile Arg Tyr Ala Ser Thr Thr Asn Leu Arg Leu Phe Val Gln Asn
            580                 585                 590

Ser Asn Asn Asp Phe Leu Val Ile Tyr Ile Asn Lys Thr Met Asn Ile
        595                 600                 605

Asp Gly Asp Leu Thr Tyr Gln Thr Phe Asp Phe Ala Thr Ser Asn Ser
    610                 615                 620

Asn Met Gly Phe Ser Gly Asp Thr Asn Asp Phe Ile Ile Gly Ala Glu
625                 630                 635                 640

Ser Phe Val Ser Asn Glu Lys Ile Tyr Ile Asp Lys Ile Glu Phe Ile
```

-continued

```
                645                 650                 655
Pro Val Gln (2) INFORMATION FOR SEQ ID NO:113:

(i) SEQUENCE CHARACTERISTICS:
        (A) LENGTH: 652 amino acids
        (B) TYPE: amino acid
        (C) STRANDEDNESS:
        (D) TOPOLOGY: linear (xi) SEQUENCE DESCRIPTION: SEQ ID NO:113:

Met Ile Arg Lys Gly Gly Arg Lys Met Asn Pro Asn Arg Ser Glu
1               5                   10                  15

His Asp Thr Ile Lys Thr Thr Glu Asn Glu Val Pro Thr Asn His
                20                  25                  30

Val Gln Tyr Pro Leu Ala Glu Thr Pro Asn Pro Thr Leu Glu Asp Leu
            35                  40                  45

Asn Tyr Lys Glu Phe Leu Arg Met Thr Ala Asp Asn Thr Glu Ala
    50                  55                  60

Leu Asp Ser Ser Thr Thr Lys Asp Val Ile Gln Lys Gly Ile Ser Val
65                  70                  75                  80

Val Gly Asp Leu Leu Gly Val Val Gly Phe Pro Phe Gly Gly Ala Leu
                85                  90                  95

Val Ser Phe Tyr Thr Asn Phe Leu Asn Thr Ile Trp Pro Ser Glu Asp
                100                 105                 110

Pro Trp Lys Ala Phe Met Glu Gln Val Glu Ala Leu Met Asp Gln Lys
            115                 120                 125

Ile Ala Asp Tyr Ala Lys Asn Lys Ala Leu Ala Glu Leu Gln Gly Leu
    130                 135                 140

Gln Asn Asn Val Glu Asp Tyr Val Ser Ala Leu Ser Ser Trp Gln Lys
145                 150                 155                 160

Asn Pro Val Ser Ser Arg Asn Pro His Ser Gln Gly Arg Ile Arg Glu
                165                 170                 175

Leu Phe Ser Gln Ala Glu Ser His Phe Arg Asn Ser Met Pro Ser Phe
                180                 185                 190

Ala Ile Ser Gly Tyr Glu Val Leu Phe Leu Thr Thr Tyr Ala Gln Ala
            195                 200                 205

Ala Asn Thr His Leu Phe Leu Leu Lys Asp Ala Gln Ile Tyr Gly Glu
    210                 215                 220

Glu Trp Gly Tyr Glu Lys Glu Asp Ile Ala Glu Phe Tyr Lys Arg Gln
225                 230                 235                 240

Leu Lys Leu Thr Gln Glu Tyr Thr Asp His Cys Val Lys Trp Tyr Asn
                245                 250                 255

Val Gly Leu Asp Lys Leu Arg Gly Ser Ser Tyr Glu Ser Trp Val Asn
                260                 265                 270

Phe Asn Arg Tyr Arg Arg Glu Met Thr Leu Thr Val Leu Asp Leu Ile
            275                 280                 285

Ala Leu Phe Pro Leu Tyr Asp Val Arg Leu Tyr Pro Lys Glu Val Lys
    290                 295                 300

Thr Glu Leu Thr Arg Asp Val Leu Thr Asp Pro Ile Val Gly Val Asn
305                 310                 315                 320

Asn Leu Arg Gly Tyr Gly Thr Thr Phe Ser Asn Ile Glu Asn Tyr Ile
                325                 330                 335

Arg Lys Pro His Leu Phe Asp Tyr Leu His Arg Ile Gln Phe His Thr
```

-continued

```
              340                 345                 350
Arg Phe Gln Pro Gly Tyr Tyr Gly Asn Asp Ser Phe Asn Tyr Trp Ser
            355                 360                 365

Gly Asn Tyr Val Ser Thr Arg Pro Ser Ile Gly Ser Asn Asp Ile Ile
    370                 375                 380

Thr Ser Pro Phe Tyr Gly Asn Lys Ser Ser Glu Pro Val Gln Asn Leu
385                 390                 395                 400

Glu Phe Asn Gly Glu Lys Val Tyr Arg Ala Val Ala Asn Thr Asn Leu
                405                 410                 415

Ala Val Trp Pro Ser Ala Val Tyr Ser Gly Val Thr Lys Val Glu Phe
            420                 425                 430

Ser Gln Tyr Asn Asp Gln Thr Asp Glu Ala Ser Thr Gln Thr Tyr Asp
        435                 440                 445

Ser Lys Arg Asn Val Gly Ala Val Ser Trp Asp Ser Ile Asp Gln Leu
    450                 455                 460

Pro Pro Glu Thr Thr Asp Glu Pro Leu Glu Lys Gly Tyr Ser His Gln
465                 470                 475                 480

Leu Asn Tyr Val Met Cys Phe Leu Met Gln Gly Ser Arg Gly Thr Ile
                485                 490                 495

Pro Val Leu Thr Trp Thr His Lys Ser Val Asp Phe Phe Asn Met Ile
            500                 505                 510

Asp Ser Lys Lys Ile Thr Gln Leu Pro Leu Val Lys Ala Tyr Lys Leu
        515                 520                 525

Gln Ser Gly Ala Ser Val Val Ala Gly Pro Arg Phe Thr Gly Gly Asp
    530                 535                 540

Ile Ile Gln Cys Thr Glu Asn Gly Ser Ala Ala Thr Ile Tyr Val Thr
545                 550                 555                 560

Pro Asp Val Ser Tyr Ser Gln Lys Tyr Arg Ala Arg Ile His Tyr Ala
                565                 570                 575

Ser Thr Ser Gln Ile Thr Phe Thr Leu Ser Leu Asp Gly Ala Pro Phe
            580                 585                 590

Asn Gln Tyr Tyr Phe Asp Lys Thr Ile Asn Lys Gly Asp Thr Leu Thr
        595                 600                 605

Tyr Asn Ser Phe Asn Leu Ala Ser Phe Ser Thr Pro Phe Glu Leu Ser
    610                 615                 620

Gly Asn Asn Leu Gln Ile Gly Val Thr Gly Leu Ser Ala Gly Asp Lys
625                 630                 635                 640

Val Tyr Ile Asp Lys Ile Glu Phe Ile Pro Val Asn
                645                 650
```